United States Patent
Shemesh et al.

(10) Patent No.: US 11,324,824 B2
(45) Date of Patent: May 10, 2022

(54) SOMATIC OPSINS FOR SINGLE CELL RESOLUTION OPTOGENETICS

(71) Applicant: Massachusetts Institute of Technology, Cambridge, MA (US)

(72) Inventors: Or A. Shemesh, Somerville, MA (US); Changyang Linghu, Cambridge, MA (US); Edward Boyden, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 177 days.

(21) Appl. No.: 16/306,627

(22) PCT Filed: Jun. 3, 2017

(86) PCT No.: PCT/US2017/035862
§ 371 (c)(1),
(2) Date: Dec. 3, 2018

(87) PCT Pub. No.: WO2017/210664
PCT Pub. Date: Dec. 7, 2017

(65) Prior Publication Data
US 2019/0307882 A1    Oct. 10, 2019

Related U.S. Application Data

(60) Provisional application No. 62/345,274, filed on Jun. 3, 2016.

(51) Int. Cl.
C07K 14/47    (2006.01)
C07K 14/405   (2006.01)
(Continued)

(52) U.S. Cl.
CPC .......... *A61K 41/0057* (2013.01); *A61K 38/17* (2013.01); *A61N 5/06* (2013.01); *A61N 5/062* (2013.01); *C07K 14/405* (2013.01); *C07K 14/4716* (2013.01); *C07K 14/705* (2013.01); *C07K 14/70571* (2013.01);
(Continued)

(58) Field of Classification Search
None
See application file for complete search history.

(56) References Cited

U.S. PATENT DOCUMENTS

| 2006/0265770 A1 | 11/2006 | Allen |
| 2014/0178381 A1 | 6/2014 | Pun et al. |
| 2016/0039902 A1 | 2/2016 | Klapoetke et al. |

OTHER PUBLICATIONS

Ren et al., "Multiple Trafficking Signals Regulate Kainate Receptor KA2 Subunit Surface Expression", Journal of Neuroscience, Jul. 23, 2003, pp. 6608-6616, vol. 23, No. 16 (Year: 2003).*

(Continued)

*Primary Examiner* — Aurora M Fontainhas
(74) *Attorney, Agent, or Firm* — Pierce Atwood LLP

(57) ABSTRACT

The invention, in some aspects, relates to polypeptide molecules and their encoding nucleic acid molecules and use of such molecules to target opsins to the soma of cells in which they are expressed. Compositions of the invention may be delivered to cells and subjects and used in methods to modulate electrical activity of cells in which they are expressed, and for treatment of diseases and conditions in subjects.

9 Claims, 25 Drawing Sheets

Specification includes a Sequence Listing.

Untargeted opsin    Soma-targeted opsin

(51) Int. Cl.

| | | |
|---|---|---|
| *A61K 41/00* | (2020.01) | |
| *A61K 38/17* | (2006.01) | |
| *C07K 14/705* | (2006.01) | |
| *C12N 5/0793* | (2010.01) | |
| *C12N 13/00* | (2006.01) | |
| *C12N 15/86* | (2006.01) | |
| *G01N 33/50* | (2006.01) | |
| *G01N 33/566* | (2006.01) | |
| *A61N 5/06* | (2006.01) | |
| *A61K 38/00* | (2006.01) | |

(52) U.S. Cl.
CPC ......... *C12N 5/0619* (2013.01); *C12N 13/00* (2013.01); *C12N 15/86* (2013.01); *G01N 33/5058* (2013.01); *G01N 33/566* (2013.01); *A61K 38/00* (2013.01); *C07K 2319/01* (2013.01)

(56) References Cited

OTHER PUBLICATIONS

Zhang et al., Channelrhodopsin-2 and optical control of excitable cells, Nature Meth., Vo. 3, No. 10, pp. 786-792 2006 (Year: 2006).*
Begue et al., "Two-photon excitation in scattering media by spatiotemporally shaped beams and their application in optogenetic stimulation." Biomedical Optics Express (2013), vol. 4, No. 12: 2869-2879.
Bianco et al., "Bicaudal-D Reglates Fragile X Mental Retardation Protein Levels, Motility, and Function during Neuronal Morphogenesis." Current Biology (2010), 20(16): 1487-1492.
Chow et al. "High-Performance Genetically Targetable Optical Neural Silencing via Light-Driven Proton Pumps." Nature. Jan. 7, 2010; 463(7277): 98-102.
Chuong et al., "Noninvasive optical inhibition with a red-shifted microbial rhodopsin." Nat. Neurosci. (2014), 17(8): 1123-1129.
Dana et al., "Sensitive red protein calcium indicators for imaging neural activity." eLife (2016), 5:e12727.
Ducros et al., "Efficient large core fiber-based detection for multichannel two-photon fluorescence microscopy and spectral unmixing." Journal of Neuroscience Methods (2011), 198: 172-180.
Garrido et al., "A Targeting Motif Involved in Sodium Channel Clustering at the Axonal Initial Segment." Science (2003), vol. 300(5628): 2091-2094.
Gerchberg et al., "A Practical Algorithm for the Determination of Phase from Image and Diffraction Plane Pictures." Optik, (1972), 35(2): 237-246.
Grubb et al., "Channelrhodopsin-2 Localised to the Axon Initial Segment." PLoS One (2010), 5(10): e13761.
Hernandez et al.,"Three-dimensional spatiotemporal focusing of holographic patterns." Nature Communications | 7:11928 | DOI: 10.1038/ncomms11928 |www.nature.com/naturecommunications.
Hofherr et al., "Selective Golgi export of Kir2.1 controls the stoichiometry of functional Kir2.x channel heteromers." Journal of Cell Science (2005), 118:1935-1943.
International Preliminary Report on Patentability dated Dec. 4, 2018 from corresponding International Application No. PCT/US2017/035862 filed on Jun. 3, 2017.
International Search Report of the International Searching Authority dated Oct. 9, 2017 from corresponding International Application No. PCT/US2017/035862 filed on Jun. 3, 2017.

Jacobs et al., "Soma-Restricted Products of the Myelin Proteolipid Gene Are Expressed Primarily in Neurons in the Developing Mouse Nervous System." Dev Neurosci 2003;25:96-104.
Jiang et al., "High Ca2+-phosphate transfection efficiency in low-density neuronal cultures." Nature Protocols (2006) vol. 1, No. 2: 695-700.
Klapoetke et al., "Independent Optical Excitation of Distinct Neural Populations." Nat. Methods (2014), 11(3):338-346.
Lewis et al., "A Role for Myosin VI in the Localization of Axonal Proteins." PLoS Biology (2011), vol. 9, Issue 3, e1001021, 18 pages.
Lewis et al., "Myosin-dependent targeting of transmembrane proteins to neuromal dendrites." Nat. Neurosci., (2009), 12(5): 568-576.
Lim et al., "A Novel Targeting Signal for Proximal Clustering of the Kv2.1 K+ Channel in Hippocampal Neurons." Neuron. Feb. 2000, vol. 25: 385-397.
Lutz et al., "Attention regulation and monitoring in mediation." Trends Cogn. Sci. (2008), 12(4): 163-169.
Ma et al., "Role of ER Export Signals in Controlling Surface Potassium Channel Numbers." Science, Jan. 12, 2001, vol. 291, Issue 5502: 316-319.
Marchler-Bauer et al., "CDD: NCBI's conserved domain database." Nucleic Acids Research (2014), vol. 43, Issue D1: D222-D226.
Mikula et al., "High-resolution whole-brain staining for electron microscopic circuit reconstruction." Nature Methods (2015), 12: 1-14.
Nicholson et al., "Extracellular space structure revealed by diffusion analysis." Trends in Neurosci. (1998), vol. 21, No. 5: 207-215.
Pallotto et al., "Extracellular space preservation aids the connectomic analysis of neural circuits." eLife 2015; 4e08206, DOI: 10.7554/eLife.08206.
Papagiakoumou et al., "Scanless two-photon excitation of channelrhodopsin-2." Nature Methods (2010), vol. 7, No. 10: 848-854.
Prakash et al., "Two-photon optogenetic toolbox for fast inhibition, excitation and bistable modulation." Nat. Methods (2012), 9(12): 1171-1179.
Ren et al., "Multiple Trafficking Signals Regulate Kainate Receptor KA2 Subunit Surface Expression." The Journal of Neuroscience, Jul. 23, 2003, vol. 23, No. 16: 6608-6616.
Rickgauer et al., "Two-photon excitation of channelrhodopsin-2 at saturation." PNAS, Sep. 1, 2009, vol. 106, No. 35: 15025-15030.
Schafer et al., "L1 syndrome mutations impair neuronal L1 function at different levels by divergent mechanisms." Neurobiology of Disease (2010): 40(1): 222-237.
Valluru et al., "Ligand Binding is a Critcal Requirement for Plasma Membrane Expression of Heteromeric Kainate Receptors" (2005), J. Biol. Chem. 280(7): 6085-6093.
Written Opinion of the International Searching Authority dated Nov. 8, 2017 from corresponding International Application No. PCT/US2017/035862 filed on Jun. 3, 2017.
Xu et al., "Measurement of two-photon excitation cross sections of molecular fluorophores with data from 690 to 1050 nm." J. Optical Society of America (1996), 13(3): 481-491.
Zhang et al., "Targeted Expression of Channelrhodopsin-2 to the Axon Initial Segment Alters the Temporal Firing Properties of Retinal Ganglon Cells." PLoS One (2015), 10(11), e0142052.
Zhang et al., "Restriction of 480/270-kD AnkyrinG to Axon Proximal Segments Requires Multiple AnkyrinG-specific Domains" (1998) J. Cell Biol. 142(6): 1571-1581.
Zipfel et al., "Nonlinear magic: multiphoton microscopy in the biosciences." Nature Biotechnology (2003), vol. 21 (11): 1369-1377.

* cited by examiner

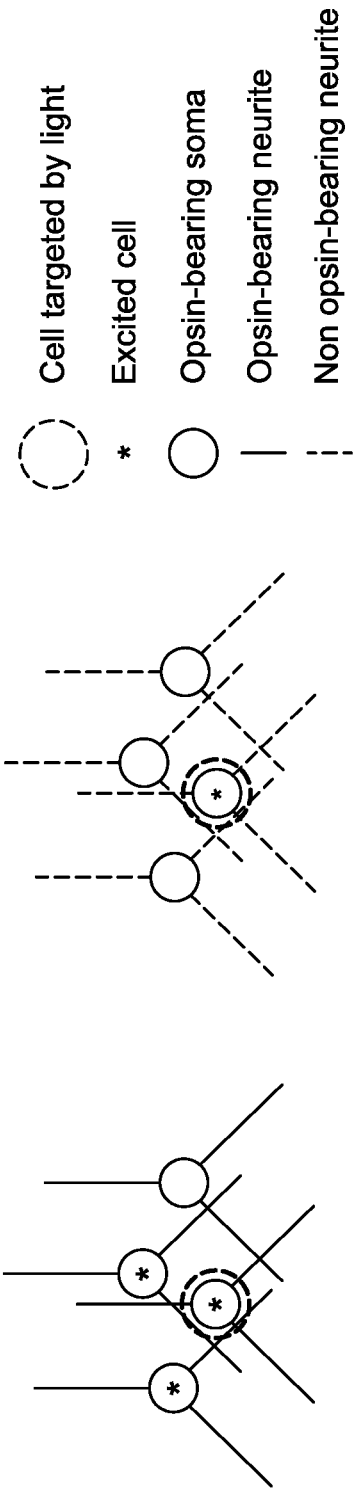

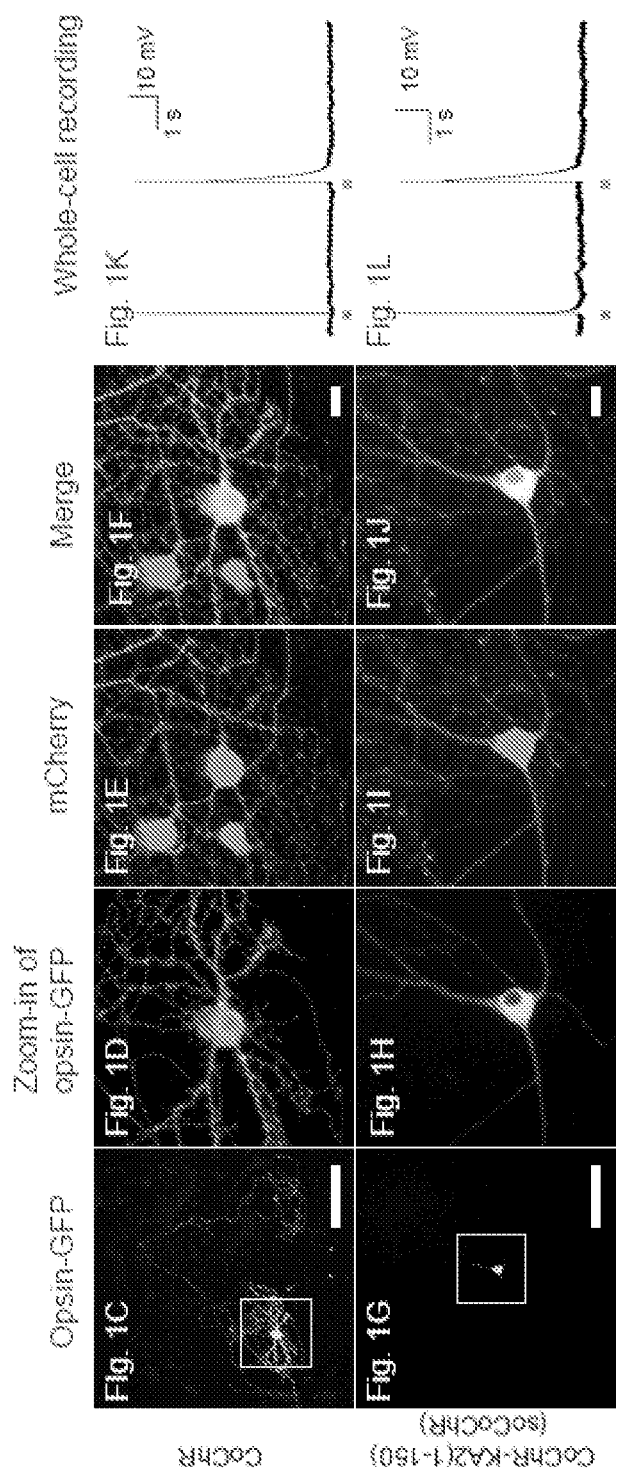

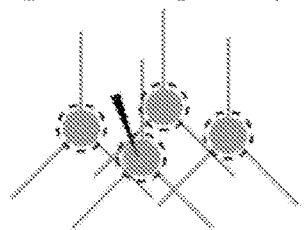 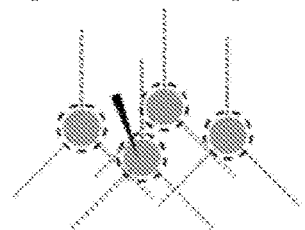 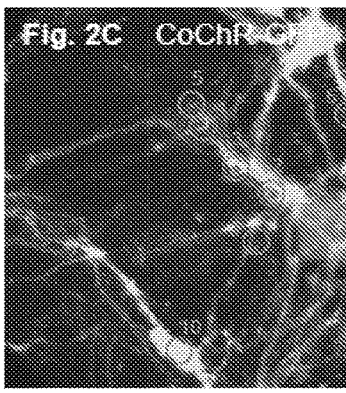 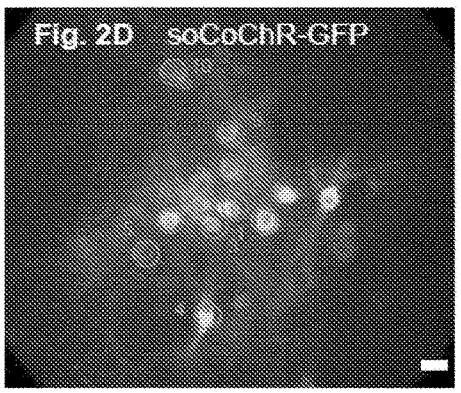 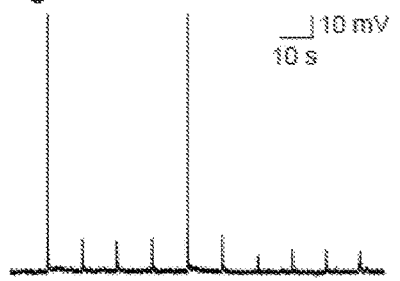 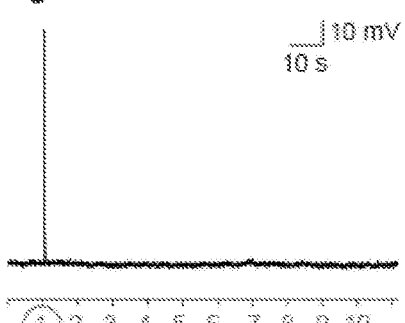

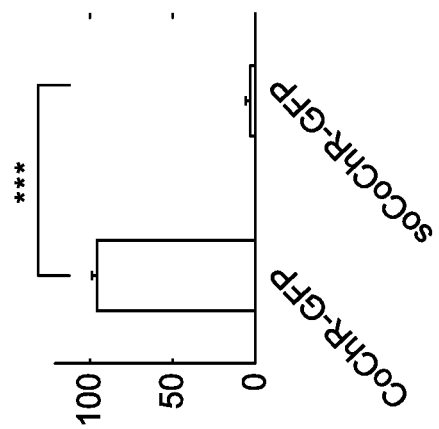
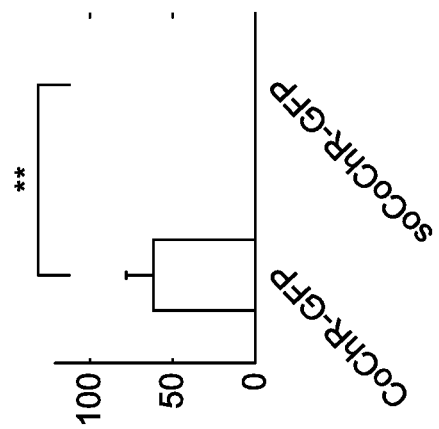
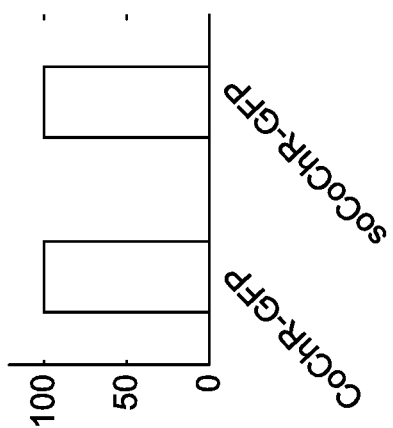
Fig. 2G
Fig. 2H
Fig. 2I

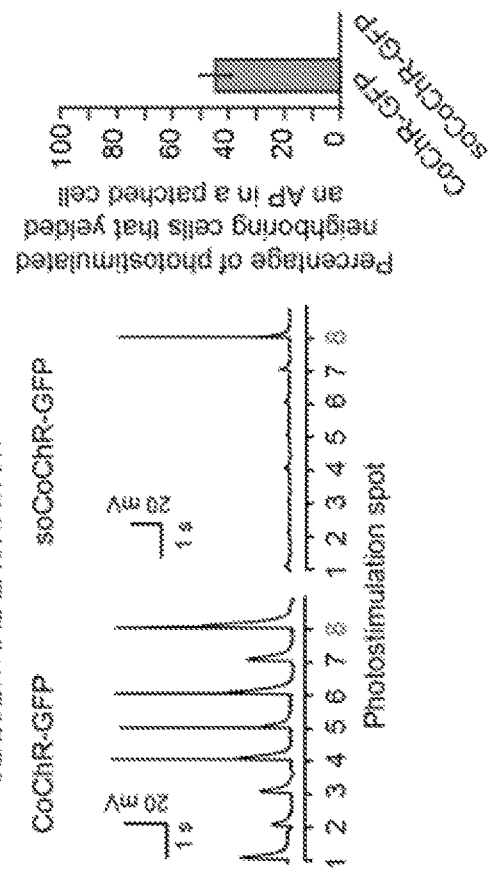
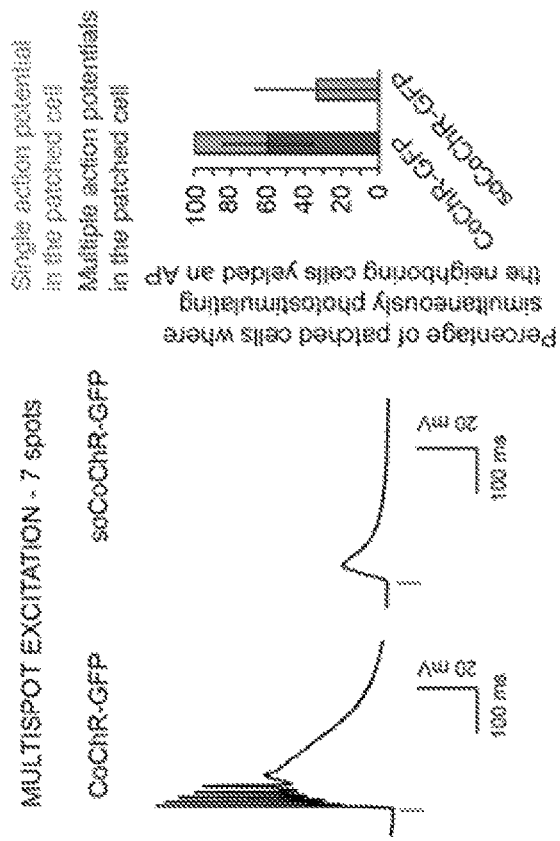
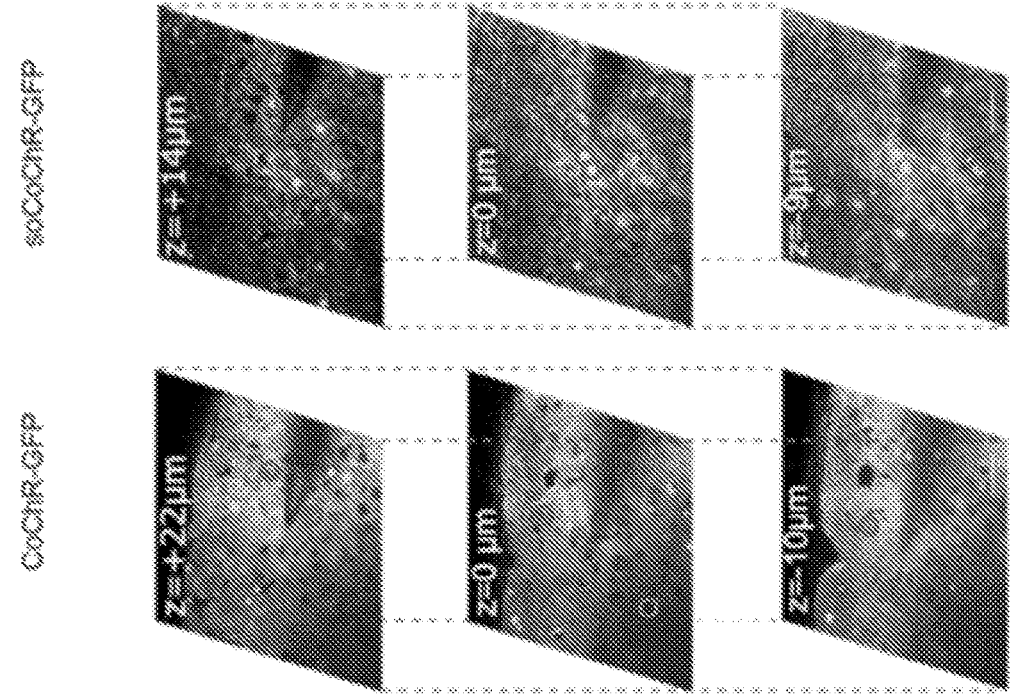

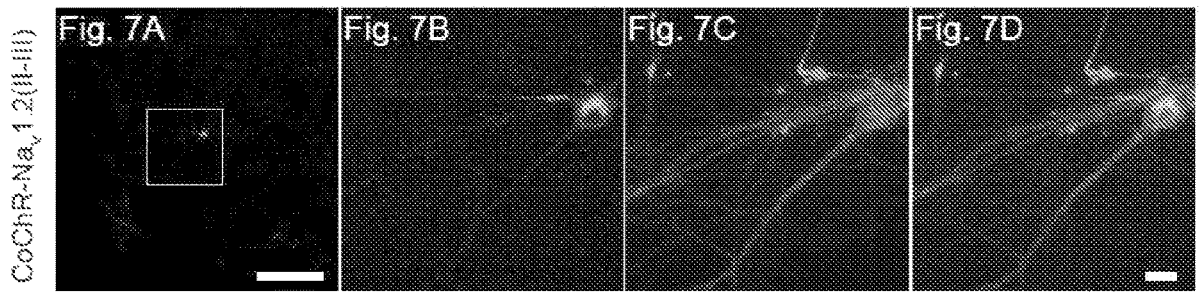
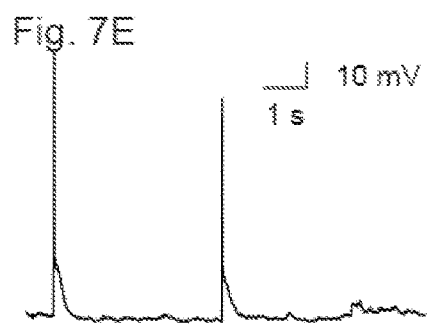
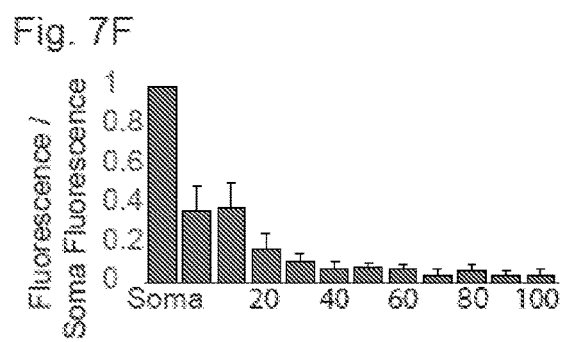

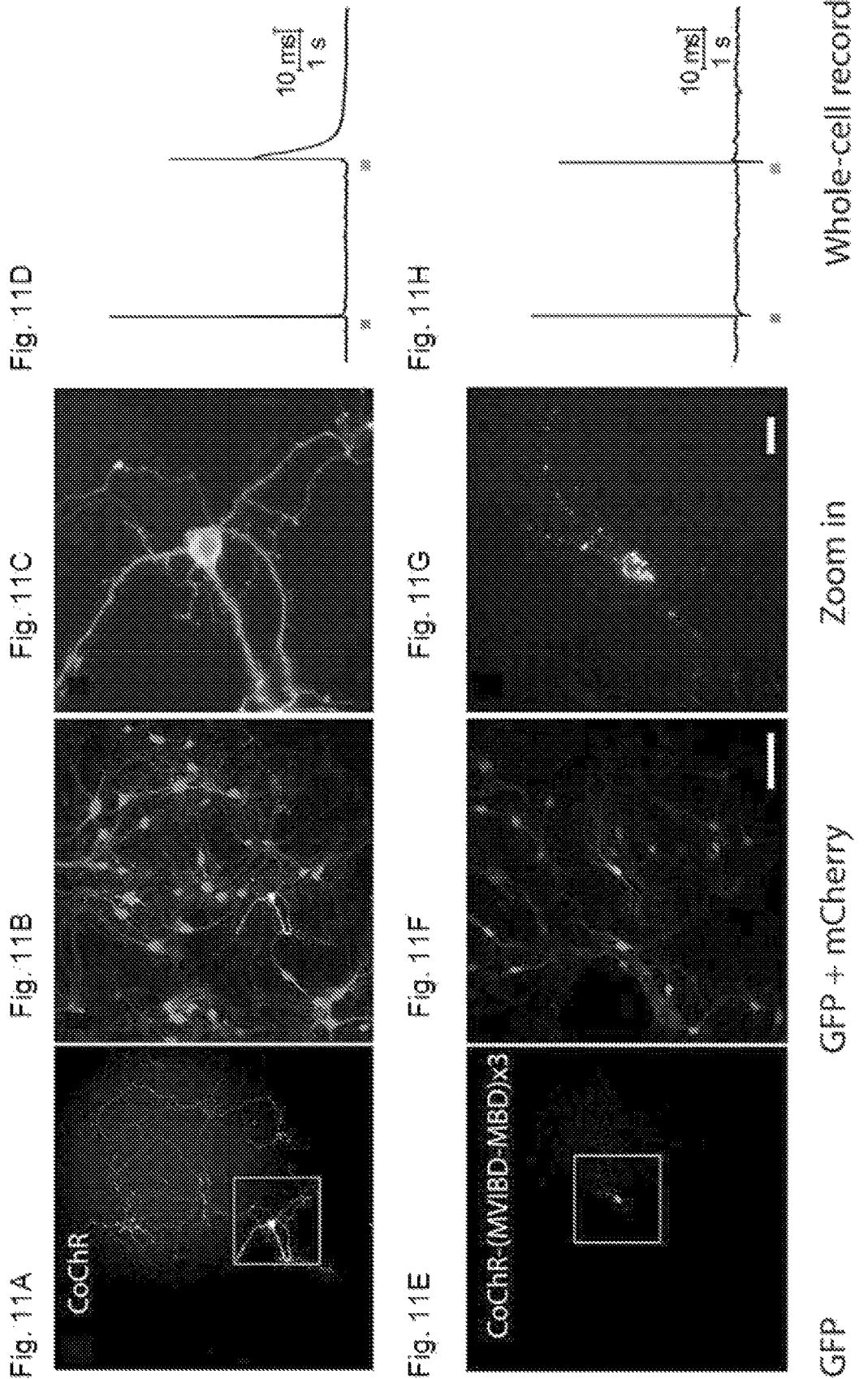

Fig. 12A
Fig. 12B
Fig. 12C
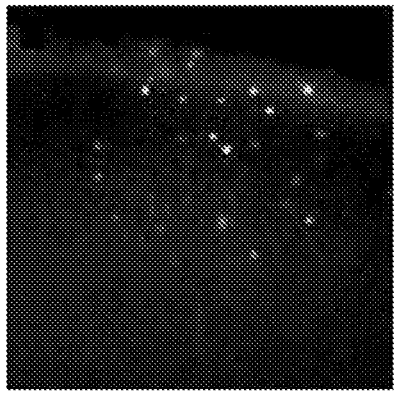
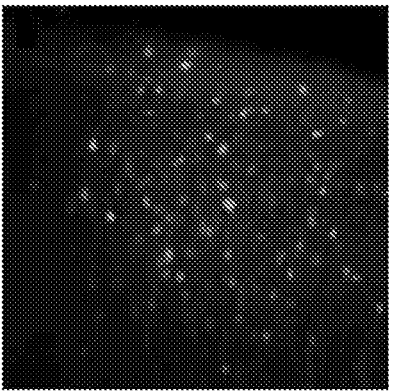
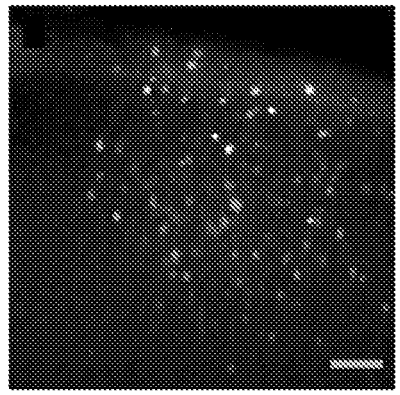

SEQUENCE LISTING

```
<160> NUMBER OF SEQ ID NOS: 59

<210> SEQ ID NO 1
<211> LENGTH: 150
<212> TYPE: PRT
<213> ORGANISM: Mus Musculus

<400> SEQUENCE: 1

Met Pro Ala Glu Leu Leu Leu Leu Ile Val Ala Phe Ala Asn Pro
1               5                   10                  15

Ser Cys Gln Val Leu Ser Ser Leu Arg Met Ala Ala Ile Leu Asp Asp
                20                  25                  30

Gln Thr Val Cys Gly Arg Gly Glu Arg Leu Ala Leu Ala Leu Ala Arg
                35                  40                  45

Glu Gln Ile Asn Gly Ile Ile Glu Val Pro Ala Lys Ala Arg Val Glu
    50                  55                  60

Val Asp Ile Phe Glu Leu Gln Arg Asp Ser Gln Tyr Glu Thr Thr Asp
65                  70                  75                  80

Thr Met Cys Gln Ile Leu Pro Lys Gly Val Val Ser Val Leu Gly Pro
                85                  90                  95

Ser Ser Ser Pro Ala Ser Ala Ser Thr Val Ser His Ile Cys Gly Glu
                100                 105                 110

Lys Glu Ile Pro His Ile Lys Val Gly Pro Glu Glu Thr Pro Arg Leu
            115                 120                 125

Gln Tyr Leu Arg Phe Ala Ser Val Ser Leu Tyr Pro Ser Asn Glu Asp
        130                 135                 140

Val Ser Leu Ala Val Ser
145                 150

<210> SEQ ID NO 2
<211> LENGTH: 450
<212> TYPE: DNA
<213> ORGANISM: Artificial Sequence
<220> FEATURE:
<223> OTHER INFORMATION: Synthetic polynucleotide

<400> SEQUENCE: 2
atgcccgccg aactgctgct gctgctgatt gtcgcttttg ctaacccttc ttgccaggtg    60
ctgtcttctc tgaggatggc cgctattctg gacgatcaga ccgtgtgcgg aagaggagag    120
aggctggcac tggcactggc tagggagcag atcaatggca tcattgaagt gcctgcaaag    180
gcccgggtcg aggtggacat tttcgaactg cagagagata gccagtacga gaccacagac    240
```

```
accatgtgcc agatcctgcc aaaaggagtg gtctccgtcc tgggaccaag ctcctctcct    300
gcttctgcaa gtaccgtgtc tcacatttgt ggcgagaagg aaatccccca tatcaaggtc    360
gggccagagg aaacacccag gctgcagtac ctgcgcttcg cctcagtgag cctgtatcca    420
tcaaacgagg atgtgtcact ggcagtcagc                                     450
```

<210> SEQ ID NO 3
<211> LENGTH: 360
<212> TYPE: PRT
<213> ORGANISM: Mus musculus

<400> SEQUENCE: 3

```
Met Pro Ala Glu Leu Leu Leu Leu Ile Val Ala Phe Ala Asn Pro
1               5                   10                  15

Ser Cys Gln Val Leu Ser Ser Leu Arg Met Ala Ala Ile Leu Asp Asp
                20                  25                  30

Gln Thr Val Cys Gly Arg Gly Glu Arg Leu Ala Leu Ala Leu Ala Arg
            35                  40                  45

Glu Gln Ile Asn Gly Ile Ile Glu Val Pro Ala Lys Ala Arg Val Glu
        50                  55                  60

Val Asp Ile Phe Glu Leu Gln Arg Asp Ser Gln Tyr Glu Thr Thr Asp
65                  70                  75                  80

Thr Met Cys Gln Ile Leu Pro Lys Gly Val Ser Val Leu Gly Pro
                85                  90                  95

Ser Ser Ser Pro Ala Ser Ala Ser Thr Val Ser His Ile Cys Gly Glu
            100                 105                 110

Lys Glu Ile Pro His Ile Lys Val Gly Pro Glu Glu Thr Pro Arg Leu
        115                 120                 125

Gln Tyr Leu Arg Phe Ala Ser Val Ser Leu Tyr Pro Ser Asn Glu Asp
    130                 135                 140

Val Ser Leu Ala Val Ser Arg Ile Leu Lys Ser Phe Asn Tyr Pro Ser
145                 150                 155                 160

Ala Ser Leu Ile Cys Ala Lys Ala Glu Cys Leu Leu Arg Leu Glu Glu
                165                 170                 175

Leu Val Arg Gly Phe Leu Ile Ser Lys Glu Thr Leu Ser Val Arg Met
            180                 185                 190

Leu Asp Asp Ser Arg Asp Pro Thr Pro Leu Leu Lys Glu Ile Arg Asp
        195                 200                 205

Asp Lys Val Ser Thr Ile Ile Ile Asp Ala Asn Ala Ser Ile Ser His
    210                 215                 220

Leu Val Leu Arg Lys Ala Ser Glu Leu Gly Met Thr Ser Ala Phe Tyr
225                 230                 235                 240

Lys Tyr Ile Leu Thr Thr Met Asp Phe Pro Ile Leu His Leu Asp Gly
                245                 250                 255

Ile Val Glu Asp Ser Ser Asn Ile Leu Gly Phe Ser Met Phe Asn Thr
            260                 265                 270

Ser His Pro Phe Tyr Pro Glu Phe Val Arg Ser Leu Asn Met Ser Trp
        275                 280                 285

Arg Glu Asn Cys Glu Ala Ser Thr Tyr Pro Gly Pro Ala Leu Ser Ala
    290                 295                 300

Ala Leu Met Phe Asp Ala Val His Val Val Ser Ala Val Arg Glu
305                 310                 315                 320

Leu Asn Arg Ser Gln Glu Ile Gly Val Lys Pro Leu Ala Cys Thr Ser
                325                 330                 335
```

Ala Asn Ile Trp Pro His Gly Thr Ser Leu Met Asn Tyr Leu Arg Met
                340                 345                 350

Val Glu Tyr Asp Gly Leu Thr Gly
        355                 360

<210> SEQ ID NO 4
<211> LENGTH: 1080
<212> TYPE: DNA
<213> ORGANISM: Artificial Sequence
<220> FEATURE:
<223> OTHER INFORMATION: Synthetic polynucleotide

<400> SEQUENCE: 4

```
atgcccgccg aactgctgct gctgctgatt gtcgcttttg ctaacccttc ttgccaggtg      60
ctgtcttctc tgaggatggc cgctattctg acgatcaga ccgtgtgcgg aagaggagag     120
aggctggcac tggcactggc tagggagcag atcaatggca tcattgaagt gcctgcaaag     180
gcccgggtcg aggtggacat tttcgaactg cagagagata ccagtacga gaccacagac     240
accatgtgcc agatcctgcc aaaaggagtg gtctccgtcc tgggaccaag ctcctctcct     300
gcttctgcaa gtaccgtgtc tcacatttgt ggcgagaagg aaatcccca tatcaaggtc     360
gggccagagg aaacacccag gctgcagtac ctgcgcttcg cctcagtgag cctgtatcca     420
tcaaacgagg atgtgtcact ggcagtcagc cgcatcctga gagctttaa ttatccctcc     480
gcctctctga tttgcgccaa agctgagtgt ctgctgcggc tggaggaact ggtgagaggc     540
ttcctgatca gcaaggaaac actgtccgtc aggatgctgg acgatagtcg cgatcccact     600
cctctgctga aggagatcag ggacgataaa gtctccacca tcattatcga cgcaaacgcc     660
agtatttcac acctggtgct gcgcaaagca agtgaactgg gatgacctc agccttctac     720
aaatatatcc tgactaccat ggactttccc atcctgcacc tggacggaat tgtggaggat     780
agttcaaaca ttctgggctt ctctatgttt aatactagtc atcccttcta ccctgaattt     840
gtgaggtccc tgaacatgtc ttggcgcgag aattgcgaag cttcaaccta tccaggacca     900
gcactgagcg cagctctgat gttcgatgcc gtgcacgtgg tcgtgtccgc tgtcagagag     960
ctgaataggt ctcaggaaat cggcgtgaag cctctggcat gtacttctgc caacatttgg    1020
ccacatggga ccagtctgat gaattacctg aggatggtgg agtatgacgg cctgaccgga    1080
```

<210> SEQ ID NO 5
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 5
ggsggtggsg gt                                                           12

<210> SEQ ID NO 6
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 6
ttctgctacg agaatgaagt g                                                 21

<210> SEQ ID NO 7

```
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 7

Phe Cys Tyr Glu Asn Glu Val
1               5

<210> SEQ ID NO 8
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 8
aaatccagaa ttacttctga agggagtat atccctctgg atcaaataga catcaatgtt    60

<210> SEQ ID NO 9
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 9

Lys Ser Arg Ile Thr Ser Glu Gly Glu Tyr Ile Pro Leu Asp Gln Ile
1               5                   10                  15

Asp Ile Asn Val
            20

<210> SEQ ID NO 10
<211> LENGTH: 100
<212> TYPE: PRT
<213> ORGANISM: Artificial Sequence
<220> FEATURE:
<223> OTHER INFORMATION: Synthetic polypeptide

<400> SEQUENCE: 10

Met Pro Ala Glu Leu Leu Leu Leu Ile Val Ala Phe Ala Asn Pro
1               5                   10                  15

Ser Cys Gln Val Leu Ser Ser Leu Arg Met Ala Ala Ile Leu Asp Asp
                20                  25                  30

Gln Thr Val Cys Gly Arg Gly Glu Arg Leu Ala Leu Ala Leu Ala Arg
            35                  40                  45

Glu Gln Ile Asn Gly Ile Ile Glu Val Pro Ala Lys Ala Arg Val Glu
    50                  55                  60

Val Asp Ile Phe Glu Leu Gln Arg Asp Ser Gln Ala Glu Thr Thr Asp
65                  70                  75                  80

Thr Met Cys Gln Ile Leu Pro Lys Gly Val Val Ser Val Leu Gly Pro
                85                  90                  95

Ser Ser Ser Pro
            100

<210> SEQ ID NO 11
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 11
```

```
atgcccgccg aactgctgct gctgctgatt gtcgcttttg ctaacccttc ttgccaggtg    60
ctgtcttctc tgaggatggc cgctattctg gacgatcaga ccgtgtgcgg aagaggagag   120
aggctggcac tggcactggc tagggagcag atcaatggca tcattgaagt gcctgcaaag   180
gcccgggtcg aggtggacat tttcgaactg cagagagata gccaggccga gaccacagac   240
accatgtgcc agatcctgcc aaaaggagtg gtctccgtcc tgggaccaag ctcctctcct   300
```

<210> SEQ ID NO 12
<211> LENGTH: 100
<212> TYPE: PRT
<213> ORGANISM: Artificial Sequence
<220> FEATURE:
<223> OTHER INFORMATION: Synthetic polypeptide

<400> SEQUENCE: 12

```
Met Pro Ala Glu Leu Leu Leu Leu Ile Val Ala Phe Ala Asn Pro
1               5                   10                  15

Ser Cys Gln Val Leu Ser Ser Leu Arg Met Ala Ala Ile Leu Asp Asp
            20                  25                  30

Gln Thr Val Cys Gly Arg Gly Glu Arg Leu Ala Leu Ala Leu Ala Arg
        35                  40                  45

Glu Gln Ile Asn Gly Ile Ile Glu Val Pro Ala Lys Ala Arg Val Glu
    50                  55                  60

Val Asp Ile Phe Glu Leu Gln Arg Asp Ser Gln Tyr Glu Thr Thr Asp
65                  70                  75                  80

Thr Met Cys Gln Ile Leu Pro Lys Gly Val Val Ser Val Leu Gly Pro
                85                  90                  95

Ser Ser Ser Pro
            100
```

<210> SEQ ID NO 13
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 13

```
atgcccgccg aactgctgct gctgctgatt gtcgcttttg ctaacccttc ttgccaggtg    60
ctgtcttctc tgaggatggc cgctattctg gacgatcaga ccgtgtgcgg aagaggagag   120
aggctggcac tggcactggc tagggagcag atcaatggca tcattgaagt gcctgcaaag   180
gcccgggtcg aggtggacat tttcgaactg cagagagata gccagtacga gaccacagac   240
accatgtgcc agatcctgcc aaaaggagtg gtctccgtcc tgggaccaag ctcctctcct   300
```

<210> SEQ ID NO 14
<211> LENGTH: 75
<212> TYPE: PRT
<213> ORGANISM: Artificial Sequence
<220> FEATURE:
<223> OTHER INFORMATION: Synthetic polypeptide

<400> SEQUENCE: 14

```
Met Pro Ala Glu Leu Leu Leu Leu Ile Val Ala Phe Ala Asn Pro
1               5                   10                  15

Ser Cys Gln Val Leu Ser Ser Leu Arg Met Ala Ala Ile Leu Asp Asp
            20                  25                  30

Gln Thr Val Cys Gly Arg Gly Glu Arg Leu Ala Leu Ala Leu Ala Arg
```

```
                35                  40                  45
Glu Gln Ile Asn Gly Ile Ile Glu Val Pro Ala Lys Ala Arg Val Glu
        50                  55                  60

Val Asp Ile Phe Glu Leu Gln Arg Asp Ser Gln
65                  70                  75

<210> SEQ ID NO 15
<211> LENGTH: 225
<212> TYPE: DNA
<213> ORGANISM: Artificial Sequence
<220> FEATURE:
<223> OTHER INFORMATION: Synthetic polynucleotide

<400> SEQUENCE: 15
atgcccgccg aactgctgct gctgctgatt gtcgcttttg ctaacccttc ttgccaggtg     60
ctgtcttctc tgaggatggc cgctattctg acgatcaga  ccgtgtgcgg aagaggagag    120
aggctggcac tggcactggc tagggagcag atcaatggca tcattgaagt gcctgcaaag    180
gcccgggtcg aggtggacat tttcgaactg cagagagata gccag                    225

<210> SEQ ID NO 16
<211> LENGTH: 979
<212> TYPE: PRT
<213> ORGANISM: Mus musculus

<400> SEQUENCE: 16

Met Pro Ala Glu Leu Leu Leu Leu Ile Val Ala Phe Ala Asn Pro
1               5                   10                  15

Ser Cys Gln Val Leu Ser Ser Leu Arg Met Ala Ala Ile Leu Asp Asp
                20                  25                  30

Gln Thr Val Cys Gly Arg Gly Glu Arg Leu Ala Leu Ala Leu Ala Arg
            35                  40                  45

Glu Gln Ile Asn Gly Ile Ile Glu Val Pro Ala Lys Ala Arg Val Glu
        50                  55                  60

Val Asp Ile Phe Glu Leu Gln Arg Asp Ser Gln Tyr Glu Thr Thr Asp
65                  70                  75                  80

Thr Met Cys Gln Ile Leu Pro Lys Gly Val Val Ser Val Leu Gly Pro
                85                  90                  95

Ser Ser Ser Pro Ala Ser Ala Ser Thr Val Ser His Ile Cys Gly Glu
            100                 105                 110

Lys Glu Ile Pro His Ile Lys Val Gly Pro Glu Glu Thr Pro Arg Leu
        115                 120                 125

Gln Tyr Leu Arg Phe Ala Ser Val Ser Leu Tyr Pro Ser Asn Glu Asp
    130                 135                 140

Val Ser Leu Ala Val Ser Arg Ile Leu Lys Ser Phe Asn Tyr Pro Ser
145                 150                 155                 160

Ala Ser Leu Ile Cys Ala Lys Ala Glu Cys Leu Leu Arg Leu Glu Glu
                165                 170                 175

Leu Val Arg Gly Phe Leu Ile Ser Lys Glu Thr Leu Ser Val Arg Met
            180                 185                 190

Leu Asp Asp Ser Arg Asp Pro Thr Pro Leu Leu Lys Glu Ile Arg Asp
        195                 200                 205

Asp Lys Val Ser Thr Ile Ile Ile Asp Ala Asn Ala Ser Ile Ser His
    210                 215                 220

Leu Val Leu Arg Lys Ala Ser Glu Leu Gly Met Thr Ser Ala Phe Tyr
225                 230                 235                 240
```

-continued

```
Lys Tyr Ile Leu Thr Thr Met Asp Phe Pro Ile Leu His Leu Asp Gly
                245                 250                 255

Ile Val Glu Asp Ser Ser Asn Ile Leu Gly Phe Ser Met Phe Asn Thr
            260                 265                 270

Ser His Pro Phe Tyr Pro Glu Phe Val Arg Ser Leu Asn Met Ser Trp
        275                 280                 285

Arg Glu Asn Cys Glu Ala Ser Thr Tyr Pro Gly Pro Ala Leu Ser Ala
    290                 295                 300

Ala Leu Met Phe Asp Ala Val His Val Val Ser Ala Val Arg Glu
305                 310                 315                 320

Leu Asn Arg Ser Gln Glu Ile Gly Val Lys Pro Leu Ala Cys Thr Ser
                325                 330                 335

Ala Asn Ile Trp Pro His Gly Thr Ser Leu Met Asn Tyr Leu Arg Met
            340                 345                 350

Val Glu Tyr Asp Gly Leu Thr Gly Arg Val Glu Phe Asn Ser Lys Gly
        355                 360                 365

Gln Arg Thr Asn Tyr Thr Leu Arg Ile Leu Glu Lys Ser Arg Gln Gly
    370                 375                 380

His Arg Glu Ile Gly Val Trp Tyr Ser Asn Arg Thr Leu Ala Met Asn
385                 390                 395                 400

Ala Thr Thr Leu Asp Ile Asn Leu Ser Gln Thr Leu Ala Asn Lys Thr
                405                 410                 415

Leu Val Val Thr Thr Ile Leu Glu Asn Pro Tyr Val Met Arg Arg Pro
            420                 425                 430

Asn Phe Gln Ala Leu Ser Gly Asn Glu Arg Phe Glu Gly Phe Cys Val
        435                 440                 445

Asp Met Leu Arg Glu Leu Ala Glu Leu Leu Arg Phe Arg Tyr Arg Leu
    450                 455                 460

Arg Leu Val Glu Asp Gly Leu Tyr Gly Ala Pro Glu Pro Asn Gly Ser
465                 470                 475                 480

Trp Thr Gly Met Val Gly Glu Leu Ile Asn Arg Lys Ala Asp Leu Ala
                485                 490                 495

Val Ala Ala Phe Thr Ile Thr Ala Glu Arg Glu Lys Val Ile Asp Phe
            500                 505                 510

Ser Lys Pro Phe Met Thr Leu Gly Ile Ser Ile Leu Tyr Arg Val His
        515                 520                 525

Met Gly Arg Lys Pro Gly Tyr Phe Ser Phe Leu Asp Pro Phe Ser Pro
    530                 535                 540

Ala Val Trp Leu Phe Met Leu Leu Ala Tyr Leu Ala Val Ser Cys Val
545                 550                 555                 560

Leu Phe Leu Ala Ala Arg Leu Ser Pro Tyr Glu Trp Tyr Asn Pro His
                565                 570                 575

Pro Cys Leu Arg Ala Arg Pro His Ile Leu Glu Asn Gln Tyr Thr Leu
            580                 585                 590

Gly Asn Ser Leu Trp Phe Pro Val Gly Gly Phe Met Gln Gln Gly Ser
        595                 600                 605

Glu Ile Met Pro Arg Ala Leu Ser Thr Arg Cys Val Ser Gly Val Trp
    610                 615                 620

Trp Ala Phe Thr Leu Ile Ile Ile Ser Ser Tyr Thr Ala Asn Leu Ala
625                 630                 635                 640

Ala Phe Leu Thr Val Gln Arg Met Glu Val Pro Val Glu Ser Ala Asp
                645                 650                 655

Asp Leu Ala Asp Gln Thr Asn Ile Glu Tyr Gly Thr Ile His Ala Gly
```

```
                   660                 665                 670
Ser Thr Met Thr Phe Gln Asn Ser Arg Tyr Gln Thr Tyr Gln Arg
                675                 680                 685

Met Trp Asn Tyr Met Gln Ser Lys Gln Pro Ser Val Phe Val Lys Ser
                690                 695                 700

Thr Glu Glu Gly Ile Ala Arg Val Leu Asn Ser Arg Tyr Ala Phe Leu
705                 710                 715                 720

Leu Glu Ser Thr Met Asn Glu Tyr His Arg Arg Leu Asn Cys Asn Leu
                725                 730                 735

Thr Gln Ile Gly Gly Leu Leu Asp Thr Lys Gly Tyr Gly Ile Gly Met
                740                 745                 750

Pro Leu Gly Ser Pro Phe Arg Asp Glu Ile Thr Leu Ala Ile Leu Gln
                755                 760                 765

Leu Gln Glu Asn Asn Arg Leu Glu Ile Leu Lys Arg Lys Trp Trp Glu
                770                 775                 780

Gly Gly Arg Cys Pro Lys Glu Glu Asp His Arg Ala Lys Gly Leu Gly
785                 790                 795                 800

Met Glu Asn Ile Gly Gly Ile Phe Val Val Leu Ile Cys Gly Leu Ile
                805                 810                 815

Ile Ala Val Phe Val Ala Val Met Glu Phe Ile Trp Ser Thr Arg Arg
                820                 825                 830

Ser Ala Glu Ser Glu Glu Val Ser Val Cys Gln Glu Met Leu Gln Glu
                835                 840                 845

Leu Arg His Ala Val Ser Cys Arg Lys Thr Ser Arg Ser Arg Arg
850                 855                 860

Arg Arg Pro Gly Gly Pro Ser Arg Ala Leu Leu Ser Leu Arg Ala Val
865                 870                 875                 880

Arg Glu Met Arg Leu Ser Asn Gly Lys Leu Tyr Ser Ala Gly Ala Gly
                885                 890                 895

Gly Asp Ala Gly Ala His Gly Gly Pro Gln Arg Leu Leu Asp Asp Pro
                900                 905                 910

Gly Pro Pro Gly Gly Pro Arg Pro Gln Ala Pro Thr Pro Cys Thr Arg
                915                 920                 925

Val Arg Val Cys Gln Glu Cys Arg Arg Ile Gln Ala Leu Arg Ala Ser
                930                 935                 940

Gly Ala Gly Ala Pro Pro Arg Gly Leu Gly Thr Pro Ala Glu Ala Thr
945                 950                 955                 960

Ser Pro Pro Arg Pro Arg Pro Gly Pro Thr Gly Pro Arg Glu Leu Thr
                965                 970                 975

Glu His Glu

<210> SEQ ID NO 17
<211> LENGTH: 2940
<212> TYPE: DNA
<213> ORGANISM: Mus musculus

<400> SEQUENCE: 17
atgccggctg agctgctgct gctgctgata gtcgccttcg ccaatcccag ctgccaggtg    60
ctgtcatcac tgcgcatggc tgcaatcctg acgaccagaa ccgtgtgtgg ccgtggtgag   120
cgtctggccc tggccctggc ccgagagcag atcaatggga tcatcgaggt cccagccaag   180
gccagagtgg aagtagacat ctttgagctg cagcgggaca gccagtacga gaccacggac   240
accatgtgtc agatcctgcc caagggggtt gtatctgtct tgggacgctc ctccagccca   300
```

```
gcttctgcct ccaccgtgag ccatatctgt ggggagaagg agattcccca catcaaggtg    360
ggtcctgagg agacgcccg  ccttcagtac cttcgcttcg catctgtcag cctgtacccc    420
agtaatgaag atgtcagcct ggcagtctcc cgaatcctca agtcctttaa ctacccctca    480
gctagcctca tctgcgccaa ggctgagtgc ctgctgcggc tagaagaact ggtgcgaggc    540
ttcctcatct ccaaggagac actgtccgtg aggatgcttg atgacagccg ggaccccacg    600
ccgctactca aggagatccg agatgacaaa gtgtccacca tcatcattga tgccaatgcg    660
tccatctccc accttgtcct ccgtaaggct tcggagctgg gaatgaccct agcgttttac    720
aagtacatcc tcaccaccat ggactttccc atcctgcatc tggatggtat cgtggaggac    780
tcctccaaca tcctgggctt ttccatgttc aacacctccc acccttcta  cccagagttt    840
gtgcgcagcc tcaacatgtc ctggagggag aactgtgaag ccagcaccta tcctggccct    900
gcgctgtccg cagccctgat gtttgacgct gtgcacgtgg tggtaagcgc tgtccgagaa    960
ctgaaccgaa gccaggagat tggcgtcaag ccactggcct gcacttcggc caacatttgg   1020
ccccatggga ccagccttat gaactacctt cgaatggtag agtatgacgg gctgaccggg   1080
cgggttgagt tcaacagcaa agggcagagg accaactaca cactacgcat cctggagaag   1140
tcccgccagg gccaccgtga gatagggggtg tggtactcta accggaccct ggccatgaat   1200
gccaccaccc tggacatcaa cctgtcacag actctagcca acaagactct ggtggtcaca   1260
actatcctgg agaacccgta tgttatgcgc cggcccaact tccaggcctt gtcagggaat   1320
gagcgcttcg agggcttctg cgtggacatg ctcaggagc  tggccgagct gctgcgcttc   1380
cgataccgcc tgcggttggt agaggacgga ctctacgggg cacctgagcc caacggttcc   1440
tggacaggca tggttggaga actcatcaac cggaaggcag acctggctgt ggcagccttc   1500
accatcaccg ccgagaggga gaaggtcatc gacttctcca agcccttcat gaccctgggg   1560
atcagcatcc tctacagggt gcacatgggc cgcaagcctg gctacttctc cttcctggac   1620
cccttctccc ctgccgtgtg gctcttcatg cttcttgcct acctggctgt cagctgtgtc   1680
ttgttcctgg ctgccaggct gagcccttat gagtggtaca cccacacccc gtgtctccgg   1740
gcgcgtcccc atatcctgga gaaccagtac acgctgggca acagcctctg gttccccgtg   1800
ggtggcttca tgcagcaggg ctcggagatc atgccgcggg cactgtccac acgctgtgtc   1860
agcggagtct ggtgggcctt caccttgatc atcatctcct cctacacggc caacctggct   1920
gccttcctca cggtgcagcg catggaggtg ccggtggagt cggctgacga cctggcggat   1980
cagaccaaca ttgagtacgg cactatccac gctggctcca ccatgacctt cttccagaac   2040
tcgcggtacc agacgtacca gcggatgtgg aactacatgc aatcgaagca gcccagcgtg   2100
tttgtcaaga gcacagagga gggaatcgcc cgcgtcctca actcccgcta tgccttcctg   2160
ctggagtcca ccatgaacga gtaccacagg cgcctcaatt gcaacctcac ccagatcggg   2220
ggcctcctcg acaccaaggg ctacggcatc ggcatgccgc tgggctcccc tttccgggat   2280
gagatcacac tggccatcct gcagctccag gagaacaaca ggctggagat cctgaagcgc   2340
aagtggtggg agggcggccg gtgccccaag gaggaggacc acagggccaa aggtttgggc   2400
atggagaaca ttggcggcat ttttgtcgtg ctgatctgtg gcctcatcat tgctgtcttc   2460
gtggcggtca tggagttcat ctggtccacg cggaggtcag cggagtccga ggaggtgtcg   2520
gtgtgccagg agatgctgca ggagctacgc cacgccgtgt cttgccgaaa gacctcgcgt   2580
tccccgccggc gccggcgccc tggtggcccg agccggggccc tgctgtcgct gcgcgcagtc   2640
cgcgagatgc gactcagcaa cggcaagctc tactcggccg gcgcggggcgg ggacgcgggc   2700
```

```
gcgcacgggg gtccgcagcg cctcctggac gaccccggac ctcctggggg accccggccc   2760
caggctccca cgccctgcac gcacgtgcgc gtctgccagg agtgcaggcg catccaggcg   2820
ctgcgagctt cggggggccgg ggcgccccca cgtggcctgg caccccagc cgaagccacc    2880 agcccgcctc ggccgcggcc aggccccacc ggaccccgcg agctgaccga gcacgaatga   2940
```

<210> SEQ ID NO 18
<211> LENGTH: 288
<212> TYPE: PRT
<213> ORGANISM: Artificial Sequence
<220> FEATURE:
<223> OTHER INFORMATION: Synthetic polypeptide

<400> SEQUENCE: 18

```
Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30

Asn Ile Leu Gln Trp Phe Ala Phe Gly Phe Ser Ile Leu Ile Leu Met
        35                  40                  45

Phe Tyr Ala Tyr Gln Thr Trp Arg Ala Thr Cys Gly Trp Glu Glu Val
    50                  55                  60

Tyr Val Cys Cys Val Glu Leu Thr Lys Val Ile Ile Glu Phe Phe His
65                  70                  75                  80

Glu Phe Asp Asp Pro Ser Met Leu Tyr Leu Ala Asn Gly His Arg Val
                85                  90                  95

Gln Trp Leu Arg Tyr Ala Glu Trp Leu Leu Thr Cys Pro Val Ile Leu
            100                 105                 110

Ile His Leu Ser Asn Leu Thr Gly Leu Lys Asp Asp Tyr Ser Lys Arg
        115                 120                 125

Thr Met Arg Leu Leu Val Ser Asp Val Gly Thr Ile Val Trp Gly Ala
    130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
    210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
            260                 265                 270

Glu Met Glu Val Glu Thr Met Val Asp Gln Glu Asp Glu Glu Thr Val
        275                 280                 285
```

<210> SEQ ID NO 19
<211> LENGTH: 864
<212> TYPE: DNA
<213> ORGANISM: Artificial Sequence
<220> FEATURE:

<223> OTHER INFORMATION: Synthetic polynucleotide

<400> SEQUENCE: 19

```
atgctgggga acggcagcgc cattgtgcct atcgaccagt gcttttgcct ggcttggacc      60
gacagcctgg gaagcgatac agagcagctg gtggccaaca tcctccagtg gttcgccttc     120
ggcttcagca tcctgatcct gatgttctac gcctaccaga cttggagagc cacttgcggt     180
tgggaggagg tctacgtctg ttgcgtcgag ctgaccaagg tcatcatcga gttcttccac     240
gagttcgacg accccagcat gctgtacctg gctaacggac accgagtcca gtggctgaga     300
tacgcagagt ggctgctgac ttgtcccgtc atcctgatcc acctgagcaa cctgaccggc     360
ctgaaggacg actacagcaa gcggaccatg aggctgctgg tgtcagacgt gggaaccatc     420
gtgtggggag ctacaagcgc catgagcaca ggctacgtca aggtcatctt cttcgtgctg     480
ggttgcatct acggcgccaa caccttcttc cacgccgcca aggtgtatat cgagagctac     540
cacgtggtgc caaagggcag acctagaacc gtcgtgcgga tcatggcttg gctgttcttc     600
ctgtcttggg gcatgttccc cgtgctgttc gtcgtgggac agaaggatt cgacgccatc     660
agcgtgtacg gctctaccat tggccacacc atcatcgacc tcatgagcaa gaattgttgg     720
ggcctgctgg acactatct gagagtgctg atccaccagc acatcatcat ctacggcgac     780
atccggaaga agaccaagat caacgtggcc ggcgaggaga tggaagtgga gaccatggtg     840
gaccaggagg acgaggagac agtg                                            864
```

<210> SEQ ID NO 20
<211> LENGTH: 694
<212> TYPE: PRT
<213> ORGANISM: Artificial Sequence
<220> FEATURE:
<223> OTHER INFORMATION: Synthetic polypeptide

<400> SEQUENCE: 20

```
Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30

Asn Ile Leu Gln Trp Phe Ala Phe Gly Phe Ser Ile Leu Ile Leu Met
        35                  40                  45

Phe Tyr Ala Tyr Gln Thr Trp Arg Ala Thr Cys Gly Trp Glu Glu Val
    50                  55                  60

Tyr Val Cys Cys Val Glu Leu Thr Lys Val Ile Ile Glu Phe Phe His
65                  70                  75                  80

Glu Phe Asp Asp Pro Ser Met Leu Tyr Leu Ala Asn Gly His Arg Val
                85                  90                  95

Gln Trp Leu Arg Tyr Ala Glu Trp Leu Leu Thr Cys Pro Val Ile Leu
            100                 105                 110

Ile His Leu Ser Asn Leu Thr Gly Leu Lys Asp Asp Tyr Ser Lys Arg
        115                 120                 125

Thr Met Arg Leu Leu Val Ser Asp Val Gly Thr Ile Val Trp Gly Ala
    130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190
```

```
Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
                260                 265                 270

Glu Met Glu Val Glu Thr Met Val Asp Gln Glu Asp Glu Glu Thr Val
            275                 280                 285

Gly Gly Ser Gly Gly Thr Gly Gly Ser Gly Gly Thr Met Pro Ala Glu
            290                 295                 300

Leu Leu Leu Leu Leu Ile Val Ala Phe Ala Asn Pro Ser Cys Gln Val
305                 310                 315                 320

Leu Ser Ser Leu Arg Met Ala Ala Ile Leu Asp Asp Gln Thr Val Cys
                325                 330                 335

Gly Arg Gly Glu Arg Leu Ala Leu Ala Leu Ala Arg Glu Gln Ile Asn
                340                 345                 350

Gly Ile Ile Glu Val Pro Ala Lys Ala Arg Val Glu Val Asp Ile Phe
            355                 360                 365

Glu Leu Gln Arg Asp Ser Gln Tyr Glu Thr Thr Asp Thr Met Cys Gln
            370                 375                 380

Ile Leu Pro Lys Gly Val Ser Val Leu Gly Pro Ser Ser Ser Pro
385                 390                 395                 400

Ala Ser Ala Ser Thr Val Ser His Ile Cys Gly Glu Lys Glu Ile Pro
                405                 410                 415

His Ile Lys Val Gly Pro Glu Thr Pro Arg Leu Gln Tyr Leu Arg
                420                 425                 430

Phe Ala Ser Val Ser Leu Tyr Pro Ser Asn Glu Asp Val Ser Leu Ala
                435                 440                 445

Val Ser Gly Ala Ser Gly Gly Thr Val Ser Lys Gly Glu Glu Leu Phe
450                 455                 460

Thr Gly Val Val Pro Ile Leu Val Glu Leu Asp Gly Asp Val Asn Gly
465                 470                 475                 480

His Lys Phe Ser Val Ser Gly Glu Gly Glu Gly Asp Ala Thr Tyr Gly
                485                 490                 495

Lys Leu Thr Leu Lys Phe Ile Cys Thr Thr Gly Lys Leu Pro Val Pro
                500                 505                 510

Trp Pro Thr Leu Val Thr Thr Leu Thr Tyr Gly Val Gln Cys Phe Ser
            515                 520                 525

Arg Tyr Pro Asp His Met Lys Gln His Asp Phe Phe Lys Ser Ala Met
530                 535                 540

Pro Glu Gly Tyr Val Gln Glu Arg Thr Ile Phe Phe Lys Asp Asp Gly
545                 550                 555                 560

Asn Tyr Lys Thr Arg Ala Glu Val Lys Phe Glu Gly Asp Thr Leu Val
                565                 570                 575

Asn Arg Ile Glu Leu Lys Gly Ile Asp Phe Lys Glu Asp Gly Asn Ile
                580                 585                 590

Leu Gly His Lys Leu Glu Tyr Asn Tyr Asn Ser His Asn Val Tyr Ile
            595                 600                 605
```

```
Met Ala Asp Lys Gln Lys Asn Gly Ile Lys Val Asn Phe Lys Ile Arg
    610                 615                 620
His Asn Ile Glu Asp Gly Ser Val Gln Leu Ala Asp His Tyr Gln Gln
625                 630                 635                 640
Asn Thr Pro Ile Gly Asp Gly Pro Val Leu Leu Pro Asp Asn His Tyr
            645                 650                 655
Leu Ser Thr Gln Ser Ala Leu Ser Lys Asp Pro Asn Glu Lys Arg Asp
            660                 665                 670
His Met Val Leu Leu Glu Phe Val Thr Ala Ala Gly Ile Thr Leu Gly
            675                 680                 685
Met Asp Glu Leu Tyr Lys
        690
```

<210> SEQ ID NO 21
<211> LENGTH: 2085
<212> TYPE: DNA
<213> ORGANISM: Artificial Sequence
<220> FEATURE:
<223> OTHER INFORMATION: Synthetic polynucleotide

<400> SEQUENCE: 21

| | | | | | |
|---|---|---|---|---|---|
| atgctgggga | acggcagcgc | cattgtgcct | atcgaccagt | gcttttgcct | ggcttggacc | 60 |
| gacagcctgg | aagcgatac | agagcagctg | gtggccaaca | tcctccagtg | gttcgccttc | 120 |
| ggcttcagca | tcctgatcct | gatgttctac | gcctaccaga | cttggagagc | cacttgcggt | 180 |
| tgggaggagg | tctacgtctg | ttgcgtcgag | ctgaccaagg | tcatcatcga | gttcttccac | 240 |
| gagttcgacg | accccagcat | gctgtacctg | gctaacggac | accgagtcca | gtggctgaga | 300 |
| tacgcagagt | ggctgctgac | ttgtcccgtc | atcctgatcc | acctgagcaa | cctgaccggc | 360 |
| ctgaaggacg | actacagcaa | gcggaccatg | aggctgctgg | tgtcagacgt | gggaaccatc | 420 |
| gtgtggggag | ctacaagcgc | catgagcaca | ggctacgtca | aggtcatctt | cttcgtgctg | 480 |
| ggttgcatct | acgcgccaa | caccttcttc | acgccgccca | aggtgtatat | cgagagctac | 540 |
| cacgtggtgc | caaagggcag | acctagaacc | gtcgtgcgga | tcatggcttg | gctgttcttc | 600 |
| ctgtcttggg | gcatgttccc | cgtgctgttc | gtcgtgggac | agaaggatt | cgacgccatc | 660 |
| agcgtgtacg | gctctaccat | tggccacacc | atcatcgacc | tcatgagcaa | gaattgttgg | 720 |
| ggcctgctgg | acactatct | gagagtgctg | atccaccagc | acatcatcat | ctacggcgac | 780 |
| atccggaaga | agaccaagat | caacgtggcc | ggcgaggaga | tggaagtgga | gaccatggtg | 840 |
| gaccaggagg | acgaggagac | agtgggaggt | tcaggtggaa | ccggtggaag | tggaggtacc | 900 |
| atgcccgccg | aactgctgct | gctgctgatt | gtcgcttttg | ctaacccttc | ttgccaggtg | 960 |
| ctgtcttctc | tgaggatggc | cgctattctg | acgatcaga | ccgtgtgcgg | aagaggagag | 1020 |
| aggctggcac | tggcactggc | tagggagcag | atcaatggca | tcattgaagt | gcctgcaaag | 1080 |
| gcccgggtcg | aggtggacat | tttcgaactg | cagagagata | gccagtacga | gaccacagac | 1140 |
| accatgtgcc | agatcctgcc | aaaaggagtg | gtctccgtcc | tgggaccaag | ctcctctcct | 1200 |
| gcttctgcaa | gtaccgtgtc | tcacatttgt | ggcgagaagg | aaatccccca | tatcaaggtc | 1260 |
| gggccagagg | aaaacacccag | gctgcagtac | ctgcgcttcg | cctcagtgag | cctgtatcca | 1320 |
| tcaaacgagg | atgtgtcact | ggcagtcagc | ggagctagcg | gaggtactgt | gagcaagggc | 1380 |
| gaggagctgt | tcaccggggt | ggtgcccatc | ctggtcgagc | tggacggcga | cgtaaacggc | 1440 |
| cacaagttca | gcgtgtccgg | cgagggcgag | ggcgatgcca | cctacggcaa | gctgaccctg | 1500 |
| aagttcattt | gcaccaccgg | caagctgccc | gtgccctggc | ccaccctcgt | gaccaccctg | 1560 |

```
acctacggcg tgcagtgctt cagccgctac cccgaccaca tgaagcagca cgacttcttc    1620
aagtccgcca tgcccgaagg ctacgtccag gagcgcacca tcttcttcaa ggacgacggc    1680
aactacaaga cccgcgccga ggtgaagttc gagggcgaca ccctggtgaa ccgcatcgag    1740
ctgaagggca tcgacttcaa ggaggacggc aacatcctgg gcacaagct ggagtacaac    1800 tacaacagcc acaacgtcta tatcatggcc gacaagcaga gaacggcat caaggtgaac    1860 ttcaagatcc gccacaacat cgaggacggc agcgtgcagc tcgccgacca ctaccagcag    1920 aacacccca tcggcgacgg ccccgtgctg ctgcccgaca ccactacct gagcacccag    1980 tccgccctga gcaaagaccc caacgagaag cgcgatcaca tggtcctgct ggagttcgtg    2040
accgccgccg ggatcactct cggcatggac gagctgtaca agtaa                    2085
```

<210> SEQ ID NO 22
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 22

```
Arg Asp Gln Pro Leu Asn Ser Lys Lys Lys Arg Leu Leu Ser Phe
1               5                   10                  15

Arg Asp Val Asp Phe Glu Glu Asp Ser Asp
            20                  25
```

<210> SEQ ID NO 23
<211> LENGTH: 178
<212> TYPE: PRT
<213> ORGANISM: Artificial Sequence
<220> FEATURE:
<223> OTHER INFORMATION: Synthetic polypeptide

<400> SEQUENCE: 23

```
Lys Val Asp Lys Met Leu Leu Gln Glu Leu Ser Glu Lys Leu Glu Leu
1               5                   10                  15

Ala Glu Gln Ala Leu Ala Ser Lys Gln Leu Gln Met Asp Glu Met Lys
                20                  25                  30

Gln Thr Leu Ala Lys Gln Glu Glu Asp Leu Glu Thr Met Ala Val Leu
        35                  40                  45

Arg Ala Gln Met Glu Val Tyr Cys Ser Asp Phe His Ala Glu Arg Ala
    50                  55                  60

Ala Arg Glu Lys Ile His Glu Glu Lys Glu Gln Leu Ala Leu Gln Leu
65                  70                  75                  80

Ala Ile Leu Leu Lys Glu Asn Asn Asp Ile Glu Glu Gly Gly Ser Arg
                85                  90                  95

Gln Ser Leu Met Glu Met Gln Cys Arg His Gly Val Lys Glu Met Phe
            100                 105                 110

Lys Asp Phe Gln Leu Arg Gln Pro Leu Val Pro Ser Arg Lys Gly
        115                 120                 125

Glu Thr Pro Pro Ser Gly Thr Ser Ser Ala Phe Ser Ser Tyr Phe Asn
    130                 135                 140

Asn Lys Val Gly Ile Pro Gln Glu His Val Asp His Asp Phe Asp
145                 150                 155                 160

Ala Asn Gln Leu Leu Asn Lys Ile Asn Glu Pro Pro Lys Pro Ala Pro
                165                 170                 175

Arg Gln
```

<210> SEQ ID NO 24
<211> LENGTH: 3054
<212> TYPE: DNA
<213> ORGANISM: Artificial Sequence
<220> FEATURE:
<223> OTHER INFORMATION: Synthetic polynucleotide

<400> SEQUENCE: 24

| | | | | | |
|---|---|---|---|---|---|
| atgagcagac | tggtcgccgc | ttcttggctg | ctggctctcc | tcctctgcgg | aattaccagc | 60 |
| acaacaacag | cctctagcgc | cccagcagct | tcttctacag | acggaacagc | cgccgcagca | 120 |
| gtgtctcact | acgccatgaa | cggcttcgac | gagctggcta | aggagccgt | ggtgccagaa | 180 |
| gaccactttg | tctgcggacc | agccgacaag | tgctattgct | ccgcttggct | gcacagcaga | 240 |
| ggcacaccag | agaaaagat | cggcgcccag | gtctgccagt | ggattgcttt | cagcatcgcc | 300 |
| atcgccctgc | tgacattcta | cggcttcagc | gcctggaagg | ccacttgcgg | ttgggaggag | 360 |
| gtctacgtct | gttgcgtcga | ggtgctgttc | gtgaccctgg | agatcttcaa | ggagttcagc | 420 |
| agccccgcca | cagtgtacct | gtctaccggc | aaccacgcct | attgcctgcg | ctacttcgag | 480 |
| tggctgctgt | cttgccccgt | gatcctgatc | aagctgagca | acctgagcgg | cctgaagaac | 540 |
| gactacagca | agcggaccat | gggcctgatc | gtgtcttgcg | tgggaatgat | cgtgttcggc | 600 |
| atggccgcag | gactggctac | cgattggctc | aagtggctgc | tgtatatcgt | gtcttgcatc | 660 |
| tacgcggct | acatgtactt | ccaggccgcc | aagtgctacg | tggaagccaa | ccacagcgtg | 720 |
| cctaaaggcc | attgccgcat | ggtcgtgaag | ctgatggcct | acgcttactt | cgcctcttgg | 780 |
| ggcagctacc | caatcctctg | gcagtgggga | ccagaaggac | tgctgaagct | gagcccttac | 840 |
| gccaacagca | tcggccacag | catctgcgac | atcatcgcca | aggagttttg | gaccttcctg | 900 |
| gcccaccacc | tgaggatcaa | gatccacgag | cacatcctga | tccacggcga | catccggaag | 960 |
| accaccaaga | tggagatcgg | aggcgaggag | gtggaagtgg | aagagttcgt | ggaggaggag | 1020 |
| gacgaggaca | cagtgggagc | tagcggaggt | actgtgtcta | agggcgaaga | gctgatcaag | 1080 |
| gaaaatatgc | gtatgaaggt | ggtcatgaa | ggttcggtca | acggccacca | attcaaatgc | 1140 |
| acaggtgaag | gagaaggcag | accgtacgag | ggagtgcaaa | ccatgaggat | caaagtcatc | 1200 |
| gagggaggac | ccctgccatt | tgcctttgac | attcttgcca | cgtcgttcat | gtatggcagc | 1260 |
| cgtaccttta | tcaagtaccc | ggccgacatc | cctgatttct | ttaaacagtc | ctttcctgag | 1320 |
| ggttttactt | gggaaagagt | tacgagatac | gaagatggtg | gagtcgtcac | cgtcacgcag | 1380 |
| gacaccagcc | ttgaggatgg | cgagctcgtc | tacaacgtca | aggtcagagg | ggtaaacttt | 1440 |
| ccctccaatg | gtcccgtgat | gcagaagaag | accaagggtt | gggagcctaa | tacagagatg | 1500 |
| atgtatccag | cagatggtgg | tctgagagga | tacactgaca | tcgcactgaa | agttgatggt | 1560 |
| ggtggccatc | tgcactgcaa | cttcgtgaca | acttacaggt | caaaaaagac | cgtcgggaac | 1620 |
| atcaagatgc | ccggtgtcca | tgccgttgat | caccgcctgg | aaaggatcga | ggagagtgac | 1680 |
| aatgaaacct | acgtagtgca | agagaagtg | gcagttgcca | atacagcaa | ccttggtggt | 1740 |
| ggcatggacg | agctgtacaa | gggaggttca | ggtggaaccg | gtggaagtgg | aggtaccaag | 1800 |
| gtcgataaga | tgctgctgca | ggagctcagt | gagaagctgg | aactggccga | acaggccctg | 1860 |
| gcctccaagc | aactgcaaat | ggatgagatg | aaacagacac | tcgccaaaca | gagggaggat | 1920 |
| ctcgaaacta | tggctgttct | gagagcacaa | atggaagtct | actgttccga | cttccacgct | 1980 |
| gaaagagcag | ccagggagaa | gattcatgaa | gagaaggagc | aactggccct | gcagctggca | 2040 |

-continued

```
atcctgctga aggagaacaa cgatattgaa aaggcggat ctaggcaatc actgatggaa    2100
atgcagtgca gacacggagt caaagaaatg ttcaaggact ttcaactgcg gcagccacct    2160
ctggtgcctt ctcggaaggg agagacacca ccatccggca catctagcgc ctttagctca    2220
tacttcaaca acaaggtggg tattcctcag gagcacgtgg atcacgacga tttcgatgcc    2280
aatcagctcc tgaacaagat caatgagcct ccaaagcctg ctcctcgcca aggaagcgct    2340
ggtaaggtcg ataagatgct gctgcaggag ctcagtgaga agctggaact ggccgaacag    2400
gccctggcct ccaagcaact gcaaatggat gagatgaaac agacactcgc caaacaagag    2460
gaggatctcg aaactatggc tgttctgaga gcacaaatgg aagtctactg ttccgacttc    2520
cacgctgaaa gagcagccag ggagaagatt catgaagaga aggagcaact ggccctgcag    2580
ctggcaatcc tgctgaagga gaacaacgat attgaagaag gcggatctag gcaatcactg    2640
atggaaatgc agtgcagaca cggagtcaaa gaaatgttca aggactttca actgcggcag    2700
ccacctctgg tgccttctcg gaagggagag acaccaccat ccggcacatc tagcgccttt    2760
agctcatact tcaacaacaa ggtgggtatt cctcaggagc acgtggatca cgacgatttc    2820
gatgccaatc agctcctgaa caagatcaat gagcctccaa agcctgctcc tagacagggt    2880
tccggacggg atcagccact caactctaag aagaagaaac gcctgctgtc ctttcgcgac    2940
gtcgactttg aggaggattc agacggttcc ggacgggatc agccactcaa ctctaagaag    3000
aagaaacgcc tgctgtcctt tcgcgacgtc gactttgagg aggattcaga ctaa          3054
```

<210> SEQ ID NO 25
<211> LENGTH: 1017
<212> TYPE: PRT
<213> ORGANISM: Artificial Sequence
<220> FEATURE:
<223> OTHER INFORMATION: Synthetic polypeptide

<400> SEQUENCE: 25

```
Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
                20                  25                  30

Thr Asp Gly Thr Ala Ala Ala Val Ser His Tyr Ala Met Asn Gly
            35                  40                  45

Phe Asp Glu Leu Ala Lys Gly Ala Val Pro Glu Asp His Phe Val
        50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
                100                 105                 110

Lys Ala Thr Cys Gly Trp Glu Glu Val Tyr Val Cys Cys Val Glu Val
            115                 120                 125

Leu Phe Val Thr Leu Glu Ile Phe Lys Glu Phe Ser Ser Pro Ala Thr
        130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Lys Arg Thr Met Gly Leu Ile Val Ser
            180                 185                 190
```

```
Cys Val Gly Met Ile Val Phe Gly Met Ala Ala Gly Leu Ala Thr Asp
            195                 200                 205

Trp Leu Lys Trp Leu Leu Tyr Ile Val Ser Cys Ile Tyr Gly Gly Tyr
    210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
            260                 265                 270

Gly Leu Leu Lys Leu Ser Pro Tyr Ala Asn Ser Ile Gly His Ser Ile
            275                 280                 285

Cys Asp Ile Ile Ala Lys Glu Phe Trp Thr Phe Leu Ala His His Leu
            290                 295                 300

Arg Ile Lys Ile His Glu His Ile Leu Ile His Gly Asp Ile Arg Lys
305                 310                 315                 320

Thr Thr Lys Met Glu Ile Gly Gly Glu Val Glu Val Glu Glu Phe
                325                 330                 335

Val Glu Glu Glu Asp Glu Asp Thr Val Gly Ala Ser Gly Gly Thr Val
            340                 345                 350

Ser Lys Gly Glu Glu Leu Ile Lys Glu Asn Met Arg Met Lys Val Val
            355                 360                 365

Met Glu Gly Ser Val Asn Gly His Gln Phe Lys Cys Thr Gly Glu Gly
            370                 375                 380

Glu Gly Arg Pro Tyr Glu Gly Val Gln Thr Met Arg Ile Lys Val Ile
385                 390                 395                 400

Glu Gly Gly Pro Leu Pro Phe Ala Phe Asp Ile Leu Ala Thr Ser Phe
                405                 410                 415

Met Tyr Gly Ser Arg Thr Phe Ile Lys Tyr Pro Ala Asp Ile Pro Asp
            420                 425                 430

Phe Phe Lys Gln Ser Phe Pro Glu Gly Phe Thr Trp Glu Arg Val Thr
            435                 440                 445

Arg Tyr Glu Asp Gly Gly Val Val Thr Val Thr Gln Asp Thr Ser Leu
    450                 455                 460

Glu Asp Gly Glu Leu Val Tyr Asn Val Lys Val Arg Gly Val Asn Phe
465                 470                 475                 480

Pro Ser Asn Gly Pro Val Met Gln Lys Lys Thr Lys Gly Trp Glu Pro
                485                 490                 495

Asn Thr Glu Met Met Tyr Pro Ala Asp Gly Gly Leu Arg Gly Tyr Thr
            500                 505                 510

Asp Ile Ala Leu Lys Val Asp Gly Gly His Leu His Cys Asn Phe
            515                 520                 525

Val Thr Thr Tyr Arg Ser Lys Lys Thr Val Gly Asn Ile Lys Met Pro
    530                 535                 540

Gly Val His Ala Val Asp His Arg Leu Glu Arg Ile Glu Glu Ser Asp
545                 550                 555                 560

Asn Glu Thr Tyr Val Val Gln Arg Glu Val Ala Val Ala Lys Tyr Ser
                565                 570                 575

Asn Leu Gly Gly Gly Met Asp Glu Leu Tyr Lys Gly Gly Ser Gly Gly
            580                 585                 590

Thr Gly Gly Ser Gly Gly Thr Lys Val Asp Lys Met Leu Leu Gln Glu
    595                 600                 605
```

```
Leu Ser Glu Lys Leu Glu Leu Ala Glu Gln Ala Leu Ala Ser Lys Gln
610             615                 620
Leu Gln Met Asp Glu Met Lys Gln Thr Leu Ala Lys Gln Glu Glu Asp
625             630                 635                 640
Leu Glu Thr Met Ala Val Leu Arg Ala Gln Met Glu Val Tyr Cys Ser
                645                 650                 655
Asp Phe His Ala Glu Arg Ala Ala Arg Glu Lys Ile His Glu Glu Lys
            660                 665                 670
Glu Gln Leu Ala Leu Gln Leu Ala Ile Leu Leu Lys Glu Asn Asn Asp
            675                 680                 685
Ile Glu Glu Gly Gly Ser Arg Gln Ser Leu Met Glu Met Gln Cys Arg
690                 695                 700
His Gly Val Lys Glu Met Phe Lys Asp Phe Gln Leu Arg Gln Pro Pro
705             710                 715                 720
Leu Val Pro Ser Arg Lys Gly Glu Thr Pro Pro Ser Gly Thr Ser Ser
                725                 730                 735
Ala Phe Ser Ser Tyr Phe Asn Asn Lys Val Gly Ile Pro Gln Glu His
            740                 745                 750
Val Asp His Asp Asp Phe Asp Ala Asn Gln Leu Leu Asn Lys Ile Asn
            755                 760                 765
Glu Pro Pro Lys Pro Ala Pro Arg Gln Gly Ser Ala Gly Lys Val Asp
770             775                 780
Lys Met Leu Leu Gln Glu Leu Ser Glu Lys Leu Glu Leu Ala Glu Gln
785             790                 795                 800
Ala Leu Ala Ser Lys Gln Leu Gln Met Asp Glu Met Lys Gln Thr Leu
                805                 810                 815
Ala Lys Gln Glu Glu Asp Leu Glu Thr Met Ala Val Leu Arg Ala Gln
            820                 825                 830
Met Glu Val Tyr Cys Ser Asp Phe His Ala Glu Arg Ala Ala Arg Glu
            835                 840                 845
Lys Ile His Glu Glu Lys Glu Gln Leu Ala Leu Gln Leu Ala Ile Leu
850                 855                 860
Leu Lys Glu Asn Asn Asp Ile Glu Glu Gly Gly Ser Arg Gln Ser Leu
865             870                 875                 880
Met Glu Met Gln Cys Arg His Gly Val Lys Glu Met Phe Lys Asp Phe
                885                 890                 895
Gln Leu Arg Gln Pro Pro Leu Val Pro Ser Arg Lys Gly Glu Thr Pro
            900                 905                 910
Pro Ser Gly Thr Ser Ser Ala Phe Ser Ser Tyr Phe Asn Asn Lys Val
            915                 920                 925
Gly Ile Pro Gln Glu His Val Asp His Asp Asp Phe Asp Ala Asn Gln
930                 935                 940
Leu Leu Asn Lys Ile Asn Glu Pro Pro Lys Pro Ala Pro Arg Gln Gly
945             950                 955                 960
Ser Gly Arg Asp Gln Pro Leu Asn Ser Lys Lys Lys Arg Leu Leu
                965                 970                 975
Ser Phe Arg Asp Val Asp Phe Glu Glu Asp Ser Asp Gly Ser Gly Arg
            980                 985                 990
Asp Gln Pro Leu Asn Ser Lys Lys  Lys Lys Arg Leu Leu  Ser Phe Arg
            995                 1000                1005
Asp Val Asp Phe Glu Glu Asp  Ser Asp
      1010                1015
```

<210> SEQ ID NO 26
<211> LENGTH: 3018
<212> TYPE: DNA
<213> ORGANISM: Artificial Sequence
<220> FEATURE:
<223> OTHER INFORMATION: Synthetic polynucleotide

<400> SEQUENCE: 26

| | | | | | |
|---|---|---|---|---|---|
| atgagcagac | tggtcgccgc | ttcttggctg | ctggctctcc | tcctctgcgg | aattaccagc | 60 |
| acaacaacag | cctctagcgc | cccagcagct | tcttctacag | acggaacagc | cgccgcagca | 120 |
| gtgtctcact | acgccatgaa | cggcttcgac | gagctggcta | aggagccgt | ggtgccagaa | 180 |
| gaccactttg | tctgcggacc | agccgacaag | tgctattgct | ccgcttggct | gcacagcaga | 240 |
| ggcacaccag | agaaaagat | cggcgcccag | gtctgccagt | ggattgcttt | cagcatcgcc | 300 |
| atcgccctgc | tgacattcta | cggcttcagc | gcctggaagg | ccacttgcgg | ttggggaggag | 360 |
| gtctacgtct | gttgcgtcga | ggtgctgttc | gtgaccctgg | agatcttcaa | ggagttcagc | 420 |
| agccccgcca | cagtgtacct | gtctaccggc | aaccacgcct | attgcctgcg | ctacttcgag | 480 |
| tggctgctgt | cttgccccgt | gatcctgatc | aagctgagca | acctgagcgg | cctgaagaac | 540 |
| gactacagca | gcggaccat | gggcctgatc | gtgtcttgcg | tgggaatgat | cgtgttcggc | 600 |
| atggccgcag | gactggctac | cgattggctc | aagtggctgc | tgtatatcgt | gtcttgcatc | 660 |
| tacgcggct | acatgtactt | ccaggccgcc | aagtgctacg | tggaagccaa | ccacagcgtg | 720 |
| cctaaaggcc | attgccgcat | ggtcgtgaag | ctgatggcct | acgcttactt | cgcctcttgg | 780 |
| ggcagctacc | caatcctctg | gcagtggga | ccagaaggac | tgctgaagct | gagcccttac | 840 |
| gccaacagca | tcggccacag | catctgcgac | atcatcgcca | aggagttttg | gaccttcctg | 900 |
| gcccaccacc | tgaggatcaa | gatccacgag | cacatcctga | tccacggcga | catccggaag | 960 |
| accaccaaga | tggagatcgg | aggcgaggag | gtggaagtgg | aagagttcgt | ggaggaggag | 1020 |
| gacgaggaca | cagtgggagc | tagcggaggt | actgtgtcta | agggcgaaga | gctgatcaag | 1080 |
| gaaaatatgc | gtatgaaggt | ggtcatggaa | ggttcggtca | acggccacca | attcaaatgc | 1140 |
| acaggtgaag | agaaggcag | accgtacgag | ggagtgcaaa | ccatgaggat | caaagtcatc | 1200 |
| gagggaggac | ccctgccatt | tgcctttgac | attcttgcca | cgtcgttcat | gtatggcagc | 1260 |
| cgtaccttta | tcaagtaccc | ggccgacatc | cctgatttct | ttaaacagtc | ctttcctgag | 1320 |
| ggtttttactt | gggaaagagt | tacgagatac | gaagatggtg | gagtcgtcac | cgtcacgcag | 1380 |
| gacaccagcc | ttgaggatgg | cgagctcgtc | tacaacgtca | aggtcagagg | ggtaaacttt | 1440 |
| ccctccaatg | gtcccgtgat | gcagaagaag | accaagggtt | gggagcctaa | tacagagatg | 1500 |
| atgtatccag | cagatggtgg | tctgagagga | tacactgaca | tcgcactgaa | agttgatggt | 1560 |
| ggtggccatc | tgcactgcaa | cttcgtgaca | acttacaggt | caaaaaagac | cgtcgggaac | 1620 |
| atcaagatgc | ccggtgtcca | tgccgttgat | caccgcctgg | aaaggatcga | ggagagtgac | 1680 |
| aatgaaacct | acgtagtgca | agagaagtg | gcagttgcca | atacagcaa | ccttggtggt | 1740 |
| ggcatggacg | agctgtacaa | gaaggtcgat | aagatgctgc | tgcaggagct | cagtgagaag | 1800 |
| ctggaactgg | ccgaacaggc | cctggcctcc | aagcaactgc | aaatggatga | gatgaaacag | 1860 |
| acactcgcca | acaagagga | ggatctcgaa | actatggctg | ttctgagagc | acaaatggaa | 1920 |
| gtctactgtt | ccgacttcca | cgctgaaaga | gcagccaggg | agaagattca | tgaagagaag | 1980 |
| gagcaactgg | ccctgcagct | ggcaatcctg | ctgaaggaga | caacgatat | tgaagaaggc | 2040 |
| ggatctaggc | aatcactgat | ggaaatgcag | tgcagacacg | gagtcaaaga | aatgttcaag | 2100 |

```
gactttcaac tgcggcagcc acctctggtg ccttctcgga agggagagac accaccatcc   2160
ggcacatcta gcgcctttag ctcatacttc aacaacaagg tgggtattcc tcaggagcac   2220
gtggatcacg acgatttcga tgccaatcag ctcctgaaca agatcaatga gcctccaaag   2280
cctgctcctc gccaaggaag cgctggtaag gtcgataaga tgctgctgca ggagctcagt   2340
gagaagctgg aactggccga acaggccctg gcctccaagc aactgcaaat ggatgagatg   2400
aaacagacac tcgccaaaca agaggaggat ctcgaaacta tggctgttct gagagcacaa   2460
atggaagtct actgttccga cttccacgct gaaagagcag ccaggagaa gattcatgaa   2520 gagaaggagc aactggccct gcagctggca atcctgctga aggagaacaa cgatattgaa   2580
gaaggcggat ctaggcaatc actgatggaa atgcagtgca gacacggagt caaagaaatg   2640
ttcaaggact tcaactgcg gcagccacct ctggtgcctt ctcggaaggg agagacacca   2700
ccatccggca catctagcgc ctttagctca tacttcaaca acaaggtggg tattcctcag   2760
gagcacgtgg atcacgacga tttcgatgcc aatcagctcc tgaacaagat caatgagcct   2820
ccaaagcctg ctcctagaca gggttccgga cgggatcagc cactcaactc taagaagaag   2880
aaacgcctgc tgtcctttcg cgacgtcgac tttgaggagg attcagacgg ttccggacgg   2940
gatcagccac tcaactctaa gaagaagaaa cgcctgctgt cctttcgcga cgtcgacttt   3000
gaggaggatt cagactaa                                                  3018
```

<210> SEQ ID NO 27
<211> LENGTH: 1005
<212> TYPE: PRT
<213> ORGANISM: Artificial Sequence
<220> FEATURE:
<223> OTHER INFORMATION: Synthetic polypeptide

<400> SEQUENCE: 27

```
Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
            20                  25                  30

Thr Asp Gly Thr Ala Ala Ala Val Ser His Tyr Ala Met Asn Gly
        35                  40                  45

Phe Asp Glu Leu Ala Lys Gly Ala Val Pro Glu Asp His Phe Val
    50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
            100                 105                 110

Lys Ala Thr Cys Gly Trp Glu Glu Val Tyr Val Cys Cys Val Glu Val
        115                 120                 125

Leu Phe Val Thr Leu Glu Ile Phe Lys Glu Phe Ser Ser Pro Ala Thr
    130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Lys Arg Thr Met Gly Leu Ile Val Ser
            180                 185                 190

Cys Val Gly Met Ile Val Phe Gly Met Ala Ala Gly Leu Ala Thr Asp
```

```
              195                 200                 205
Trp Leu Lys Trp Leu Leu Tyr Ile Val Ser Cys Ile Tyr Gly Gly Tyr
210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                    245                 250                 255

Phe Ala Ser Trp Gly Ser Tyr Pro Ile Leu Trp Ala Val Gly Pro Glu
                260                 265                 270

Gly Leu Leu Lys Leu Ser Pro Tyr Ala Asn Ser Ile Gly His Ser Ile
                275                 280                 285

Cys Asp Ile Ile Ala Lys Glu Phe Trp Thr Phe Leu Ala His His Leu
290                 295                 300

Arg Ile Lys Ile His Glu His Ile Leu Ile His Gly Asp Ile Arg Lys
305                 310                 315                 320

Thr Thr Lys Met Glu Ile Gly Gly Glu Val Glu Val Glu Glu Phe
                325                 330                 335

Val Glu Glu Glu Asp Glu Asp Thr Val Gly Ala Ser Gly Gly Thr Val
                340                 345                 350

Ser Lys Gly Glu Glu Leu Ile Lys Glu Asn Met Arg Met Lys Val Val
                355                 360                 365

Met Glu Gly Ser Val Asn Gly His Gln Phe Lys Cys Thr Gly Glu Gly
370                 375                 380

Glu Gly Arg Pro Tyr Glu Gly Val Gln Thr Met Arg Ile Lys Val Ile
385                 390                 395                 400

Glu Gly Gly Pro Leu Pro Phe Ala Phe Asp Ile Leu Ala Thr Ser Phe
                405                 410                 415

Met Tyr Gly Ser Arg Thr Phe Ile Lys Tyr Pro Ala Asp Ile Pro Asp
                420                 425                 430

Phe Phe Lys Gln Ser Phe Pro Glu Gly Phe Thr Trp Glu Arg Val Thr
                435                 440                 445

Arg Tyr Glu Asp Gly Gly Val Val Thr Val Thr Gln Asp Thr Ser Leu
450                 455                 460

Glu Asp Gly Glu Leu Val Tyr Asn Val Lys Val Arg Gly Val Asn Phe
465                 470                 475                 480

Pro Ser Asn Gly Pro Val Met Gln Lys Lys Thr Lys Gly Trp Glu Pro
                485                 490                 495

Asn Thr Glu Met Met Tyr Pro Ala Asp Gly Gly Leu Arg Gly Tyr Thr
                500                 505                 510

Asp Ile Ala Leu Lys Val Asp Gly Gly His Leu His Cys Asn Phe
                515                 520                 525

Val Thr Thr Tyr Arg Ser Lys Lys Thr Val Gly Asn Ile Lys Met Pro
530                 535                 540

Gly Val His Ala Val Asp His Arg Leu Glu Arg Ile Glu Glu Ser Asp
545                 550                 555                 560

Asn Glu Thr Tyr Val Val Gln Arg Glu Val Ala Val Ala Lys Tyr Ser
                565                 570                 575

Asn Leu Gly Gly Gly Met Asp Glu Leu Tyr Lys Lys Val Asp Lys Met
                580                 585                 590

Leu Leu Gln Glu Leu Ser Glu Lys Leu Glu Leu Ala Glu Gln Ala Leu
                595                 600                 605

Ala Ser Lys Gln Leu Gln Met Asp Glu Met Lys Gln Thr Leu Ala Lys
610                 615                 620
```

Gln Glu Glu Asp Leu Glu Thr Met Ala Val Leu Arg Ala Gln Met Glu
625                 630                 635                 640

Val Tyr Cys Ser Asp Phe His Ala Glu Arg Ala Ala Arg Glu Lys Ile
            645                 650                 655

His Glu Glu Lys Glu Gln Leu Ala Leu Gln Leu Ala Ile Leu Leu Lys
        660                 665                 670

Glu Asn Asn Asp Ile Glu Glu Gly Gly Ser Arg Gln Ser Leu Met Glu
    675                 680                 685

Met Gln Cys Arg His Gly Val Lys Glu Met Phe Lys Asp Phe Gln Leu
690                 695                 700

Arg Gln Pro Pro Leu Val Pro Ser Arg Lys Gly Glu Thr Pro Pro Ser
705                 710                 715                 720

Gly Thr Ser Ser Ala Phe Ser Ser Tyr Phe Asn Asn Lys Val Gly Ile
                725                 730                 735

Pro Gln Glu His Val Asp His Asp Asp Phe Asp Ala Asn Gln Leu Leu
            740                 745                 750

Asn Lys Ile Asn Glu Pro Pro Lys Pro Ala Pro Arg Gln Gly Ser Ala
        755                 760                 765

Gly Lys Val Asp Lys Met Leu Leu Gln Glu Leu Ser Glu Lys Leu Glu
    770                 775                 780

Leu Ala Glu Gln Ala Leu Ala Ser Lys Gln Leu Gln Met Asp Glu Met
785                 790                 795                 800

Lys Gln Thr Leu Ala Lys Gln Glu Glu Asp Leu Glu Thr Met Ala Val
                805                 810                 815

Leu Arg Ala Gln Met Glu Val Tyr Cys Ser Asp Phe His Ala Glu Arg
            820                 825                 830

Ala Ala Arg Glu Lys Ile His Glu Glu Lys Glu Gln Leu Ala Leu Gln
        835                 840                 845

Leu Ala Ile Leu Leu Lys Glu Asn Asn Asp Ile Glu Glu Gly Gly Ser
    850                 855                 860

Arg Gln Ser Leu Met Glu Met Gln Cys Arg His Gly Val Lys Glu Met
865                 870                 875                 880

Phe Lys Asp Phe Gln Leu Arg Gln Pro Pro Leu Val Pro Ser Arg Lys
                885                 890                 895

Gly Glu Thr Pro Pro Ser Gly Thr Ser Ser Ala Phe Ser Ser Tyr Phe
            900                 905                 910

Asn Asn Lys Val Gly Ile Pro Gln Glu His Val Asp His Asp Asp Phe
        915                 920                 925

Asp Ala Asn Gln Leu Leu Asn Lys Ile Asn Glu Pro Pro Lys Pro Ala
    930                 935                 940

Pro Arg Gln Gly Ser Gly Arg Asp Gln Pro Leu Asn Ser Lys Lys Lys
945                 950                 955                 960

Lys Arg Leu Leu Ser Phe Arg Asp Val Asp Phe Glu Glu Asp Ser Asp
                965                 970                 975

Gly Ser Gly Arg Asp Gln Pro Leu Asn Ser Lys Lys Lys Arg Leu
            980                 985                 990

Leu Ser Phe Arg Asp Val Asp Phe  Glu Glu Asp Ser Asp
        995                 1000                1005

<210> SEQ ID NO 28
<211> LENGTH: 55
<212> TYPE: PRT
<213> ORGANISM: Artificial Sequence
<220> FEATURE:

<223> OTHER INFORMATION: Synthetic polypeptide

<400> SEQUENCE: 28

Arg Asp Gln Pro Leu Asn Ser Lys Lys Lys Arg Leu Leu Ser Phe
1               5                   10                  15

Arg Asp Val Asp Phe Glu Glu Asp Ser Asp Gly Ser Gly Arg Asp Gln
            20                  25                  30

Pro Leu Asn Ser Lys Lys Lys Arg Leu Leu Ser Phe Arg Asp Val
                35                  40                  45

Asp Phe Glu Glu Asp Ser Asp
    50                  55

<210> SEQ ID NO 29
<211> LENGTH: 359
<212> TYPE: PRT
<213> ORGANISM: Artificial Sequence
<220> FEATURE:
<223> OTHER INFORMATION: Synthetic polypeptide

<400> SEQUENCE: 29

Lys Val Asp Lys Met Leu Leu Gln Glu Leu Ser Glu Lys Leu Glu Leu
1               5                   10                  15

Ala Glu Gln Ala Leu Ala Ser Lys Gln Leu Gln Met Asp Glu Met Lys
            20                  25                  30

Gln Thr Leu Ala Lys Gln Glu Glu Asp Leu Glu Thr Met Ala Val Leu
        35                  40                  45

Arg Ala Gln Met Glu Val Tyr Cys Ser Asp Phe His Ala Glu Arg Ala
50                  55                  60

Ala Arg Glu Lys Ile His Glu Glu Lys Glu Gln Leu Ala Leu Gln Leu
65                  70                  75                  80

Ala Ile Leu Leu Lys Glu Asn Asn Asp Ile Glu Glu Gly Gly Ser Arg
                85                  90                  95

Gln Ser Leu Met Glu Met Gln Cys Arg His Gly Val Lys Glu Met Phe
            100                 105                 110

Lys Asp Phe Gln Leu Arg Gln Pro Pro Leu Val Pro Ser Arg Lys Gly
        115                 120                 125

Glu Thr Pro Pro Ser Gly Thr Ser Ser Ala Phe Ser Ser Tyr Phe Asn
    130                 135                 140

Asn Lys Val Gly Ile Pro Gln Glu His Val Asp His Asp Phe Asp
145                 150                 155                 160

Ala Asn Gln Leu Leu Asn Lys Ile Asn Glu Pro Pro Lys Pro Ala Pro
                165                 170                 175

Arg Gln Gly Ser Gly Lys Val Asp Lys Met Leu Leu Gln Glu Leu Ser
            180                 185                 190

Glu Lys Leu Glu Leu Ala Glu Gln Ala Leu Ala Ser Lys Gln Leu Gln
        195                 200                 205

Met Asp Glu Met Lys Gln Thr Leu Ala Lys Gln Glu Glu Asp Leu Glu
    210                 215                 220

Thr Met Ala Val Leu Arg Ala Gln Met Glu Val Tyr Cys Ser Asp Phe
225                 230                 235                 240

His Ala Glu Arg Ala Ala Arg Glu Lys Ile His Glu Glu Lys Glu Gln
                245                 250                 255

Leu Ala Leu Gln Leu Ala Ile Leu Leu Lys Glu Asn Asn Asp Ile Glu
            260                 265                 270

Glu Gly Gly Ser Arg Gln Ser Leu Met Glu Met Gln Cys Arg His Gly
        275                 280                 285

```
Val Lys Glu Met Phe Lys Asp Phe Gln Leu Arg Gln Pro Pro Leu Val
    290                 295                 300

Pro Ser Arg Lys Gly Glu Thr Pro Pro Ser Gly Thr Ser Ser Ala Phe
305                 310                 315                 320

Ser Ser Tyr Phe Asn Asn Lys Val Gly Ile Pro Gln Glu His Val Asp
                325                 330                 335

His Asp Asp Phe Asp Ala Asn Gln Leu Leu Asn Lys Ile Asn Glu Pro
                340                 345                 350

Pro Lys Pro Ala Pro Arg Gln
            355
```

<210> SEQ ID NO 30
<211> LENGTH: 324
<212> TYPE: DNA
<213> ORGANISM: Rattus norvegicus

<400> SEQUENCE: 30

```
caggcgcaga agctccggac tgtgaagatt gaacaaggga aggtgaatga tcaggccaac    60
acgctggctg acctggccaa ggcacagagc atcgcatatg aggtggtgtc ggagctgcag   120
gcccagcagg aggagttgga ggcccgtctg gctgccctgg agagccgcct ggatgtccta   180
ggcgcctccc tgcaggccct accaagtctc atagcccaag ccatatgccc tctaccacca   240
ccctggcccg ggcccagtca cctgaccaca gccgcccaga gccacaaag ccactggctg   300 cccaccacgg catcagactg tggg                                           324
```

<210> SEQ ID NO 31
<211> LENGTH: 108
<212> TYPE: PRT
<213> ORGANISM: Rattus norvegicus

<400> SEQUENCE: 31

```
Gln Ala Gln Lys Leu Arg Thr Val Lys Ile Glu Gln Gly Lys Val Asn
1               5                   10                  15

Asp Gln Ala Asn Thr Leu Ala Asp Leu Ala Lys Ala Gln Ser Ile Ala
            20                  25                  30

Tyr Glu Val Val Ser Glu Leu Gln Ala Gln Gln Glu Glu Leu Glu Ala
        35                  40                  45

Arg Leu Ala Ala Leu Glu Ser Arg Leu Asp Val Leu Gly Ala Ser Leu
    50                  55                  60

Gln Ala Leu Pro Ser Leu Ile Ala Gln Ala Ile Cys Pro Leu Pro Pro
65                  70                  75                  80

Pro Trp Pro Gly Pro Ser His Leu Thr Thr Ala Ala Gln Ser Pro Gln
                85                  90                  95

Ser His Trp Leu Pro Thr Thr Ala Ser Asp Cys Gly
            100                 105
```

<210> SEQ ID NO 32
<211> LENGTH: 417
<212> TYPE: PRT
<213> ORGANISM: Artificial Sequence
<220> FEATURE:
<223> OTHER INFORMATION: Synthetic polypeptide

<400> SEQUENCE: 32

```
Lys Val Asp Lys Met Leu Leu Gln Glu Leu Ser Glu Lys Leu Glu Leu
1               5                   10                  15

Ala Glu Gln Ala Leu Ala Ser Lys Gln Leu Gln Met Asp Glu Met Lys
```

```
                    20                  25                  30
Gln Thr Leu Ala Lys Gln Glu Glu Asp Leu Glu Thr Met Ala Val Leu
         35                  40                  45
Arg Ala Gln Met Glu Val Tyr Cys Ser Asp Phe His Ala Glu Arg Ala
 50                  55                  60
Ala Arg Glu Lys Ile His Glu Glu Lys Glu Gln Leu Ala Leu Gln Leu
 65                  70                  75                  80
Ala Ile Leu Leu Lys Glu Asn Asn Asp Ile Glu Glu Gly Gly Ser Arg
             85                  90                  95
Gln Ser Leu Met Glu Met Gln Cys Arg His Gly Val Lys Glu Met Phe
            100                 105                 110
Lys Asp Phe Gln Leu Arg Gln Pro Pro Leu Val Pro Ser Arg Lys Gly
            115                 120                 125
Glu Thr Pro Pro Ser Gly Thr Ser Ser Ala Phe Ser Tyr Phe Asn
            130                 135                 140
Asn Lys Val Gly Ile Pro Gln Glu His Val Asp His Asp Phe Asp
145                 150                 155                 160
Ala Asn Gln Leu Leu Asn Lys Ile Asn Glu Pro Pro Lys Pro Ala Pro
                165                 170                 175
Arg Gln Gly Ser Gly Lys Val Asp Lys Met Leu Leu Gln Glu Leu Ser
            180                 185                 190
Glu Lys Leu Glu Leu Ala Glu Gln Ala Leu Ala Ser Lys Gln Leu Gln
            195                 200                 205
Met Asp Glu Met Lys Gln Thr Leu Ala Lys Gln Glu Glu Asp Leu Glu
            210                 215                 220
Thr Met Ala Val Leu Arg Ala Gln Met Glu Val Tyr Cys Ser Asp Phe
225                 230                 235                 240
His Ala Glu Arg Ala Ala Arg Glu Lys Ile His Glu Glu Lys Glu Gln
                245                 250                 255
Leu Ala Leu Gln Leu Ala Ile Leu Leu Lys Glu Asn Asn Asp Ile Glu
            260                 265                 270
Glu Gly Gly Ser Arg Gln Ser Leu Met Glu Met Gln Cys Arg His Gly
            275                 280                 285
Val Lys Glu Met Phe Lys Asp Phe Gln Leu Arg Gln Pro Pro Leu Val
            290                 295                 300
Pro Ser Arg Lys Gly Glu Thr Pro Pro Ser Gly Thr Ser Ser Ala Phe
305                 310                 315                 320
Ser Ser Tyr Phe Asn Asn Lys Val Gly Ile Pro Gln Glu His Val Asp
                325                 330                 335
His Asp Asp Phe Asp Ala Asn Gln Leu Leu Asn Lys Ile Asn Glu Pro
            340                 345                 350
Pro Lys Pro Ala Pro Arg Gln Gly Ser Gly Arg Asp Gln Pro Leu Asn
            355                 360                 365
Ser Lys Lys Lys Arg Leu Leu Ser Phe Arg Asp Val Asp Phe Glu
            370                 375                 380
Glu Asp Ser Asp Gly Ser Gly Arg Asp Gln Pro Leu Asn Ser Lys Lys
385                 390                 395                 400
Lys Lys Arg Leu Leu Ser Phe Arg Asp Val Asp Phe Glu Glu Asp Ser
                405                 410                 415
Asp

<210> SEQ ID NO 33
<211> LENGTH: 2035
```

<212> TYPE: DNA
<213> ORGANISM: Artificial Sequence
<220> FEATURE:
<223> OTHER INFORMATION: Synthetic polynucleotide

<400> SEQUENCE: 33

| | | | | | |
|---|---|---|---|---|---|
| atgaccgccg | tgagcaccac | agccactacc | gtgctgcagg | ccacacagag | cgacgtgctg | 60 |
| caggagatcc | agtccaactt | cctgctgaat | agctccatct | gggtgaacat | tgctctggcc | 120 |
| ggagtggtca | tcctgctgtt | tgtggccatg | gggagggatc | tggaatcccc | tagagctaag | 180 |
| ctgatctggg | tggccacaat | gctggtgcca | ctggtgtcta | tttctagtta | cgctggactg | 240 |
| gccagtgggc | tgactgtggg | cttcctgcag | atgccacctg | acacgctct | ggccggacag | 300 |
| gaggtgctga | gcccatgggg | ccggtatctg | acatggactt | tctccactcc | catgatcctg | 360 |
| ctggctctgg | gactgctggc | cgacaccgat | attgccagcc | tgttcaccgc | catcacaatg | 420 |
| gacattggca | tgtgcgtgac | aggactggcc | gctgccctga | tcactagctc | ccatctgctg | 480 |
| cgctgggtgt | tctacggaat | tcttgtgct | ttctttgtgg | ccgtgctgta | tgtgctgctg | 540 |
| gtgcagtggc | cagctgatgc | tgaggctgct | gggaccagtg | aaatctttgg | cactctgagg | 600 |
| attctgaccg | tggtgctgtg | gctggggtac | cctatcctgt | tcgctctggg | ctctgaggga | 660 |
| gtggccctgc | tgagtgtggg | agtgaccagc | tggggatact | ccggactgga | catcctggct | 720 |
| aaatacgtgt | tcgcctttct | gctgctgaga | tgggtggctg | ccaatgaagg | cacagtgtct | 780 |
| gggagtggaa | tgggaatcgg | gtccggagga | gctgctccag | ccgacgatcg | accggtagta | 840 |
| aaatccagaa | ttacttctga | agggagtat | atccctctgg | atcaaataga | catcaatgtt | 900 |
| gcacctgcag | gggcaggttc | cggaccggta | gtagcagtga | gcaagggcga | ggagctgttc | 960 |
| accggggtgg | tgcccatcct | ggtcgagctg | gacggcgacg | taaacggcca | caagttcagc | 1020 |
| gtgtccggcg | agggcgaggg | cgatgccacc | tacggcaagc | tgaccctgaa | gttcatttgc | 1080 |
| accaccggca | agctgcccgt | gccctggccc | accctcgtga | ccaccctgac | ctacggcgtg | 1140 |
| cagtgcttca | gccgctaccc | cgaccacatg | aagcagcacg | acttcttcaa | gtccgccatg | 1200 |
| cccgaaggct | acgtccagga | gcgcaccatc | ttcttcaagg | acgacggcaa | ctacaagacc | 1260 |
| cgcgccgagg | tgaagttcga | gggcgacacc | ctggtgaacc | gcatcgagct | gaagggcatc | 1320 |
| gacttcaagg | aggacggcaa | catcctgggg | cacaagctgg | agtacaacta | caacagccac | 1380 |
| aacgtctata | tcatggccga | caagcagaag | aacggcatca | aggtgaactt | caagatccgc | 1440 |
| cacaacatcg | aggacggcag | cgtgcagctc | gccgaccact | accagcagaa | cacccccatc | 1500 |
| ggcgacggcc | ccgtgctgct | gcccgacaac | cactacctga | gcacccagtc | cgccctgagc | 1560 |
| aaagacccca | acgagaagcg | cgatcacatg | gtcctgctgg | agttcgtgac | cgccgccggg | 1620 |
| atcactctcg | gcatggacga | gctgtacaag | ggaggttcag | gtggaaccgg | tggaagtgga | 1680 |
| ggtaccccag | gcgcagaagc | tccggactgt | gaagattgaa | caagggaagg | tgaatgatca | 1740 |
| ggccaacacg | ctggctgacc | tggccaaggc | acagagcatc | gcatatgagg | tggtgtcgga | 1800 |
| gctgcaggcc | cagcaggagg | agttggaggc | ccgtctggct | gccctggaga | gccgcctgga | 1860 |
| tgtcctaggc | gcctccctgc | aggccctacc | aagtctcata | gcccaagcca | tatgccctct | 1920 |
| accaccaccc | tggcccgggc | ccagtcacct | gaccacagcc | gccagagcc | acaaagcca | 1980 |
| ctggctgccc | accacggcat | cagactgtgg | gttctgctac | gagaatgaag | tgtaa | 2035 |

<210> SEQ ID NO 34
<211> LENGTH: 677
<212> TYPE: PRT

<213> ORGANISM: Artificial Sequence
<220> FEATURE:
<223> OTHER INFORMATION: Synthetic polypeptide

<400> SEQUENCE: 34

Met Thr Ala Val Ser Thr Thr Ala Thr Thr Val Leu Gln Ala Thr Gln
1               5                   10                  15

Ser Asp Val Leu Gln Glu Ile Gln Ser Asn Phe Leu Leu Asn Ser Ser
                20                  25                  30

Ile Trp Val Asn Ile Ala Leu Ala Gly Val Val Ile Leu Leu Phe Val
            35                  40                  45

Ala Met Gly Arg Asp Leu Glu Ser Pro Arg Ala Lys Leu Ile Trp Val
        50                  55                  60

Ala Thr Met Leu Val Pro Leu Val Ser Ile Ser Ser Tyr Ala Gly Leu
65                  70                  75                  80

Ala Ser Gly Leu Thr Val Gly Phe Leu Gln Met Pro Pro Gly His Ala
                85                  90                  95

Leu Ala Gly Gln Glu Val Leu Ser Pro Trp Gly Arg Tyr Leu Thr Trp
            100                 105                 110

Thr Phe Ser Thr Pro Met Ile Leu Leu Ala Leu Gly Leu Leu Ala Asp
        115                 120                 125

Thr Asp Ile Ala Ser Leu Phe Thr Ala Ile Thr Met Asp Ile Gly Met
130                 135                 140

Cys Val Thr Gly Leu Ala Ala Ala Leu Ile Thr Ser Ser His Leu Leu
145                 150                 155                 160

Arg Trp Val Phe Tyr Gly Ile Ser Cys Ala Phe Phe Val Ala Val Leu
                165                 170                 175

Tyr Val Leu Leu Val Gln Trp Pro Ala Asp Ala Glu Ala Ala Gly Thr
            180                 185                 190

Ser Glu Ile Phe Gly Thr Leu Arg Ile Leu Thr Val Val Leu Trp Leu
        195                 200                 205

Gly Tyr Pro Ile Leu Phe Ala Leu Gly Ser Glu Gly Val Ala Leu Leu
210                 215                 220

Ser Val Gly Val Thr Ser Trp Gly Tyr Ser Gly Leu Asp Ile Leu Ala
225                 230                 235                 240

Lys Tyr Val Phe Ala Phe Leu Leu Leu Arg Trp Val Ala Ala Asn Glu
                245                 250                 255

Gly Thr Val Ser Gly Ser Gly Met Gly Ile Gly Ser Gly Ala Ala
            260                 265                 270

Pro Ala Asp Asp Arg Pro Val Val Lys Ser Arg Ile Thr Ser Glu Gly
        275                 280                 285

Glu Tyr Ile Pro Leu Asp Gln Ile Asp Ile Asn Val Ala Pro Ala Gly
    290                 295                 300

Ala Gly Ser Gly Pro Val Val Ala Val Ser Lys Gly Glu Glu Leu Phe
305                 310                 315                 320

Thr Gly Val Val Pro Ile Leu Val Glu Leu Asp Gly Asp Val Asn Gly
                325                 330                 335

His Lys Phe Ser Val Ser Gly Glu Gly Glu Gly Asp Ala Thr Tyr Gly
            340                 345                 350

Lys Leu Thr Leu Lys Phe Ile Cys Thr Thr Gly Lys Leu Pro Val Pro
        355                 360                 365

Trp Pro Thr Leu Val Thr Thr Leu Thr Tyr Gly Val Gln Cys Phe Ser
    370                 375                 380

Arg Tyr Pro Asp His Met Lys Gln His Asp Phe Phe Lys Ser Ala Met

```
                385                 390                 395                 400
Pro Glu Gly Tyr Val Gln Glu Arg Thr Ile Phe Phe Lys Asp Asp Gly
                    405                 410                 415

Asn Tyr Lys Thr Arg Ala Glu Val Lys Phe Glu Gly Asp Thr Leu Val
                420                 425                 430

Asn Arg Ile Glu Leu Lys Gly Ile Asp Phe Lys Glu Asp Gly Asn Ile
            435                 440                 445

Leu Gly His Lys Leu Glu Tyr Asn Tyr Asn Ser His Asn Val Tyr Ile
        450                 455                 460

Met Ala Asp Lys Gln Lys Asn Gly Ile Lys Val Asn Phe Lys Ile Arg
465                 470                 475                 480

His Asn Ile Glu Asp Gly Ser Val Gln Leu Ala Asp His Tyr Gln Gln
                485                 490                 495

Asn Thr Pro Ile Gly Asp Gly Pro Val Leu Leu Pro Asn His Tyr
                    500                 505                 510

Leu Ser Thr Gln Ser Ala Leu Ser Lys Asp Pro Asn Glu Lys Arg Asp
                515                 520                 525

His Met Val Leu Leu Glu Phe Val Thr Ala Ala Gly Ile Thr Leu Gly
    530                 535                 540

Met Asp Glu Leu Tyr Lys Gly Gly Ser Gly Gly Thr Gly Gly Ser Gly
545                 550                 555                 560

Gly Thr Gln Ala Gln Lys Leu Arg Thr Val Lys Ile Glu Gln Gly Lys
                    565                 570                 575

Val Asn Asp Gln Ala Asn Thr Leu Ala Asp Leu Ala Lys Ala Gln Ser
                580                 585                 590

Ile Ala Tyr Glu Val Val Ser Glu Leu Gln Ala Gln Gln Glu Glu Leu
            595                 600                 605

Glu Ala Arg Leu Ala Ala Leu Glu Ser Arg Leu Asp Val Leu Gly Ala
        610                 615                 620

Ser Leu Gln Ala Leu Pro Ser Leu Ile Ala Gln Ala Ile Cys Pro Leu
625                 630                 635                 640

Pro Pro Pro Trp Pro Gly Pro Ser His Leu Thr Thr Ala Ala Gln Ser
                    645                 650                 655

Pro Gln Ser His Trp Leu Pro Thr Thr Ala Ser Asp Cys Gly Phe Cys
                660                 665                 670

Tyr Glu Asn Glu Val
            675

<210> SEQ ID NO 35
<211> LENGTH: 1984
<212> TYPE: DNA
<213> ORGANISM: Artificial Sequence
<220> FEATURE:
<223> OTHER INFORMATION: Synthetic polynucleotide

<400> SEQUENCE: 35
atgctgggga acggcagcgc cattgtgcct atcgaccagt gctttttgcct ggcttggacc      60 gacagcctgg aagcgatac agagcagctg gtggccaaca tcctccagtg gttcgccttc     120
ggcttcagca tcctgatcct gatgttctac gcctaccaga cttggagagc cacttgcggt     180
tgggaggagg tctacgtctg ttgcgtcgag ctgaccaagg tcatcatcga gttcttccac     240
gagttcgacg accccagcat gctgtacctg gctaacggac accgagtcca gtggctgaga     300
tacgcagagt ggctgctgac ttgtcccgtc atcctgatcc acctgagcaa cctgaccggc     360
ctgaaggacg actacagcaa gcggaccatg aggctgctgg tgtcagacgt gggaaccatc     420
```

```
gtgtggggag ctacaagcgc catgagcaca ggctacgtca aggtcatctt cttcgtgctg    480
ggttgcatct acggcgccaa caccttcttc cacgccgcca aggtgtatat cgagagctac    540
cacgtggtgc caaagggcag acctagaacc gtcgtgcgga tcatggcttg gctgttcttc    600
ctgtcttggg gcatgttccc cgtgctgttc gtcgtgggac cagaaggatt cgacgccatc    660
agcgtgtacg gctctaccat tggccacacc atcatcgacc tcatgagcaa gaattgttgg    720
ggcctgctgg gacactatct gagagtgctg atccaccagc acatcatcat ctacggcgac    780
atccggaaga agaccaagat caacgtggcc ggcgaggaga tggaagtgga gaccatggtg    840
gaccaggagg acgaggagac agtgggttcc ggaccggtag tagcagtgag caagggcgag    900
gagctgttca ccggggtggt gcccatcctg gtcgagctgg acggcgacgt aaacggccac    960
aagttcagcg tgtccggcga gggcgagggc gatgccacct acggcaagct gaccctgaag   1020
ttcatttgca ccaccggcaa gctgcccgtg ccctggccca ccctcgtgac caccctgacc   1080
tacggcgtgc agtgcttcag ccgctacccc gaccacatga gcagcacga cttcttcaag   1140 tccgccatgc ccgaaggcta cgtccaggag cgcaccatct tcttcaagga cgacggcaac   1200
tacaagaccc gcgccgaggt gaagttcgag ggcgacaccc tggtgaaccg catcgagctg   1260
aagggcatcg acttcaagga ggacggcaac atcctggggc acaagctgga gtacaactac   1320
aacagccaca acgtctatat catggccgac aagcagaaga acggcatcaa ggtgaacttc   1380
aagatccgcc acaacatcga ggacggcagc gtgcagctcg ccgaccacta ccagcagaac   1440
acccccatcg gcgacggccc cgtgctgctg cccgacaacc actacctgag cacccagtcc   1500
gccctgagca agaccccaa cgagaagcgc gatcacatgg tcctgctgga gttcgtgacc   1560
gccgccggga tcactctcgg catggacgag ctgtacaagg aggttcagg tggaaccggt   1620 ggaagtggag gtaccccagg cgcagaagct ccggactgtg aagattgaac aagggaaggt   1680
gaatgatcag gccaacacgc tggctgacct ggccaaggca cagagcatcg catatgaggt   1740
ggtgtcggag ctgcaggccc agcaggagga gttggaggcc cgtctggctg ccctggagag   1800
ccgcctggat gtcctaggcg cctccctgca ggccctacca agtctcatag cccaagccat   1860
atgccctcta ccaccaccct ggcccgggcc cagtcacctg accacagccg cccagagccc   1920
acaaagccac tggctgccca ccacggcatc agactgtggg ttctgctacg agaatgaagt   1980
gtaa                                                                  1984
```

<210> SEQ ID NO 36
<211> LENGTH: 660
<212> TYPE: PRT
<213> ORGANISM: Artificial Sequence
<220> FEATURE:
<223> OTHER INFORMATION: Synthetic polypeptide

<400> SEQUENCE: 36

```
Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30

Asn Ile Leu Gln Trp Phe Ala Phe Gly Phe Ser Ile Leu Ile Leu Met
        35                  40                  45

Phe Tyr Ala Tyr Gln Thr Trp Arg Ala Thr Cys Gly Trp Glu Glu Val
    50                  55                  60

Tyr Val Cys Cys Val Glu Leu Thr Lys Val Ile Ile Glu Phe Phe His
65                  70                  75                  80
```

```
Glu Phe Asp Asp Pro Ser Met Leu Tyr Leu Ala Asn Gly His Arg Val
            85                  90                  95

Gln Trp Leu Arg Tyr Ala Glu Trp Leu Leu Thr Cys Pro Val Ile Leu
            100                 105                 110

Ile His Leu Ser Asn Leu Thr Gly Leu Lys Asp Asp Tyr Ser Lys Arg
            115                 120                 125

Thr Met Arg Leu Leu Val Ser Asp Val Gly Thr Ile Val Trp Gly Ala
            130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
            195                 200                 205

Leu Phe Val Val Gly Pro Glu Gly Phe Asp Ala Ile Ser Val Tyr Gly
    210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
                260                 265                 270

Glu Met Glu Val Glu Thr Met Val Asp Gln Glu Asp Glu Glu Thr Val
            275                 280                 285

Gly Ser Gly Pro Val Val Ala Val Ser Lys Gly Glu Glu Leu Phe Thr
    290                 295                 300

Gly Val Val Pro Ile Leu Val Glu Leu Asp Gly Asp Val Asn Gly His
305                 310                 315                 320

Lys Phe Ser Val Ser Gly Glu Gly Glu Gly Asp Ala Thr Tyr Gly Lys
                325                 330                 335

Leu Thr Leu Lys Phe Ile Cys Thr Thr Gly Lys Leu Pro Val Pro Trp
            340                 345                 350

Pro Thr Leu Val Thr Thr Leu Thr Tyr Gly Val Gln Cys Phe Ser Arg
            355                 360                 365

Tyr Pro Asp His Met Lys Gln His Asp Phe Phe Lys Ser Ala Met Pro
    370                 375                 380

Glu Gly Tyr Val Gln Glu Arg Thr Ile Phe Phe Lys Asp Asp Gly Asn
385                 390                 395                 400

Tyr Lys Thr Arg Ala Glu Val Lys Phe Glu Gly Asp Thr Leu Val Asn
                405                 410                 415

Arg Ile Glu Leu Lys Gly Ile Asp Phe Lys Glu Asp Gly Asn Ile Leu
            420                 425                 430

Gly His Lys Leu Glu Tyr Asn Tyr Asn Ser His Asn Val Tyr Ile Met
            435                 440                 445

Ala Asp Lys Gln Lys Asn Gly Ile Lys Val Asn Phe Lys Ile Arg His
    450                 455                 460

Asn Ile Glu Asp Gly Ser Val Gln Leu Ala Asp His Tyr Gln Gln Asn
465                 470                 475                 480

Thr Pro Ile Gly Asp Gly Pro Val Leu Leu Pro Asp Asn His Tyr Leu
                485                 490                 495
```

```
Ser Thr Gln Ser Ala Leu Ser Lys Asp Pro Asn Glu Lys Arg Asp His
            500                 505                 510

Met Val Leu Leu Glu Phe Val Thr Ala Ala Gly Ile Thr Leu Gly Met
        515                 520                 525

Asp Glu Leu Tyr Lys Gly Gly Ser Gly Gly Thr Gly Gly Ser Gly Gly
        530                 535                 540

Thr Gln Ala Gln Lys Leu Arg Thr Val Lys Ile Glu Gln Gly Lys Val
545                 550                 555                 560

Asn Asp Gln Ala Asn Thr Leu Ala Asp Leu Ala Lys Ala Gln Ser Ile
                565                 570                 575

Ala Tyr Glu Val Val Ser Glu Leu Gln Ala Gln Gln Glu Glu Leu Glu
            580                 585                 590

Ala Arg Leu Ala Ala Leu Glu Ser Arg Leu Asp Val Leu Gly Ala Ser
        595                 600                 605

Leu Gln Ala Leu Pro Ser Leu Ile Ala Gln Ala Ile Cys Pro Leu Pro
        610                 615                 620

Pro Pro Trp Pro Gly Pro Ser His Leu Thr Thr Ala Ala Gln Ser Pro
625                 630                 635                 640

Gln Ser His Trp Leu Pro Thr Thr Ala Ser Asp Cys Gly Phe Cys Tyr
                645                 650                 655

Glu Asn Glu Val
            660

<210> SEQ ID NO 37
<211> LENGTH: 2112
<212> TYPE: DNA
<213> ORGANISM: Artificial Sequence
<220> FEATURE:
<223> OTHER INFORMATION: Synthetic polynucleotide

<400> SEQUENCE: 37
atgagcagac tggtcgccgc ttcttggctg ctggctctcc tcctctgcgg aattaccagc      60
acaacaacag cctctagcgc cccagcagct tcttctacag acggaacagc cgccgcagca     120
gtgtctcact acgccatgaa cggcttcgac gagctggcta aggagccgt ggtgccagaa      180 gaccactttg tctgcggacc agccgacaag tgctattgct ccgcttggct gcacagcaga     240
ggcacaccag agaaaagat cggcgcccag gtctgccagt ggattgcttt cagcatcgcc      300
atcgccctgc tgacattcta cggcttcagc gcctggaagg ccacttgcgg ttgggaggag     360
gtctacgtct gttgcgtcga ggtgctgttc gtgaccctgg agatcttcaa ggagttcagc     420
agccccgcca gtgtacct gtctaccggc aaccacgcct attgcctgcg ctacttcgag      480
tggctgctgt cttgccccgt gatcctgatc aagctgagca acctgagcgg cctgaagaac     540
gactacagca gcggaccat gggcctgatc gtgtcttgcg tgggaatgat cgtgttcggc     600
atggccgcag actggctac cgattggctc aagtggctgc tgtatatcgt gtcttgcatc     660
tacgcgggct acatgtactt ccaggccgcc aagtgctacg tggaagccaa ccacagcgtg     720
cctaaaggcc attgccgcat ggtcgtgaag ctgatggcct acgcttactt cgcctcttgg    780
ggcagctacc caatcctctg ggcagtggga ccagaaggac tgctgaagct gagcccttac     840
gccaacagca tcggcacag catctgcgac atcatcgcca ggagttttg gaccttcctg      900 gcccaccacc tgaggatcaa gatccacgag cacatcctga tccacggcga catccggaag    960
accaccaaga tggagatcgg aggcgaggag gtggaagtgg aagagttcgt ggaggaggag    1020
gacgaggaca cagtgggagc tagcggaggt actatggcct cctccgagga cgtcatcaag    1080
```

```
gagttcatgc gcttcaaggt gcgcatggag ggctccgtga acggccacga gttcgagatc    1140
gagggcgagg gcgagggccg cccctacgag ggcacccaga ccgccaagct gaaggtgacc    1200
aagggcggcc ccctgccctt cgcctgggac atcctgtccc cccagttcca gtacggctcc    1260
aaggtgtacg tgaagcaccc cgccgacatc cccgactaca agaagctgtc cttccccgag    1320
ggcttcaagt gggagcgcgt gatgaacttc gaggacggcg gcgtggtgac cgtgacccag    1380
gactcctccc tgcaggacgg ctgcttcatc tacaaggtga agttcatcgg cgtgaacttc    1440
ccctccgacg gccccgtaat gcagaagaag actatgggct gggagccctc caccgagcgc    1500
ctgtaccccc gcgacggcgt gctgaagggc gagatccaca aggccctgaa gctgaaggac    1560
ggcggccact acctggtgga gttcaagtcc atctacatgg ccaagaagcc cgtgcagctg    1620
cccggctact actacgtgga ctccaagctg gacatcacct cccacaacga ggactacacc    1680
atcgtggagc agtacgagcg caccgagggc cgccaccacc tgttcctggg aggttcaggt    1740
ggaaccggtg aagtggagg tacccaggcg cagaagctcc ggactgtgaa gattgaacaa    1800
gggaaggtga atgatcaggc caacacgctg gctgacctgg ccaaggcaca gagcatcgca    1860
tatgaggtgg tgtcggagct gcaggcccag caggaggagt ggaggcccg tctggctgcc    1920 ctggagagcc gcctggatgt cctaggcgcc tccctgcagg ccctaccaag tctcatagcc    1980
caagccatat gccctctacc accaccctgg cccgggccca gtcacctgac cacagccgcc    2040
cagagcccac aaagccactg gctgcccacc acggcatcag actgtgggtt ctgctacgag    2100
aatgaagtgt aa                                                        2112
```

<210> SEQ ID NO 38
<211> LENGTH: 703
<212> TYPE: PRT
<213> ORGANISM: Artificial Sequence
<220> FEATURE:
<223> OTHER INFORMATION: Synthetic polypeptide

<400> SEQUENCE: 38

```
Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
            20                  25                  30

Thr Asp Gly Thr Ala Ala Ala Val Ser His Tyr Ala Met Asn Gly
        35                  40                  45

Phe Asp Glu Leu Ala Lys Gly Ala Val Pro Glu Asp His Phe Val
    50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
            100                 105                 110

Lys Ala Thr Cys Gly Trp Glu Glu Val Tyr Val Cys Cys Val Glu Val
        115                 120                 125

Leu Phe Val Thr Leu Glu Ile Phe Lys Glu Phe Ser Ser Pro Ala Thr
    130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175
```

```
Gly Leu Lys Asn Asp Tyr Ser Lys Arg Thr Met Gly Leu Ile Val Ser
                180                 185                 190

Cys Val Gly Met Ile Val Phe Gly Met Ala Ala Gly Leu Ala Thr Asp
            195                 200                 205

Trp Leu Lys Trp Leu Leu Tyr Ile Val Ser Cys Ile Tyr Gly Gly Tyr
        210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
            260                 265                 270

Gly Leu Leu Lys Leu Ser Pro Tyr Ala Asn Ser Ile Gly His Ser Ile
        275                 280                 285

Cys Asp Ile Ile Ala Lys Glu Phe Trp Thr Phe Leu Ala His His Leu
290                 295                 300

Arg Ile Lys Ile His Glu His Ile Leu Ile His Gly Asp Ile Arg Lys
305                 310                 315                 320

Thr Thr Lys Met Glu Ile Gly Gly Glu Val Glu Val Glu Glu Phe
                325                 330                 335

Val Glu Glu Glu Asp Glu Asp Thr Val Gly Ala Ser Gly Gly Thr Met
            340                 345                 350

Ala Ser Ser Glu Asp Val Ile Lys Glu Phe Met Arg Phe Lys Val Arg
            355                 360                 365

Met Glu Gly Ser Val Asn Gly His Glu Phe Glu Ile Glu Gly Glu Gly
370                 375                 380

Glu Gly Arg Pro Tyr Glu Gly Thr Gln Thr Ala Lys Leu Lys Val Thr
385                 390                 395                 400

Lys Gly Gly Pro Leu Pro Phe Ala Trp Asp Ile Leu Ser Pro Gln Phe
                405                 410                 415

Gln Tyr Gly Ser Lys Val Tyr Val Lys His Pro Ala Asp Ile Pro Asp
            420                 425                 430

Tyr Lys Lys Leu Ser Phe Pro Glu Gly Phe Lys Trp Glu Arg Val Met
        435                 440                 445

Asn Phe Glu Asp Gly Gly Val Val Thr Val Thr Gln Asp Ser Ser Leu
450                 455                 460

Gln Asp Gly Cys Phe Ile Tyr Lys Val Lys Phe Ile Gly Val Asn Phe
465                 470                 475                 480

Pro Ser Asp Gly Pro Val Met Gln Lys Lys Thr Met Gly Trp Glu Pro
                485                 490                 495

Ser Thr Glu Arg Leu Tyr Pro Arg Asp Gly Val Leu Lys Gly Glu Ile
            500                 505                 510

His Lys Ala Leu Lys Leu Lys Asp Gly Gly His Tyr Leu Val Glu Phe
        515                 520                 525

Lys Ser Ile Tyr Met Ala Lys Lys Pro Val Gln Leu Pro Gly Tyr Tyr
530                 535                 540

Tyr Val Asp Ser Lys Leu Asp Ile Thr Ser His Asn Glu Asp Tyr Thr
545                 550                 555                 560

Ile Val Glu Gln Tyr Glu Arg Thr Glu Gly Arg His His Leu Phe Leu
                565                 570                 575

Gly Gly Ser Gly Gly Thr Gly Gly Ser Gly Gly Thr Gln Ala Gln Lys
            580                 585                 590

Leu Arg Thr Val Lys Ile Glu Gln Gly Lys Val Asn Asp Gln Ala Asn
```

```
                  595                 600                 605
Thr Leu Ala Asp Leu Ala Lys Ala Gln Ser Ile Ala Tyr Glu Val Val
    610                 615                 620

Ser Glu Leu Gln Ala Gln Gln Glu Glu Leu Glu Ala Arg Leu Ala Ala
625                 630                 635                 640

Leu Glu Ser Arg Leu Asp Val Leu Gly Ala Ser Leu Gln Ala Leu Pro
                645                 650                 655

Ser Leu Ile Ala Gln Ala Ile Cys Pro Leu Pro Pro Trp Pro Gly
            660                 665                 670

Pro Ser His Leu Thr Thr Ala Ala Gln Ser Pro Gln Ser His Trp Leu
            675                 680                 685

Pro Thr Thr Ala Ser Asp Cys Gly Phe Cys Tyr Glu Asn Glu Val
            690                 695                 700

<210> SEQ ID NO 39
<211> LENGTH: 2145
<212> TYPE: DNA
<213> ORGANISM: Artificial Sequence
<220> FEATURE:
<223> OTHER INFORMATION: Synthetic polynucleotide

<400> SEQUENCE: 39
atgagcagac tggtcgccgc ttcttggctg ctggctctcc tcctctgcgg aattaccagc      60
acaacaacag cctctagcgc cccagcagct tcttctacag acggaacagc cgccgcagca     120
gtgtctcact acgccatgaa cggcttcgac gagctggcta aggagccgt ggtgccagaa     180 gaccactttg tctgcggacc agccgacaag tgctattgct ccgcttggct gcacagagaa    240
ggcacaccag agaaaagat cggcgcccag gtctgccagt ggattgcttt cagcatcgcc    300
atcgccctgc tgacattcta cggcttcagc gcctggaagg ccacttgcgg ttgggaggag    360
gtctacgtct gttgcgtcga ggtgctgttc gtgaccctgg agatcttcaa ggagttcagc    420
agccccgcca cagtgtacct gtctaccgga accacgccc attgcctgcg ctacttcgag    480
tggctgctgt cttgccccgt gatcctgatc aagctgagca acctgagcgg cctgaagaac    540
gactacagca gcggaccat gggcctgatc gtgtcttgcg tgggaatgat cgtgttcggc    600
atggccgcag gactggctac cgattggctc aagtggctgc tgtatatcgt gtcttgcatc    660
tacgccggct acatgtactt ccaggccgcc aagtgctacg tggaagccaa ccacagcgtg    720
cctaaaggcc attgccgcat ggtcgtgaag ctgatggcct acgcttactt cgcctcttgg    780
ggcagctacc caatcctctg ggcagtggga ccagaaggac tgctgaagct gagcccttac    840
gccaacagca tcggccacag catctgcgac atcatcgcca aggagttttg gaccttcctg    900
gcccaccacc tgaggatcaa gatccacgag cacatcctga tccacggcga catccggaag    960
accaccaaga tggagatcgg aggcgaggag gtggaagtgg aagagttcgt ggaggaggag   1020
gacgaggaca cagtgggagc tagcggaggt actgtgtcta agggcgaaga gctgatcaag   1080
gaaaatatgc gtatgaaggt ggtcatgaa ggttcggtca acggccacca attcaaatgc   1140
acaggtgaag agaaggcag accgtacgag ggagtgcaaa ccatgaggat caaagtcatc   1200
gagggaggac ccctgccatt tgcctttgac attcttgcca cgtcgttcat gtatggcagc   1260
cgtaccttta tcaagtaccc ggccgacatc cctgattttt taaacagtc ctttcctgag   1320 ggttttactt gggaaagagt tacgagatac gaagatggtg gagtcgtcac cgtcacgcag   1380
gacaccagcc ttgaggatgg cgagctcgtc tacaacgtca aggtcagagg ggtaaacttt   1440
ccctccaatg gtcccgtgat gcagaagaag accaagggtt gggagcctaa tacagagatg   1500
```

```
atgtatccag cagatggtgg tctgagagga tacactgaca tcgcactgaa agttgatggt   1560
ggtggccatc tgcactgcaa cttcgtgaca acttacaggt caaaaaagac cgtcgggaac   1620
atcaagatgc ccggtgtcca tgccgttgat caccgcctgg aaaggatcga ggagagtgac   1680
aatgaaacct acgtagtgca aagagaagtg gcagttgcca atacagcaa ccttggtggt    1740 ggcatggacg agctgtacaa gggaggttca ggtggaaccg gtggaagtgg aggtacccag   1800
gcgcagaagc tccggactgt gaagattgaa caagggaagg tgaatgatca ggccaacacg   1860
ctggctgacc tggccaaggc acagagcatc gcatatgagg tggtgtcgga gctgcaggcc   1920
cagcaggagg agttggaggc ccgtctggct gccctggaga gccgcctgga tgtcctaggc   1980
gcctccctgc aggccctacc aagtctcata gcccaagcca tatgccctct accaccaccc   2040
tggcccgggc ccagtcacct gaccacagcc gcccagagcc cacaaagcca ctggctgccc   2100
accacggcat cagactgtgg gttctgctac gagaatgaag tgtaa               2145

<210> SEQ ID NO 40
<211> LENGTH: 714
<212> TYPE: PRT
<213> ORGANISM: Artificial Sequence
<220> FEATURE:
<223> OTHER INFORMATION: Synthetic polypeptide

<400> SEQUENCE: 40

Met Ser Arg Leu Val Ala Ala Ser Trp Leu Ala Leu Leu Cys
1               5                   10                  15

Gly Ile Thr Ser Thr Thr Thr Ala Ser Ser Ala Pro Ala Ala Ser Ser
            20                  25                  30

Thr Asp Gly Thr Ala Ala Ala Val Ser His Tyr Ala Met Asn Gly
        35                  40                  45

Phe Asp Glu Leu Ala Lys Gly Ala Val Val Pro Glu Asp His Phe Val
    50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
            100                 105                 110

Lys Ala Thr Cys Gly Trp Glu Glu Val Tyr Val Cys Cys Val Glu Val
        115                 120                 125

Leu Phe Val Thr Leu Glu Ile Phe Lys Glu Phe Ser Ser Pro Ala Thr
    130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Arg Thr Met Gly Leu Ile Val Ser
            180                 185                 190

Cys Val Gly Met Ile Val Phe Gly Met Ala Ala Gly Leu Ala Thr Asp
        195                 200                 205

Trp Leu Lys Trp Leu Leu Tyr Ile Val Ser Cys Ile Tyr Gly Gly Tyr
    210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
```

```
                    245                 250                 255
Phe Ala Ser Trp Gly Ser Tyr Pro Ile Leu Trp Ala Val Gly Pro Glu
                260                 265                 270
Gly Leu Leu Lys Leu Ser Pro Tyr Ala Asn Ser Ile Gly His Ser Ile
                275                 280                 285
Cys Asp Ile Ile Ala Lys Glu Phe Trp Thr Phe Leu Ala His His Leu
                290                 295                 300
Arg Ile Lys Ile His Glu His Ile Leu Ile His Gly Asp Ile Arg Lys
305                 310                 315                 320
Thr Thr Lys Met Glu Ile Gly Gly Glu Val Glu Val Glu Glu Phe
                325                 330                 335
Val Glu Glu Glu Asp Glu Asp Thr Val Gly Ala Ser Gly Gly Thr Val
                340                 345                 350
Ser Lys Gly Glu Glu Leu Ile Lys Glu Asn Met Arg Met Lys Val Val
                355                 360                 365
Met Glu Gly Ser Val Asn Gly His Gln Phe Lys Cys Thr Gly Glu Gly
                370                 375                 380
Glu Gly Arg Pro Tyr Glu Gly Val Gln Thr Met Arg Ile Lys Val Ile
385                 390                 395                 400
Glu Gly Gly Pro Leu Pro Phe Ala Phe Asp Ile Leu Ala Thr Ser Phe
                405                 410                 415
Met Tyr Gly Ser Arg Thr Phe Ile Lys Tyr Pro Ala Asp Ile Pro Asp
                420                 425                 430
Phe Phe Lys Gln Ser Phe Pro Glu Gly Phe Thr Trp Glu Arg Val Thr
                435                 440                 445
Arg Tyr Glu Asp Gly Gly Val Val Thr Val Thr Gln Asp Thr Ser Leu
                450                 455                 460
Glu Asp Gly Glu Leu Val Tyr Asn Val Lys Val Arg Gly Val Asn Phe
465                 470                 475                 480
Pro Ser Asn Gly Pro Val Met Gln Lys Lys Thr Lys Gly Trp Glu Pro
                485                 490                 495
Asn Thr Glu Met Met Tyr Pro Ala Asp Gly Gly Leu Arg Gly Tyr Thr
                500                 505                 510
Asp Ile Ala Leu Lys Val Asp Gly Gly His Leu His Cys Asn Phe
                515                 520                 525
Val Thr Thr Tyr Arg Ser Lys Lys Thr Val Gly Asn Ile Lys Met Pro
                530                 535                 540
Gly Val His Ala Val Asp His Arg Leu Glu Arg Ile Glu Glu Ser Asp
545                 550                 555                 560
Asn Glu Thr Tyr Val Val Gln Arg Glu Val Ala Val Ala Lys Tyr Ser
                565                 570                 575
Asn Leu Gly Gly Gly Met Asp Glu Leu Tyr Lys Gly Gly Ser Gly Gly
                580                 585                 590
Thr Gly Gly Ser Gly Gly Thr Gln Ala Gln Lys Leu Arg Thr Val Lys
                595                 600                 605
Ile Glu Gln Gly Lys Val Asn Asp Gln Ala Asn Thr Leu Ala Asp Leu
                610                 615                 620
Ala Lys Ala Gln Ser Ile Ala Tyr Glu Val Val Ser Glu Leu Gln Ala
625                 630                 635                 640
Gln Gln Glu Glu Leu Glu Ala Arg Leu Ala Leu Glu Ser Arg Leu
                645                 650                 655
Asp Val Leu Gly Ala Ser Leu Gln Ala Leu Pro Ser Leu Ile Ala Gln
                660                 665                 670
```

```
Ala Ile Cys Pro Leu Pro Pro Trp Pro Gly Pro Ser His Leu Thr
        675                 680                 685

Thr Ala Ala Gln Ser Pro Gln Ser His Trp Leu Pro Thr Thr Ala Ser
    690                 695                 700

Asp Cys Gly Phe Cys Tyr Glu Asn Glu Val
705                 710

<210> SEQ ID NO 41
<211> LENGTH: 309
<212> TYPE: PRT
<213> ORGANISM: Artificial Sequence
<220> FEATURE:
<223> OTHER INFORMATION: Synthetic polypeptide

<400> SEQUENCE: 41

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65              70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val
305
```

```
<210> SEQ ID NO 42
<211> LENGTH: 345
<212> TYPE: PRT
<213> ORGANISM: Artificial Sequence
<220> FEATURE:
<223> OTHER INFORMATION: Synthetic polypeptide

<400> SEQUENCE: 42

Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
            20                  25                  30

Thr Asp Gly Thr Ala Ala Ala Val Ser His Tyr Ala Met Asn Gly
        35                  40                  45

Phe Asp Glu Leu Ala Lys Gly Ala Val Val Pro Glu Asp His Phe Val
    50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
            100                 105                 110

Lys Ala Thr Cys Gly Trp Glu Glu Val Tyr Val Cys Cys Val Glu Val
            115                 120                 125

Leu Phe Val Thr Leu Glu Ile Phe Lys Glu Phe Ser Ser Pro Ala Thr
    130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Lys Arg Thr Met Gly Leu Ile Val Ser
            180                 185                 190

Cys Val Gly Met Ile Val Phe Gly Met Ala Ala Gly Leu Ala Thr Asp
            195                 200                 205

Trp Leu Lys Trp Leu Leu Tyr Ile Val Ser Cys Ile Tyr Gly Gly Tyr
    210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
            260                 265                 270

Gly Leu Leu Lys Leu Ser Pro Tyr Ala Asn Ser Ile Gly His Ser Ile
    275                 280                 285

Cys Asp Ile Ile Ala Lys Glu Phe Trp Thr Phe Leu Ala His His Leu
290                 295                 300

Arg Ile Lys Ile His Glu His Ile Leu Ile His Gly Asp Ile Arg Lys
305                 310                 315                 320

Thr Thr Lys Met Glu Ile Gly Gly Glu Val Glu Val Glu Glu Phe
                325                 330                 335

Val Glu Glu Glu Asp Glu Asp Thr Val
            340                 345

<210> SEQ ID NO 43
```

```
<211> LENGTH: 350
<212> TYPE: PRT
<213> ORGANISM: Artificial Sequence
<220> FEATURE:
<223> OTHER INFORMATION: Synthetic polypeptide

<400> SEQUENCE: 43

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
        35                  40                  45

Asp Pro Ser Tyr Gly Leu Ser Asp Ala Gly Tyr Gly Tyr Cys Phe Val
    50                  55                  60

Glu Ala Thr Gly Gly Tyr Leu Val Val Gly Val Glu Lys Lys Gln Ala
65                  70                  75                  80

Trp Leu His Ser Arg Gly Thr Pro Gly Glu Lys Ile Gly Ala Gln Val
                85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
        115                 120                 125

Cys Cys Val Glu Val Leu Phe Val Thr Leu Glu Ile Phe Lys Glu Phe
130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Lys
                165                 170                 175

Leu Ser Asn Leu Ser Gly Leu Lys Asn Asp Tyr Ser Lys Arg Thr Met
            180                 185                 190

Gly Leu Ile Val Ser Cys Val Gly Met Ile Val Phe Gly Met Ala Ala
        195                 200                 205

Gly Leu Ala Thr Asp Trp Leu Lys Trp Leu Leu Tyr Ile Val Ser Cys
    210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
                245                 250                 255

Met Ala Tyr Ala Tyr Phe Ala Ser Trp Gly Ser Tyr Pro Ile Leu Trp
            260                 265                 270

Ala Val Gly Pro Glu Gly Leu Leu Lys Leu Ser Pro Tyr Ala Asn Ser
        275                 280                 285

Ile Gly His Ser Ile Cys Asp Ile Ile Ala Lys Glu Phe Trp Thr Phe
    290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Glu Val
                325                 330                 335

Glu Val Glu Glu Phe Val Glu Glu Glu Asp Glu Asp Thr Val
            340                 345                 350

<210> SEQ ID NO 44
<211> LENGTH: 325
<212> TYPE: PRT
<213> ORGANISM: Artificial Sequence
```

<220> FEATURE:
<223> OTHER INFORMATION: Synthetic polypeptide

<400> SEQUENCE: 44

```
Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Ala Val Val
            20                  25                  30

Thr Pro Ala Ala Asp Ala His Gly Glu Thr Ser Asn Ala Thr Thr Ala
        35                  40                  45

Gly Ala Asp His Gly Cys Phe Pro His Ile Asn His Gly Thr Glu Leu
    50                  55                  60

Gln His Lys Ile Ala Val Gly Leu Gln Trp Phe Thr Val Ile Val Ala
65              70                  75                  80

Ile Val Gln Leu Ile Phe Tyr Gly Trp His Ser Phe Lys Ala Thr Thr
                85                  90                  95

Gly Trp Glu Glu Val Tyr Val Cys Val Ile Glu Leu Val Lys Cys Phe
            100                 105                 110

Ile Glu Leu Phe His Glu Val Asp Ser Pro Ala Thr Val Tyr Gln Thr
        115                 120                 125

Asn Gly Gly Ala Val Ile Trp Leu Arg Tyr Ser Met Trp Leu Leu Thr
    130                 135                 140

Cys Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                165                 170                 175

Ile Val Trp Gly Ile Thr Ala Ala Phe Thr Lys Gly Pro Leu Lys Ile
            180                 185                 190

Leu Phe Phe Met Ile Gly Leu Phe Tyr Gly Val Thr Cys Phe Phe Gln
        195                 200                 205

Ile Ala Lys Val Tyr Ile Glu Ser Tyr His Thr Leu Pro Lys Gly Val
    210                 215                 220

Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
                245                 250                 255

Ile Thr Pro Tyr Thr Ser Gly Ile Gly His Leu Ile Leu Asp Leu Ile
            260                 265                 270

Ser Lys Asn Thr Trp Gly Phe Leu Gly His His Leu Arg Val Lys Ile
        275                 280                 285

His Glu His Ile Leu Ile His Gly Asp Ile Arg Lys Thr Thr Thr Ile
    290                 295                 300

Asn Val Ala Gly Glu Asn Met Glu Ile Glu Thr Phe Val Asp Glu Glu
305                 310                 315                 320

Glu Glu Gly Gly Val
                325
```

<210> SEQ ID NO 45
<211> LENGTH: 1172
<212> TYPE: PRT
<213> ORGANISM: Artificial Sequence
<220> FEATURE:
<223> OTHER INFORMATION: Synthetic polypeptide

<400> SEQUENCE: 45

Met Leu Gly Asn Gly Ser Ala Ile Val Pro Ile Asp Gln Cys Phe Cys

-continued

```
1               5                    10                   15
Leu Ala Trp Thr Asp Ser Leu Gly Ser Asp Thr Glu Gln Leu Val Ala
                20                  25                  30
Asn Ile Leu Gln Trp Phe Ala Phe Gly Phe Ser Ile Leu Ile Leu Met
                35                  40                  45
Phe Tyr Ala Tyr Gln Thr Trp Arg Ala Thr Cys Gly Trp Glu Glu Val
                50                  55                  60
Tyr Val Cys Cys Val Glu Leu Thr Lys Val Ile Ile Glu Phe Phe His
65                  70                  75                  80
Glu Phe Asp Asp Pro Ser Met Leu Tyr Leu Ala Asn Gly His Arg Val
                85                  90                  95
Gln Trp Leu Arg Tyr Ala Glu Trp Leu Leu Thr Cys Pro Val Ile Leu
                100                 105                 110
Ile His Leu Ser Asn Leu Thr Gly Leu Lys Asp Asp Tyr Ser Lys Arg
                115                 120                 125
Thr Met Arg Leu Leu Val Ser Asp Val Gly Thr Ile Val Trp Gly Ala
                130                 135                 140
Thr Ser Ala Met Ser Thr Gly Tyr Val Lys Val Ile Phe Phe Val Leu
145                 150                 155                 160
Gly Cys Ile Tyr Gly Ala Asn Thr Phe Phe His Ala Ala Lys Val Tyr
                165                 170                 175
Ile Glu Ser Tyr His Val Val Pro Lys Gly Arg Pro Arg Thr Val Val
                180                 185                 190
Arg Ile Met Ala Trp Leu Phe Phe Leu Ser Trp Gly Met Phe Pro Val
                195                 200                 205
Leu Phe Val Val Gly Pro Glu Gly Phe Asp Ala Ile Ser Val Tyr Gly
                210                 215                 220
Ser Thr Ile Gly His Thr Ile Ile Asp Leu Met Ser Lys Asn Cys Trp
225                 230                 235                 240
Gly Leu Leu Gly His Tyr Leu Arg Val Leu Ile His Gln His Ile Ile
                245                 250                 255
Ile Tyr Gly Asp Ile Arg Lys Lys Thr Lys Ile Asn Val Ala Gly Glu
                260                 265                 270
Glu Met Glu Val Glu Thr Met Val Asp Gln Glu Asp Glu Glu Thr Val
                275                 280                 285
Gly Ala Ser Gly Gly Thr Val Ser Lys Gly Glu Glu Leu Phe Thr Gly
                290                 295                 300
Val Val Pro Ile Leu Val Glu Leu Asp Gly Asp Val Asn Gly His Lys
305                 310                 315                 320
Phe Ser Val Ser Gly Glu Gly Glu Gly Asp Ala Thr Tyr Gly Lys Leu
                325                 330                 335
Thr Leu Lys Phe Ile Cys Thr Thr Gly Lys Leu Pro Val Pro Trp Pro
                340                 345                 350
Thr Leu Val Thr Thr Leu Thr Tyr Gly Val Gln Cys Phe Ser Arg Tyr
                355                 360                 365
Pro Asp His Met Lys Gln His Asp Phe Phe Lys Ser Ala Met Pro Glu
                370                 375                 380
Gly Tyr Val Gln Glu Arg Thr Ile Phe Phe Lys Asp Asp Gly Asn Tyr
385                 390                 395                 400
Lys Thr Arg Ala Glu Val Lys Phe Glu Gly Asp Thr Leu Val Asn Arg
                405                 410                 415
Ile Glu Leu Lys Gly Ile Asp Phe Lys Glu Asp Gly Asn Ile Leu Gly
                420                 425                 430
```

```
His Lys Leu Glu Tyr Asn Tyr Asn Ser His Asn Val Tyr Ile Met Ala
            435                 440                 445

Asp Lys Gln Lys Asn Gly Ile Lys Val Asn Phe Lys Ile Arg His Asn
    450                 455                 460

Ile Glu Asp Gly Ser Val Gln Leu Ala Asp His Tyr Gln Gln Asn Thr
465                 470                 475                 480

Pro Ile Gly Asp Gly Pro Val Leu Leu Pro Asp Asn His Tyr Leu Ser
                485                 490                 495

Thr Gln Ser Ala Leu Ser Lys Asp Pro Asn Glu Lys Arg Asp His Met
                500                 505                 510

Val Leu Leu Glu Phe Val Thr Ala Ala Gly Ile Thr Leu Gly Met Asp
            515                 520                 525

Glu Leu Tyr Lys Gly Gly Ser Gly Gly Thr Gly Gly Ser Gly Gly Thr
            530                 535                 540

Lys Val Asp Lys Met Leu Leu Gln Glu Leu Ser Glu Lys Leu Glu Leu
545                 550                 555                 560

Ala Glu Gln Ala Leu Ala Ser Lys Gln Leu Gln Met Asp Glu Met Lys
                565                 570                 575

Gln Thr Leu Ala Lys Gln Glu Glu Asp Leu Glu Thr Met Ala Val Leu
            580                 585                 590

Arg Ala Gln Met Glu Val Tyr Cys Ser Asp Phe His Ala Glu Arg Ala
            595                 600                 605

Ala Arg Glu Lys Ile His Glu Glu Lys Glu Gln Leu Ala Leu Gln Leu
    610                 615                 620

Ala Ile Leu Leu Lys Glu Asn Asn Asp Ile Glu Glu Gly Gly Ser Arg
625                 630                 635                 640

Gln Ser Leu Met Glu Met Gln Cys Arg His Gly Val Lys Glu Met Phe
                645                 650                 655

Lys Asp Phe Gln Leu Arg Gln Pro Pro Leu Val Pro Ser Arg Lys Gly
            660                 665                 670

Glu Thr Pro Pro Ser Gly Thr Ser Ser Ala Phe Ser Ser Tyr Phe Asn
            675                 680                 685

Asn Lys Val Gly Ile Pro Gln Glu His Val Asp His Asp Phe Asp
    690                 695                 700

Ala Asn Gln Leu Leu Asn Lys Ile Asn Glu Pro Pro Lys Pro Ala Pro
705                 710                 715                 720

Arg Gln Gly Ser Gly Arg Asp Gln Pro Leu Asn Ser Lys Lys Lys Lys
                725                 730                 735

Arg Leu Leu Ser Phe Arg Asp Val Asp Phe Glu Asp Ser Asp Gly
            740                 745                 750

Ser Gly Lys Val Asp Lys Met Leu Leu Gln Glu Leu Ser Glu Lys Leu
            755                 760                 765

Glu Leu Ala Glu Gln Ala Leu Ala Ser Lys Gln Leu Gln Met Asp Glu
    770                 775                 780

Met Lys Gln Thr Leu Ala Lys Gln Glu Glu Asp Leu Glu Thr Met Ala
785                 790                 795                 800

Val Leu Arg Ala Gln Met Glu Val Tyr Cys Ser Asp Phe His Ala Glu
                805                 810                 815

Arg Ala Ala Arg Glu Lys Ile His Glu Glu Lys Glu Gln Leu Ala Leu
            820                 825                 830

Gln Leu Ala Ile Leu Leu Lys Glu Asn Asn Asp Ile Glu Glu Gly Gly
            835                 840                 845
```

```
Ser Arg Gln Ser Leu Met Glu Met Gln Cys Arg His Gly Val Lys Glu
    850                 855                 860

Met Phe Lys Asp Phe Gln Leu Arg Gln Pro Pro Leu Val Pro Ser Arg
865                 870                 875                 880

Lys Gly Glu Thr Pro Pro Ser Gly Thr Ser Ser Ala Phe Ser Ser Tyr
                885                 890                 895

Phe Asn Asn Lys Val Gly Ile Pro Gln Glu His Val Asp His Asp Asp
            900                 905                 910

Phe Asp Ala Asn Gln Leu Leu Asn Lys Ile Asn Glu Pro Pro Lys Pro
        915                 920                 925

Ala Pro Arg Gln Gly Ser Ala Gly Arg Asp Gln Pro Leu Asn Ser Lys
    930                 935                 940

Lys Lys Lys Arg Leu Leu Ser Phe Arg Asp Val Asp Phe Glu Glu Asp
945                 950                 955                 960

Ser Asp Gly Ser Gly Lys Val Asp Lys Met Leu Leu Gln Glu Leu Ser
                965                 970                 975

Glu Lys Leu Glu Leu Ala Glu Gln Ala Leu Ala Ser Lys Gln Leu Gln
            980                 985                 990

Met Asp Glu Met Lys Gln Thr Leu Ala Lys Gln Glu Glu Asp Leu Glu
        995                 1000                1005

Thr Met Ala Val Leu Arg Ala Gln Met Glu Val Tyr Cys Ser Asp
   1010                1015                1020

Phe His Ala Glu Arg Ala Ala Arg Glu Lys Ile His Glu Glu Lys
   1025                1030                1035

Glu Gln Leu Ala Leu Gln Leu Ala Ile Leu Leu Lys Glu Asn Asn
   1040                1045                1050

Asp Ile Glu Glu Gly Gly Ser Arg Gln Ser Leu Met Glu Met Gln
   1055                1060                1065

Cys Arg His Gly Val Lys Glu Met Phe Lys Asp Phe Gln Leu Arg
   1070                1075                1080

Gln Pro Pro Leu Val Pro Ser Arg Lys Gly Glu Thr Pro Pro Ser
   1085                1090                1095

Gly Thr Ser Ser Ala Phe Ser Ser Tyr Phe Asn Asn Lys Val Gly
   1100                1105                1110

Ile Pro Gln Glu His Val Asp His Asp Asp Phe Asp Ala Asn Gln
   1115                1120                1125

Leu Leu Asn Lys Ile Asn Glu Pro Pro Lys Pro Ala Pro Arg Gln
   1130                1135                1140

Gly Ser Gly Arg Asp Gln Pro Leu Asn Ser Lys Lys Lys Lys Arg
   1145                1150                1155

Leu Leu Ser Phe Arg Asp Val Asp Phe Glu Glu Asp Ser Asp
   1160                1165                1170

<210> SEQ ID NO 46
<211> LENGTH: 1172
<212> TYPE: PRT
<213> ORGANISM: Artificial Sequence
<220> FEATURE:
<223> OTHER INFORMATION: Synthetic polypeptide

<400> SEQUENCE: 46

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30
```

-continued

```
Asn Ile Leu Gln Trp Phe Ala Phe Gly Phe Ser Ile Leu Ile Leu Met
             35                  40                  45

Phe Tyr Ala Tyr Gln Thr Trp Arg Ala Thr Cys Gly Trp Glu Glu Val
 50                  55                  60

Tyr Val Cys Cys Val Glu Leu Thr Lys Val Ile Ile Glu Phe Phe His
 65                  70                  75                  80

Glu Phe Asp Asp Pro Ser Met Leu Tyr Leu Ala Asn Gly His Arg Val
                 85                  90                  95

Gln Trp Leu Arg Tyr Ala Glu Trp Leu Leu Thr Cys Pro Val Ile Leu
                100                 105                 110

Ile His Leu Ser Asn Leu Thr Gly Leu Lys Asp Asp Tyr Ser Lys Arg
             115                 120                 125

Thr Met Arg Leu Leu Val Ser Asp Val Gly Thr Ile Val Trp Gly Ala
        130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
        210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
            260                 265                 270

Glu Met Glu Val Glu Thr Met Val Asp Gln Asp Glu Glu Thr Val
        275                 280                 285

Gly Ala Ser Gly Gly Thr Val Ser Lys Gly Glu Glu Leu Phe Thr Gly
290                 295                 300

Val Val Pro Ile Leu Val Glu Leu Asp Gly Asp Val Asn Gly His Lys
305                 310                 315                 320

Phe Ser Val Ser Gly Glu Gly Glu Gly Asp Ala Thr Tyr Gly Lys Leu
                325                 330                 335

Thr Leu Lys Phe Ile Cys Thr Thr Gly Lys Leu Pro Val Pro Trp Pro
            340                 345                 350

Thr Leu Val Thr Thr Leu Thr Tyr Gly Val Gln Cys Phe Ser Arg Tyr
        355                 360                 365

Pro Asp His Met Lys Gln His Asp Phe Phe Lys Ser Ala Met Pro Glu
        370                 375                 380

Gly Tyr Val Gln Glu Arg Thr Ile Phe Phe Lys Asp Asp Gly Asn Tyr
385                 390                 395                 400

Lys Thr Arg Ala Glu Val Lys Phe Glu Gly Asp Thr Leu Val Asn Arg
                405                 410                 415

Ile Glu Leu Lys Gly Ile Asp Phe Lys Glu Asp Gly Asn Ile Leu Gly
            420                 425                 430

His Lys Leu Glu Tyr Asn Tyr Asn Ser His Asn Val Tyr Ile Met Ala
        435                 440                 445

Asp Lys Gln Lys Asn Gly Ile Lys Val Asn Phe Lys Ile Arg His Asn
```

```
            450                 455                 460
Ile Glu Asp Gly Ser Val Gln Leu Ala Asp His Tyr Gln Gln Asn Thr
465                 470                 475                 480

Pro Ile Gly Asp Gly Pro Val Leu Leu Pro Asp Asn His Tyr Leu Ser
                    485                 490                 495

Thr Gln Ser Ala Leu Ser Lys Asp Pro Asn Glu Lys Arg Asp His Met
                500                 505                 510

Val Leu Leu Glu Phe Val Thr Ala Ala Gly Ile Thr Leu Gly Met Asp
                515                 520                 525

Glu Leu Tyr Lys Gly Gly Ser Gly Gly Thr Gly Gly Ser Gly Gly Thr
                530                 535                 540

Lys Val Asp Lys Met Leu Leu Gln Glu Leu Ser Glu Lys Leu Glu Leu
545                 550                 555                 560

Ala Glu Gln Ala Leu Ala Ser Lys Gln Leu Gln Met Asp Glu Met Lys
                565                 570                 575

Gln Thr Leu Ala Lys Gln Glu Glu Asp Leu Glu Thr Met Ala Val Leu
                580                 585                 590

Arg Ala Gln Met Glu Val Tyr Cys Ser Asp Phe His Ala Glu Arg Ala
                595                 600                 605

Ala Arg Glu Lys Ile His Glu Glu Lys Glu Gln Leu Ala Leu Gln Leu
                610                 615                 620

Ala Ile Leu Leu Lys Glu Asn Asn Asp Ile Glu Glu Gly Gly Ser Arg
625                 630                 635                 640

Gln Ser Leu Met Glu Met Gln Cys Arg His Gly Val Lys Glu Met Phe
                645                 650                 655

Lys Asp Phe Gln Leu Arg Gln Pro Pro Leu Val Pro Ser Arg Lys Gly
                660                 665                 670

Glu Thr Pro Pro Ser Gly Thr Ser Ser Ala Phe Ser Ser Tyr Phe Asn
                675                 680                 685

Asn Lys Val Gly Ile Pro Gln Glu His Val Asp His Asp Asp Phe Asp
                690                 695                 700

Ala Asn Gln Leu Leu Asn Lys Ile Asn Glu Pro Pro Lys Pro Ala Pro
705                 710                 715                 720

Arg Gln Gly Ser Gly Lys Val Asp Lys Met Leu Leu Gln Glu Leu Ser
                725                 730                 735

Glu Lys Leu Glu Leu Ala Glu Gln Ala Leu Ala Ser Lys Gln Leu Gln
                740                 745                 750

Met Asp Glu Met Lys Gln Thr Leu Ala Lys Gln Glu Glu Asp Leu Glu
                755                 760                 765

Thr Met Ala Val Leu Arg Ala Gln Met Glu Val Tyr Cys Ser Asp Phe
770                 775                 780

His Ala Glu Arg Ala Ala Arg Glu Lys Ile His Glu Glu Lys Glu Gln
785                 790                 795                 800

Leu Ala Leu Gln Leu Ala Ile Leu Leu Lys Glu Asn Asn Asp Ile Glu
                805                 810                 815

Glu Gly Gly Ser Arg Gln Ser Leu Met Glu Met Gln Cys Arg His Gly
                820                 825                 830

Val Lys Glu Met Phe Lys Asp Phe Gln Leu Arg Gln Pro Pro Leu Val
                835                 840                 845

Pro Ser Arg Lys Gly Glu Thr Pro Pro Ser Gly Thr Ser Ser Ala Phe
                850                 855                 860

Ser Ser Tyr Phe Asn Asn Lys Val Gly Ile Pro Gln Glu His Val Asp
865                 870                 875                 880
```

```
His Asp Asp Phe Asp Ala Asn Gln Leu Leu Asn Lys Ile Asn Glu Pro
            885                 890                 895
Pro Lys Pro Ala Pro Arg Gln Gly Ser Ala Gly Lys Val Asp Lys Met
        900                 905                 910
Leu Leu Gln Glu Leu Ser Glu Lys Leu Glu Leu Ala Glu Gln Ala Leu
            915                 920                 925
Ala Ser Lys Gln Leu Gln Met Asp Glu Met Lys Gln Thr Leu Ala Lys
930                 935                 940
Gln Glu Glu Asp Leu Glu Thr Met Ala Val Leu Arg Ala Gln Met Glu
945                 950                 955                 960
Val Tyr Cys Ser Asp Phe His Ala Glu Arg Ala Ala Arg Glu Lys Ile
            965                 970                 975
His Glu Glu Lys Glu Gln Leu Ala Leu Gln Leu Ala Ile Leu Leu Lys
            980                 985                 990
Glu Asn Asn Asp Ile Glu Glu Gly  Gly Ser Arg Gln Ser  Leu Met Glu
            995                 1000                1005
Met Gln Cys Arg His Gly Val  Lys Glu Met Phe Lys  Asp Phe Gln
    1010                1015                1020
Leu Arg  Gln Pro Pro Leu Val  Pro Ser Arg Lys Gly  Glu Thr Pro
    1025                1030                1035
Pro Ser  Gly Thr Ser Ser Ala  Phe Ser Ser Tyr Phe  Asn Asn Lys
    1040                1045                1050
Val Gly  Ile Pro Gln Glu His  Val Asp His Asp  Phe Asp Ala
    1055                1060                1065
Asn Gln  Leu Leu Asn Lys Ile  Asn Glu Pro Pro Lys  Pro Ala Pro
    1070                1075                1080
Arg Gln  Gly Ser Gly Arg Asp  Gln Pro Leu Asn Ser  Lys Lys Lys
    1085                1090                1095
Lys Arg  Leu Leu Ser Phe Arg  Asp Val Asp Phe Glu  Glu Asp Ser
    1100                1105                1110
Asp Gly  Ser Gly Arg Asp Gln  Pro Leu Asn Ser Lys  Lys Lys Lys
    1115                1120                1125
Arg Leu  Leu Ser Phe Arg Asp  Val Asp Phe Glu Glu  Asp Ser Asp
    1130                1135                1140
Gly Ser  Gly Arg Asp Gln Pro  Leu Asn Ser Lys Lys  Lys Lys Arg
    1145                1150                1155
Leu Leu  Ser Phe Arg Asp Val  Asp Phe Glu Glu Asp  Ser Asp
    1160                1165                1170

<210> SEQ ID NO 47
<211> LENGTH: 967
<212> TYPE: PRT
<213> ORGANISM: Artificial Sequence
<220> FEATURE:
<223> OTHER INFORMATION: Synthetic polypeptide

<400> SEQUENCE: 47

Met Leu Gly Asn Gly Ser Ala Ile Val Pro Ile Asp Gln Cys Phe Cys
1               5                   10                  15
Leu Ala Trp Thr Asp Ser Leu Gly Ser Asp Thr Glu Gly Leu Val Ala
            20                  25                  30
Asn Ile Leu Gln Trp Phe Ala Phe Gly Phe Ser Ile Leu Ile Leu Met
        35                  40                  45
Phe Tyr Ala Tyr Gln Thr Trp Arg Ala Thr Cys Gly Trp Glu Glu Val
    50                  55                  60
```

```
Tyr Val Cys Cys Val Glu Leu Thr Lys Val Ile Ile Glu Phe Phe His
 65                  70                  75                  80

Glu Phe Asp Asp Pro Ser Met Leu Tyr Leu Ala Asn Gly His Arg Val
                 85                  90                  95

Gln Trp Leu Arg Tyr Ala Glu Trp Leu Leu Thr Cys Pro Val Ile Leu
            100                 105                 110

Ile His Leu Ser Asn Leu Thr Gly Leu Lys Asp Asp Tyr Ser Lys Arg
        115                 120                 125

Thr Met Arg Leu Leu Val Ser Asp Val Gly Thr Ile Val Trp Gly Ala
    130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
    210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
            260                 265                 270

Glu Met Glu Val Glu Thr Met Val Asp Gln Glu Asp Glu Glu Thr Val
        275                 280                 285

Gly Ala Ser Gly Gly Thr Val Ser Lys Gly Glu Glu Leu Ile Lys Glu
    290                 295                 300

Asn Met His Met Lys Leu Tyr Met Glu Gly Thr Val Asn Asn His His
305                 310                 315                 320

Phe Lys Cys Thr Thr Glu Gly Glu Gly Lys Pro Tyr Glu Gly Thr Gln
                325                 330                 335

Thr Gln Arg Ile Lys Val Val Glu Gly Gly Pro Leu Pro Phe Ala Phe
            340                 345                 350

Asp Ile Leu Ala Thr Cys Phe Met Tyr Gly Ser Lys Thr Phe Ile Asn
        355                 360                 365

His Thr Gln Gly Ile Pro Asp Phe Phe Lys Gln Ser Phe Pro Glu Gly
    370                 375                 380

Phe Thr Trp Glu Arg Val Thr Thr Tyr Glu Asp Gly Gly Val Leu Thr
385                 390                 395                 400

Val Thr Gln Asp Thr Ser Leu Gln Asp Gly Cys Leu Ile Tyr Asn Val
                405                 410                 415

Lys Leu Arg Gly Val Asn Phe Pro Ser Asn Gly Pro Val Met Gln Lys
            420                 425                 430

Lys Thr Leu Gly Trp Glu Ala Thr Thr Glu Thr Leu Tyr Pro Ala Asp
        435                 440                 445

Gly Gly Leu Glu Gly Arg Cys Asp Met Ala Leu Lys Leu Val Gly Gly
    450                 455                 460

Gly His Leu His Cys Asn Leu Lys Thr Thr Tyr Arg Ser Lys Lys Pro
465                 470                 475                 480
```

-continued

```
Ala Lys Asn Leu Lys Met Pro Gly Val Tyr Phe Val Asp Arg Arg Leu
                485                 490                 495
Glu Arg Ile Lys Glu Ala Asp Asn Glu Thr Tyr Val Glu Gln His Glu
            500                 505                 510
Val Ala Val Ala Arg Tyr Cys Asp Leu Pro Ser Lys Leu Gly His Lys
        515                 520                 525
Leu Asn Gly Met Asp Glu Leu Tyr Lys Gly Gly Ser Gly Gly Thr Gly
    530                 535                 540
Gly Ser Gly Gly Thr Lys Val Asp Lys Met Leu Leu Gln Glu Leu Ser
545                 550                 555                 560
Glu Lys Leu Glu Leu Ala Glu Gln Ala Leu Ala Ser Lys Gln Leu Gln
                565                 570                 575
Met Asp Glu Met Lys Gln Thr Leu Ala Lys Gln Glu Glu Asp Leu Glu
            580                 585                 590
Thr Met Ala Val Leu Arg Ala Gln Met Glu Val Tyr Cys Ser Asp Phe
        595                 600                 605
His Ala Glu Arg Ala Ala Arg Glu Lys Ile His Glu Glu Lys Glu Gln
    610                 615                 620
Leu Ala Leu Gln Leu Ala Ile Leu Leu Lys Glu Asn Asn Asp Ile Glu
625                 630                 635                 640
Glu Gly Gly Ser Arg Gln Ser Leu Met Glu Met Gln Cys Arg His Gly
                645                 650                 655
Val Lys Glu Met Phe Lys Asp Phe Gln Leu Arg Gln Pro Pro Leu Val
            660                 665                 670
Pro Ser Arg Lys Gly Glu Thr Pro Pro Ser Gly Thr Ser Ser Ala Phe
        675                 680                 685
Ser Ser Tyr Phe Asn Asn Lys Val Gly Ile Pro Gln Glu His Val Asp
    690                 695                 700
His Asp Asp Phe Asp Ala Asn Gln Leu Leu Asn Lys Ile Asn Glu Pro
705                 710                 715                 720
Pro Lys Pro Ala Pro Arg Gln Gly Ser Ala Gly Lys Val Asp Lys Met
                725                 730                 735
Leu Leu Gln Glu Leu Ser Glu Lys Leu Glu Leu Ala Glu Gln Ala Leu
            740                 745                 750
Ala Ser Lys Gln Leu Gln Met Asp Glu Met Lys Gln Thr Leu Ala Lys
        755                 760                 765
Gln Glu Glu Asp Leu Glu Thr Met Ala Val Leu Arg Ala Gln Met Glu
    770                 775                 780
Val Tyr Cys Ser Asp Phe His Ala Glu Arg Ala Ala Arg Glu Lys Ile
785                 790                 795                 800
His Glu Glu Lys Glu Gln Leu Ala Leu Gln Leu Ala Ile Leu Leu Lys
                805                 810                 815
Glu Asn Asn Asp Ile Glu Glu Gly Gly Ser Arg Gln Ser Leu Met Glu
            820                 825                 830
Met Gln Cys Arg His Gly Val Lys Glu Met Phe Lys Asp Phe Gln Leu
        835                 840                 845
Arg Gln Pro Pro Leu Val Pro Ser Arg Lys Gly Glu Thr Pro Pro Ser
    850                 855                 860
Gly Thr Ser Ser Ala Phe Ser Ser Tyr Phe Asn Asn Lys Val Gly Ile
865                 870                 875                 880
Pro Gln Glu His Val Asp His Asp Asp Phe Asp Ala Asn Gln Leu Leu
                885                 890                 895
Asn Lys Ile Asn Glu Pro Pro Lys Pro Ala Pro Arg Gln Gly Ser Gly
```

```
                900             905             910
Arg Asp Gln Pro Leu Asn Ser Lys Lys Lys Arg Leu Leu Ser Phe
            915             920             925

Arg Asp Val Asp Phe Glu Glu Asp Ser Asp Gly Ser Gly Arg Asp Gln
        930             935             940

Pro Leu Asn Ser Lys Lys Lys Arg Leu Leu Ser Phe Arg Asp Val
945             950             955             960

Asp Phe Glu Glu Asp Ser Asp
            965

<210> SEQ ID NO 48
<211> LENGTH: 960
<212> TYPE: PRT
<213> ORGANISM: Artificial Sequence
<220> FEATURE:
<223> OTHER INFORMATION: Synthetic polypeptide

<400> SEQUENCE: 48

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30

Asn Ile Leu Gln Trp Phe Ala Phe Gly Phe Ser Ile Leu Ile Leu Met
        35                  40                  45

Phe Tyr Ala Tyr Gln Thr Trp Arg Ala Thr Cys Gly Trp Glu Glu Val
    50                  55                  60

Tyr Val Cys Cys Val Glu Leu Thr Lys Val Ile Ile Glu Phe Phe His
65                  70                  75                  80

Glu Phe Asp Asp Pro Ser Met Leu Tyr Leu Ala Asn Gly His Arg Val
                85                  90                  95

Gln Trp Leu Arg Tyr Ala Glu Trp Leu Leu Thr Cys Pro Val Ile Leu
            100                 105                 110

Ile His Leu Ser Asn Leu Thr Gly Leu Lys Asp Asp Tyr Ser Lys Arg
        115                 120                 125

Thr Met Arg Leu Leu Val Ser Asp Val Gly Thr Ile Val Trp Gly Ala
    130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
    210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
            260                 265                 270

Glu Met Glu Val Glu Thr Met Val Asp Gln Glu Asp Glu Glu Thr Val
        275                 280                 285

Gly Ser Gly Pro Val Val Ala Val Ser Lys Gly Glu Glu Leu Ile Lys
```

```
            290                 295                 300
Glu Asn Met His Met Lys Leu Tyr Met Glu Gly Thr Val Asn Asn His
305                 310                 315                 320

His Phe Lys Cys Thr Thr Glu Gly Glu Gly Lys Pro Tyr Glu Gly Thr
                325                 330                 335

Gln Thr Gln Arg Ile Lys Val Val Glu Gly Gly Pro Leu Pro Phe Ala
                340                 345                 350

Phe Asp Ile Leu Ala Thr Cys Phe Met Tyr Gly Ser Lys Thr Phe Ile
                355                 360                 365

Asn His Thr Gln Gly Ile Pro Asp Phe Phe Lys Gln Ser Phe Pro Glu
            370                 375                 380

Gly Phe Thr Trp Glu Arg Val Thr Thr Tyr Glu Asp Gly Gly Val Leu
385                 390                 395                 400

Thr Val Thr Gln Asp Thr Ser Leu Gln Asp Gly Cys Leu Ile Tyr Asn
                405                 410                 415

Val Lys Leu Arg Gly Val Asn Phe Pro Ser Asn Gly Pro Val Met Gln
                420                 425                 430

Lys Lys Thr Leu Gly Trp Glu Ala Thr Thr Glu Thr Leu Tyr Pro Ala
                435                 440                 445

Asp Gly Gly Leu Glu Gly Arg Cys Asp Met Ala Leu Lys Leu Val Gly
            450                 455                 460

Gly Gly His Leu His Cys Asn Leu Lys Thr Thr Tyr Arg Ser Lys Lys
465                 470                 475                 480

Pro Ala Lys Asn Leu Lys Met Pro Gly Val Tyr Phe Val Asp Arg Arg
                485                 490                 495

Leu Glu Arg Ile Lys Glu Ala Asp Asn Glu Thr Tyr Val Glu Gln His
                500                 505                 510

Glu Val Ala Val Ala Arg Tyr Cys Asp Leu Pro Ser Lys Leu Gly His
                515                 520                 525

Lys Leu Asn Gly Met Asp Glu Leu Tyr Lys Gly Ala Ser Gly Lys Val
            530                 535                 540

Asp Lys Met Leu Leu Gln Glu Leu Ser Glu Lys Leu Glu Leu Ala Glu
545                 550                 555                 560

Gln Ala Leu Ala Ser Lys Gln Leu Gln Met Asp Glu Met Lys Gln Thr
                565                 570                 575

Leu Ala Lys Gln Glu Glu Asp Leu Glu Thr Met Ala Val Leu Arg Ala
                580                 585                 590

Gln Met Glu Val Tyr Cys Ser Asp Phe His Ala Glu Arg Ala Ala Arg
                595                 600                 605

Glu Lys Ile His Glu Glu Lys Glu Gln Leu Ala Leu Gln Leu Ala Ile
                610                 615                 620

Leu Leu Lys Glu Asn Asn Asp Ile Glu Glu Gly Gly Ser Arg Gln Ser
625                 630                 635                 640

Leu Met Glu Met Gln Cys Arg His Gly Val Lys Glu Met Phe Lys Asp
                645                 650                 655

Phe Gln Leu Arg Gln Pro Pro Leu Val Pro Ser Arg Lys Gly Glu Thr
                660                 665                 670

Pro Pro Ser Gly Thr Ser Ser Ala Phe Ser Ser Tyr Phe Asn Asn Lys
                675                 680                 685

Val Gly Ile Pro Gln Glu His Val Asp His Asp Phe Asp Ala Asn
            690                 695                 700

Gln Leu Leu Asn Lys Ile Asn Glu Pro Pro Lys Pro Ala Pro Arg Gln
705                 710                 715                 720
```

```
Gly Ser Gly Arg Asp Gln Pro Leu Asn Ser Lys Lys Lys Arg Leu
            725                 730                 735

Leu Ser Phe Arg Asp Val Asp Phe Glu Asp Ser Asp Gly Ser Gly
            740                 745                 750

Lys Val Asp Lys Met Leu Leu Gln Glu Leu Ser Glu Lys Leu Glu Leu
            755                 760                 765

Ala Glu Gln Ala Leu Ala Ser Lys Gln Leu Gln Met Asp Glu Met Lys
            770                 775                 780

Gln Thr Leu Ala Lys Gln Glu Glu Asp Leu Glu Thr Met Ala Val Leu
785                 790                 795                 800

Arg Ala Gln Met Glu Val Tyr Cys Ser Asp Phe His Ala Glu Arg Ala
            805                 810                 815

Ala Arg Glu Lys Ile His Glu Glu Lys Glu Gln Leu Ala Leu Gln Leu
            820                 825                 830

Ala Ile Leu Leu Lys Glu Asn Asn Asp Ile Glu Glu Gly Gly Ser Arg
            835                 840                 845

Gln Ser Leu Met Glu Met Gln Cys Arg His Gly Val Lys Glu Met Phe
            850                 855                 860

Lys Asp Phe Gln Leu Arg Gln Pro Pro Leu Val Pro Ser Arg Lys Gly
865                 870                 875                 880

Glu Thr Pro Pro Ser Gly Thr Ser Ser Ala Phe Ser Ser Tyr Phe Asn
            885                 890                 895

Asn Lys Val Gly Ile Pro Gln Glu His Val Asp His Asp Phe Asp
            900                 905                 910

Ala Asn Gln Leu Leu Asn Lys Ile Asn Glu Pro Pro Lys Pro Ala Pro
            915                 920                 925

Arg Gln Gly Ser Ala Gly Arg Asp Gln Pro Leu Asn Ser Lys Lys Lys
            930                 935                 940

Lys Arg Leu Leu Ser Phe Arg Asp Val Asp Phe Glu Glu Asp Ser Asp
945                 950                 955                 960

<210> SEQ ID NO 49
<211> LENGTH: 1006
<212> TYPE: PRT
<213> ORGANISM: Artificial Sequence
<220> FEATURE:
<223> OTHER INFORMATION: Synthetic polypeptide

<400> SEQUENCE: 49

Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
            20                  25                  30

Thr Asp Gly Thr Ala Ala Ala Val Ser His Tyr Ala Met Asn Gly
            35                  40                  45

Phe Asp Glu Leu Ala Lys Gly Ala Val Val Pro Glu Asp His Phe Val
            50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
            85                  90                  95

Phe Ser Ile Ala Ile Ala Leu Leu Thr Phe Tyr Gly Phe Ser Ala Trp
            100                 105                 110

Lys Ala Thr Cys Gly Trp Glu Glu Val Tyr Val Cys Cys Val Glu Val
            115                 120                 125
```

```
Leu Phe Val Thr Leu Glu Ile Phe Lys Glu Phe Ser Ser Pro Ala Thr
        130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Lys Arg Thr Met Gly Leu Ile Val Ser
            180                 185                 190

Cys Val Gly Met Ile Val Phe Gly Met Ala Ala Gly Leu Ala Thr Asp
        195                 200                 205

Trp Leu Lys Trp Leu Leu Tyr Ile Val Ser Cys Ile Tyr Gly Gly Tyr
    210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
            260                 265                 270

Gly Leu Leu Lys Leu Ser Pro Tyr Ala Asn Ser Ile Gly His Ser Ile
        275                 280                 285

Cys Asp Ile Ile Ala Lys Glu Phe Trp Thr Phe Leu Ala His His Leu
290                 295                 300

Arg Ile Lys Ile His Glu His Ile Leu Ile His Gly Asp Ile Arg Lys
305                 310                 315                 320

Thr Thr Lys Met Glu Ile Gly Gly Glu Val Glu Val Glu Glu Phe
                325                 330                 335

Val Glu Glu Glu Asp Glu Asp Thr Val Gly Ala Ser Gly Gly Thr Met
                340                 345                 350

Ala Ser Ser Glu Asp Val Ile Lys Glu Phe Met Arg Phe Lys Val Arg
            355                 360                 365

Met Glu Gly Ser Val Asn Gly His Glu Phe Glu Ile Glu Gly Glu Gly
370                 375                 380

Glu Gly Arg Pro Tyr Glu Gly Thr Gln Thr Ala Lys Leu Lys Val Thr
385                 390                 395                 400

Lys Gly Gly Pro Leu Pro Phe Ala Trp Asp Ile Leu Ser Pro Gln Phe
                405                 410                 415

Gln Tyr Gly Ser Lys Val Tyr Val Lys His Pro Ala Asp Ile Pro Asp
            420                 425                 430

Tyr Lys Lys Leu Ser Phe Pro Glu Gly Phe Lys Trp Glu Arg Val Met
        435                 440                 445

Asn Phe Glu Asp Gly Gly Val Val Thr Val Thr Gln Asp Ser Ser Leu
450                 455                 460

Gln Asp Gly Cys Phe Ile Tyr Lys Val Lys Phe Ile Gly Val Asn Phe
465                 470                 475                 480

Pro Ser Asp Gly Pro Val Met Gln Lys Lys Thr Met Gly Trp Glu Pro
                485                 490                 495

Ser Thr Glu Arg Leu Tyr Pro Arg Asp Gly Val Leu Lys Gly Glu Ile
            500                 505                 510

His Lys Ala Leu Lys Leu Lys Asp Gly Gly His Tyr Leu Val Glu Phe
        515                 520                 525

Lys Ser Ile Tyr Met Ala Lys Lys Pro Val Gln Leu Pro Gly Tyr Tyr
530                 535                 540
```

-continued

Tyr Val Asp Ser Lys Leu Asp Ile Thr Ser His Asn Glu Asp Tyr Thr
545                 550                 555                 560

Ile Val Glu Gln Tyr Glu Arg Thr Glu Arg His His Leu Phe Leu
            565                 570                 575

Gly Gly Ser Gly Gly Thr Gly Gly Ser Gly Gly Thr Lys Val Asp Lys
                580                 585                 590

Met Leu Leu Gln Glu Leu Ser Glu Lys Leu Glu Leu Ala Glu Gln Ala
            595                 600                 605

Leu Ala Ser Lys Gln Leu Gln Met Asp Glu Met Lys Gln Thr Leu Ala
            610                 615                 620

Lys Gln Glu Glu Asp Leu Glu Thr Met Ala Val Leu Arg Ala Gln Met
625                 630                 635                 640

Glu Val Tyr Cys Ser Asp Phe His Ala Glu Arg Ala Ala Arg Glu Lys
                645                 650                 655

Ile His Glu Glu Lys Glu Gln Leu Ala Leu Gln Leu Ala Ile Leu Leu
            660                 665                 670

Lys Glu Asn Asn Asp Ile Glu Glu Gly Gly Ser Arg Gln Ser Leu Met
            675                 680                 685

Glu Met Gln Cys Arg His Gly Val Lys Glu Met Phe Lys Asp Phe Gln
690                 695                 700

Leu Arg Gln Pro Pro Leu Val Pro Ser Arg Lys Gly Glu Thr Pro Pro
705                 710                 715                 720

Ser Gly Thr Ser Ser Ala Phe Ser Ser Tyr Phe Asn Asn Lys Val Gly
            725                 730                 735

Ile Pro Gln Glu His Val Asp His Asp Phe Asp Ala Asn Gln Leu
            740                 745                 750

Leu Asn Lys Ile Asn Glu Pro Pro Lys Pro Ala Pro Arg Gln Gly Ser
            755                 760                 765

Ala Gly Lys Val Asp Lys Met Leu Leu Gln Glu Leu Ser Glu Lys Leu
            770                 775                 780

Glu Leu Ala Glu Gln Ala Leu Ala Ser Lys Gln Leu Gln Met Asp Glu
785                 790                 795                 800

Met Lys Gln Thr Leu Ala Lys Gln Glu Glu Asp Leu Glu Thr Met Ala
            805                 810                 815

Val Leu Arg Ala Gln Met Glu Val Tyr Cys Ser Asp Phe His Ala Glu
            820                 825                 830

Arg Ala Ala Arg Glu Lys Ile His Glu Glu Lys Glu Gln Leu Ala Leu
            835                 840                 845

Gln Leu Ala Ile Leu Leu Lys Glu Asn Asn Asp Ile Glu Glu Gly Gly
            850                 855                 860

Ser Arg Gln Ser Leu Met Glu Met Gln Cys Arg His Gly Val Lys Glu
865                 870                 875                 880

Met Phe Lys Asp Phe Gln Leu Arg Gln Pro Pro Leu Val Pro Ser Arg
                885                 890                 895

Lys Gly Glu Thr Pro Pro Ser Gly Thr Ser Ser Ala Phe Ser Ser Tyr
            900                 905                 910

Phe Asn Asn Lys Val Gly Ile Pro Gln Glu His Val Asp His Asp Asp
            915                 920                 925

Phe Asp Ala Asn Gln Leu Leu Asn Lys Ile Asn Glu Pro Pro Lys Pro
            930                 935                 940

Ala Pro Arg Gln Gly Ser Gly Arg Asp Gln Pro Leu Asn Ser Lys Lys
945                 950                 955                 960

Lys Lys Arg Leu Leu Ser Phe Arg Asp Val Asp Phe Glu Glu Asp Ser

```
                        965                 970                 975
Asp Gly Ser Gly Arg Asp Gln Pro Leu Asn Ser Lys Lys Lys Lys Arg
            980                 985                 990

Leu Leu Ser Phe Arg Asp Val Asp  Phe Glu Glu Asp Ser  Asp
        995                 1000                1005

<210> SEQ ID NO 50
<211> LENGTH: 994
<212> TYPE: PRT
<213> ORGANISM: Artificial Sequence
<220> FEATURE:
<223> OTHER INFORMATION: Synthetic polypeptide

<400> SEQUENCE: 50

Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
            20                  25                  30

Thr Asp Gly Thr Ala Ala Ala Val Ser His Tyr Ala Met Asn Gly
        35                  40                  45

Phe Asp Glu Leu Ala Lys Gly Ala Val Val Pro Glu Asp His Phe Val
    50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
            100                 105                 110

Lys Ala Thr Cys Gly Trp Glu Glu Val Tyr Val Cys Cys Val Glu Val
        115                 120                 125

Leu Phe Val Thr Leu Glu Ile Phe Lys Glu Phe Ser Ser Pro Ala Thr
130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Lys Arg Thr Met Gly Leu Ile Val Ser
            180                 185                 190

Cys Val Gly Met Ile Val Phe Gly Met Ala Ala Gly Leu Ala Thr Asp
        195                 200                 205

Trp Leu Lys Trp Leu Leu Tyr Ile Val Ser Cys Ile Tyr Gly Gly Tyr
    210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
            260                 265                 270

Gly Leu Leu Lys Leu Ser Pro Tyr Ala Asn Ser Ile Gly His Ser Ile
        275                 280                 285

Cys Asp Ile Ile Ala Lys Glu Phe Trp Thr Phe Leu Ala His His Leu
    290                 295                 300

Arg Ile Lys Ile His Glu His Ile Leu Ile His Gly Asp Ile Arg Lys
305                 310                 315                 320

Thr Thr Lys Met Glu Ile Gly Gly Glu Glu Val Glu Val Glu Glu Phe
```

```
            325                 330                 335
Val Glu Glu Glu Asp Glu Asp Thr Val Gly Ala Ser Gly Gly Thr Met
            340                 345                 350
Ala Ser Ser Glu Asp Val Ile Lys Glu Phe Met Arg Phe Lys Val Arg
            355                 360                 365
Met Glu Gly Ser Val Asn Gly His Glu Phe Glu Ile Glu Gly Glu Gly
            370                 375                 380
Glu Gly Arg Pro Tyr Glu Gly Thr Gln Thr Ala Lys Leu Lys Val Thr
385                 390                 395                 400
Lys Gly Gly Pro Leu Pro Phe Ala Trp Asp Ile Leu Ser Pro Gln Phe
                405                 410                 415
Gln Tyr Gly Ser Lys Val Tyr Val Lys His Pro Ala Asp Ile Pro Asp
                420                 425                 430
Tyr Lys Lys Leu Ser Phe Pro Glu Gly Phe Lys Trp Glu Arg Val Met
                435                 440                 445
Asn Phe Glu Asp Gly Gly Val Val Thr Val Thr Gln Asp Ser Ser Leu
450                 455                 460
Gln Asp Gly Cys Phe Ile Tyr Lys Val Lys Phe Ile Gly Val Asn Phe
465                 470                 475                 480
Pro Ser Asp Gly Pro Val Met Gln Lys Lys Thr Met Gly Trp Glu Pro
                485                 490                 495
Ser Thr Glu Arg Leu Tyr Pro Arg Asp Gly Val Leu Lys Gly Glu Ile
                500                 505                 510
His Lys Ala Leu Lys Leu Lys Asp Gly Gly His Tyr Leu Val Glu Phe
                515                 520                 525
Lys Ser Ile Tyr Met Ala Lys Lys Pro Val Gln Leu Pro Gly Tyr Tyr
                530                 535                 540
Tyr Val Asp Ser Lys Leu Asp Ile Thr Ser His Asn Glu Asp Tyr Thr
545                 550                 555                 560
Ile Val Glu Gln Tyr Glu Arg Thr Glu Gly Arg His His Leu Phe Leu
                565                 570                 575
Lys Val Asp Lys Met Leu Leu Gln Glu Leu Ser Glu Lys Leu Glu Leu
                580                 585                 590
Ala Glu Gln Ala Leu Ala Ser Lys Gln Leu Gln Met Asp Glu Met Lys
                595                 600                 605
Gln Thr Leu Ala Lys Gln Glu Glu Asp Leu Glu Thr Met Ala Val Leu
                610                 615                 620
Arg Ala Gln Met Glu Val Tyr Cys Ser Asp Phe His Ala Glu Arg Ala
625                 630                 635                 640
Ala Arg Glu Lys Ile His Glu Lys Glu Gln Leu Ala Leu Gln Leu
                645                 650                 655
Ala Ile Leu Leu Lys Glu Asn Asn Asp Ile Glu Glu Gly Gly Ser Arg
                660                 665                 670
Gln Ser Leu Met Glu Met Gln Cys Arg His Gly Val Lys Glu Met Phe
                675                 680                 685
Lys Asp Phe Gln Leu Arg Gln Pro Pro Leu Val Pro Ser Arg Lys Gly
                690                 695                 700
Glu Thr Pro Pro Ser Gly Thr Ser Ser Ala Phe Ser Ser Tyr Phe Asn
705                 710                 715                 720
Asn Lys Val Gly Ile Pro Gln Glu His Val Asp His Asp Phe Asp
                725                 730                 735
Ala Asn Gln Leu Leu Asn Lys Ile Asn Glu Pro Pro Lys Pro Ala Pro
                740                 745                 750
```

```
Arg Gln Gly Ser Ala Gly Lys Val Asp Lys Met Leu Leu Gln Glu Leu
            755                 760                 765

Ser Glu Lys Leu Glu Leu Ala Glu Gln Ala Leu Ala Ser Lys Gln Leu
        770                 775                 780

Gln Met Asp Glu Met Lys Gln Thr Leu Ala Lys Gln Glu Glu Asp Leu
785                 790                 795                 800

Glu Thr Met Ala Val Leu Arg Ala Gln Met Glu Val Tyr Cys Ser Asp
                805                 810                 815

Phe His Ala Glu Arg Ala Ala Arg Glu Lys Ile His Glu Glu Lys Glu
                    820                 825                 830

Gln Leu Ala Leu Gln Leu Ala Ile Leu Leu Lys Glu Asn Asn Asp Ile
                835                 840                 845

Glu Glu Gly Gly Ser Arg Gln Ser Leu Met Glu Met Gln Cys Arg His
            850                 855                 860

Gly Val Lys Glu Met Phe Lys Asp Phe Gln Leu Arg Gln Pro Pro Leu
865                 870                 875                 880

Val Pro Ser Arg Lys Gly Glu Thr Pro Pro Ser Gly Thr Ser Ser Ala
                885                 890                 895

Phe Ser Tyr Phe Asn Asn Lys Val Gly Ile Pro Glu His Val
                    900                 905                 910

Asp His Asp Asp Phe Asp Ala Asn Gln Leu Leu Asn Lys Ile Asn Glu
                915                 920                 925

Pro Pro Lys Pro Ala Pro Arg Gln Gly Ser Gly Arg Asp Gln Pro Leu
            930                 935                 940

Asn Ser Lys Lys Lys Arg Leu Leu Ser Phe Arg Asp Val Asp Phe
945                 950                 955                 960

Glu Glu Asp Ser Asp Gly Ser Gly Arg Asp Gln Pro Leu Asn Ser Lys
                965                 970                 975

Lys Lys Lys Arg Leu Leu Ser Phe Arg Asp Val Asp Phe Glu Glu Asp
                980                 985                 990

Ser Asp

<210> SEQ ID NO 51
<211> LENGTH: 206
<212> TYPE: PRT
<213> ORGANISM: Artificial Sequence
<220> FEATURE:
<223> OTHER INFORMATION: Synthetic polypeptide

<400> SEQUENCE: 51

Val Asp Lys Met Leu Leu Gln Glu Leu Ser Glu Lys Leu Glu Leu Ala
1               5                   10                  15

Glu Gln Ala Leu Ala Ser Lys Gln Leu Gln Met Asp Glu Met Lys Gln
            20                  25                  30

Thr Leu Ala Lys Gln Glu Glu Asp Leu Glu Thr Met Ala Val Leu Arg
        35                  40                  45

Ala Gln Met Glu Val Tyr Cys Ser Asp Phe His Ala Glu Arg Ala Ala
    50                  55                  60

Arg Glu Lys Ile His Glu Glu Lys Glu Gln Leu Ala Leu Gln Leu Ala
65                  70                  75                  80

Ile Leu Leu Lys Glu Asn Asn Asp Ile Glu Glu Gly Gly Ser Arg Gln
                85                  90                  95

Ser Leu Met Glu Met Gln Cys Arg His Gly Val Lys Glu Met Phe Lys
            100                 105                 110
```

```
Asp Phe Gln Leu Arg Gln Pro Pro Leu Val Pro Ser Arg Lys Gly Glu
            115                 120                 125

Thr Pro Pro Ser Gly Thr Ser Ser Ala Phe Ser Ser Tyr Phe Asn Asn
    130                 135                 140

Lys Val Gly Ile Pro Gln Glu His Val Asp His Asp Asp Phe Asp Ala
145             150                 155                 160

Asn Gln Leu Leu Asn Lys Ile Asn Glu Pro Pro Lys Pro Ala Pro Arg
                165                 170                 175

Gln Gly Ser Gly Arg Asp Gln Pro Leu Asn Ser Lys Lys Lys Lys Arg
            180                 185                 190

Leu Leu Ser Phe Arg Asp Val Asp Phe Glu Glu Asp Ser Asp
            195                 200                 205
```

<210> SEQ ID NO 52
<211> LENGTH: 207
<212> TYPE: PRT
<213> ORGANISM: Artificial Sequence
<220> FEATURE:
<223> OTHER INFORMATION: Synthetic polypeptide

<400> SEQUENCE: 52

```
Arg Asp Gln Pro Leu Asn Ser Lys Lys Lys Arg Leu Leu Ser Phe
1               5                   10                  15

Arg Asp Val Asp Phe Glu Glu Asp Ser Asp Gly Ser Gly Lys Val Asp
            20                  25                  30

Lys Met Leu Leu Gln Glu Leu Ser Glu Lys Leu Glu Leu Ala Glu Gln
            35                  40                  45

Ala Leu Ala Ser Lys Gln Leu Gln Met Asp Glu Met Lys Gln Thr Leu
50                  55                  60

Ala Lys Gln Glu Glu Asp Leu Glu Thr Met Ala Val Leu Arg Ala Gln
65                  70                  75                  80

Met Glu Val Tyr Cys Ser Asp Phe His Ala Glu Arg Ala Ala Arg Glu
                85                  90                  95

Lys Ile His Glu Glu Lys Glu Gln Leu Ala Leu Gln Leu Ala Ile Leu
            100                 105                 110

Leu Lys Glu Asn Asn Asp Ile Glu Glu Gly Gly Ser Arg Gln Ser Leu
            115                 120                 125

Met Glu Met Gln Cys Arg His Gly Val Lys Glu Met Phe Lys Asp Phe
130                 135                 140

Gln Leu Arg Gln Pro Pro Leu Val Pro Ser Arg Lys Gly Glu Thr Pro
145                 150                 155                 160

Pro Ser Gly Thr Ser Ser Ala Phe Ser Ser Tyr Phe Asn Asn Lys Val
                165                 170                 175

Gly Ile Pro Gln Glu His Val Asp His Asp Asp Phe Asp Ala Asn Gln
            180                 185                 190

Leu Leu Asn Lys Ile Asn Glu Pro Pro Lys Pro Ala Pro Arg Gln
            195                 200                 205
```

<210> SEQ ID NO 53
<211> LENGTH: 417
<212> TYPE: PRT
<213> ORGANISM: Artificial Sequence
<220> FEATURE:
<223> OTHER INFORMATION: Synthetic polypeptide

<400> SEQUENCE: 53

```
Lys Val Asp Lys Met Leu Leu Gln Glu Leu Ser Glu Lys Leu Glu Leu
1               5                   10                  15
```

Ala Glu Gln Ala Leu Ala Ser Lys Gln Leu Gln Met Asp Glu Met Lys
            20                  25                  30

Gln Thr Leu Ala Lys Gln Glu Asp Leu Glu Thr Met Ala Val Leu
        35                  40                  45

Arg Ala Gln Met Glu Val Tyr Cys Ser Asp Phe His Ala Glu Arg Ala
50                  55                  60

Ala Arg Glu Lys Ile His Glu Glu Lys Glu Gln Leu Ala Leu Gln Leu
65                  70                  75                  80

Ala Ile Leu Leu Lys Glu Asn Asn Asp Ile Glu Gly Gly Ser Arg
                85                  90                  95

Gln Ser Leu Met Glu Met Gln Cys Arg His Gly Val Lys Glu Met Phe
            100                 105                 110

Lys Asp Phe Gln Leu Arg Gln Pro Pro Leu Val Pro Ser Arg Lys Gly
        115                 120                 125

Glu Thr Pro Pro Ser Gly Thr Ser Ser Ala Phe Ser Ser Tyr Phe Asn
130                 135                 140

Asn Lys Val Gly Ile Pro Gln Glu His Val Asp His Asp Asp Phe Asp
145                 150                 155                 160

Ala Asn Gln Leu Leu Asn Lys Ile Asn Glu Pro Pro Lys Pro Ala Pro
                165                 170                 175

Arg Gln Gly Ser Gly Arg Asp Gln Pro Leu Asn Ser Lys Lys Lys Lys
            180                 185                 190

Arg Leu Leu Ser Phe Arg Asp Val Asp Phe Glu Glu Asp Ser Asp Gly
        195                 200                 205

Ser Gly Lys Val Asp Lys Met Leu Leu Gln Glu Leu Ser Glu Lys Leu
    210                 215                 220

Glu Leu Ala Glu Gln Ala Leu Ala Ser Lys Gln Leu Gln Met Asp Glu
225                 230                 235                 240

Met Lys Gln Thr Leu Ala Lys Gln Glu Glu Asp Leu Glu Thr Met Ala
                245                 250                 255

Val Leu Arg Ala Gln Met Glu Val Tyr Cys Ser Asp Phe His Ala Glu
            260                 265                 270

Arg Ala Ala Arg Glu Lys Ile His Glu Glu Lys Glu Gln Leu Ala Leu
        275                 280                 285

Gln Leu Ala Ile Leu Leu Lys Glu Asn Asn Asp Ile Glu Gly Gly Gly
    290                 295                 300

Ser Arg Gln Ser Leu Met Glu Met Gln Cys Arg His Gly Val Lys Glu
305                 310                 315                 320

Met Phe Lys Asp Phe Gln Leu Arg Gln Pro Pro Leu Val Pro Ser Arg
                325                 330                 335

Lys Gly Glu Thr Pro Pro Ser Gly Thr Ser Ser Ala Phe Ser Ser Tyr
            340                 345                 350

Phe Asn Asn Lys Val Gly Ile Pro Gln Glu His Val Asp His Asp Asp
        355                 360                 365

Phe Asp Ala Asn Gln Leu Leu Asn Lys Ile Asn Glu Pro Pro Lys Pro
    370                 375                 380

Ala Pro Arg Gln Gly Ser Gly Arg Asp Gln Pro Leu Asn Ser Lys Lys
385                 390                 395                 400

Lys Lys Arg Leu Leu Ser Phe Arg Asp Val Asp Phe Glu Glu Asp Ser
                405                 410                 415

Asp

-continued

```
<210> SEQ ID NO 54
<211> LENGTH: 417
<212> TYPE: PRT
<213> ORGANISM: Artificial Sequence
<220> FEATURE:
<223> OTHER INFORMATION: Synthetic polypeptide

<400> SEQUENCE: 54

Arg Asp Gln Pro Leu Asn Ser Lys Lys Lys Arg Leu Leu Ser Phe
1               5                   10                  15

Arg Asp Val Asp Phe Glu Glu Asp Ser Asp Gly Ser Gly Lys Val Asp
            20                  25                  30

Lys Met Leu Leu Gln Glu Leu Ser Glu Lys Leu Glu Leu Ala Glu Gln
        35                  40                  45

Ala Leu Ala Ser Lys Gln Leu Gln Met Asp Glu Met Lys Gln Thr Leu
    50                  55                  60

Ala Lys Gln Glu Glu Asp Leu Glu Thr Met Ala Val Leu Arg Ala Gln
65                  70                  75                  80

Met Glu Val Tyr Cys Ser Asp Phe His Ala Glu Arg Ala Ala Arg Glu
                85                  90                  95

Lys Ile His Glu Glu Lys Glu Gln Leu Ala Leu Gln Leu Ala Ile Leu
            100                 105                 110

Leu Lys Glu Asn Asn Asp Ile Glu Glu Gly Gly Ser Arg Gln Ser Leu
        115                 120                 125

Met Glu Met Gln Cys Arg His Gly Val Lys Glu Met Phe Lys Asp Phe
    130                 135                 140

Gln Leu Arg Gln Pro Pro Leu Val Pro Ser Arg Lys Gly Glu Thr Pro
145                 150                 155                 160

Pro Ser Gly Thr Ser Ser Ala Phe Ser Ser Tyr Phe Asn Asn Lys Val
                165                 170                 175

Gly Ile Pro Gln Glu His Val Asp His Asp Phe Asp Ala Asn Gln
            180                 185                 190

Leu Leu Asn Lys Ile Asn Glu Pro Pro Lys Pro Ala Pro Arg Gln Gly
        195                 200                 205

Ser Gly Arg Asp Gln Pro Leu Asn Ser Lys Lys Lys Arg Leu Leu
    210                 215                 220

Ser Phe Arg Asp Val Asp Phe Glu Glu Asp Ser Asp Gly Ser Gly Lys
225                 230                 235                 240

Val Asp Lys Met Leu Leu Gln Glu Leu Ser Glu Lys Leu Glu Leu Ala
                245                 250                 255

Glu Gln Ala Leu Ala Ser Lys Gln Leu Gln Met Asp Glu Met Lys Gln
            260                 265                 270

Thr Leu Ala Lys Gln Glu Glu Asp Leu Glu Thr Met Ala Val Leu Arg
        275                 280                 285

Ala Gln Met Glu Val Tyr Cys Ser Asp Phe His Ala Glu Arg Ala Ala
    290                 295                 300

Arg Glu Lys Ile His Glu Glu Lys Glu Gln Leu Ala Leu Gln Leu Ala
305                 310                 315                 320

Ile Leu Leu Lys Glu Asn Asn Asp Ile Glu Glu Gly Gly Ser Arg Gln
                325                 330                 335

Ser Leu Met Glu Met Gln Cys Arg His Gly Val Lys Glu Met Phe Lys
            340                 345                 350

Asp Phe Gln Leu Arg Gln Pro Pro Leu Val Pro Ser Arg Lys Gly Glu
        355                 360                 365

Thr Pro Pro Ser Gly Thr Ser Ser Ala Phe Ser Ser Tyr Phe Asn Asn
```

```
                370                 375                 380
Lys Val Gly Ile Pro Gln Glu His Val Asp His Asp Phe Asp Ala
385                 390                 395                 400

Asn Gln Leu Leu Asn Lys Ile Asn Glu Pro Pro Lys Pro Ala Pro Arg
                405                 410                 415

Gln

<210> SEQ ID NO 55
<211> LENGTH: 627
<212> TYPE: PRT
<213> ORGANISM: Artificial Sequence
<220> FEATURE:
<223> OTHER INFORMATION: Synthetic polypeptide

<400> SEQUENCE: 55

Lys Val Asp Lys Met Leu Leu Gln Glu Leu Ser Glu Lys Leu Glu Leu
1               5                   10                  15

Ala Glu Gln Ala Leu Ala Ser Lys Gln Leu Gln Met Asp Glu Met Lys
            20                  25                  30

Gln Thr Leu Ala Lys Gln Glu Glu Asp Leu Glu Thr Met Ala Val Leu
        35                  40                  45

Arg Ala Gln Met Glu Val Tyr Cys Ser Asp Phe His Ala Glu Arg Ala
    50                  55                  60

Ala Arg Glu Lys Ile His Glu Glu Lys Glu Gln Leu Ala Leu Gln Leu
65                  70                  75                  80

Ala Ile Leu Leu Lys Glu Asn Asn Asp Ile Glu Glu Gly Gly Ser Arg
                85                  90                  95

Gln Ser Leu Met Glu Met Gln Cys Arg His Gly Val Lys Glu Met Phe
            100                 105                 110

Lys Asp Phe Gln Leu Arg Gln Pro Pro Leu Val Pro Ser Arg Lys Gly
        115                 120                 125

Glu Thr Pro Pro Ser Gly Thr Ser Ser Ala Phe Ser Ser Tyr Phe Asn
    130                 135                 140

Asn Lys Val Gly Ile Pro Gln Glu His Val Asp His Asp Phe Asp
145                 150                 155                 160

Ala Asn Gln Leu Leu Asn Lys Ile Asn Glu Pro Pro Lys Pro Ala Pro
                165                 170                 175

Arg Gln Gly Ser Gly Arg Asp Gln Pro Leu Asn Ser Lys Lys Lys Lys
            180                 185                 190

Arg Leu Leu Ser Phe Arg Asp Val Asp Phe Glu Glu Asp Ser Asp Gly
        195                 200                 205

Ser Gly Lys Val Asp Lys Met Leu Leu Gln Glu Leu Ser Glu Lys Leu
    210                 215                 220

Glu Leu Ala Glu Gln Ala Leu Ala Ser Lys Gln Leu Gln Met Asp Glu
225                 230                 235                 240

Met Lys Gln Thr Leu Ala Lys Gln Glu Glu Asp Leu Glu Thr Met Ala
                245                 250                 255

Val Leu Arg Ala Gln Met Glu Val Tyr Cys Ser Asp Phe His Ala Glu
            260                 265                 270

Arg Ala Ala Arg Glu Lys Ile His Glu Glu Lys Glu Gln Leu Ala Leu
        275                 280                 285

Gln Leu Ala Ile Leu Leu Lys Glu Asn Asn Asp Ile Glu Glu Gly Gly
    290                 295                 300

Ser Arg Gln Ser Leu Met Glu Met Gln Cys Arg His Gly Val Lys Glu
305                 310                 315                 320
```

Met Phe Lys Asp Phe Gln Leu Arg Gln Pro Pro Leu Val Pro Ser Arg
            325                 330                 335

Lys Gly Glu Thr Pro Pro Ser Gly Thr Ser Ser Ala Phe Ser Ser Tyr
            340                 345                 350

Phe Asn Asn Lys Val Gly Ile Pro Gln Glu His Val Asp His Asp Asp
            355                 360                 365

Phe Asp Ala Asn Gln Leu Leu Asn Lys Ile Asn Glu Pro Pro Lys Pro
            370                 375                 380

Ala Pro Arg Gln Gly Ser Gly Arg Asp Gln Pro Leu Asn Ser Lys Lys
385                 390                 395                 400

Lys Lys Arg Leu Leu Ser Phe Arg Asp Val Asp Phe Glu Glu Asp Ser
            405                 410                 415

Asp Gly Ser Gly Lys Val Asp Lys Met Leu Leu Gln Glu Leu Ser Glu
            420                 425                 430

Lys Leu Glu Leu Ala Glu Gln Ala Leu Ala Ser Lys Gln Leu Gln Met
            435                 440                 445

Asp Glu Met Lys Gln Thr Leu Ala Lys Gln Glu Glu Asp Leu Glu Thr
            450                 455                 460

Met Ala Val Leu Arg Ala Gln Met Glu Val Tyr Cys Ser Asp Phe His
465                 470                 475                 480

Ala Glu Arg Ala Ala Arg Glu Lys Ile His Glu Glu Lys Glu Gln Leu
            485                 490                 495

Ala Leu Gln Leu Ala Ile Leu Leu Lys Glu Asn Asn Asp Ile Glu Glu
            500                 505                 510

Gly Gly Ser Arg Gln Ser Leu Met Glu Met Gln Cys Arg His Gly Val
            515                 520                 525

Lys Glu Met Phe Lys Asp Phe Gln Leu Arg Gln Pro Pro Leu Val Pro
            530                 535                 540

Ser Arg Lys Gly Glu Thr Pro Pro Ser Gly Thr Ser Ser Ala Phe Ser
545                 550                 555                 560

Ser Tyr Phe Asn Asn Lys Val Gly Ile Pro Gln Glu His Val Asp His
            565                 570                 575

Asp Asp Phe Asp Ala Asn Gln Leu Leu Asn Lys Ile Asn Glu Pro Pro
            580                 585                 590

Lys Pro Ala Pro Arg Gln Gly Ser Gly Arg Asp Gln Pro Leu Asn Ser
            595                 600                 605

Lys Lys Lys Lys Arg Leu Leu Ser Phe Arg Asp Val Asp Phe Glu Glu
            610                 615                 620

Asp Ser Asp
625

<210> SEQ ID NO 56
<211> LENGTH: 627
<212> TYPE: PRT
<213> ORGANISM: Artificial Sequence
<220> FEATURE:
<223> OTHER INFORMATION: Synthetic polypeptide

<400> SEQUENCE: 56

Arg Asp Gln Pro Leu Asn Ser Lys Lys Lys Lys Arg Leu Leu Ser Phe
1               5                   10                  15

Arg Asp Val Asp Phe Glu Glu Asp Ser Asp Gly Ser Gly Lys Val Asp
            20                  25                  30

Lys Met Leu Leu Gln Glu Leu Ser Glu Lys Leu Glu Leu Ala Glu Gln
            35                  40                  45

```
Ala Leu Ala Ser Lys Gln Leu Gln Met Asp Glu Met Lys Gln Thr Leu
     50                  55                  60
Ala Lys Gln Glu Glu Asp Leu Glu Thr Met Ala Val Leu Arg Ala Gln
 65                  70                  75                  80
Met Glu Val Tyr Cys Ser Asp Phe His Ala Glu Arg Ala Ala Arg Glu
                 85                  90                  95
Lys Ile His Glu Glu Lys Glu Gln Leu Ala Leu Gln Leu Ala Ile Leu
            100                 105                 110
Leu Lys Glu Asn Asn Asp Ile Glu Glu Gly Gly Ser Arg Gln Ser Leu
        115                 120                 125
Met Glu Met Gln Cys Arg His Gly Val Lys Glu Met Phe Lys Asp Phe
    130                 135                 140
Gln Leu Arg Gln Pro Pro Leu Val Pro Ser Arg Lys Gly Glu Thr Pro
145                 150                 155                 160
Pro Ser Gly Thr Ser Ser Ala Phe Ser Ser Tyr Phe Asn Asn Lys Val
                165                 170                 175
Gly Ile Pro Gln Glu His Val Asp His Asp Phe Asp Ala Asn Gln
            180                 185                 190
Leu Leu Asn Lys Ile Asn Glu Pro Pro Lys Pro Ala Pro Arg Gln Gly
        195                 200                 205
Ser Gly Arg Asp Gln Pro Leu Asn Ser Lys Lys Lys Arg Leu Leu
    210                 215                 220
Ser Phe Arg Asp Val Asp Phe Glu Glu Asp Ser Asp Gly Ser Gly Lys
225                 230                 235                 240
Val Asp Lys Met Leu Leu Gln Glu Leu Ser Glu Lys Leu Glu Leu Ala
                245                 250                 255
Glu Gln Ala Leu Ala Ser Lys Gln Leu Gln Met Asp Glu Met Lys Gln
            260                 265                 270
Thr Leu Ala Lys Gln Glu Glu Asp Leu Glu Thr Met Ala Val Leu Arg
        275                 280                 285
Ala Gln Met Glu Val Tyr Cys Ser Asp Phe His Ala Glu Arg Ala Ala
    290                 295                 300
Arg Glu Lys Ile His Glu Glu Lys Glu Gln Leu Ala Leu Gln Leu Ala
305                 310                 315                 320
Ile Leu Leu Lys Glu Asn Asn Asp Ile Glu Glu Gly Gly Ser Arg Gln
                325                 330                 335
Ser Leu Met Glu Met Gln Cys Arg His Gly Val Lys Glu Met Phe Lys
            340                 345                 350
Asp Phe Gln Leu Arg Gln Pro Pro Leu Val Pro Ser Arg Lys Gly Glu
        355                 360                 365
Thr Pro Pro Ser Gly Thr Ser Ser Ala Phe Ser Ser Tyr Phe Asn Asn
    370                 375                 380
Lys Val Gly Ile Pro Gln Glu His Val Asp His Asp Phe Asp Ala
385                 390                 395                 400
Asn Gln Leu Leu Asn Lys Ile Asn Glu Pro Pro Lys Pro Ala Pro Arg
                405                 410                 415
Gln Gly Ser Gly Arg Asp Gln Pro Leu Asn Ser Lys Lys Lys Arg
            420                 425                 430
Leu Leu Ser Phe Arg Asp Val Asp Phe Glu Glu Asp Ser Asp Gly Ser
        435                 440                 445
Gly Lys Val Asp Lys Met Leu Leu Gln Glu Leu Ser Glu Lys Leu Glu
    450                 455                 460
```

Leu Ala Glu Gln Ala Leu Ala Ser Lys Gln Leu Gln Met Asp Glu Met
465                 470                 475                 480

Lys Gln Thr Leu Ala Lys Gln Glu Glu Asp Leu Glu Thr Met Ala Val
            485                 490                 495

Leu Arg Ala Gln Met Glu Val Tyr Cys Ser Asp Phe His Ala Glu Arg
        500                 505                 510

Ala Ala Arg Glu Lys Ile His Glu Glu Lys Glu Gln Leu Ala Leu Gln
    515                 520                 525

Leu Ala Ile Leu Leu Lys Glu Asn Asn Asp Ile Glu Glu Gly Gly Ser
530                 535                 540

Arg Gln Ser Leu Met Glu Met Gln Cys Arg His Gly Val Lys Glu Met
545                 550                 555                 560

Phe Lys Asp Phe Gln Leu Arg Gln Pro Pro Leu Val Pro Ser Arg Lys
            565                 570                 575

Gly Glu Thr Pro Pro Ser Gly Thr Ser Ser Ala Phe Ser Ser Tyr Phe
        580                 585                 590

Asn Asn Lys Val Gly Ile Pro Gln Glu His Val Asp His Asp Asp Phe
    595                 600                 605

Asp Ala Asn Gln Leu Leu Asn Lys Ile Asn Glu Pro Pro Lys Pro Ala
610                 615                 620

Pro Arg Gln
625

<210> SEQ ID NO 57
<211> LENGTH: 837
<212> TYPE: PRT
<213> ORGANISM: Artificial Sequence
<220> FEATURE:
<223> OTHER INFORMATION: Synthetic polypeptide

<400> SEQUENCE: 57

Lys Val Asp Lys Met Leu Leu Gln Glu Leu Ser Glu Lys Leu Glu Leu
1               5                   10                  15

Ala Glu Gln Ala Leu Ala Ser Lys Gln Leu Gln Met Asp Glu Met Lys
            20                  25                  30

Gln Thr Leu Ala Lys Gln Glu Glu Asp Leu Glu Thr Met Ala Val Leu
        35                  40                  45

Arg Ala Gln Met Glu Val Tyr Cys Ser Asp Phe His Ala Glu Arg Ala
50                  55                  60

Ala Arg Glu Lys Ile His Glu Glu Lys Glu Gln Leu Ala Leu Gln Leu
65                  70                  75                  80

Ala Ile Leu Leu Lys Glu Asn Asn Asp Ile Glu Glu Gly Gly Ser Arg
                85                  90                  95

Gln Ser Leu Met Glu Met Gln Cys Arg His Gly Val Lys Glu Met Phe
            100                 105                 110

Lys Asp Phe Gln Leu Arg Gln Pro Pro Leu Val Pro Ser Arg Lys Gly
        115                 120                 125

Glu Thr Pro Pro Ser Gly Thr Ser Ser Ala Phe Ser Ser Tyr Phe Asn
130                 135                 140

Asn Lys Val Gly Ile Pro Gln Glu His Val Asp His Asp Asp Phe Asp
145                 150                 155                 160

Ala Asn Gln Leu Leu Asn Lys Ile Asn Glu Pro Pro Lys Pro Ala Pro
                165                 170                 175

Arg Gln Gly Ser Gly Arg Asp Gln Pro Leu Asn Ser Lys Lys Lys Lys
            180                 185                 190

-continued

```
Arg Leu Leu Ser Phe Arg Asp Val Asp Phe Glu Glu Asp Ser Asp Gly
            195                 200                 205

Ser Gly Lys Val Asp Lys Met Leu Leu Gln Glu Leu Ser Glu Lys Leu
        210                 215                 220

Glu Leu Ala Glu Gln Ala Leu Ala Ser Lys Gln Leu Gln Met Asp Glu
225                 230                 235                 240

Met Lys Gln Thr Leu Ala Lys Gln Glu Glu Asp Leu Glu Thr Met Ala
            245                 250                 255

Val Leu Arg Ala Gln Met Glu Val Tyr Cys Ser Asp Phe His Ala Glu
        260                 265                 270

Arg Ala Ala Arg Glu Lys Ile His Glu Glu Lys Glu Gln Leu Ala Leu
        275                 280                 285

Gln Leu Ala Ile Leu Leu Lys Glu Asn Asn Asp Ile Glu Glu Gly Gly
        290                 295                 300

Ser Arg Gln Ser Leu Met Glu Met Gln Cys Arg His Gly Val Lys Glu
305                 310                 315                 320

Met Phe Lys Asp Phe Gln Leu Arg Gln Pro Pro Leu Val Pro Ser Arg
            325                 330                 335

Lys Gly Glu Thr Pro Pro Ser Gly Thr Ser Ser Ala Phe Ser Ser Tyr
            340                 345                 350

Phe Asn Asn Lys Val Gly Ile Pro Gln Glu His Val Asp His Asp Asp
        355                 360                 365

Phe Asp Ala Asn Gln Leu Leu Asn Lys Ile Asn Glu Pro Pro Lys Pro
        370                 375                 380

Ala Pro Arg Gln Gly Ser Gly Arg Asp Gln Pro Leu Asn Ser Lys Lys
385                 390                 395                 400

Lys Lys Arg Leu Leu Ser Phe Arg Asp Val Asp Phe Glu Glu Asp Ser
            405                 410                 415

Asp Gly Ser Gly Lys Val Asp Lys Met Leu Leu Gln Glu Leu Ser Glu
        420                 425                 430

Lys Leu Glu Leu Ala Glu Gln Ala Leu Ala Ser Lys Gln Leu Gln Met
        435                 440                 445

Asp Glu Met Lys Gln Thr Leu Ala Lys Gln Glu Glu Asp Leu Glu Thr
450                 455                 460

Met Ala Val Leu Arg Ala Gln Met Glu Val Tyr Cys Ser Asp Phe His
465                 470                 475                 480

Ala Glu Arg Ala Ala Arg Glu Lys Ile His Glu Glu Lys Glu Gln Leu
            485                 490                 495

Ala Leu Gln Leu Ala Ile Leu Leu Lys Glu Asn Asn Asp Ile Glu Glu
        500                 505                 510

Gly Gly Ser Arg Gln Ser Leu Met Glu Met Gln Cys Arg His Gly Val
        515                 520                 525

Lys Glu Met Phe Lys Asp Phe Gln Leu Arg Gln Pro Pro Leu Val Pro
530                 535                 540

Ser Arg Lys Gly Glu Thr Pro Pro Ser Gly Thr Ser Ser Ala Phe Ser
545                 550                 555                 560

Ser Tyr Phe Asn Asn Lys Val Gly Ile Pro Gln Glu His Val Asp His
            565                 570                 575

Asp Asp Phe Asp Ala Asn Gln Leu Leu Asn Lys Ile Asn Glu Pro Pro
        580                 585                 590

Lys Pro Ala Pro Arg Gln Gly Ser Gly Arg Asp Gln Pro Leu Asn Ser
        595                 600                 605

Lys Lys Lys Lys Arg Leu Leu Ser Phe Arg Asp Val Asp Phe Glu Glu
```

```
            610                 615                 620
Asp Ser Asp Gly Ser Gly Lys Val Asp Lys Met Leu Leu Gln Glu Leu
625                 630                 635                 640

Ser Glu Lys Leu Glu Leu Ala Glu Gln Ala Leu Ala Ser Lys Gln Leu
                645                 650                 655

Gln Met Asp Glu Met Lys Gln Thr Leu Ala Lys Gln Glu Glu Asp Leu
            660                 665                 670

Glu Thr Met Ala Val Leu Arg Ala Gln Met Glu Val Tyr Cys Ser Asp
        675                 680                 685

Phe His Ala Glu Arg Ala Ala Arg Glu Lys Ile His Glu Glu Lys Glu
    690                 695                 700

Gln Leu Ala Leu Gln Leu Ala Ile Leu Leu Lys Glu Asn Asn Asp Ile
705                 710                 715                 720

Glu Glu Gly Gly Ser Arg Gln Ser Leu Met Glu Met Gln Cys Arg His
                725                 730                 735

Gly Val Lys Glu Met Phe Lys Asp Phe Gln Leu Arg Gln Pro Pro Leu
            740                 745                 750

Val Pro Ser Arg Lys Gly Glu Thr Pro Pro Ser Gly Thr Ser Ser Ala
        755                 760                 765

Phe Ser Ser Tyr Phe Asn Asn Lys Val Gly Ile Pro Gln Glu His Val
    770                 775                 780

Asp His Asp Asp Phe Asp Ala Asn Gln Leu Leu Asn Lys Ile Asn Glu
785                 790                 795                 800

Pro Pro Lys Pro Ala Pro Arg Gln Gly Ser Gly Arg Asp Gln Pro Leu
                805                 810                 815

Asn Ser Lys Lys Lys Arg Leu Leu Ser Phe Arg Asp Val Asp Phe
            820                 825                 830

Glu Glu Asp Ser Asp
            835

<210> SEQ ID NO 58
<211> LENGTH: 837
<212> TYPE: PRT
<213> ORGANISM: Artificial Sequence
<220> FEATURE:
<223> OTHER INFORMATION: Synthetic polypeptide

<400> SEQUENCE: 58

Arg Asp Gln Pro Leu Asn Ser Lys Lys Lys Arg Leu Leu Ser Phe
1               5                   10                  15

Arg Asp Val Asp Phe Glu Glu Asp Ser Asp Gly Ser Gly Lys Val Asp
                20                  25                  30

Lys Met Leu Leu Gln Glu Leu Ser Glu Lys Leu Glu Leu Ala Glu Gln
            35                  40                  45

Ala Leu Ala Ser Lys Gln Leu Gln Met Asp Glu Met Lys Gln Thr Leu
50                  55                  60

Ala Lys Gln Glu Glu Asp Leu Glu Thr Met Ala Val Leu Arg Ala Gln
65                  70                  75                  80

Met Glu Val Tyr Cys Ser Asp Phe His Ala Glu Arg Ala Ala Arg Glu
                85                  90                  95

Lys Ile His Glu Glu Lys Glu Gln Leu Ala Leu Gln Leu Ala Ile Leu
            100                 105                 110

Leu Lys Glu Asn Asn Asp Ile Glu Glu Gly Gly Ser Arg Gln Ser Leu
        115                 120                 125

Met Glu Met Gln Cys Arg His Gly Val Lys Glu Met Phe Lys Asp Phe
```

```
            130                 135                 140
Gln Leu Arg Gln Pro Pro Leu Val Pro Ser Arg Lys Gly Glu Thr Pro
145                 150                 155                 160
Pro Ser Gly Thr Ser Ser Ala Phe Ser Ser Tyr Phe Asn Asn Lys Val
                165                 170                 175
Gly Ile Pro Gln Glu His Val Asp His Asp Asp Phe Asp Ala Asn Gln
                180                 185                 190
Leu Leu Asn Lys Ile Asn Glu Pro Pro Lys Pro Ala Pro Arg Gln Gly
                195                 200                 205
Ser Gly Arg Asp Gln Pro Leu Asn Ser Lys Lys Lys Arg Leu Leu
            210                 215                 220
Ser Phe Arg Asp Val Asp Phe Glu Glu Asp Ser Asp Gly Ser Gly Lys
225                 230                 235                 240
Val Asp Lys Met Leu Leu Gln Glu Leu Ser Glu Lys Leu Glu Leu Ala
                245                 250                 255
Glu Gln Ala Leu Ala Ser Lys Gln Leu Gln Met Asp Glu Met Lys Gln
                260                 265                 270
Thr Leu Ala Lys Gln Glu Glu Asp Leu Glu Thr Met Ala Val Leu Arg
                275                 280                 285
Ala Gln Met Glu Val Tyr Cys Ser Asp Phe His Ala Glu Arg Ala Ala
                290                 295                 300
Arg Glu Lys Ile His Glu Glu Lys Glu Gln Leu Ala Leu Gln Leu Ala
305                 310                 315                 320
Ile Leu Leu Lys Glu Asn Asn Asp Ile Glu Glu Gly Gly Ser Arg Gln
                325                 330                 335
Ser Leu Met Glu Met Gln Cys Arg His Gly Val Lys Glu Met Phe Lys
                340                 345                 350
Asp Phe Gln Leu Arg Gln Pro Pro Leu Val Pro Ser Arg Lys Gly Glu
                355                 360                 365
Thr Pro Pro Ser Gly Thr Ser Ser Ala Phe Ser Ser Tyr Phe Asn Asn
                370                 375                 380
Lys Val Gly Ile Pro Gln Glu His Val Asp His Asp Asp Phe Asp Ala
385                 390                 395                 400
Asn Gln Leu Leu Asn Lys Ile Asn Glu Pro Pro Lys Pro Ala Pro Arg
                405                 410                 415
Gln Gly Ser Gly Arg Asp Gln Pro Leu Asn Ser Lys Lys Lys Arg
                420                 425                 430
Leu Leu Ser Phe Arg Asp Val Asp Phe Glu Glu Asp Ser Asp Gly Ser
                435                 440                 445
Gly Lys Val Asp Lys Met Leu Leu Gln Glu Leu Ser Glu Lys Leu Glu
            450                 455                 460
Leu Ala Glu Gln Ala Leu Ala Ser Lys Gln Leu Gln Met Asp Glu Met
465                 470                 475                 480
Lys Gln Thr Leu Ala Lys Gln Glu Glu Asp Leu Glu Thr Met Ala Val
                485                 490                 495
Leu Arg Ala Gln Met Glu Val Tyr Cys Ser Asp Phe His Ala Glu Arg
                500                 505                 510
Ala Ala Arg Glu Lys Ile His Glu Glu Lys Glu Gln Leu Ala Leu Gln
                515                 520                 525
Leu Ala Ile Leu Leu Lys Glu Asn Asn Asp Ile Glu Glu Gly Gly Ser
            530                 535                 540
Arg Gln Ser Leu Met Glu Met Gln Cys Arg His Gly Val Lys Glu Met
545                 550                 555                 560
```

```
Phe Lys Asp Phe Gln Leu Arg Gln Pro Pro Leu Val Pro Ser Arg Lys
            565                 570                 575

Gly Glu Thr Pro Pro Ser Gly Thr Ser Ser Ala Phe Ser Ser Tyr Phe
        580                 585                 590

Asn Asn Lys Val Gly Ile Pro Gln Glu His Val Asp His Asp Asp Phe
        595                 600                 605

Asp Ala Asn Gln Leu Leu Asn Lys Ile Asn Glu Pro Pro Lys Pro Ala
    610                 615                 620

Pro Arg Gln Gly Ser Gly Arg Asp Gln Pro Leu Asn Ser Lys Lys Lys
625                 630                 635                 640

Lys Arg Leu Leu Ser Phe Arg Asp Val Asp Phe Glu Glu Asp Ser Asp
                645                 650                 655

Gly Ser Gly Lys Val Asp Lys Met Leu Leu Gln Glu Leu Ser Glu Lys
                660                 665                 670

Leu Glu Leu Ala Glu Gln Ala Leu Ala Ser Lys Gln Leu Gln Met Asp
            675                 680                 685

Glu Met Lys Gln Thr Leu Ala Lys Gln Glu Glu Asp Leu Glu Thr Met
        690                 695                 700

Ala Val Leu Arg Ala Gln Met Glu Val Tyr Cys Ser Asp Phe His Ala
705                 710                 715                 720

Glu Arg Ala Ala Arg Glu Lys Ile His Glu Glu Lys Glu Gln Leu Ala
                725                 730                 735

Leu Gln Leu Ala Ile Leu Leu Lys Glu Asn Asn Asp Ile Glu Glu Gly
            740                 745                 750

Gly Ser Arg Gln Ser Leu Met Glu Met Gln Cys Arg His Gly Val Lys
        755                 760                 765

Glu Met Phe Lys Asp Phe Gln Leu Arg Gln Pro Pro Leu Val Pro Ser
    770                 775                 780

Arg Lys Gly Glu Thr Pro Pro Ser Gly Thr Ser Ser Ala Phe Ser Ser
785                 790                 795                 800

Tyr Phe Asn Asn Lys Val Gly Ile Pro Gln Glu His Val Asp His Asp
                805                 810                 815

Asp Phe Asp Ala Asn Gln Leu Leu Asn Lys Ile Asn Glu Pro Pro Lys
            820                 825                 830

Pro Ala Pro Arg Gln
        835

<210> SEQ ID NO 59
<211> LENGTH: 630
<212> TYPE: PRT
<213> ORGANISM: Artificial Sequence
<220> FEATURE:
<223> OTHER INFORMATION: Synthetic polypeptide

<400> SEQUENCE: 59

Lys Val Asp Lys Met Leu Leu Gln Glu Leu Ser Glu Lys Leu Glu Leu
1               5                   10                  15

Ala Glu Gln Ala Leu Ala Ser Lys Gln Leu Gln Met Asp Glu Met Lys
            20                  25                  30

Gln Thr Leu Ala Lys Gln Glu Glu Asp Leu Glu Thr Met Ala Val Leu
        35                  40                  45

Arg Ala Gln Met Glu Val Tyr Cys Ser Asp Phe His Ala Glu Arg Ala
    50                  55                  60

Ala Arg Glu Lys Ile His Glu Glu Lys Glu Gln Leu Ala Leu Gln Leu
65                  70                  75                  80
```

```
Ala Ile Leu Leu Lys Glu Asn Asn Asp Ile Glu Gly Gly Ser Arg
             85                  90                  95

Gln Ser Leu Met Glu Met Gln Cys Arg His Gly Val Lys Glu Met Phe
            100                 105                 110

Lys Asp Phe Gln Leu Arg Gln Pro Pro Leu Val Pro Ser Arg Lys Gly
            115                 120                 125

Glu Thr Pro Pro Ser Gly Thr Ser Ser Ala Phe Ser Ser Tyr Phe Asn
130                 135                 140

Asn Lys Val Gly Ile Pro Gln Glu His Val Asp His Asp Phe Asp
145                 150                 155                 160

Ala Asn Gln Leu Leu Asn Lys Ile Asn Glu Pro Pro Lys Pro Ala Pro
                165                 170                 175

Arg Gln Gly Ser Gly Lys Val Asp Lys Met Leu Leu Gln Glu Leu Ser
            180                 185                 190

Glu Lys Leu Glu Leu Ala Glu Gln Ala Leu Ala Ser Lys Gln Leu Gln
            195                 200                 205

Met Asp Glu Met Lys Gln Thr Leu Ala Lys Gln Glu Glu Asp Leu Glu
            210                 215                 220

Thr Met Ala Val Leu Arg Ala Gln Met Glu Val Tyr Cys Ser Asp Phe
225                 230                 235                 240

His Ala Glu Arg Ala Ala Arg Glu Lys Ile His Glu Glu Lys Glu Gln
                245                 250                 255

Leu Ala Leu Gln Leu Ala Ile Leu Leu Lys Glu Asn Asn Asp Ile Glu
            260                 265                 270

Glu Gly Gly Ser Arg Gln Ser Leu Met Glu Met Gln Cys Arg His Gly
            275                 280                 285

Val Lys Glu Met Phe Lys Asp Phe Gln Leu Arg Gln Pro Pro Leu Val
            290                 295                 300

Pro Ser Arg Lys Gly Glu Thr Pro Pro Ser Gly Thr Ser Ser Ala Phe
305                 310                 315                 320

Ser Ser Tyr Phe Asn Asn Lys Val Gly Ile Pro Gln Glu His Val Asp
                325                 330                 335

His Asp Phe Asp Ala Asn Gln Leu Leu Asn Lys Ile Asn Glu Pro
            340                 345                 350

Pro Lys Pro Ala Pro Arg Gln Gly Ser Gly Lys Val Asp Lys Met Leu
            355                 360                 365

Leu Gln Glu Leu Ser Glu Lys Leu Glu Leu Ala Glu Gln Ala Leu Ala
            370                 375                 380

Ser Lys Gln Leu Gln Met Asp Glu Met Lys Gln Thr Leu Ala Lys Gln
385                 390                 395                 400

Glu Glu Asp Leu Glu Thr Met Ala Val Leu Arg Ala Gln Met Glu Val
                405                 410                 415

Tyr Cys Ser Asp Phe His Ala Glu Arg Ala Ala Arg Glu Lys Ile His
            420                 425                 430

Glu Glu Lys Glu Gln Leu Ala Leu Gln Leu Ala Ile Leu Leu Lys Glu
            435                 440                 445

Asn Asn Asp Ile Glu Glu Gly Gly Ser Arg Gln Ser Leu Met Glu Met
450                 455                 460

Gln Cys Arg His Gly Val Lys Glu Met Phe Lys Asp Phe Gln Leu Arg
465                 470                 475                 480

Gln Pro Pro Leu Val Pro Ser Arg Lys Gly Glu Thr Pro Pro Ser Gly
                485                 490                 495
```

```
Thr Ser Ser Ala Phe Ser Ser Tyr Phe Asn Asn Lys Val Gly Ile Pro
            500             505                 510

Gln Glu His Val Asp His Asp Phe Asp Ala Asn Gln Leu Leu Asn
        515             520             525

Lys Ile Asn Glu Pro Pro Lys Pro Ala Pro Arg Gln Gly Ser Gly Arg
        530             535                 540

Asp Gln Pro Leu Asn Ser Lys Lys Lys Arg Leu Leu Ser Phe Arg
545             550             555                 560

Asp Val Asp Phe Glu Glu Asp Ser Asp Gly Ser Gly Arg Asp Gln Pro
                565             570                 575

Leu Asn Ser Lys Lys Lys Arg Leu Leu Ser Phe Arg Asp Val Asp
            580             585             590

Phe Glu Glu Asp Ser Asp Gly Ser Gly Arg Asp Gln Pro Leu Asn Ser
        595             600             605

Lys Lys Lys Lys Arg Leu Leu Ser Phe Arg Asp Val Asp Phe Glu Glu
            610             615             620

Asp Ser Asp Gly Ser Gly
625             630
```

US 11,324,824 B2

SOMATIC OPSINS FOR SINGLE CELL RESOLUTION OPTOGENETICS

RELATED APPLICATIONS

This application is a National Stage Filing under U.S.C. § 371 of PCT International Application PCT/US2017/035862, filed Jun. 3, 2017, which was published under PCT Article 21(2) in English, which claims benefit under 35 U.S.C. § 119(e) of U.S. Provisional application Ser. No. 62/345,274 filed Jun. 3, 2016, the disclosure of each of which is incorporated by reference herein in its entirety.

GOVERNMENT INTEREST

This invention was made with government support under NIH 6928706 and NIH 6931693 awarded by the National Institutes of Health. The government has certain rights in the invention.

FIELD OF THE INVENTION

The invention, in some aspects, relates to polypeptide molecules and their encoding nucleic acid molecules and use of such molecules to target opsins to the soma of cells in which they are expressed. Compositions of the invention may be delivered to cells and subjects and used in methods to modulate electrical activity of the cells. The invention, in part, also includes methods to test candidate modulatory agents and methods to treat diseases and conditions in subjects.

BACKGROUND OF THE INVENTION

In recent years, a great deal of interest has arisen around the possibility of two-photon (2P) stimulation of individual neurons expressing optogenetic proteins. 2P activation is essential for selective targeting of single neurons because it excites opsins precisely where the laser light is aimed, due to the quadratic dependence of 2P opsin excitation on light intensity. In contrast, in one photon illumination, the linear dependence of the opsin excitation on the light intensity results in out-of-focus light powerful enough to excite neurons other than the targeted ones. 2P activation of opsins is robust at a biophysical level, with excellent cross section for opsin photoactivation (Rickgauer, J. P., & Tank, D. W. (2009). PNAS US, 106(35), 15025-15030), but a challenge is to generate enough photo-evoked current using the micrometer-sized excitation volume of conventional 2P microscopy.

In a neuronal network, cell bodies are densely surrounded by neurites of neighboring cells, whose membranes are separated by very thin gaps of extracellular space, smaller than the diffraction limit of light (Mikula, S., & Denk, W. (2015). Nature Methods, 12(6), 541-6; Nicholson, C., & Sykova, E. (1998). Trends in Neurosci., 21(5), 207-215; Pallotto, M., et al., (2015). eLife, 4, e08206. doi:10.7554/eLife.08206). Thus, if neurons within a region are bearing densely expressed opsins, even 2P stimulation of a single neuron's cell body may excite opsins on dendrites or axons that are passing by, causing stray excitation of those nearby neurons. As a result, stimulating single cells without artifactual drive of nearby cells remains a challenge, because light aimed at one cell body or soma would cause not only activation of that particular neuron, but recruitment of other neurons whose processes cross the illumination volume. This crosstalk problem prevents single cell resolution, while performing both single- and multiple-cell stimulation. Thus, although there have been recent advances in 2P stimulation technology in optogenetic methods, there remain difficulties that reduce efficiency and usefulness of these methods.

SUMMARY OF THE INVENTION

According to an aspect of the invention, compositions that include a soma-targeting polypeptide are provided, wherein the soma-targeting polypeptide includes at least one of: a KA2 polypeptide or functional variant thereof, a myosin 5-myosin-6 binding repeat (M5M6BR) polypeptide or functional variant thereof; and an rSK-1-tail polypeptide or functional variant thereof. In some embodiments, the soma-targeting polypeptide also includes a cargo polypeptide. In some embodiments, the cargo polypeptide includes an opsin polypeptide. In certain embodiments, the opsin is a channelrhodopsin. In some embodiments, the channelrhodopsin is a CoChR channelrhodopsin, a JAWS opsin, or a CsChrimson opsin. In some embodiments, the composition is a fusion protein and includes one or more of the soma-targeting polypeptide and the opsin polypeptide. In certain embodiments, the soma-targeting polypeptide comprises a KA2 polypeptide including an amino acid sequence set forth as SEQ ID NO: 1. In some embodiments, the amino acid sequence of the KA2 polypeptide is a sequence set forth as: SEQ ID NO: 3, 10, 12, 14, or a functional variant thereof. In some embodiments, the KA2 polypeptide functional variant includes an amino acid sequence of SEQ ID NO: 1 with 1, 2, 3, 4, 5, 6, 7, 8, 9, 10, or more sequence modifications. In some embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of SEQ ID NO: 1. In certain embodiments, the functional variant includes an amino acid sequence of SEQ ID NO: 3, 10, 12, or 14 with 1, 2, 3, 4, 5, 6, 7, 8, 9, 10, or more sequence modifications to the amino acid sequence of SEQ ID NO: 3, 10, 12, or 14, respectively. In some embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of at least one of SEQ ID NOs: 3, 10, 12, and 14. In some embodiments, the soma-targeting polypeptide includes a myosin 5 binding repeat-myosin 6 binding repeat polypeptide (M5M6BR) including one or more of the amino acid sequence set forth as SEQ ID NO: 22 and one or more of the amino acid sequence set forth as SEQ ID NO: 23. In certain embodiments, the M5M6BR polypeptide includes the amino acid sequence set forth as one of: SEQ ID NOs: 32 and 51-59. In some embodiments, the M5M6BR polypeptide functional variant includes an amino acid sequence of a parent M5M6BR polypeptide with 1, 2, 3, 4, 5, 6, 7, 8, 9, 10, or more sequence modifications in the parent M5M6BR amino acid sequence. In certain embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of the parent M5M6BR sequence. In some embodiments, the soma-targeting polypeptide includes an rSK-1-tail polypeptide comprising an amino acid sequence set forth as SEQ ID NO: 31.

In some embodiments, the rSK-1-tail polypeptide functional variant includes an amino acid sequence of SEQ ID NO: 31 with 1, 2, 3, 4, 5, 6, 7, 8, 9, 10, or more sequence modifications. In some embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of SEQ ID NO: 31. In certain embodiments, when expressed in a cell, the KA2 polypeptide or functional variant thereof, the M5M6BR polypeptide or functional variant thereof, or the rSK-1-tail polypeptide or functional variant thereof targets the composition to the soma of the cell. In some embodiments, the composition is in a cell. In some embodiments, the cell is a vertebrate cell and optionally is a mammalian cell. In certain embodiments, the cell is an excitable cell. In some embodiments, the composition is a pharmaceutical composition and comprises a pharmaceutically acceptable carrier. In some embodiments, the composition also includes one or more of a: trafficking agent, targeting agent, and detectable label.

According to another aspect of the invention, a polynucleotide with a nucleic acid sequence encoding the KA2 polypeptide or functional variant thereof, the myosin 5-myosin-6 binding repeat (M5M6BR) polypeptide or functional variant thereof, or the rSK-1-tail polypeptide or functional variant thereof of any embodiment of the aforementioned aspect of the invention is provided. In certain embodiments, the nucleic acid sequence also includes a nucleic acid sequence encoding an opsin polypeptide. In some embodiments, the nucleic acid sequence is a mammalian codon-optimized DNA sequence.

According to another aspect of the invention, compositions that include a polynucleotide having a nucleic acid sequence of any aforementioned embodiment of the invention are provided. In some embodiments, the composition is a pharmaceutical composition and comprises a pharmaceutically acceptable carrier. In certain embodiments, the composition also includes one or more of a trafficking agent, a targeting agent, and a detectable label.

According to another aspect of the invention, vectors that include the nucleic acid sequence of any aforementioned embodiments of nucleic acid sequences are provided. In some embodiments, the nucleic acid sequence is operatively linked to a promoter sequence. In some embodiments, the vector also includes one, two, or more nucleic acid signal sequences operatively linked to a nucleic acid sequence encoding an opsin polypeptide. In certain embodiments, the vector is a plasmid vector, cosmid vector, viral vector, or an artificial chromosome. In some embodiments, the vector also includes one or more of: a nucleic acid sequence encoding an opsin polypeptide. In some embodiments, an expression product of the vector is a fusion protein comprising the KA2 polypeptide or functional variant thereof fused to the opsin polypeptide. In some embodiments, an expression product of the vector is a fusion protein comprising the M5M6BR polypeptide or functional variant thereof fused to the opsin polypeptide. In certain embodiments, an expression product of the vector is a fusion protein comprising the rSK-1-tail polypeptide or functional variant thereof fused to the opsin polypeptide. In some embodiments, the vector also includes a nucleic acid sequence encoding one or more of a trafficking agent, a targeting agent, and a detectable label. In some embodiments, the vector is in a cell. In some embodiments, the cell is a vertebrate cell and optionally is a mammalian cell. In some embodiments, the cell is an excitable cell. In certain embodiments, the amino acid sequence of the KA2 polypeptide is set forth as SEQ ID NO:1. In some embodiments, the amino acid sequence of M5M6BR polypeptide is set forth as one of SEQ ID NO: 32 and 51-59. In some embodiments, the amino acid sequence of the rSK-1-tail polypeptide is set forth as SEQ ID NO: 31.

According to another aspect of the invention, a cell that includes any of the aforementioned embodiments of a vector is provided.

According to another aspect of the invention, pharmaceutical compositions that include any aforementioned embodiment of a vector are provided. In certain embodiments, the pharmaceutical compositions also include one or more of: a pharmaceutically acceptable carrier, a trafficking agent, a targeting agent, and a detectable label.

According to another aspect of the invention, fusion proteins that include a soma-targeting polypeptide are provided wherein the soma-targeting polypeptide comprises at least one of: a KA2 polypeptide or functional variant thereof, a myosin 5-myosin-6 binding repeat (M5M6BR) polypeptide or functional variant thereof; and a rSK-1-tail polypeptide or functional variant thereof. In some embodiments, the fusion protein includes a KA2 polypeptide having the amino acid sequence set forth as SEQ ID NO: 1, 3, 10, 12, 14, or a functional variant thereof. In some embodiments, the fusion protein also includes an opsin polypeptide. In some embodiments, the fusion protein also includes a detectable label. In certain embodiments, the fusion protein is in a cell. In some embodiments, the cell is a vertebrate cell, and optionally is a mammalian cell. In some embodiments, the cell is an excitable cell. In some embodiments, the functional variant includes an amino acid sequence of SEQ ID NO: 1 with 1, 2, 3, 4, 5, 6, 7, 8, 9, 10, or more sequence modifications. In certain embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of SEQ ID NO: 1. In some embodiments, the functional variant includes an amino acid sequence of SEQ ID NO: 3, 10, 12, or 14 with 1, 2, 3, 4, 5, 6, 7, 8, 9, 10, or more sequence modifications to the amino acid sequence of SEQ ID NO: 3, 10, 12, or 14, respectively. In some embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of at least one of SEQ ID NOs: 3, 10, 12, and 14. In certain embodiments, when expressed in a cell, the KA2 polypeptide or functional variant thereof, the M5M6BR polypeptide or functional variant thereof, and the rSK-1-tail polypeptide or functional variant thereof, targets the fusion protein to the soma of the cell. In some embodiments, the soma-targeting polypeptide comprises a M5M6BR polypeptide comprising an amino acid sequence set forth as one of SEQ ID Nos: 32 and 51-59. In some embodiments, the M5M6BR polypeptide includes two or more fused myosin 5-myosin 6 tandem repeats. In some embodiments, the M5M6BR polypeptide functional variant includes an amino acid sequence of a parent M5M6BR polypeptide with 1, 2, 3, 4, 5, 6, 7, 8, 9, 10, or more sequence modifications. In certain embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of the parent M5M6BR polypeptide. In some embodiments, the soma-targeting polypeptide includes an rSK-1-tail polypeptide comprising an amino acid sequence set forth as SEQ ID NO: 31. In some embodiments, the rSK-1-tail polypeptide functional variant includes an amino acid sequence of SEQ ID NO: 31 with 1, 2, 3, 4, 5, 6, 7, 8, 9, 10, or more sequence modifications. In certain embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of SEQ ID NO: 31.

According to another aspect of the invention, a cell including any embodiment of an aforementioned fusion protein is provided. In some embodiments, the cell is an in vitro, ex vivo, or in vivo cell.

According to another aspect of the invention, methods of modulating electrical activity in a cell are provided, the method including a) expressing in a host cell any embodiment of an aforementioned fusion protein aspect of the invention that includes a soma-targeting polypeptide and an opsin polypeptide; and contacting the expressed opsin polypeptide with a light under suitable conditions to activate the opsin polypeptide and modulate an electrical activity in the host cell. In certain embodiments, the host cell is a vertebrate cell, optionally a mammalian cell. In some embodiments, the host cell is a human cell. In some embodiments, the opsin is a CoChR opsin, CsChrimson, JAWS, or Chronos. In certain embodiments, the host cell is a neuronal cell, a nervous system cell, a cardiac cell, a circulatory system cell, a visual system cell, or an auditory system cell. In some embodiments, the cell is an: in vitro, ex vivo, or in vivo cell. In some embodiments, the functional variant includes an amino acid sequence of SEQ ID NO: 1 with 1, 2, 3, 4, 5, 6, 7, 8, 9, 10, or more sequence modifications. In some embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of SEQ ID NO: 1. In certain embodiments, the functional variant comprises an amino acid sequence of SEQ ID NO: 3, 10, 12, or 14 with 1, 2, 3, 4, 5, 6, 7, 8, 9, 10, or more sequence modifications to the amino acid sequence of SEQ ID NO: 3, 10, 12, or 14, respectively. In some embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of at least one of SEQ ID NOs: 3, 10, 12, and 14. In some embodiments, the soma-targeting polypeptide includes a M5M6BR polypeptide that includes an amino acid sequence set forth as one of SEQ ID NOs: 32 and 51-59. In certain embodiments, the M5M6BR polypeptide includes two or more fused myosin 5-myosin 6 tandem repeats. In some embodiments, the M5M6BR polypeptide functional variant includes an amino acid sequence of a parent M5M6BR polypeptide with 1, 2, 3, 4, 5, 6, 7, 8, 9, 10, or more sequence modifications to the parent M5M6BR amino acid sequence. In some embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of the M5M6BR polypeptide. In some embodiments, the soma-targeting polypeptide includes an rSK-1-tail polypeptide that includes an amino acid sequence set forth as SEQ ID NO: 31. In certain embodiments, the rSK-1-tail polypeptide functional variant includes an amino acid sequence of SEQ ID NO: 31 with 1, 2, 3, 4, 5, 6, 7, 8, 9, 10, or more sequence modifications. In some embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of SEQ ID NO: 31. In some embodiments, the KA2 polypeptide or functional variant thereof, the M5M6BR polypeptide or functional variant thereof, and the rSK-1-tail polypeptide or functional variant thereof, targets the fusion protein to the soma of the host cell.

According to another aspect of the invention, methods of treating a disease or condition in a subject are provided, the method including expressing in a cell of a subject in need of such treatment, a therapeutically effective amount of a fusion protein of any embodiment of any of the aforementioned fusion protein aspects of the invention, that includes a soma-targeting polypeptide and an opsin polypeptide to treat the disorder; and b) contacting the opsin polypeptide expressed in the cell with an activating stimulus under conditions suitable to modulate an electrical activity of the cell, wherein the modulated electrical activity of the cell treats the disease or condition in the subject. In certain embodiments, the opsin is a light-activated opsin and the activating stimulus is light. In some embodiments, the disease or condition is injury, brain damage, spinal cord injury, epilepsy, cardiac dysfunction, vision loss, blindness, deafness, hearing loss, ALS, Alzheimer's disease, Parkinson's disease, seizures, or a psychiatric condition. In certain embodiments, the modulation is an increase in electrical activity in the cell compared to a control activity in a cell that does not include the fusion protein. In some embodiments, the subject is a vertebrate, optionally a mammal. In some embodiments, the subject is a human. In certain embodiments, the functional variant includes an amino acid sequence of SEQ ID NO: 1 with 1, 2, 3, 4, 5, 6, 7, 8, 9, 10, or more sequence modifications. In some embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of SEQ ID NO: 1. In some embodiments, the functional variant includes an amino acid sequence of SEQ ID NO: 3, 10, 12, or 14 with 1, 2, 3, 4, 5, 6, 7, 8, 9, 10, or more sequence modifications to the amino acid sequence of SEQ ID NO: 3, 10, 12, or 14, respectively. In some embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of at least one of SEQ ID NOs: 3, 10, 12, and 14. In certain embodiments, the soma-targeting polypeptide includes a M5M6BR polypeptide that includes an amino acid sequence of one of SEQ ID NO: 32 and 51-59. In certain embodiments, the M5M6BR polypeptide comprises two or more M5M6BRs. In some embodiments, the M5M6BR polypeptide functional variant includes an amino acid sequence of a parent M5M6BR polypeptide with 1, 2, 3, 4, 5, 6, 7, 8, 9, 10, or more sequence modifications to the parent M5M6BR amino acid sequence. In some embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of its parent M5M6BR amino acid sequence. In certain embodiments, the soma-targeting polypeptide includes a rSK-1-tail polypeptide comprising an amino acid sequence set forth as SEQ ID NO: 31. In some embodiments, the rSK-1-tail polypeptide functional variant includes an amino acid sequence of SEQ ID NO: 31 with 1, 2, 3, 4, 5, 6, 7, 8, 9, 10, or more sequence modifications. In some embodiments, the amino acid sequence of the functional variant has at least: 75%, 80%, 85%, 90%, 91%, 92%, 93%, 94%, 95%, 96%, 97%, 98%, or 99% sequence identity to the amino acid sequence of SEQ ID NO: 31. In certain embodiments, the KA2 polypeptide or functional variant thereof, the M5M6BR polypeptide or functional variant thereof, and the rSK-1-tail polypeptide or functional variant thereof, targets the fusion protein to the soma of the cell.

The present invention is not intended to be limited to a system or method that must satisfy one or more of any stated objects or features of the invention. It is also important to note that the present invention is not limited to the exemplary or primary embodiments described herein. Modifications and substitutions by one of ordinary skill in the art are considered to be within the scope of the present invention.

BRIEF DESCRIPTION OF THE DRAWINGS

FIG. 1A-Q provides schematic diagrams, bar plots, graphs, traces, and photomicrographic images of embodiments of soma-targeted optogenetics methods.

Untargeted opsins express over the entire neural membrane. One can aim light at a given neural soma, but each cell body is surrounded by opsin-bearing neurites from other cells (FIG. 1A), which results in artifactual activation of those cells. Restricting opsin expression to the cell body prevents such side effects, enabling single cell optogenetic stimulation (FIG. 1B). In FIG. 1C-J photomicroscopic images are presented for cultured hippocampal neurons expressing wild-type vs. selectively trafficked CoChR fused to GFP, along with the countermarker mCherry. FIG. 1C shows a hippocampal neuron in culture expressing CoChR-GFP and mCherry, seen in the GFP channel (scale bar: 100 µm). FIG. 1D presents a zoomed-in image from the rectangle of FIG. 1C. FIG. 1E shows the neuron of FIG. 1C, seen in the mCherry channel (magenta), along with surrounding neurons. FIG. 1F provides a merged image of FIGS. 1D and E. The scale bar for FIG. 1D-F is 20 µm. Parameters for FIG. 1G-J are similar to those described for FIG. 1C-F, except procedures were performed with a neuron expressing CoChR-KA2(1-150)-GFP (abbreviated soCoChR-GFP). FIG. 1K shows a trace of whole cell current clamp recording of a cultured hippocampal neuron expressing CoChR-GFP, under current injection (10 ms duration; at left rectangle) and optical stimulation (480 nm, 34.84 mW/mm$^2$, 1 ms duration; at right rectangle). Rectangles are not to scale. FIG. 1L shows a trace under same parameters of FIG. 1K, except for a neuron expressing CoChR-KA2(1-150)-GFP (soCoChR-GFP). FIG. 1Q is a bar plot showing photocurrent decay time (τoff, in ms) for CoChR-GFP and CoChR-KA2(1-150)-GFP (soCoChR-GFP) in cultured hippocampal neurons illuminated with blue light (480 nm, 34.84 mW/mW$^2$, 5 ms) (n=10 neurons from 3 cultures, 13 neurons from 3 cultures for CoChR-GFP, CoChR-KA2(1-150)-GFP (soCoChR-GFP)). **P<0.01; see Table 3 for full statistics.

FIG. 2A-I provides schematic diagrams, photomicrographic images, traces, and bar plots showing embodiments of the invention demonstrating zero-crosstalk single cell optogenetic control of cultured neurons with one-photon illumination. FIG. 2A-B provides a schematic of the experiment. Diagrams represent cultured hippocampal neurons two weeks after transduction with AAV8-Syn-CoChR-GFP (untargeted CoChR, FIG. 2A) or AAV8-Syn-soCoChR-GFP (somatic CoChR, FIG. 2B). One cell in the field of view was patched (current-clamp). The patched cell, along with 9 neighboring cells, was photostimulated using a digital micromirror device (DMD) consecutively. FIG. 2C is an image of cultured hippocampal neurons expressing CoChR-GFP; regions of stimulation are highlighted by the circles. Numbers denote the order of stimulation. Scale bar: 20 µm. FIG. 2D has same parameters as FIG. 2C, except for soCoChR-GFP. FIG. 2e shows traces of representative current-clamp recording for a cultured hippocampal neuron expressing CoChR-GFP. Cells were photostimulated sequentially using the DMD (470 nm, 40.7 mW/mm$^2$, 1 ms light pulse). The order of the photo-stimulation, as indicated by the numbers in FIG. 2C, is given in the x-axis. The patched cell is numbered 1. FIG. 2F has same parameters as FIG. 2E, except for soCoChR-GFP. FIG. 2G is a bar plot showing the percentage of cultured hippocampal neurons which fired an action potential (AP) upon direct photostimulation, using light pulses as above (n=5 cells from 4 cultures for CoChR-GFP; n=5 cells from 5 cultures for soCoChR-GFP). FIG. 2H is a bar plot showing, averaged across all patched neurons, the percentage of photostimulated neighboring cells that yielded an AP in each patched cell (n=5 cells from 4 cultures for CoChR-GFP; n=5 cells from 5 cultures for soCoChR-GFP). Values are mean±s.e.m. P<0.01, T-test (t=3.82, P=0.0051). FIG. 2I is a bar plot showing, averaged across all patched neurons, the percentage of photostimulated neighboring cells that yielded a depolarization in each patched cell (n=5 cells, in 4 cultures for CoChR-GFP; n=5 cells, in 5 cultures for soCoChR-GFP). Values are mean±s.e.m. *P<0.001, T-test (t=19.6, P<0.0001).

FIG. 3A is a schematic representation of the two experimental setups used for holographic illumination. In setup 1 holographic photo-stimulation was achieved using an amplified fiber laser and was coupled with a two-photon (2P) scanning imaging system. In setup 2 holographic photo-stimulation was achieved using a conventional Ti:Sapphire pulsed laser and was coupled with a wide-field epifluorescence imaging system. FIG. 3B is a schematic of 2P holographic stimulation along one neurite, showing Alexa 594 fluorescence (obtained via 2P scanning at 780 nm) injected into a patched CoChR-GFP expressing neuron (GFP not shown). The Alexa 594 fluorescence was used to guide holographic spot placement (spot diameter 10 µm, λ=1030 nm, using setup 1) to different points along a neurite, at different distances from the soma. The bright emission to the right of the cell represents the patch pipette filled with Alexa 594 (scale bar, 30 µm along all three axes). FIG. 3C are traces of representative whole-cell currents recorded from a CoChR-GFP expressing neuron (left) and a soCoChR-GFP expressing neuron (right), when illuminated with a power density corresponding to the spiking threshold power density (18 µW/µm$^2$ and 101 µW/µm$^2$ for the CoChR-GFP and the soCoChR-GFP expressing cells respectively; setup used as in FIG. 3B). FIG. 3D is a bar plot of the integral of the elicited photo-current, normalized to that obtained with the spot at the soma, as a function of distance from the soma, for CoChR-GFP [darker (black) bars] and soCoChR-GFP [lighter (grey) bars] expressing neurons (spacing between spots, ~10 µm, $\lambda$=1030 nm or 920 nm for setup 1 or setup 2 respectively). For each cell, the photo-stimulation was done at the power density threshold determined for that cell (average across cells, 25±15 µW/µm$^2$ for CoChR-GFP expressing cells; 105±136 µW/µm$^2$ for soCoChR-GFP expressing cells). The normalized current values were binned into intervals of 15 µm. The normalized current integral was significantly higher in CoChR-GFP relative to soCoChR-GFP expressing cells for distances of 30 µm or more from the soma. * $P<0.05$ for distances ≥30 µm; ** $P<0.01$ for distances ≥60 µm; Kolmogorov-Smirnov (KS) test (n=16 neurites from 7 CoChR-GFP cells from 6 mice; n=22 neurites from 13 soCoChR-GFP cells from 9 mice; see Table 4 for full statistics for FIG. 3.

FIG. 4A shows the rise time of soCoChR-GFP [lighter (grey) lines] and CoChR-GFP [darker (black) lines]-mediated photocurrents, measured in mouse brain slice cortical neurons, decreased as 2P stimulation power increased (n=4-13 photostimulation powers per cell, 5 cells from 5 mice for CoChR-GFP; n=4-13 photostimulation powers per cell, for 5 cells from 5 mice for soCoChR-GFP). Data collected from setup 1 are plotted with circles, and correspond to the power scale on the bottom x-axis; data collected from setup 2 are plotted with asterisks, and correspond to the top x-axis. Dark (black) and lighter (grey) arrows indicate average threshold powers relative to setup 1 for CoChR-GFP and soCoChR-GFP expressing neurons respectively (for CoChR-GFP: 28±10 µW/µm$^2$, n=7 cells; for soCoChR-GFP: 83±39 µW/µm, n=4 cells). FIG. 4B shows the action potential (AP) latency, defined as the time from the onset of 2P stimulation to the peak of the AP, plotted vs. 2P stimulation power (n=3-5 powers per cell, for 4 cells from 3 mice for CoChR-GFP, dark (black) dots; n=3-5 powers per cell, for 3 cells from 3 mice for soCoChR-GFP, lighter (grey) dots). Lines connect data acquired from the same neuron. Horizontal dashed line denotes 15 ms latency, and vertical dashed line denotes 70 µW/µm$^2$ stimulation power, for comparison to FIG. 4C. Setups 1 and 2 were used interchangeably; power values used on setup 2 were scaled to equivalent power values for setup 1. FIG. 4C shows AP temporal jittering (measured as standard deviation of the AP latency across a series of 5 photostimulations for a given cell) plotted as a function of AP latency (n=3-5 powers per cell, for 4 cells from 3 mice for CoChR-GFP, dark (black) dots; n=3-5 powers per cell, for 3 cells from 3 mice for soCoChR-GFP, lighter (grey) dots). Lines connect data acquired from the same neuron. Setups 1 and 2 were used interchangeably. Jittering below 1 ms (horizontal dashed line) was ensured when the latency was kept below 15 ms (vertical dashed line), corresponding to a photo-stimulation power higher than approximately 70 µW/µm$^2$. The boxed areas (shaded) in both FIG. 4B and FIG. 4C mark the region at which such conditions were satisfied.

FIG. 5A-G provides schematic images, images, traces, and bar plots showing that soma-targeted opsin enables single cell control with 3D photo-activation in brain slices. FIG. 5A is a schematic of 3D holographic activation. One cell expressing CoChR-GFP or soCoChR-GFP could be patched, then neighboring cells at different z-planes illuminated with 10-15 µm diameter holographic spots. FIG. 5B provides an image of a 3D reconstruction of a multi-spot 3D holographic pattern obtained by creating a holographic illumination pattern on a thin layer of rhodamine 6G (spin coated on a glass coverslip), imaging through a second microscope objective (contoured volume size (x-y-z): 130*174*280 µm, spot diameter: 10 µm). FIG. 5C provides 2P images (imaging $\lambda$=920 nm) from a 3D z-stack used to draw 10-15 µm holographic spots (1=1030 nm, setup 1) on neighboring cells expressing CoChR-GFP (left, circles numbered 1-7) or soCoChR-GFP (right, circles numbered 1-7) and on the patched cell (circle, numbered 8), inside a volume of approximately 200×200×80 µm (scale bars: 50 µm). FIG. 5D shows results of whole-cell recording of a CoChR-GFP expressing cell (left) and a soCoChR-GFP expressing cell (right) while sequentially positioning the holographic spot on neighboring cells one at a time (represented in panel c; $\lambda$=1030 nm, setup 1, photostimulation power: 40 µW/µm$^2$ for CoChR-GFP, 43 µW/µm$^2$ for soCoChR, 30 ms duration). FIG. 5E is a bar plot showing the percentage of neighboring cells that, when stimulated, yielded an AP in a given patched cell (and averaged across all patched cells; n=5 cells from 3 mice for CoChR-GFP; n=4 cells from 4 mice for soCoChR-GFP). Values are mean±s.e.m. $\lambda$=1030 nm, setup 1, average photostimulation power: CoChR-GFP 73±33 µW/µm$^2$ soCoChR-GFP: 150±76 µW/µm$^2$, 30 ms duration. *$P<0.01$, Student's T-test (t=7.1, p=0.002). FIG. 5F provides traces from whole-cell recording of a CoChR-GFP expressing cell (left) and a soCoChR-GFP cell (right; both cells presented in FIG. 5D) during simultaneous photostimulation of neighboring cells as represented in FIG. 5C, without a stimulation spot on the soma of the patched cell. Photostimulation power density for each spot was equal to the one used in FIG. 5D (1=1030 nm, setup 1, photostimulation power: µW/µm$^2$ for CoChR-GFP, 43 µW/µm$^2$ for soCoChR-GFP, 30 ms duration). FIG. 5G is a bar plot showing the percentage of simultaneous photostimulations of neighboring cells that yielded APs in a given patched cell (and averaged across patched cells). Grey bars indicate the generation of 1 AP; blue bars indicate the generation of >1 AP (n=5 cells expressing CoChR-GFP from 3 mice; n=3 cells expressing soCoChR-GFP from 3 mice). Values are mean±s.e.m. $\lambda$=1030 nm, setup 1, average photostimulation power: 73±33 µW/µm$^2$ and 150±76 µW/µm$^2$ for CoChR-GFP expressing cells and for soCoChR-GFP expressing cells respectively; 30 ms duration. For generation of 1AP: *$P<0.01$ (Student's T-test; t=3.7, p=0.005).

FIG. 6A is an image of a hippocampal neuron expressing GFP. FIG. 6B is an image of a hippocampal neuron expressing KA2-GFP. FIG. 6C is an image of a hippocampal neuron expressing KA2(1-150)-GFP. Scale bars for FIG. 6A-C: 50 µm. FIG. 6D-F provides bar plots of GFP brightness versus position along a neurite, normalized to GFP brightness at the soma for GFP (n=5 neurites from 3 cells), KA2-GFP (n=5 neurites from 3 cells) and KA2(1-150)-GFP (n=5 neurites from 3 cells) respectively. Plotted data are mean+s.e.m. For KA2-GFP, P=0.0085525, Tukey's post hoc test (after two-way repeated measures ANOVA with factors of gene identity and distance along neurite) with GFP as the reference (see Table 3 for full statistics for FIG. 6). For KA2(1-150)-GFP, P=0.0010053, Tukey's post hoc test (after two-way repeated measures ANOVA with factors of gene identity and distance along neurite) with CoChR-GFP as the reference.

FIG. 7A-F provides photomicrographic images, traces, and a bar plot obtained from CoChR-Na$_V$1.2(II-III)-GFP expression and photostimulation in cultured hippocampal neurons. FIG. 7A-D presents images for cultured hippocampal neurons expressing CoChR-Na$_V$1.2(II-III)-GFP, along with the countermarker mCherry. FIG. 7A shows a hippocampal neuron in culture expressing CoChR-Na$_V$1.2(II-III)-GFP and mCherry, seen in the GFP channel (scale bar: 100 μm). FIG. 7B is a zoomed-in image from the rectangle of FIG. 7A. FIG. 7C shows the neuron of FIG. 7B, seen in the mCherry channel (magenta), along with other nearby neurons. FIG. 7D is a merged image of FIG. 7B and FIG. 7C (scale bar for FIG. 7B-D: 20 μm). FIG. 7E shows results from whole cell current clamp recording of a cultured hippocampal neuron expressing CoChR-Na$_V$1.2(II-III)-GFP, under current injection (10 ms duration) and optical stimulation (480 nm, 34.84 mW/mm$^2$, 1 ms duration). Rectangles are not to scale. FIG. 7F is a bar plot of GFP brightness versus position along a neurite, normalized to GFP brightness at the soma, extracted from neurites of cultured hippocampal neurons expressing CoChR-Na$_V$1.2 (II-III)-GFP (n=5 neurites taken from 5 cells from 4 cultures). See Table 3 for statistics for FIG. 7.

FIG. 8A shows resting potential. P=0.8232, one-way ANOVA with factor of gene identity (see Table 5 for full statistics for FIG. 8). FIG. 8B shows membrane capacitance. P=0.8448, one-way ANOVA with factor of gene identity. FIG. 8C shows holding current. P=0.9215, one-way ANOVA with factor of gene identity. FIG. 8D shows membrane resistance. P=0.9814, one-way ANOVA with factor of gene identity.

FIGS. 10A and B provide a top view (FIG. 10A) and lateral view (FIG. 10B) of the fluorescence emission generated by a 10 μm diameter holographic spot on a thin fluorescent layer of rhodamine 6G spin-coated on a glass coverslip. The fluorescence was collected by a second bottom objective and relayed to a CCD camera, and a z-stack is acquired by scanning the vertical position of the main upper objective. FIG. 10C is a graph showing the normalized axial intensity profile of the holographic spot corresponding to FIG. 10A and FIG. 10B. FIG. 10D shows a max projection of the fluorescence generated by a sequence of 15 μm diameter holographic spots placed on points of a square grid. Scale bar: 30 μm. FIG. 10E provides vertical and horizontal intensity profiles of FIG. 10E with and without the application of the algorithm (see Examples section for methods) for the correction of the diffraction efficiency for sequential illumination. FIG. 10F shows fluorescence generated by the simultaneous projection of 8 randomly placed holographic spots with equal intensity. Scale bar: 30 μm. FIG. 10G shows an input pattern of the GS algorithm used to calculate the hologram corresponding to FIG. 10F. Different input intensities were assigned to each spot to compensate diffraction efficiency in the plane and obtain the same power density on each spot. Scale bar: 15 μm. FIG. 10H shows an axial intensity profile of the fluorescence induced by a 10 μm holographic spot displaced over different axial positions relative to the microscope focal plane. Darker (black) and lighter (grey) curves represent intensities obtained respectively with and without the correction of diffraction efficiency for sequential illumination. FIG. 10I provides a lateral view of the 3D fluorescence pattern generated by 3 holographic spots (diameter 10 μm) of equal intensity and axial position of z=−120 μm; 0; +120 μm. Scale bar: 30 μm. FIG. 10J shows an input pattern of the GS algorithm used to calculate the hologram corresponding to FIG. 10I. Similarly to FIG. 10G, different input intensities were assigned to each spot to compensate diffraction efficiency on the vertical axis and obtain the same output power density on each spot.

FIG. 11A-H provides photomicrographic images and recording traces illustrating embodiments of strategies for soma-targeting of opsins (punctate somatic opsins). FIG. 11A provides image of CoChR-GFP expressed in a cultured hippocampal neuron. FIG. 11B shows image of the same cultured neurons expressing mCherry (additional labelling in image compared to FIG. 11A). CoChR-GFP is the labeling in same position as in FIG. 11A. FIG. 11C shows a zoomed in image of the neuron shown in FIG. 11A. FIG. 11D shows trace from a neuron expressing CoChR-GFP that was patched and stimulated electrically (10 ms, left-hand rectangle) and optically (1 ms, right-hand rectangle). FIG. 11E shows image from CHR86-GFP-MVIBDx2-MBDx3 expressed in a cultured hippocampal neuron. FIG. 11F is an image of the same cultured neurons expressing mCherry (additional labelling in image compared to FIG. 11E). CHR86-GFP-MVIBDx2-MBDx3 is the labeling in the same position in FIG. 11E. FIG. 11G shows a zoomed in image of the neuron in FIG. 11E. FIG. 11H is a trace from a neuron expressing CoChR-GFP that was patched and stimulated electrically (10 ms, left-hand rectangle) and optically (1 ms, right-hand rectangle). Scale bars: 100 μm in FIG. 11F, 10 μm in FIG. 11G FIG. 12A-C provides photomicrographic images showing expression of punctate somatic opsins (CHR86-GFP-MVIBDx2-MBDx2) in a brain slice. FIG. 12A shows labelled neurons that expressed CHR86-GFP-MVIBDx2-MBDx2 in a brain slice. FIG. 12B shows the same brain slice expressing mCherry. FIG. 12C shows merged image that shows the expressed CHR86-GFP-MVIBDx2-MBDx2 and mCherry. Scale bar: 100 μm.

Figure 1N:
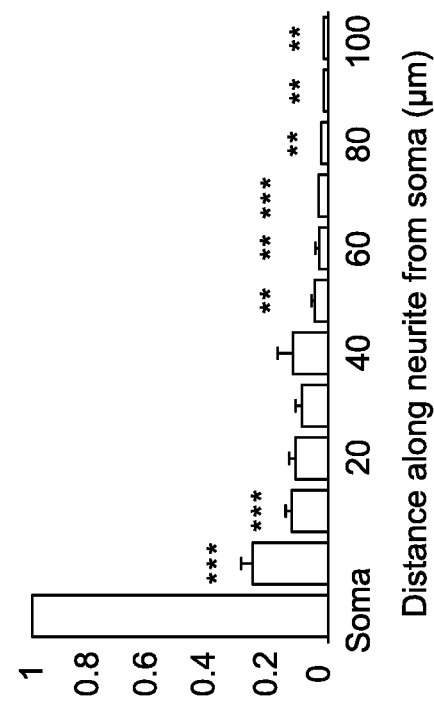
FIG. 1N includes same parameters as in FIG. 1M, except for neurons expressing CoChR-KA2(1-150)-GFP (soCoChR-GFP; n=9 neurites taken from 7 cells from 3 cultures). P<0.01 and *P<0.001, Bonferroni-corrected Kolmogorov-Smirnov test of brightness between wild-type and soma-targeted; see Table 3 for full statistics for FIG. 1). Plotted data are mean+s.e.m (standard error of the mean).
Figure 1M:
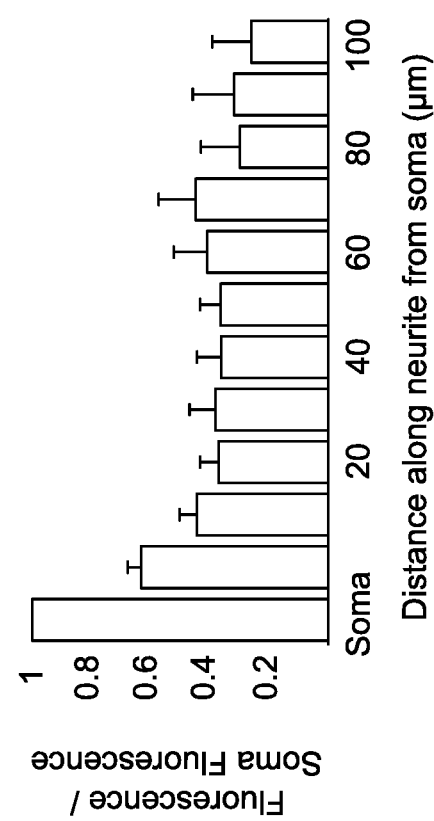
FIG. 1M is a bar plot of GFP brightness versus position along a neurite, normalized to GFP brightness at the soma, extracted from neurites of cultured hippocampal neurons expressing CoChR-GFP (n=7 neurites taken from 5 cells from 2 cultures).
Figure 1O:
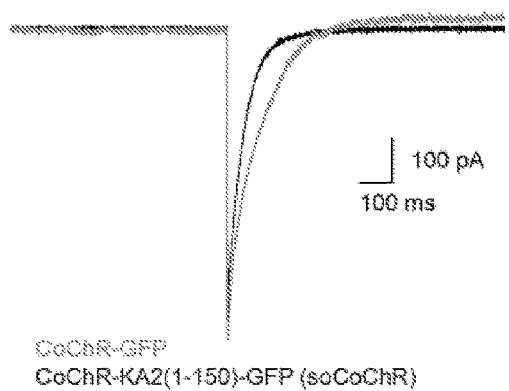
FIG. 1O shows representative photocurrents for cultured hippocampal neurons expressing CoChR-GFP (magenta) and CoChR-KA2 (1-150)-GFP (soCoChR-GFP; black), under voltage clamp conditions, using 5 ms light pulses (480 nm, 34.84 mW/mm$^2$; at rectangle).
Figure 1P:
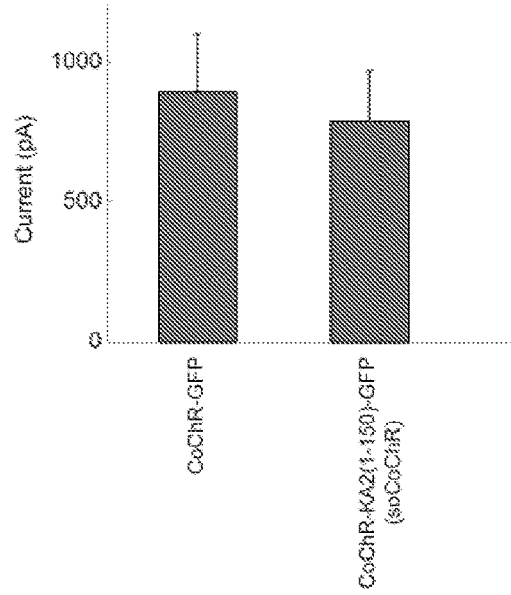
FIG. 1P is a bar plot showing peak current amplitudes (pA) for CoChR-GFP and CoChR-KA2 (1-150)-GFP (soCoChR-GFP) in cultured hippocampal neurons illuminated with blue light (480 nm, 34.84 mW/mW$^2$, 5 ms) (n=13 neurons from 3 cultures and 13 neurons from 3 cultures for CoChR-GFP and CoChR-KA2(1-150)-GFP respectively). Not significant; see Table 3 for full statistics.

BRIEF DESCRIPTION OF THE SEQUENCES
SEQ ID NO: 1 is the amino acid sequence of the KA2 polypeptide that also is referred to herein as KA2(1-150) polypeptide:
MPAELLLLLIVAFANPSCQVLSSLRMAAILDDQTVCGRGERLALALAREQINGIIE

VPAKARVEVDIFELQRDSQYETTDTMCQILPKGVVSVLGPSSSPASASTVSHICGE

KEIPHIKVGPEETPRLQYLRFASVSLYPSNEDVSLAVS.

SEQ ID NO: 2 is mammalian-codon optimized nucleic acid sequence encoding
the KA2 polypeptide set forth as SEQ ID NO: 1:
atgcccgccgaactgctgctgctgctgattgtcgcttttgctaaccttcttgccaggtgctgtcttctctgaggatggc cgctattctggacgatcagaccgtgtgcggaagaggagagaggctggcactggcactggctagggagcagatcaatggca tcattgaagtgcctgcaaaggcccgggtcgaggtggacattttcgaactgcagagagatagccagtacgagaccacagac accatgtgccagatcctgccaaaaggagtggtctccgtcctgggaccaagctcctctcctgcttctgcaagtaccgtgtc tcacatttgtggcgagaaggaaatcccccatatcaaggtcgggccagaggaaacacccaggctgcagtacctgcgcttcg cctcagtgagcctgtatccatcaaacgaggatgtgtcactggcagtcagc.

SEQ ID NO: 3 is the amino acid sequence of a 360 amino acid KA2 polypeptide:
MPAELLLLLIVAFANPSCQVLSSLRMAAILDDQTVCGRGERLALALAREQINGIIE

VPAKARVEVDIFELQRDSQYETTDTMCQILPKGVVSVLGPSSSPASASTVSHICGE

KEIPHIKVGPEETPRLQYLRFASVSLYPSNEDVSLAVSRILKSFNYPSASLICAKA

ECLLRLEELVRGFLISKETLSVRMLDDSRDPTPLLKEIRDDKVSTIIIDANASISH

LVLRKASELGMTSAFYKYILTTMDFPILHLDGIVEDSSNILGFSMFNTSHPFYPEF

VRSLNMSWRENCEASTYPGPALSAALMFDAVHVVVSAVRELNRSQEIGVKPLACTS

ANIWPHGTSLMNYLRMVEYDGLTG.

SEQ ID NO: 4 is mammalian-codon optimized nucleic acid sequence encoding the KA2
polypeptide set forth as SEQ ID NO: 3:
atgcccgccgaactgctgctgctgctgattgtcgcttttgctaaccttcttgccaggtgctgtcttctctgaggatggc cgctattctggacgatcagaccgtgtgcggaagaggagagaggctggcactggcactggctagggagcagatcaatggca tcattgaagtgcctgcaaaggcccgggtcgaggtggacattttcgaactgcagagagatagccagtacgagaccacagac accatgtgccagatcctgccaaaaggagtggtctccgtcctgggaccaagctcctctcctgcttctgcaagtaccgtgtc tcacatttgtggcgagaaggaaatcccccatatcaaggtcgggccagaggaaacacccaggctgcagtacctgcgcttcg cctcagtgagcctgtatccatcaaacgaggatgtgtcactggcagtcagccgcatcctgaagagattaattatccctccg cctctctgatttgcgccaaagctgagtgtctgctgcggctggaggaactggtgagaggcttcctgatcagcaaggaaaca ctgtccgtcaggatgctggacgatagtcgcgatcccactcctctgctgaaggagatcagggacgataaagtctccaccat cattatcgacgcaaacgccagtatttcacacctggtgctgcgcaaagcaagtgaactggggatgacctcagccttctaca aatatatcctgactaccatggactttcccatcctgcacctggacggaattgtggaggatagttcaaacattctgggcttc tctatgtttaatactagtcatcccttctaccctgaatttgtgaggtccctgaacatgtcttggcgcgagaattgcgaagc ttcaacctatccaggaccagcactgagcgcagctctgatgttcgatgccgtgcacgtggtcgtgtccgctgtcagagagc tgaataggtctcaggaaatcggcgtgaagcctctggcatgtacttctgccaacatttggccacatgggaccagtctgatg aattacctgaggatggtggagtatgacggcctgaccgga.

SEQ ID NO: 5 is: nucleic acid sequence:
ggsggtggsggt.

SEQ ID NO: 6 is the DNA sequence of the ER export sequence (also referred to
herein as "ER2":
ttctgctacgagaatgaagtg.

SEQ ID NO: 7 is the amino acid sequence of the ER export sequence (also
referred to herein as "ER2":
FCYENEV.

SEQ ID NO: 8 is the DNA sequence of KGC, which is a C terminal export sequence
from the potassium channel Kir2.1:
aaatccagaattacttctgaagggagtatatccctctggatcaaatagacatcaatgtt.

SEQ ID NO: 9 is the amino acid sequence of KGC, which is a C terminal export
sequence from the potassium channel Kir2.1:
KSRITSEGEYIPLDQIDINV.

SEQ ID NO: 10 amino acid sequence of a variant of KA2(1-100) that has Y76A substitution and lacks a natural dimerization site on Tyrosine 76:
MPAELLLLLIVAFANPSCQVLSSLRMAAILDDQTVCGRGERLALALAREQINGIIE

VPAKARVEVDIFELQRDSQAETTDTMCQILPKGVVSVLGPSSSP.

SEQ ID NO: 11 nucleic acid encoding SEQ ID NO: 10, a variant of KA2(1-100) that has Y76A substitution and lacks a natural dimerization site on Tyrosine 76:
atgcccgccgaactgctgctgctgctgattgtcgcttttgctaaccatcttgccaggtgctgtatctctgaggatggccg ctattctggacgatcagaccgtgtgcggaagaggagagaggctggcactggcactggctagggagcagatcaatggcatc attgaagtgcctgcaaaggcccgggtcgaggtggacattttcgaactgcagagagatagccaggccgagaccacagacac catgtgccagatcctgccaaaaggagtggtctccgtcctgggaccaagctcctctcct.

SEQ ID NO: 12 is the amino acid sequence of a KA2 (1-100) polypeptide:
MPAELLLLLIVAFANPSCQVLSSLRMAAILDDQTVCGRGERLALALAREQINGIIE

VPAKARVEVDIFELQRDSQYETTDTMCQILPKGVVSVLGPSSSP.

SEQ ID NO: 13 is the nucleic acid sequence of KA2 (1-100) [SEQ ID NO: 12]:
atgcccgccgaactgctgctgctgctgattgtcgcttttgctaaccatcttgccaggtgctgtatctctgaggatggccg ctattctggacgatcagaccgtgtgcggaagaggagagaggctggcactggcactggctagggagcagatcaatggcatc attgaagtgcctgcaaaggcccgggtcgaggtggacattttcgaactgcagagagatagccagtacgagaccacagacac catgtgccagatcctgccaaaaggagtggtctccgtcctgggaccaagctcctctcct.

SEQ ID NO: 14 is the amino acid sequence of a KA2(1-75) polypeptide:
MPAELLLLLIVAFANPSCQVLSSLRMAAILDDQTVCGRGERLALALAREQINGIIE

VPAKARVEVDIFELQRDSQ.

SEQ ID NO: 15 is the nucleic acid sequence of KA2(1-75) [SEQ ID NO: 14]:
atgcccgccgaactgctgctgctgctgattgtcgcttttgctaaccatcttgccaggtgctgtatctctgaggatggccg ctattctggacgatcagaccgtgtgcggaagaggagagaggctggcactggcactggctagggagcagatcaatggcatc attgaagtgcctgcaaaggcccgggtcgaggtggacattttcgaactgcagagagatagccag.

SEQ ID NO: 16 is amino acid sequence of a full-length (979 aa) mus musculus Kainate Receptor Subunit 2, also referred to as: KA2 (grik5), and having GenBank Accession No. AAI10683.1:
MPAELLLLLIVAFANPSCQVLSSLRMAAILDDQTVCGRGERLALALAREQINGIIE

VPAKARVEVDIFELQRDSQYETTDTMCQILPKGVVSVLGPSSSPASASTVSHICGE

KEIPHIKVGPEETPRLQYLRFASVSLYPSNEDVSLAVSRILKSFNYPSASLICAKA

ECLLRLEELVRGFLISKETLSVRMLDDSRDPTPLLKEIRDDKVSTIIIDANASISH

LVLRKASELGMTSAFYKYILTTMDFPILHLDGIVEDSSNILGFSMFNTSHPFYPEF

VRSLNMSWRENCEASTYPGPALSAALMFDAVHVVVSAVRELNRSQEIGVKPLACTS

ANIWPHGTSLMNYLRMVEYDGLTGRVEFNSKGQRTNYTLRILEKSRQGHREIGVWY

SNRTLAMNATTLDINLSQTLANKTLVVTTILENPYVMRRPNFQALSGNERFEGFCV

DMLRELAELLRFRYRLRLVEDGLYGAPEPNGSWTGMVGELINRKADLAVAAFTITA

EREKVIDFSKPFMTLGISILYRVHMGRKPGYFSFLDPFSPAVWLFMLLAYLAVSCV

LFLAARLSPYEWYNPHPCLRARPHILENQYTLGNSLWFPVGGEMQQGSEIMPRALS

TRCVSGVWWAFTLIIISSYTANLAAFLTVQRMEVPVESADDLADQTNIEYGTIHAG

STMTFFQNSRYQTYQRMWNYMQSKQPSVFVKSTEEGIARVLNSRYAELLESTMNEY

HRRLNCNLTQIGGLLDTKGYGIGMPLGSPERDEITLAILQLQENNRLEILKRKWWE

GGRCPKEEDHRAKGLGMENIGGIFVVLICGLIIAVEVAVMEFIWSTRRSAESEEVS

VCQEMLQELRHAVSCRKTSRSRRRRRPGGPSRALLSLRAVREMRLSNGKLYSAGAG

GDAGAHGGPQRLLDDPGPPGGPRPQAPTPCTRVRVCQECRRIQALRASGAGAPPRG

LGTPAEATSPPRPRPGPTGPRELTEHE.

SEQ ID NO: 17 is the (2940 nt) nucleic acid sequence that encodes SEQ ID NO: 16:
atgccggctgagctgctgctgctgctgatagtcgccttcgccaatcccagctgccaggtgctgtcatcactgcgcatggc tgcaatcctggacgaccagaccgtgtgtggccgtggtgagcgtctggccctggccctggcccgagagcagatcaatggga tcatcgaggtcccagccaaggccagagtggaagtagacatctttgagctgcagcgggacagccagtacgagaccacggac accatgtgtcagatcctgcccaagggggttgtatctgtcttgggaccctcctccagcccagcttctgcctccaccgtgag ccatatctgtggggagaaggagattccccacatcaaggtgggtcctgaggagacgccccgccttcagtaccttcgcttcg catctgtcagcctgtacccagtaatgaagatgtcagcctggcagtctcccgaatcctcaagtcctttaactaccctca gctagcctcatctgcgccaaggctgagtgcctgctgcggctagaagaactggtgcgaggcttcctcatctccaaggagac actgtccgtgaggatgcttgatgacagccgggaccccacgccgctactcaaggagatccgagatgacaaagtgtccacca tcatcattgatgccaatgcgtccatctcccaccttgtcctccgtaaggatcggagctgggaatgacctcagcgtMacaag tacatcctcaccaccatggactttcccatcctgcatctggatggtatcgtggaggactcctccaacatcctgggcttttc catgttcaacacctcccacccttctacccagagtttgtgcgcagcctcaacatgtcctggagggagaactgtgaagcca gcacctatcctggccctgcgctgtccgcagccctgatgtttgacgctgtgcacgtggtggtaagcgctgtccgagaactg aaccgaagccaggagattggcgtcaagccactggcctgcacttcggccaacatttggccccatgggaccagccttatgaa ctaccttcgaatggtagagtatgacgggctgaccgggcgggttgagttcaacagcaaagggcagaggaccaactacacac tacgcatcctggagaagtcccgccagggccaccgtgagataggggtgtggtactctaaccggaccctggccatgaatgcc accaccctggacatcaacctgtcacagactctagccaacaagactctggtggtcacaactatcctggagaacccgtatgt tatgcgccggcccaacttccaggccttgtcagggaatgagcgcttcgagggcttctgcgtggacatgctcagggagctgg ccgagctgctgcgcttccgataccgcctgcggttggtagaggacggactctacggggcacctgagcccaacggttcctgg acaggcatggttggagaactcatcaaccggaaggcagacctggctgtggcagccttcaccatcaccgccgagagggagaa ggtcatcgacttctccaagcccttcatgaccctggggatcagcatcctctacagggtgcacatgggccgcaagcctggct acttctccttcctggaccccttctcccctgccgtgtggctcttcatgcttcttgcctacctggctgtcagctgtgtcttg ttcctggctgccaggctgagcccttatgagtggtacaacccacaccccgtgtctccgggcgcgtcccatatcctggagaa ccagtacacgctgggcaacagcctctggttccccgtgggtggcttcatgcagcagggctcggagatcatgccgcgggcac tgtccacacgctgtgtcagcggagtctggtgggccttcaccttgatcatcatctcctcctacacggccaacctggctgcc ttcctcacggtgcagcgcatggaggtgccggtggagtcggctgacgacctggcggatcagaccaacattgagtacgcac tatccacgctggctccaccatgaccttcttccagaactcgcggtaccagacgtaccagcggatgtggaactacatgcaat cgaagcagcccagcgtgtttgtcaagagcacagaggagggaatcgcccgcgtcctcaactcccgctatgccttcctgctg gagtccaccatgaacgagtaccacaggcgcctcaattgcaacctcacccagatcggggggcctcctcgacaccaagggcta cggcatcggcatgccgctgggctccccttccggggatgagatcacactggccatcctgcagctccaggagaacaacaggc tggagatcctgaagcgcaagtggtgggagggcggccggtgccccaaggaggaggaccacagggccaaaggtttgggcatg gagaacattggcggcatttttgtcgtgctgatctgtggcctcatcattgctgtcttcgtggcggtcatggagttcatctg gtccacgcggaggtcagcggagtccgaggaggtgtcggtgtgccaggagatgctgcaggagctacgccacgccgtgtctt gccgaaagacctcgcgttcccgccggcgccggcgccctggtggcccgagccgggccctgctgtcgctgcgcgcagtccgc gagatgcgactcagcaacggcaagctctactcggccggcgcgggcggggacgcgggcgcacggggtccgcagcgcct cctggacgaccccgacctcctgggggaccccggcccaggctcccacgccctgcacgcacgtgcgcgtctgccaggagt gcaggcgcatccaggcgctgcgagcttcgggggccggggcgccccacgtggcctgggcaccccagccaagccaccagc ccgcctcggccgcggccaggccccaccggaccccgcgagctgaccgagcacgaatga.

SEQ ID NO: 18 is the amino acid sequence of CoChR:
MLGNGSAIVPIDQCFCLAWTDSLGSDTEQLVANILQWFAFGFSILILMFYAYQTW

RATCGWEEVYVCCVELTKVIIEFFHEFDDPSMLYLANGHRVQWLRYAEWLLTCPV

ILIHLSNLTGLKDDYSKRTMRLLVSDVGTIVWGATSAMSTGYVKVIFFVLGCIYG

ANTFFHAAKVYIESYHVVPKGRPRTVVRIMAWLFFLSWGMFPVLFVVGPEGFDAI

SVYGSTIGHTIIDLMSKNCWGLLGHYLRVLIHQHIIIYGDIRKKTKINVAGEEME

VETMVDQEDEETV.

SEQ ID NO: 19 is mammalian codon optimized nucleic acid sequence of CoChR
[SEQ ID NO: 18]:
atgctggggaacggcagcgccattgtgcctatcgaccagtgatttgcctggcttggaccgacagcctgggaagcgataca gagcagctggtggccaacatcctccagtggttcgccttcggcttcagcatcctgatcctgatgttctacgcctaccagac ttggagagccacttgcggttgggaggaggtctacgtctgttgcgtcgagctgaccaaggtcatcatcgagttcttccacg agttcgacgaccccagcatgctgtacctggctaacggacaccgagtccagtggctgagatacgcagagtggctgctgact tgtcccgtcatcctgatccacctgagcaacctgaccggcctgaaggacgactacagcaagcggaccatgaggctgctggt gtcagacgtgggaaccatcgtgtggggagctacaagcgccatgagcacaggctacgtcaaggtcatcttcttcgtgctgg gttgcatctacggcgccaacaccttcttccacgccgccaaggtgtatatcgagagctaccacgtggtgccaaagggcaga cctagaaccgtcgtgcggatcatggcttggctgttcttcctgtcttgggcatgttccccgtgctgttcgtcgtgggacc agaaggattcgacgccatcagcgtgtacggctctaccattggccacaccatcatcgacctcatgagcaagaattgttggg gcctgctgggacactatctgagagtgctgatccaccagcacatcatcatctacggcgacatccggaagaagaccaagatc aacgtggccggcgaggagatggaagtggagaccatggtggaccaggaggacgaggagacagtg.

SEQ ID NO: 20 is amino acid sequence of soCoChR:
MLGNGSAIVPIDQCFCLAWTDSLGSDTEQLVANILQWFAFGFSILILMFYAYQTW

RATCGWEEVYVCCVELTKVIIEFFHEFDDPSMLYLANGHRVQWLRYAEWLLTCPV

ILIHLSNLTGLKDDYSKRTMRLLVSDVGTIVWGATSAMSTGYVKVIFFVLGCIYG

ANTFFHAAKVYIESYHVVPKGRPRTVVRIMAWLFFLSWGMFPVLFVVGPEGFDAI

SVYGSTIGHTIIDLMSKNCWGLLGHYLRVLIHQHIIIYGDIRKKTKINVAGEEME

VETMVDQEDEETVGGSGGTGGSGGTMPAELLLLLIVAFANPSCQVLSSLRMAAIL

DDQTVCGRGERLALALAREQINGIIEVPAKARVEVDIFELQRDSQYETTDTMCQI

LPKGVVSVLGPSSSPASASTVSHICGEKEIPHIKVGPEETPRLQYLRFASVSLYP

SNEDVSLAVSGASGGTVSKGEELFTGVVPILVELDGDVNGHKFSVSGEGEGDATY

GKLTLKFICTTGKLPVPWPTLVTTLTYGVQCFSRYPDHMKQHDFFKSAMPEGYVQ

ERTIFFKDDGNYKTRAEVKFEGDTLVNRIELKGIDEKEDGNILGHKLEYNYNSHN

VYIMADKQKNGIKVNEKIRHNIEDGSVQLADHYQQNTPIGDGPVLLPDNHYLSTQ

SALSKDPNEKRDHMVLLEFVTAAGITLGMDELYK.

SEQ ID NO: 21 is the mammalian codon optimized nucleic acid sequence encoding
soCoChR [SEQ ID NO: 20]:
atgctggggaacggcagcgccattgtgcctatcgaccagtgatttgcctggcttggaccgacagcctgggaagcgataca gagcagctggtggccaacatcctccagtggttcgccttcggcttcagcatcctgatcctgatgttctacgcctaccagac ttggagagccacttgcggttgggaggaggtctacgtctgttgcgtcgagctgaccaaggtcatcatcgagttcttccacg agttcgacgaccccagcatgctgtacctggctaacggacaccgagtccagtggctgagatacgcagagtggctgctgact tgtcccgtcatcctgatccacctgagcaacctgaccggcctgaaggacgactacagcaagcggaccatgaggctgctggt gtcagacgtgggaaccatcgtgtggggagctacaagcgccatgagcacaggctacgtcaaggtcatcttcttcgtgctgg gttgcatctacggcgccaacaccttcttccacgccgccaaggtgtatatcgagagctaccacgtggtgccaaagggcaga cctagaaccgtcgtgcggatcatggcttggctgttcttcctgtcttgggcatgttccccgtgctgttcgtcgtgggacc agaaggattcgacgccatcagcgtgtacggctctaccattggccacaccatcatcgacctcatgagcaagaattgttggg gcctgctgggacactatctgagagtgctgatccaccagcacatcatcatctacggcgacatccggaagaagaccaagatc aacgtggccggcgaggagatggaagtggagaccatggtggaccaggaggacgaggagacagtgggaggttcaggtggaac -continued

```
cggtggaagtggaggtaccatgcccgccgaactgctgctgctgctgattgtcgcttttgctaaccttcttgccaggtgc tgtcttctctgaggatggccgctattctggacgatcagaccgtgtgcggaagaggagagaggctggcactggcactggct agggagcagatcaatggcatcattgaagtgcctgcaaaggcccgggtcgaggtggacattttcgaactgcagagagatag ccagtacgagaccacagacaccatgtgccagatcctgccaaaaggagtggtctccgtcctgggaccaagctcctctcctg cttctgcaagtaccgtgtctcacatttgtggcgagaaggaaatcccccatatcaaggtcgggccagaggaaacacccagg ctgcagtacctgcgcttcgcctcagtgagcctgtatccatcaaacgaggatgtgtcactggcagtcagcggagctagcgg aggtactgtgagcaagggcgaggagctgttcaccggggtggtgcccatcctggtcgagctggacggcgacgtaaacggcc acaagttcagcgtgtccggcgagggcgagggcgatgccacctacggcaagctgacccctgaagttcatttgcaccaccggc aagctgcccgtgccctggcccaccctcgtgaccaccctgacctacggcgtgcagtgcttcagccgctaccccgaccacat gaagcagcacgacttcttcaagtccgccatgcccgaaggctacgtccaggagcgcaccatcttcttcaaggacgacggca actacaagacccgcgccgaggtgaagttcgagggcgacaccctggtgaaccgcatcgagctgaagggcatcgacttcaag gaggacggcaacatcctggggcacaagctggagtacaactacaacgccacaacgtctatatcatggccgacaagcagaa gaacggcatcaaggtgaacttcaagatccgccacaacatcgaggacggcagcgtgcagctcgccgaccactaccagaga acaccccatcggcgacggccccgtgctgctgcccgacaaccactacctgagcacccagtccgccctgagcaaagacccc aacgagaagcgcgatcacatggtcctgctggagttcgtgaccgccgccgggatcactctcggcatggacgagctgtacaa gtaa.
```

SEQ ID NO: 22 amino acid sequence of myosin 5 binding repeat (MBD):
RDQPLNSKKKKRLLSFRDVDFEEDSD.

SEQ ID NO: 23 is amino acid sequence of myosin 6 binding repeat (MVIBD):
KVDKMLLQELSEKLELAEQALASKQLQMDEMKQTLAKQEEDLETMAVLRAQME

VYCSDFHAERAAREKIHEEKEQLALQLAILLKENNDIEEGGSRQSLMEMQCRH

GVKEMEKDFQLRQPPLVPSRKGETPPSGTSSAFSSYFNNKVGIPQEHVDHDDF

DANQLLNKINEPPKPAPRQ.

SEQ ID NO: 24 is DNA sequence of CsChrimson-mRuby3-12-MVIBDx2-MBDx2, which encodes the CsChrimson-mRuby3-12-MVIBDx2-MBDx2 polypeptide.

```
atgagcagactggtcgccgcttcttggctgctggctctcctcctctgcgaattaccagcacaacaacagcctctagcgc cccagcagcttcttctacagacggaacagccgccgcagcagtgtctcactacgccatgaacggcttcgacgagctggcta aaggagccgtggtgccagaagaccactttgtctgcggaccagccgacaagtgctattgctccgcttggctgcacagcaga ggcacaccaggagaaaagatcggcgccccaggtctgccagtggattgctttcagcatcgccatcgccctgctgacattcta cggcttcagcgcctggaaggccacttgcggttgggaggaggtctacgtctgttgcgtcgaggtgctgttcgtgaccctgg agatcttcaaggagttcagcagccccgccacagtgtacctgtctaccggcaaccacgctattgcctgcgctacttcgag tggctgctgtcttgccccgtgatcctgatcaagctgagcaacctgagcggcctgaagaacgactacagcaagcggaccat gggcctgatcgtgtcttgcgtgggaatgatcgtgttcggcatggccgcaggactggctaccgattggctcaagtggctgc tgtatatcgtgtcttgcatctacggcggctacatgtacttccaggccgccaagtgctacgtggaagccaaccacagcgtg cctaaaggccattgccgcatggtcgtgaagctgatggcctacgcttacttcgcctcttgggggcagctacccaatcctctg ggcagtgggaccagaaggactgctgaagctgagcccttacgccaacagcatcggccacagcatctgcgacatcatcgcca aggagttttggaccttcctggcccaccacctgaggatcaagatccacgagcacatcctgatccacggcgacatccggaag accaccaagatggagatcggaggcgaggaggtggaagtggaagagttcgtggaggaggaggacgaggacacagtgggagc tagcggaggtactgtgtctaagggcgaagagctgatcaaggaaatatgcgtatgaaggtggtcatggaaggttcggtca acggccaccaattcaaatgcacaggtgaaggagaaggcagaccgtacgagggagtgcaaaccatgaggatcaaagtcatc gagggaggaccccctgccatttgcctttgacattcttgccacgtcgttcatgtatggcagccgtacctttatcaagtaccc ggccgacatccctgatttctttaaacagtcctttcctgagggttttacttgggaaagagttacgagatacgaagatggtg
```

-continued

```
gagtcgtcaccgtcacgcaggacaccagccttgaggatggcgagctcgtctacaacgtcaaggtcagaggggtaaacttt ccctccaatggtcccgtgatgcagaagaagaccaagggttgggagcctaatacagagatgatgtatccagcagatggtgg tctgagaggatacactgacatcgcactgaaagttgatggtggtggccatctgcactgcaacttcgtgacaacttacaggt caaaaaagaccgtcgggaacatcaagatgcccggtgtccatgccgttgatcaccgcctggaaaggatcgaggagagtgac aatgaaacctacgtagtgcaaagagaagtggcagttgccaaatacagcaaccttggtggtggcatggacgagctgtacaa gggaggttcaggtggaaccggtggaagtggaggtaccaaggtcgataagatgctgctgcaggagctcagtgagaagctgg aactggccgaacaggccctggcctccaagcaactgcaaatggatgagatgaaacagacactcgccaaacaagaggaggat ctcgaaactatggctgttctgagagcacaaatggaagtctactgttccgacttccacgctgaaagagcagccagggagaa gattcatgaagaaggagcaactggccctgcagctggcaatcctgctgaaggagaacaacgatattgaagaaggcggat ctaggcaatcactgatggaaatgcagtgcagacacggagtcaaagaaatgttcaaggactttcaactgcggcagccacct ctggtgccttctcggaaggagagacaccaccatccggcacatctagcgcctttagctcatacttcaacaacaaggtgggg tattcctcaggagcacgtggatcacgacgatttcgatgccaatcagctcctgaacaagatcaatgagcctccaaagcctg ctcctcgccaaggaagcgctggtaaggtcgataagatgctgctgcaggagctcagtgagaagctggaactggccgaacag gccctggcctccaagcaactgcaaatggatgagatgaaacagacactcgccaaacaagaggaggatctcgaaactatggc tgttctgagagcacaaatggaagtctactgttccgacttccacgctgaaagagcagccagggagaagattcatgaagaga aggagcaactggccctgcagctggcaatcctgctgaaggagaacaacgatattgaagaaggcggatctaggcaatcactg atggaaatgcagtgcagacacggagtcaaagaaatgttcaaggactttcaactgcggcagccacctctggtgccttctcg gaagggagagacaccaccatccggcacatctagcgcctttagctcatacttcaacaacaaggtgggtattcctcaggagc acgtggatcacgacgatttcgatgccaatcagctcctgaacaagatcaatgagcctccaaagcctgctcctagacaggt tccggacgggatcagccactcaactctaagaagaagaaacgcctgctgtcctttcgcgacgtcgactttgaggaggattc agacggttccggacgggatcagccactcaactctaagaagaagaaacgcctgctgtcctttcgcgacgtcgactttgagg aggattcagactaa.
```

SEQ ID NO: 25 is amino acid sequence encoded by SEQ ID NO: 24
MSRLVAASWLLALLLCGITSTTTASSAPAASSTDGTAAAAVSHYAMNGFDEL

AKGAVVPEDHFVCGPADKCYCSAWLHSRGTPGEKIGAQVCQWIAFSIAIALL

TFYGFSAWKATCGWEEVYVCCVEVLFVTLEIFKEFSSPATVYLSTGNHAYCL

RYFEWLLSCPVILIKLSNLSGLKNDYSKRTMGLIVSCVGMIVFGMAAGLATD

WLKWLLYIVSCIYGGYMYFQAAKCYVEANHSVPKGHCRMVVKLMAYAYFASW

GSYPILWAVGPEGLLKLSPYANSIGHSICDIIAKEFWTFLAHHLRIKIHEHI

LIHGDIRKTTKMEIGGEEVEVEEFVEEEDEDTVGASGGTVSKGEELIKENMI

RMKVVMEGSVNGHQFKCTGEGEGRPYEGVQTMRIKVIEGGPLPFAFDILATS

FMYGSRTFIKYPADIPDFFKQSFPEGFTWERVTRYEDGGVVTVTQDTSLEDG

ELVYNVKVRGVNFPSNGPVMQKKTKGWEPNTEMMYPADGGLRGYTDIALKVD

GGGHLHCNFVTTYRSKKTVGNIKMPGVHAVDHRLERIEESDNETYVVQREVA

VAKYSNLGGGMDELYKGGSGGTGGSGGTKVDKMLLQELSEKLELAEQALASK

QLQMDEMKQTLAKQEEDLETMAVLRAQMEVYCSDFHAERAAREKIHEEKEQL

ALQLAILLKENNDIEEGGSRQSLMEMQCRHGVKEMFKDFQLRQPPLVPSRKG

ETPPSGTSSAFSSYFNNKVGIPQEHVDHDDFDANQLLNKINEPPKPAPRQGS

AGKVDKMLLQELSEKLELAEQALASKQLQMDEMKQTLAKQEEDLETMAVLRA

QMEVYCSDFHAERAAREKIHEEKEQLALQLAILLKENNDIEEGGSRQSLMEM

QCRHGVKEMFKDFQLRQPPLVPSRKGETPPSGTSSAFSSYFNNKVGIPQEHV

-continued

DHDDFDANQLLNKINEPPKPAPRQGSGRDQPLNSKKKKRLLSFRDVDFEEDS

DGSGRDQPLNSKKKKRLLSFRDVDFEEDSD.

SEQ ID NO: 26 is DNA sequence of CsChrimson-mRuby3-MVIBDx2-MBDx2, which encodes the CsChrimson-mRuby3-MVIBDx2-MBDx2 polypeptide.

```
atgagcagactggtcgccgcttcttggctgctggctctcctcctctgcggaattaccagcacaacaacagcctctagcgc
cccagcagcttcttctacagacggaacagccgccgcagcagtgtctcactacgccatgaacggcttcgacgagctggcta
aaggagccgtggtgccagaagaccactttgtctgcggaccagccgacaagtgctattgctccgcttggctgcacagcaga
ggcacaccaggagaaaagatcggcgcccaggtctgccagtggattgctttcagcatcgccatcgccctgctgacattcta
cggcttcagcgcctggaaggccacttgccggttgggaggaggtctacgtctgttgcgtcgaggtgctgttcgtgaccctgg
agatcttcaaggagttcagcagccccgccacagtgtacctgtctaccggcaaccacgcctattgcctgcgctacttcgag
tggctgctgtcttgccccgtgatcctgatcaagctgagcaacctgagcggcctgaagaacgactacagcaagcggaccat
gggcctgatcgtgtcttgcgtgggaatgatcgtgttcggcatggccgcaggactggctaccgattggctcaagtggctgc
tgtatatcgtgtcttgcatctacggcggctacatgtacttccaggccgccaagtgctacgtggaagccaaccacagcgtg
cctaaaggccattgccgcatggtcgtgaagctgatggcctacgcttacttcgcctcttggggcagctacccaatcctctg
ggcagtgggaccagaaggactgctgaagctgagcccttacgccaacagcatcggccacagcatctgcgacatcatcgcca
aggagttttggaccttcctggcccaccacctgaggatcaagatccacgagcacatcctgatccacgcgacatccggaag
accaccaagatggagatcggaggcgaggaggtggaagtggaagagttcgtggaggaggaggacgaggacacagtgggagc
tagcggaggtactgtgtctaagggcgaagagctgatcaaggaaaatatgcgtatgaaggtggtcatggaaggttcggtca
acggccaccaattcaaatgcacaggtgaaggagaaggcagaccgtacgagggagtgcaaaccatgaggatcaaagtcatc
gagggaggacccctgccattgcctttgacattcttgccacgtcgttcatgtatggcagccgtacctttatcaagtaccc
ggccgacatccctgatttctttaaacagtcctttcctgagggttttacttgggaaagagttacgagatacgaagatggtg
gagtcgtcaccgtcacgcaggacaccagccttgaggatggcgagctcgtctacaacgtcaaggtcagaggggtaaactttt
ccctccaatggtcccgtgatgcagaagaagaccaagggttgggagcctaatacagagatgatgtatccagcagatggtgg
tctgagaggatacactgacatcgcactgaaagttgatggtggtggccatctgcactgcaacttcgtgacaacttacaggt
caaaaaagaccgtcgggaacatcaagatgcccgtgtccatgccgttgatcaccgcctggaaaggatcgaggagagtgac
aatgaaacctacgtagtgcaaagagaagtggcagttgccaaatacagcaaccttggtggtggcatggacgagctgtacaa
gaaggtcgataagatgctgctgcaggagctcagtgagaagctggaactggccgaacaggccctggcctccaagcaactgc
aaatggatgagatgaaacagacactcgccaaacaagaggaggatctcgaaactatggctgttctgagagcacaaatggaa
gtctactgttccgacttccacgctgaaagagcagccagggagaagattcatgaagagaaggagcaactggccctgcagct
ggcaatcctgctgaaggagaacaacgatattgaagaaggcggatctaggcaatcactgatggaaatgcagtgcagacacg
gagtcaaagaaatgttcaaggactttcaactgcggcagccacctctggtgccttctcggaagggagagacaccaccatcc
ggcacatctagcgcctttagctcatacttcaacaacaaggtgggtattcctcaggagcacgtggatcacgacgatttcga
tgccaatcagctcctgaacaagatcaatgagcctccaaagcctgctcctcgccaaggaagcgctggtaaggtcgataaga
tgctgctgcaggagctcagtgagaagctggaactggccgaacaggccctggcctccaagcaactgcaaatggatgagatg
aaacagacactcgccaaacaagaggaggatctcgaaactatggctgttctgagagcacaaatggaagtctactgttccga
cttccacgctgaaagagcagccagggagaagattcatgaagagaaggagcaactggccctgcagctggcaatcctgctga
aggagaacaacgatattgaagaaggcggatctaggcaatcactgatggaaatgcagtgcagacacggagtcaaagaaatg
ttcaaggactttcaactgcggcagccacctctggtgccttctcggaagggagagacaccaccatccggcacatctagcgc
ctttagctcatacttcaacaacaaggtgggtattcctcaggagcacgtggatcacgacgatttcgatgccaatcagctcc
tgaacaagatcaatgagcctccaaagcctgctcctagacagggttccggacgggatcagccactcaactctaagaagaag
aaacgcctgctgtccttcgcgacgtcgactttgaggaggattcagacggttccggacgggatcagccactcaactctaa
gaagaagaaacgcctgctgtcctttcgcgacgtcgactttgaggaggattcagactaa.
```

-continued

SEQ ID NO: 27 is amino acid sequence encoded by SEQ ID NO: 26
MSRLVAASWLLALLLCGITSTTTASSAPAASSTDGTAAAAVSHYAMNGFDEL

AKGAVVPEDHFVCGPADKCYCSAWLHSRGTPGEKIGAQVCQWIAFSIAIALL

TFYGFSAWKATCGWEEVYVCCVEVLFVTLEIFKEFSSPATVYLSTGNHAYCL

RYFEWLLSCPVILIKLSNLSGLKNDYSKRTMGLIVSCVGMIVFGMAAGLATD

WLKWLLYIVSCIYGGYMYFQAAKCYVEANHSVPKGHCRMVVKLMAYAYFASW

GSYPILWAVGPEGLLKLSPYANSIGHSICDIIAKEFWTFLAHHLRIKIHEHI

LIHGDIRKTTKMEIGGEEVEVEEFVEEEDEDTVGASGGTVSKGEELIKENMI

RMKVVMEGSVNGHQFKCTGEGEGRPYEGVQTMRIKVIEGGPLPFAFDILATS

FMYGSRTFIKYPADIPDFFKQSFPEGFTWERVTRYEDGGVVTVTQDTSLEDG

ELVYNVKVRGVNFPSNGPVMQKKTKGWEPNTEMMYPADGGLRGYTDIALKVD

GGGHLHCNFVTTYRSKKTVGNIKMPGVHAVDHRLERIEESDNETYVVQREVA

VAKYSNLGGGMDELYKKVDKMLLQELSEKLELAEQALASKQLQMDEMKQTLA

KQEEDLETMAVLRAQMEVYCSDFHAERAAREKIHEEKEQLALQLAILLKENN

DIEEGGSRQSLMEMQCRHGVKEMFKDFQLRQPPLVPSRKGETPPSGTSSAFS

SYFNNKVGIPQEHVDHDDFDANQLLNKINEPPKPAPRQGSAGKVDKMLLQEL

SEKLELAEQALASKQLQMDEMKQTLAKQEEDLETMAVLRAQMEVYCSDFHAE

RAAREKIHEEKEQLALQLAILLKENNDIEEGGSRQSLMEMQCRHGVKEMFKD

FQLRQPPLVPSRKGETPPSGTSSAFSSYFNNKVGIPQEHVDHDDFDANQLLN

KINEPPKPAPRQGSGRDQPLNSKKKKRLLSFRDVDFEEDSDGSGRDQPLNSK

KKKRLLSFRDVDFEEDSD.

SEQ ID NO: 28 is amino acid sequence of MBD-GSG linker-MBD
RDQPLNSKKKKRLLSFRDVDFEEDSDGSGRDQPLNSKKKKRLLSFRDVDFEEDSD.

SEQ ID NO: 29 is amino acid sequence of MVIBD-GSG linker-MVIBD:
KVDKMLLQELSEKLELAEQALASKQLQMDEMKQTLAKQEEDLETMAVLRAQME

VYCSDFHAERAAREKIHEEKEQLALQLAILLKENNDIEEGGSRQSLMEMQCRH

GVKEMFKDFQLRQPPLVPSRKGETPPSGTSSAFSSYFNNKVGIPQEHVDHDDF

DANQLLNKINEPPKPAPRQGSGKVDKMLLQELSEKLELAEQALASKQLQMDEM

KQTLAKQEEDLETMAVLRAQMEVYCSDFHAERAAREKIHEEKEQLALQLAILL

KENNDIEEGGSRQSLMEMQCRHGVKEMFKDFQLRQPPLVPSRKGETPPSGTSS

AFSSYFNNKVGIPQEHVDHDDFDANQLLNKINEPPKPAPRQ.

SEQ ID NO: 30 is the DNA sequence of rSK1-tail, which encodes the rSK1-tail
polypeptide.
caggcgcagaagctccggactgtgaagattgaacaagggaaggtgaatgatcaggccaacacgctggctgacctggccaa ggcacagagcatcgcatatgaggtggtgtcggagctgcaggcccagcaggaggagttggaggcccgtctggctgccctgg agagccgcctggatgtcctaggcgcctccctgcaggccctaccaagtctcatagcccaagccatatgccctctaccacca ccctggcccgggcccagtcacctgaccacagccgcccagagcccacaaagccactggctgcccaccacggcatcagactg tggg.

SEQ ID NO: 31 is amino acid sequence encoded by SEQ ID NO: 30
QAQKLRTVKIEQGKVNDQANTLADLAKAQSIAYEVVSELQAQQEELEARLAALE

SRLDVLGASLQALPSLIAQAICPLPPPWPGPSHLTTAAQSPQSHWLPTTASDCG.

SEQ ID NO: 32 is the amino acid sequence of MVIBD-GSG linker-MVIBD-GSG linker-MBD-GSG linker-MBD:
KVDKMLLQELSEKLELAEQALASKQLQMDEMKQTLAKQEEDLETMAVLRAQME

VYCSDFHAERAAREKIHEEKEQLALQLAILLKENNDIEEGGSRQSLMEMQCRH

GVKEMFKDFQLRQPPLVPSRKGETPPSGTSSAFSSYFNNKVGIPQEHVDHDDF

DANQLLNKINEPPKPAPRQGSGKVDKMLLQELSEKLELAEQALASKQLQMDEM

KQTLAKQEEDLETMAVLRAQMEVYCSDFHAERAAREKIHEEKEQLALQLAILL

KENNDIEEGGSRQSLMEMQCRHGVKEMFKDFQLRQPPLVPSRKGETPPSGTSS

AFSSYFNNKVGIPQEHVDHDDFDANQLLNKINEPPKPAPRQGSGRDQPLNSKK

KKRLLSFRDVDFEEDSDGSGRDQPLNSKKKKRLLSFRDVDFEEDSD.

SEQ ID NO: 33 is DNA sequence of construct of: Jaws-GFP-rSK1-tail-ER2.
atgaccgccgtgagcaccacagccactaccgtgctgcaggccacacagagcgacgtgctgcaggagatccagtccaactt cctgctgaatagctccatctgggtgaacattgctctggccggagtggtcatcctgctgtttgtggccatggggagggatc tggaatcccctagagctaagctgatctgggtggccacaatgctggtgccactggtgtctatttctagttacgctggactg gccagtgggctgactgtgggcttcctgcagatgccacctggacacgctctggccggacaggaggtgctgagcccatgggg ccggtatctgacatggactttctccactcccatgatcctgctggctctgggactgctggccgacaccgatattgccagcc tgttcaccgccatcacaatggacattggcatgtgcgtgacaggactggccgctgccctgatcactagctcccatctgctg cgctgggtgttctacggaatttcttgtgcttcttttgtggccgtgctgtatgtgctgctggtgcagtggccagctgatgc tgaggctgctgggaccagtgaaatctttggcactctgaggattctgaccgtggtgctgtggctggggtaccctatcctgt tcgctctgggctctgagggagtggccctgctgagtgtgggagtgaccagctggggatactccggactggacatcctggct aaatacgtgttcgcctttctgctgctgagatgggtggctgccaatgaaggcacagtgtctgggagtggaatgggaatcgg gtccggaggagctgctccagccgacgatcgaccggtagtaaaatccagaattacttctgaagggagtatatccctctgg atcaaatagacatcaatgttgcacctgcaggggcaggttccggaccggtagtagcagtgagcaagggcgaggagctgttc accggggtggtgcccatcctggtcgagctggacggcgacgtaaacggccacaagttcagcgtgtccggcgagggcgaggg cgatgccacctacggcaagctgaccctgaagttcatttgcaccaccggcaagctgccgtgccctggcccaccctcgtga ccaccctgacctacggcgtgcagtgcttcagccgctaccccgaccacatgaagcagcacgacttcttcaagtccgccatg cccgaaggctacgtccaggagcgcaccatcttcttcaaggacgacggcaactacaagacccgcgccgaggtgaagttcga gggcgacaccctggtgaaccgcatcgagctgaagggcatcgacttcaaggaggacggcaacatcctggggcacaagctgg agtacaactacaacagccacaacgtctatatcatggccgacaagcagaagaacggcatcaaggtgaacttcaagatccgc cacaacatcgaggacggcagcgtgcagctcgccgaccactaccagcagaacacccccatcggcgacggccccgtgctgct gcccgacaaccactacctgagcacccagtccgccctgagcaaagaccccaacgagaagcgcgatcacatggtcctgctgg agttcgtgaccgccgccgggatcactctcggcatggacgagctgtacaagggaggttcaggtggaaccggtggaagtgga ggtaccccaggcgcagaagctccggactgtgaagattgaacaagggaaggtgaatgatcaggccaacacgctggctgacc tggccaaggcacagagcatcgcatatgaggtggtgtcggagctgcaggcccagcaggaggagttggaggcccgtctggct gccctggagagccgcctggatgtcctaggcgcctccctgcaggccctaccaagtctcatagcccaagccatatgccctct accaccaccctggcccgggcccagtcacctgaccacagccgcccagagcccacaaagccactggctgcccaccacggcat cagactgtgggttctgctacgagaatgaagtgtaa.

SEQ ID NO: 34 is amino acid sequence of Jaws-GFP-rSK1-tail-ER2 fusion protein.
MTAVSTTATTVLQATQSDVLQEIQSNFLLNSSIWVNIALAGVVILLFVAMG

RDLESPRAKLIWVATMLVPLVSISSYAGLASGLTVGFLQMPPGHALAGQEV

LSPWGRYLTWTFSTPMILLALGLLADTDIASLFTAITMDIGMCVTGLAAAL

ITSSHLLRWVFYGISCAFFVAVLYVLLVQWPADAEAAGTSEIFGTLRILTV

VLWLGYPILFALGSEGVALLSVGVTSWGYSGLDILAKYVFAFLLLRWVAAN

-continued

```
EGTVSGSGMGIGSGGAAPADDRPVVKSRITSEGEYIPLDQIDINVAPAGAG

SGPVVAVSKGEELFTGVVPILVELDGDVNGHKFSVSGEGEGDATYGKLTLK

FICTTGKLPVPWPTLVTTLTYGVQCFSRYPDHMKQHDFFKSAMPEGYVQER

TIFFKDDGNYKTRAEVKFEGDTLVNRIELKGIDEKEDGNILGHKLEYNYNS

HNVYIMADKQKNGIKVNFKIRHNIEDGSVQLADHYQQNTPIGDGPVLLPDN

HYLSTQSALSKDPNEKRDHMVLLEFVTAAGITLGMDELYKGGSGGTGGSGG

TQAQKLRTVKIEQGKVNDQANTLADLAKAQSIAYEVVSELQAQQEELEARL

AALESRLDVLGASLQALPSLIAQAICPLPPPWPGPSHLTTAAQSPQSHWLP

TTASDCGFCYENEV.
```

SEQ ID NO: 35 is DNA sequence of construct: CoChR-GFP-rSK1-tail-ER2.
```
atgctggggaacggcagcgccattgtgcctatcgaccagtgcttttgcctggcttggaccgacagcctgggaagcgatac agagcagctggtggccaacatcctccagtggttcgccttcggcttcagcatcctgatcctgatgttctacgcctaccaga cttggagagccacttgcggttggggaggaggtctacgtctgttgcgtcgagctgaccaaggtcatcatcgagttcttccac gagttcgacgaccccagcatgctgtacctggctaacggacaccgagtccagtggctgagatacgcagagtggctgctgac ttgtcccgtcatcctgatccacctgagcaacctgaccggcctgaaggacgactacagcaagcggaccatgaggctgctgg tgtcagacgtgggaaccatcgtgtggggagctacaagcgccatgagcacaggctacgtcaaggtcatcttcttcgtgctg ggttgcatctacggcgccaacacctcttccacgccgccaaggtgtatatcgagagctaccacgtggtgccaaagggcag acctagaaccgtcgtgcggatcatggcttggctgttcttcctgtcttggggcatgttccccgtgctgttcgtcgtgggac cagaaggattcgacgccatcagcgtgtacggctctaccattggccacaccatcatcgacctcatgagcaagaattgttgg ggcctgctgggacactatctgagagtgctgatccaccagcacatcatcatctacggcgacatccggaagaagaccaagat caacgtggccgcgaggagatggaagtggagaccatggtggaccaggaggacgaggagacagtgggttccggaccggtag tagcagtgagcaagggcgaggagctgttcaccggggtggtgcccatcctggtcgagctggacggcgacgtaaacggccac aagttcagcgtgtccggcgagggcgagggcgatgccacctacggcaagctgaccctgaagttcatttgcaccaccggcaa gctgccgtgcctggcccacctcgtgaccaccctgacctacggcgtgcagtgcttcagccgctaccccgaccacatga agcagcacgacttcttcaagtccgccatgcccgaaggctacgtccaggagcgcaccatcttcttcaaggacgacggcaac tacaagacccgcgccgaggtgaagttcgagggcgacaccctggtgaaccgcatcgagctgaagggcatcgacttcaagga ggacggcaacatcctggggcacaagctggagtacaactacaacagccacaacgtctatatcatggccgacaagcagaaga acggcatcaaggtgaacttcaagatccgccacaacatcgaggacggcagcgtgcagctcgccgaccactaccagcagaac accccatcggcgacggccccgtgctgctgcccgacaaccactacctgagcacccagtccgccctgagcaaagaccccaa cgagaagcgcgatcacatggtcctgctggagttcgtgaccgccgccgggatcactctcggcatggacgagctgtacaagg gaggttcaggtggaaccggtggaagtggaggtaccccaggcgcagaagctccggactgtgaagattgaacaaggggaaggt gaatgatcaggccaacacgctggctgacctggccaaggcacagagcatcgcatatgaggtggtgtcggagctgcaggccc agcaggaggagttggaggcccgtctggctgccctggagagccgcctggatgtcctaggcgcctccctgcaggccctacca agtctcatagcccaagccatatgccctctaccaccacctggcccgggcccagtcacctgaccacagccgcccagagccc acaaagccactggctgccaccacggcatcagactgtgggttctgctacgagaatgaagtgtaa.
```

SEQ ID NO: 36 is amino acid sequence of CoChR-GFP-rSK1-tail-ER2 fusion protein.
```
MLGNGSAIVPIDQCFCLAWTDSLGSDTEQLVANILQWFAFGFSILILMFYA

YQTWRATCGWEEVYVCCVELTKVIIEFFHEFDDPSMLYLANGHRVQWLRYA

EWLLTCPVILIHLSNLTGLKDDYSKRTMRLLVSDVGTIVWGATSAMSTGYV

KVIFFVLGCIYGANTFFHAAKVYIESYHVVPKGRPRTVVREVIAWLFFLSW

GMFPVLFVVGPEGFDAISVYGSTIGHTIIDLMSKNCWGLLGHYLRVLIHQH
```

-continued

IIIYGDIRKKTKINVAGEEMEVETMVDQEDEETVGSGPVVAVSKGEELFTG

VVPILVELDGDVNGHKFSVSGEGEGDATYGKLTLKFICTTGKLPVPWPTLV

TTLTYGVQCFSRYPDHMKQHDFFKSAMPEGYVQERTIFFKDDGNYKTRAEV

KFEGDTLVNRIELKGIDFKEDGNILGHKLEYNYNSHNVYIMADKQKNGIKV

NFKIRHNIEDGSVQLADHYQQNTPIGDGPVLLPDNHYLSTQSALSKDPNEK

RDHMVLLEFVTAAGITLGMDELYKGGSGGTGGSGGTQAQKLRTVKIEQGKV

NDQANTLADLAKAQSIAYEVVSELQAQQEELEARLAALESRLDVLGASLQA

LPSLIAQAICPLPPPWPGPSHLTTAAQSPQSHWLPTTASDCGFCYENEV

SEQ ID NO: 37 is DNA sequence of construct: CsChrimson-DsRed-12-rSK1-tail-ER2.
atgagcagactggtcgccgcttcttggctgctggctctcctcctctgcggaattaccagcacaacaacagcctctagcgc cccagcagatatctacagacggaacagccgccgcagcagtgtctcactacgccatgaacggcttcgacgagctggctaaa ggagccgtggtgccagaagaccactttgtctgcggaccagccgacaagtgctattgctccgcttggctgcacagcagagg cacaccaggagaaaagatcggcgcccaggtctgccagtggattgctttcagcatcgccatcgccctgctgacattctacg gcttcagcgcctggaaggccacttgcggttgggaggaggtctacgtctgttgcgtcgaggtgctgttcgtgaccctggag atcttcaaggagttcagcagccccgccacagtgtacctgtctaccggcaaccacgcctattgcctgcgctacttcgagtg gctgctgtatgccccgtgatcctgatcaagctgagcaacctgagcggcctgaagaacgactacagcaagcggaccatggg cctgatcgtgtatgcgtgggaatgatcgtgttcggcatggccgcaggactggctaccgattggctcaagtggctgctgta tatcgtgtatgcatctacggcggctacatgtacttccaggccgccaagtgctacgtggaagccaaccacagcgtgcctaa aggccattgccgcatggtcgtgaagctgatggcctacgcttacttcgcctcttgggcagctacccaatcctctgggcag tgggaccagaaggactgctgaagctgagcccttacgccaacagcatcggccacagcatctgcgacatcatcgccaaggag ttttggaccttcctggcccaccacctgaggatcaagatccacgagcacatcctgatccacggcgacatccggaagaccac caagatggagatcggaggcgaggaggtggaagtggaagagttcgtggaggaggaggacgaggacacagtgggagctagcg gaggtactatggcctcctccgaggacgtcatcaaggagttcatgcgcttcaaggtgcgcatggagggctccgtgaacggc cacgagttcgagatcgagggcgagggcgagggccgcccctacgagggcacccagaccgccaagctgaaggtgaccaaggg cggccccctgcccttcgcctgggacatcctgtcccccagttccagtacggctccaaggtgtacgtgaagcaccccgccg acatccccgactacaagaagctgtccttccccgagggcttcaagtgggagcgcgtgatgaacttcgaggacggcggcgtg gtgaccgtgacccaggactcctccctgcaggacggctgcttcatctacaaggtgaagttcatcggcgtgaacttcccctc cgacggccccgtaatgcagaagaagactatgggctgggagccctccaccgagcgcctgtaccccgcgacggcgtgctga agggcgagatccacaaggccctgaagctgaaggacggcggccactacctggtggagttcaagtccatctacatggccaag aagcccgtgcagctgcccggctactactacgtggactccaagctggacatcacctcccacaacgaggactacaccatcgt ggagcagtacgagcgcaccgagggccgccaccacctgttcctgggaggttcaggtggaaccggtggaagtggaggtaccc aggcgcagaagctccggactgtgaagattgaacaaggggaaggtgaatgatcaggccaacacgctggctgacctggccaag gcacagagcatcgcatatgaggtggtgtcggagctgcaggcccagcaggaggagttggaggcccgtctggctgccctgga gagccgcctggatgtcctaggcgcctccctgcaggccctaccaagtctcatagcccaagccatatgccctctaccaccac cctggcccgggcccagtcacctgaccacagccgcccagagcccacaaagccactggctgcccaccacggcatcagactgt gggttctgctacgagaatgaagtgtaa.

SEQ ID NO: 38 is amino acid sequence of polypeptide encoded by SEQ ID NO: 37
MSRLVAASWLLALLLCGITSTTTASSAPAASSTDGTAAAAVSHYAMNGFDEL

AKGAVVPEDHFVCGPADKCYCSAWLHSRGTPGEKIGAQVCQWIAFSIAIALL

TFYGFSAWKATCGWEEVYVCCVEVLFVTLEIFKEFSSPATVYLSTGNHAYCL

RYFEWLLSCPVILIKLSNLSGLKNDYSKRTMGLIVSCVGMIVFGMAAGLATD

WLKWLLYIVSCIYGGYMYFQAAKCYVEANHSVPKGHCRMVVKLMAYAYFASW

-continued

GSYPILWAVGPEGLLKLSPYANSIGHSICDIIAKEFWTFLAHHLRIKIHEHI

LIHGDIRKTTKMEIGGEEVEVEEFVEEEDEDTVGASGGTMASSEDVIKEFMR

FKVRMEGSVNGHEFEIEGEGEGRPYEGTQTAKLKVTKGGPLPFAWDILSPQF

QYGSKVYVKHPADIPDYKKLSFPEGFKWERVMNFEDGGVVTVTQDSSLQDGC

FIYKVKFIGVNFPSDGPVMQKKTMGWEPSTERLYPRDGVLKGEIHKALKLKD

GGHYLVEFKSIYMAKKPVQLPGYYYVDSKLDITSHNEDYTIVEQYERTEGRH

HLFLGGSGGTGGSGGTQAQKLRTVKIEQGKVNDQANTLADLAKAQSIAYEVV

SELQAQQEELEARLAALESRLDVLGASLQALPSLIAQAICPLPPPWPGPSHL

TTAAQSPQSHWLPTTASDCGFCYENEV.

SEQ ID NO: 39 is DNA sequence of construct: CsChrimson-mRuby3-12-rSK1-tail-ER2.
atgagcagactggtcgccgcttcttggctgctggctctcctcctctgcggaattaccagcacaacaacagcctctagcgc cccagcagcttcttctacagacggaacagccgccgcagcagtgtctcactacgccatgaacggcttcgacgagctggcta aaggagccgtggtgccagaagaccactttgtctgcggaccagccgacaagtgctattgctccgcttggctgcacagcaga ggcacaccaggagaaaagatcggcgcccaggtctgccagtggattgctttcagcatcgccatcgccctgctgacattcta cggcttcagcgcctggaaggccacttgcggttgggaggaggtctacgtctgttgcgtcgaggtgctgttcgtgaccctgg agatcttcaaggagttcagcagccccgccacagtgtacctgtctaccggcaaccacgcctattgcctgcgctacttcgag tggctgctgtcttgccccgtgatcctgatcaagctgagcaacctgagcggcctgaagaacgactacagcaagcggaccat gggcctgatcgtgtcttgcgtgggaatgatcgtgttcggcatggccgcaggactggctaccgattggctcaagtggctgc tgtatatcgtgtcttgcatctacggcggctacatgtacttccaggccgccaagtgctacgtggaagccaaccacagcgtg cctaaaggccattgccgcatggtcgtgaagctgatggcctacgcttacttcgcctcttggggcagctacccaatcctctg ggcagtgggaccagaaggactgctgaagctgagcccttacgccaacagcatcggccacagcatctgcgacatcatcgcca aggagttttggaccttcctggcccaccacctgaggatcaagatccacgagcacatcctgatccacggcgacatccggaag accaccaagatggagatcggaggcgaggaggtggaagtggaagagttcgtggaggaggaggacgaggacacagtgggagc tagcggaggtactgtgtctaagggcgaagagctgatcaaggaaaatatgcgtatgaaggtggtcatggaaggttcggtca acggccaccaattcaaatgcacaggtgaaggagaaggcagaccgtacgagggagtgcaaaccatgaggatcaaagtcatc gagggaggacccctgccatttgcctttgacattcttgccacgtcgttcatgtatggcagccgtacctttatcaagtaccc ggccgacatccctgatttctttaaacagtcctttcctgagggttttacttgggaaagagttacgagatacgaagatggtg gagtcgtcaccgtcacgcaggacaccagccttgaggatggcgagctcgtctacaacgtcaaggtcagaggggtaaacttt ccctccaatggtcccgtgatgcagaagaagaccaagggttgggagcctaatacagagatgatgtatccagcagatggtgg tctgagaggatacactgacatcgcactgaaagttgatggtggtggccatctgcactgcaacttcgtgacaacttacaggt caaaaaagaccgtcgggaacatcaagatgcccggtgtccatgccgttgatcaccgcctggaaaggatcgaggagagtgac aatgaaacctacgtagtgcaaagagaagtggcagttgccaaatacagcaaccttggtggtggcatggacgagctgtacaa gggaggttcaggtggaaccggtggaagtggaggtacccaggcgcagaagctccggactgtgaagattgaacaagggaagg tgaatgatcaggccaacacgctggctgacctggccaaggcacagagcatcgcatatgaggtggtgtcggagctgcaggcc cagcaggaggagttggaggcccgtctggctgccctggagagccgcctggatgtcctaggcgcctccctgcaggccctacc aagtctcatagcccaagccatgccctcctaccaccaccctggcccgggcccagtcacctgaccacagccgcccagagcc cacaaagccactggctgccaccacgcatcagactgtgggttctgctacgagaatgaagtgtaa.

SEQ ID NO: 40 is amino acid sequence of polypeptide encoded by SEQ ID NO: 39.
MSRLVAASWLLALLLCGITSTTTASSAPAASSTDGTAAAAVSHYAMNGFDEL

AKGAVVPEDHFVCGPADKCYCSAWLHSRGTPGEKIGAQVCQWIAFSIAIALL

TFYGFSAWKATCGWEEVYVCCVEVLEVTLEIFKEFSSPATVYLSTGNHAYCL

```
RYFEWLLSCPVILIKLSNLSGLKNDYSKRTMGLIVSCVGMIVEGMAAGLATD

WLKWLLYIVSCIYGGYMYFQAAKCYVEANHSVPKGHCRMVVKLMAYAYFASW

GSYPILWAVGPEGLLKLSPYANSIGHSICDIIAKEFWTFLAHHLRIKIHEHI

LIHGDIRKTTKMEIGGEEVEVEEFVEEEDEDTVGASGGTVSKGEELIKENMI

RMKVVMEGSVNGHQFKCTGEGEGRPYEGVQTMRIKVIEGGPLPFAFDILATS

EMYGSRTFIKYPADIPDFFKQSFPEGFTWERVTRYEDGGVVTVTQDTSLEDG

ELVYNVKVRGVNFPSNGPVMQKKTKGWEPNTEMMYPADGGLRGYTDIALKVD

GGGHLHCNEVTTYRSKKTVGNIKMPGVHAVDHRLERIEESDNETYVVQREVA

VAKYSNLGGGMDELYKGGSGGTGGSGGTQAQKLRTVKIEQGKVNDQANTLAD

LAKAQSIAYEVVSELQAQQEELEARLAALESRLDVLGASLQALPSLIAQAIC

PLPPPWPGPSHLTTAAQSPQSHWLPTTASDCGFCYENEV.
```

SEQ ID NO: 41 is amino acid sequence of light-activated opsin polypeptide ChR2.
[Klapoetke, N., et al. (2014) Nature Methods 11.3: 338]
```
MDYGGALSAVGRELLFVTNPVVVNGSVLVPEDQCYCAGWIESRGTNGAQTAS

NVLQWLAAGFSILLLMFYAYQTWKSTCGWEEIYVCAIEMVKVILEFFFEFKN

PSMLYLATGHRVQWLRYAEWLLTCPVILIHLSNLTGLSNDYSRRTMGLLVSD

IGTIVWGATSAMATGYVKVIFFCLGLCYGANTFFHAAKAYIEGYHTVPKGRC

RQVVTGMAWLFFVSWGMFPILFILGPEGFGVLSVYGSTVGHTIIDLMSKNCW

GLLGHYLRVLIHEHILIHGDIRKTTKLNIGGTEIEVETLVEDEAEAGAV.
```

SEQ ID NO: 42 is amino acid sequence of light-activated opsin polypeptide CsChrimson. [Klapoetke, N., et al. (2014) Nature Methods 11.3: 338]
```
MSRLVAASWLLALLLCGITSTTTASSAPAASSTDGTAAAAVSHYAMNGFDEL

AKGAVVPEDHFVCGPADKCYCSAWLHSRGTPGEKIGAQVCQWIAFSIAIALL

TFYGFSAWKATCGWEEVYVCCVEVLFVTLEIFKEFSSPATVYLSTGNHAYCL

RYFEWLLSCPVILIKLSNLSGLKNDYSKRTMGLIVSCVGMIVFGMAAGLATD

WLKWLLYIVSCIYGGYMYFQAAKCYVEANHSVPKGHCRMVVKLMAYAYFASW

GSYPILWAVGPEGLLKLSPYANSIGHSICDIIAKEFWTFLAHHLRIKIHEHI

LIHGDIRKTTKMEIGGEEVEVEEFVEEEDEDTV.
```

SEQ ID NO: 43 is amino acid sequence of light-activated opsin polypeptide Chrimson. [Klapoetke, N., et al. (2014) Nature Methods 11.3: 338]
```
MAELISSATRSLFAAGGINPWPNPYHHEDMGCGGMTPTGECFSTEWWCDPSY

GLSDAGYGYCFVEATGGYLVVGVEKKQAWLHSRGTPGEKIGAQVCQWIAFSI

AIALLTFYGFSAWKATCGWEEVYVCCVEVLFVTLEIFKEFSSPATVYLSTGN

HAYCLRYFEWLLSCPVILIKLSNLSGLKNDYSKRTMGLIVSCVGMIVFGMAA

GLATDWLKWLLYIVSCIYGGYMYFQAAKCYVEANHSVPKGHCRMVVKLMAYA

YFASWGSYPILWAVGPEGLLKLSPYANSIGHSICDIIAKEFWTFLAHHLRIK

IHEHHILIHGDIRKTTKMEIGGEEVEVEEFVEEEDEDTV.
```

SEQ ID NO: 44 is amino acid sequence of light-activated opsin polypeptide Chronos. [Klapoetke, N., et al. (2014) Nature Methods 11.3: 338]
```
METAATMTHAFISAVPSAEATIRGLLSAAAVTPAADAHGETSNATTAGADHG

CFPHINHGTELQHKIAVGLQWFTVIVAIVQLIFYGWHSFKATTGWEEVYVCV

IELVKCFIELFHEVDSPATVYQTNGGAVIWLRYSMWLLTCPVILIHLSNLTG

LHEEYSKRTMTILVTDIGNIVWGITAAFTKGPLKILFFMIGLFYGVTCFFQI
```

-continued

AKVYIESYHTLPKGVCRKICKIMAYVFFCSWLMFPVMFIAGHEGLGLITPYT

SGIGHLILDLISKNTWGFLGHHLRVKIHEHILIHGDIRKTTTINVAGENMEI

ETFVDEEEEGGV.

SEQ ID NO: 45 is amino acid sequence of: CoChR-GFP-12-(MVIBD-MBD)x3
MLGNGSAIVPIDQCFCLAWTDSLGSDTEQLVANILQWFAFGFSILILMFYAY

QTWRATCGWEEVYVCCVELTKVIIEFFHEFDDPSMLYLANGHRVQWLRYAEW

LLTCPVILIHLSNLTGLKDDYSKRTMRLLVSDVGTIVWGATSAMSTGYVKVI

FFVLGCIYGANTFFHAAKVYIESYHVVPKGRPRTVVRIMAWLFFLSWGMFPV

LFVVGPEGFDAISVYGSTIGHTIIDLMSKNCWGLLGHYLRVLIHQHIIIYGD

IRKKTKINVAGEEMEVETMVDQEDEETVGASGGTVSKGEELFTGVVPILVEL

DGDVNGHKFSVSGEGEGDATYGKLTLKFICTTGKLPVPWPTLVTTLTYGVQC

FSRYPDHMKQHDFFKSAMPEGYVQERTIFFKDDGNYKTRAEVKFEGDTLVNR

IELKGIDFKEDGNILGHKLEYNYNSHNVYIMADKQKNGIKVNFKIRHNIEDG

SVQLADHYQQNTPIGDGPVLLPDNHYLSTQSALSKDPNEKRDHMVLLEFVTA

AGITLGMDELYKGGSGGTGGSGGTKVDKMLLQELSEKLELAEQALASKQLQM

DEMKQTLAKQEEDLETMAVLRAQMEVYCSDFHAERAAREKIHEEKEQLALQL

AILLKENNDIEEGGSRQSLMEMQCRHGVKEMFKDFQLRQPPLVPSRKGETPP

SGTSSAFSSYFNNKVGIPQEHVDHDDFDANQLLNKINEPPKPAPRQGSGRDQ

PLNSKKKKRLLSFRDVDFEEDSDGSGKVDKMLLQELSEKLELAEQALASKQL

QMDEMKQTLAKQEEDLETMAVLRAQMEVYCSDFHAERAAREKIHEEKEQLAL

QLAILLKENNDIEEGGSRQSLMEMQCRHGVKEMFKDFQLRQPPLVPSRKGET

PPSGTSSAFSSYFNNKVGIPQEHVDHDDFDANQLLNKINEPPKPAPRQGSAG

RDQPLNSKKKKRLLSFRDVDFEEDSDGSGKVDKMLLQELSEKLELAEQALAS

KQLQMDEMKQTLAKQEEDLETMAVLRAQMEVYCSDFHAERAAREKIHEEKEQ

LALQLAILLKENNDIEEGGSRQSLMEMQCRHGVKEMFKDFQLRQPPLVPSRK

GETPPSGTSSAFSSYFNNKVGIPQEHVDHDDFDANQLLNKINEPPKPAPRQG

SGRDQPLNSKKKKRLLSFRDVDFEEDSD.

SEQ ID NO: 46 is amino acid sequence of: CoChR-GFP-12-MVIBDx3-MBDx3
MLGNGSAIVPIDQCFCLAWTDSLGSDTEQLVANILQWFAFGFSILILMFYAY

QTWRATCGWEEVYVCCVELTKVIIEFFHEFDDPSMLYLANGHRVQWLRYAEWL

LTCPVILIHLSNLTGLKDDYSKRTMRLLVSDVGTIVWGATSAMSTGYVKVIF

FVLGCIYGANTFFHAAKVYIESYHVVPKGRPRTVVRIMAWLFFLSWGMFPVL

FVVGPEGFDAISVYGSTIGHTIIDLMSKNCWGLLGHYLRVLIHQHIIIYGDI

RKKTKINVAGEEMEVETMVDQEDEETVGASGGTVSKGEELFTGVVPILVELD

GDVNGHKFSVSGEGEGDATYGKLTLKFICTTGKLPVPWPTLVTTLTYGVQCF

SRYPDHMKQHDFFKSAMPEGYVQERTIFFKDDGNYKTRAEVKFEGDTLVNRI

ELKGIDFKEDGNILGHKLEYNYNSHNVYIMADKQKNGIKVNFKIRHNIEDGS

VQLADHYQQNTPIGDGPVLLPDNHYLSTQSALSKDPNEKRDHMVLLEFVTAA

GITLGMDELYKGGSGGTGGSGGTKVDKMLLQELSEKLELAEQALASKQLQMD

EMKQTLAKQEEDLETMAVLRAQMEVYCSDFHAERAAREKIHEEKEQLALQLA

ILLKENNDIEEGGSRQSLMEMQCRHGVKEMFKDFQLRQPPLVPSRKGETPPS

GTSSAFSSYFNNKVGIPQEHVDHDDFDANQLLNKINEPPKPAPRQGSGKVDK

MLLQELSEKLELAEQALASKQLQMDEMKQTLAKQEEDLETMAVLRAQMEVYC
SEFHAERAAREKIHEEKEQLALQLAILLKENNDIEEGGSRQSLMEMQCRHGV
KEMFKDFQLRQPPLVPSRKGETPPSGTSSAFSSYFNNKVGIPQEHVDHDDFD
ANQLLNKINEPPKPAPRQGSAGKVDKMLLQELSEKLELAEQALASKQLQMDE
MKQTLAKQEEDLETMAVLRAQMEVYCSDFHAERAAREKIHEEKEQLALQLAI
LLKENNDIEEGGSRQSLMEMQCRHGVKEMFKDFQLRQPPLVPSRKGETPPSG
TSSAFSSYFNNKVGIPQEHVDHDDFDANQLLNKINEPPKPAPRQGSRDQPL
NSKKKKRLLSFRDVDFEEDSDGSGRDQPLNSKKKKRLLSFRDVDFEEDSDGS
GRDQPLNSKKKKRLLSFRDVDFEEDSD.

SEQ ID NO: 47 is amino acid sequence of: CoChR-mCardinal-12-MVIBDx2-MBDx2
MLGNGSAIVPIDQCFCLAWTDSLGSDTEQLVANILQWFAFGFSILILMFYAY
QTWRATCGWEEVYVCCVELTKVIIEFFHEFDDPSMLYLANGHRVQWLRYAEW
LLTCPVILIHLSNLTGLKDDYSKRTMERLLVSDVGTIVWGATSAMSTGYVKV
IFFVLGCIYGANTFFHAAKVYIESYHVVPKGRPRTVVRIMAWLFFLSWGMFP
VLFVVGPEGFDAISVYGSTIGHTIIDLMSKNCWGLLGHYLRVLIHQHIIIYG
DIRKKTKINVAGEEMEVETMVDQEDEETVGASGGTVSKGEELIKENMHMKLY
MEGTVNNHHFKCTTEGEGKPYEGTQTQRIKVVEGGPLPFAFDILATCFMYGS
KTFINHTQGIPDFFKQSFPEGFTWERVTTYEDGGVLTVTQDTSLQDGCLIYN
VKLRGVNFPSNGPVMQKKTLGWEATTETLYPADGGLEGRCDMALKLVGGGHL
HCNLKTTYRSKKPAKNLKMPGVYFVDRRLERIKEADNETYVEQHEVAVARYC
DLPSKLGHKLNGMDELYKGGSGGTGGSGGTKVDKMLLQELSEKLELAEQALA
SKQLQMDEMKQTLAKQEEDLETMAVLRAQMEVYCSDFHAERAAREKIHEEKE
QLALQLAILLKENNDIEEGGSRQSLMEMQCRHGVKEMFKDFQLRQPPLVPSR
KGETPPSGTSSAFSSYFNNKVGIPQEHVDHDDFDANQLLNKINEPPKPAPRQ
GSAGKVDKMLLQELSEKLELAEQALASKQLQMDEMKQTLAKQEEDLETMAVL
RAQMEVYCSDFHAERAAREKIHEEKEQLALQLAILLKENNDIEEGGSRQSLM
EMQCRHGVKEMFKDFQLRQPPLVPSRKGETPPSGTSSAFSSYFNNKVGIPQE
HVDHDDFDANQLLNKINEPPKPAPRQGSRDQPLNSKKKKRLLSFRDVDFEE
DSDGSGRDQPLNSKKKKRLLSFRDVDFEEDSD.

SEQ ID NO: 48 is amino acid sequence of: CoChR-mCardinal-(MVIBD-MBD)x2
MLGNGSAIVPIDQCFCLAWTDSLGSDTEQLVANILQWFAFGFSILILMFYAY
QTWRATCGWEEVYVCCVELTKVIIEFFHEFDDPSMLYLANGHRVQWLRYAEW
LLTCPVILIHLSNLTGLKDDYSKRTMRLLVSDVGTIVWGATSAMSTGYVKI
FFVLGCIYGANTFFHAAKVYIESYHVVPKGRPRTVVRIMAWLFFLSWGMFPV
LFVVGPEGFDAISVYGSTIGHTIIDLMSKNCWGLLGHYLRVLIHQHIIIYGD
IRKKTKINVAGEEMEVETMVDQEDEETVGSGPVVAVSKGEELIKENMHMKLY
MEGTVNNHHFKCTTEGEGKPYEGTQTQRIKVVEGGPLPFAFDILATCFMYGS
KTFINHTQGIPDFFKQSFPEGFTWERVTTYEDGGVLTVTQDTSLQDGCLIYN
VKLRGVNFPSNGPVMQKKTLGWEATTETLYPADGGLEGRCDMALKLVGGGHL
HCNLKTTYRSKKPAKNLKMPGVYFVDRRLERIKEADNETYVEQHEVAVARYC
DLPSKLGHKLNGMDELYKGASGKVDKMLLQELSEKLELAEQALASKQLQMDE -continued

MKQTLAKQEEDLETMAVLRAQMEVYCSDFHAERAAREKIHEEKEQLALQLAI

LLKENNDIEEGGSRQSLMEMQCRHGVKEMFKDFQLRQPPLVPSRKGETPPSG

TSSAFSSYFNNKVGIPQEHVDHDDFDANQLLNKINEPPKPAPRQGSGRDQPL

NSKKKKRLLSFRDVDFEEDSDGSGKVDKMLLQELSEKLELAEQALASKQLQM

DEMKQTLAKQEEDLETMAVLRAQMEVYCSDFHAERAAREKIHEEKEQLALQL

AILKENNDIEEGGSRQSLMEMQCRHGVKEMFKDFQLRQPPLVPSRKGETPPS

GTSSAFSSYFNNKVGIPQEHVDHDDFDANQLLNKINEPPKPAPRQGSAGRDQ

PLNSKKKKRLLSFRDVDFEEDSD.

SEQ ID NO: 49 is amino acid sequence of: CsChrimson-DsRed-12-MVIBDx2-MBDx2
MSRLVAASWLLALLLCGITSTTTASSAPAASSTDGTAAAAVSHYAMNGFDEL

AKGAVVPEDHFVCGPADKCYCSAWLHSRGTPGEKIGAQVCQWIAFSIAIALL

TFYGFSAWKATCGWEEVYVCCVEVLFVTLEIFKEFSSPATVYLSTGNHAYCL

RYFEWLLSCPVILIKLSNLSGLKNDYSKRTMGLIVSCVGMIVFGMAAGLATD

WLKWLLYIVSCIYGGYMYFQAAKCYVEANHSVPKGHCRMVVKLMAYAYFASW

GSYPILWAVGPEGLLKLSPYANSIGHSICDIIAKEFWTFLAHHLRIKIHEHI

LIHGDIRKTTKMEIGGEEVEVEEFVEEEDEDTVGASGGTMASSEDVIKEFMR

FKVRMEGSVNGHEFEIEGEGEGRPYEGTQTAKLKVTKGGPLPFAWDILSPQF

QYGSKVYVKHPADIPDYKKLSFPEGFKWERVMNFEDGGVVTVTQDSSLQDGC

FIYKVKFIGVNFPSDGPVMQKKTMGWEPSTERLYPRDGVLKGEIHKALKLKD

GGHYLVEFKSIYMAKKPVQLPGYYYVDSKLDITSHNEDYTIVEQYERTEGRH

HLFLGGSGGTGGSGGTKVDKMLLQELSEKLELAEQALASKQLQMDEMKQTLA

KQEEDLETMAVLRAQMEVYCSDFHAERAAREKIHEEKEQLALQLAILLKENN

DIEEGGSRQSLMEMQCRHGVKEMFKDFQLRQPPLVPSRKGETPPSGTSSAFS

SYFNNKVGIPQEHVDHDDFDANQLLNKINEPPKPAPRQGSAGKVDKMLLQEL

SEKLELAEQALASKQLQMDEMKQTLAKQEEDLETMAVLRAQMEVYCSDFHAE

RAAREKIHEEKEQLALQLAILLKENNDIEEGGSRQSLMEMQCRHGVKEMFKD

FQLRQPPLVPSRKGETPPSGTSSAFSSYFNNKVGIPQEHVDHDDFDANQLLN

KINEPPKPAPRQGSGRDQPLNSKKKKRLLSFRDVDFEEDSDGSGRDQPLNSK

KKKRLLSFRDVDFEEDSD.

SEQ ID NO: 50 is amino acid sequence of: CsChrimson-DsRed-MVIBDx2-MBDx2
MSRLVAASWLLALLLCGITSTTTASSAPAASSTDGTAAAAVSHYAMNGFDEL

AKGAVVPEDHFVCGPADKCYCSAWLHSRGTPGEKIGAQVCQWIAFSIAIALL

TFYGFSAWKATCGWEEVYVCCVEVLFVTLEIFKEFSSPATVYLSTGNHAYCL

RYFEWLLSCPVILIKLSNLSGLKNDYSKRTMGLIVSCVGMIVFGMAAGLATD

WLKWLLYIVSCIYGGYMYFQAAKCYVEANHSVPKGHCRMVVKLMAYAYFASW

GSYPILWAVGPEGLLKLSPYANSIGHSICDIIAKEFWTFLAHHLRIKIHEHI

LIHGDIRKTTKMEIGGEEVEVEEFVEEEDEDTVGASGGTMASSEDVIKEFMR

FKVRMEGSVNGHEFEIEGEGEGRPYEGTQTAKLKVTKGGPLPFAWDILSPQF

QYGSKVYVKHPADIPDYKKLSFPEGFKWERVMNFEDGGVVTVTQDSSLQDGC

FIYKVKFIGVNFPSDGPVMQKKTMGWEPSTERLYPRDGVLKGEIHKALKLKD

GGHYLVEFKSIYMAKKPVQLPGYYYVDSKLDITSHNEDYTIVEQYERTEGRH

HLFLKVDKMLLQELSEKLELAEQALASKQLQMDLMKQTLAKQEEDLETMAVL

-continued

RAQMEVYCSDFHAERAAREKIHEEKEQLALQLAILLKENNDIEEGGSRQSLM

EMQCRHGVKEMFKDFQLRQPPLVPSRKGETPPSGTSSAFSSYFNNKVGIPQE

HVDHDDFDANQLLNKINEPPKPAPRQGSAGKVDKMLLQELSEKLELAEQALA

SKQLQMDEMKQTLAKQEEDLETMAVLRAQMEVYCSDFHAERAAREKIHEEKE

QLALQLAILLKENNDIEEGGSRQSLMEMQCRHGVKEMFKDFQLRQPPLVPSR

KGETPPSGTSSAFSSYFNNKVGIPQEHVDHDDFDANQLLNKINEPPKPAPRQ

GSGRDQPLNSKKKKRLLSFRDVDFEEDSDGSGRDQPLNSKKKKRLLSFRDVD

FEEDSD.

SEQ ID NO: 51 amino acid sequence of an embodiment of a M5M6BR polypeptide
(MVIBD-MBD)
KVDKMLLQELSEKLELAEQALASKQLQMDEMKQTLAKQEEDLETMAVLRAQM

EVYCSDFHAERAAREKIHEEKEQLALQLAILLKENNDIEEGGSRQSLMEMQC

RHGVKEMFKDFQLRQPPLVPSRKGETPPSGTSSAFSSYFNNKVGIPQEHVDH

DDFDANQLLNKINEPPKPAPRQGSGRDQPLNSKKKKRLLSFRDVDFEEDSD.

SEQ ID NO: 52 is amino acid sequence of an embodiment of a M5M6BR polypeptide
(MBD-MVIBD)
RDQPLNSKKKKRLLSFRDVDFEEDSDGSGKVDKMLLQELSEKLELAEQALAS

KQLQMDEMKQTLAKQEEDLETMAVLRAQMEVYCSDFHAERAAREKIHEEKEQ

LALQLAILLKENNDIEEGGSRQSLMEMQCRHGVKEMFKDFQLRQPPLVPSRK

GETPPSGTSSAFSSYFNNKVGIPQEHVDHDDFDANQLLNKINEPPKPAPRQ.

SEQ ID NO: 53 is amino acid sequence of an embodiment of M5M6BR polypeptide
(MVIBD-MBD-MVIBD-MBD)
KVDKMLLQELSEKLELAEQALASKQLQMDEMKQTLAKQEEDLETMAVLRAQM

EVYCSDFHAERAAREKIHEEKEQLALQLAILLKENNDIEEGGSRQSLMEMQC

RHGVKEMFKDFQLRQPPLVPSRKGETPPSGTSSAFSSYFNNKVGIPQEHVDH

DDFDANQLLNKINEPPKPAPRQGSGRDQPLNSKKKKRLLSFRDVDFEEDSDG

SGKVDKMLLQELSEKLELAEQALASKQLQMDEMKQTLAKQEEDLETMAVLRA

QMEVYCSDFHAERAAREKIHEEKEQLALQLAILLKENNDIEEGGSRQSLMEM

QCRHGVKEMFKDFQLRQPPLVPSRKGETPPSGTSSAFSSYFNNKVGIPQEHV

DHDDFDANQLLNKINEPPKPAPRQGSGRDQPLNSKKKKRLLSFRDVDFEEDS

D.

SEQ ID NO: 54 is amino acid sequence of an embodiment of an M5M6BR polypeptide
(MBD-MVIBD-MBD-MVIBD)
RDQPLNSKKKKRLLSFRDVDFEEDSDGSGKVDKMLLQELSEKLELAEQALAS

KQLQMDEMKQTLAKQEEDLETMAVLRAQMEVYCSDFHAERAAREKIHEEKEQ

LALQLAILLKENNDIEEGGSRQSLMEMQCRHGVKEMFKDFQLRQPPLVPSRK

GETPPSGTSSAFSSYFNNKVGIPQEHVDHDDFDANQLLNKINEPPKPAPRQG

SGRDQPLNSKKKKRLLSFRDVDFEEDSDGSGKVDKMLLQELSEKLELAEQAL

ASKQLQMDEMKQTLAKQEEDLETMAVLRAQMEVYCSDFHAERAAREKIHEEK

EQLALQLAILLKENNDIEEGGSRQSLMEMQCRHGVKEMFKDFQLRQPPLVPS

RKGETPPSGTSSAFSSYFNNKVGIPQEHVDHDDFDANQLLNKINEPPKPAPR

Q.

-continued

SEQ ID NO: 55 is amino acid sequence of an embodiment of an M5M6BR polypeptide
(MVIBD-MBD-MVIBD-MBD-MVIBD-MBD)
KVDKMLLQELSEKLELAEQALASKQLQMDEMKQTLAKQEEDLETMAVLRAQM

EVYCSDFHAERAAREKIHEEKEQLALQLAILLLKENNDIEEGGSRQSLMEMQC

RHGVKEMFKDFQLRQPPLVPSRKGETPPSGTSSAFSSYFNNKVGIPQEHVDH

DDFDANQLLNKINEPPKPAPRQGSGRDQPLNSKKKKRLLSFRDVDFEEDSDG

SGKVDKMLLQELSEKLELAEQALASKQLQMDEMKQTLAKQEEDLETMAVLRA

QMEVYCSDFHAERAAREKIHEEKEQLALQLAILLLKENNDIEEGGSRQSLMEM

QCRHGVKEMFKDFQLRQPPLVPSRKGETPPSGTSSAFSSYFNNKVGIPQEHV

DHDDFDANQLLNKINEPPKPAPRQGSGRDQPLNSKKKKRLLSFRDVDFEEDS

DGSGKVDKMLLQELSEKLELAEQALASKQLQMDEMKQTLAKQEEDLETMAVL

RAQMEVYCSDFHAERAAREKIHEEKEQLALQLAILLLKENNDIEEGGSRQSLM

EMQCRHGVKEMFKDFQLRQPPLVPSRKGETPPSGTSSAFSSYFNNKVGIPQE

HVDHDDFDANQLLNKINEPPKPAPRQGSGRDQPLNSKKKKRLLSFRDVDFEE

DSD.

SEQ ID NO: 56 is amino acid sequence of an embodiment of an M5M6BR polypeptide
(MBD-MVIBD-MBD-MVIBD-MBD-MVIBD)
RDQPLNSKKKKRLLSFRDVDFEEDSDGSGKVDKMLLQELSEKLELAEQALAS

KQLQMDEMKQTLAKQEEDLETMAVLRAQMEVYCSDFHAERAAREKIHEEKEQ

LALQLAILLLKENNDIEEGGSRQSLMEMQCRHGVKEMFKDFQLRQPPLVPSRK

GETPPSGTSSAFSSYFNNKVGIPQEHVDHDDFDANQLLNKINEPPKPAPRQG

SGRDQPLNSKKKKRLLSFRDVDFEEDSDGSGKVDKMLLQELSEKLELAEQAL

ASKQLQMDEMKQTLAKQEEDLETMAVLRAQMEVYCSDFHAERAAREKIHEEK

EQLALQLAILLLKENNDIEEGGSRQSLMEMQCRHGVKEMFKDFQLRQPPLVPS

RKGETPPSGTSSAFSSYFNNKVGIPQEHVDHDDFDANQLLNKINEPPKPAPR

QGSGRDQPLNSKKKKRLLSFRDVDFEEDSDGSGKVDKMLLQELSEKLELAEQ

ALASKQLQMDEMKQTLAKQEEDLETMAVLRAQMEVYCSDFHAERAAREKIHE

EKEQLALQLAILLLKENNDIEEGGSRQSLMEMQCRHGVKEMFKDFQLRQPPLV

PSRKGETPPSGTSSAFSSYFNNKVGIPQEHVDHDDFDANQLLNKINEPPKPA

PRQ.

SEQ ID NO: 57 is amino acid sequence of an embodiment of an M5M6BR polypeptide
(MVIBD-MBD-MVIBD-MBD-MVIBD-MBD-MVIBD-MBD)
KVDKMLLQELSEKLELAEQALASKQLQMDEMKQTLAKQEEDLETMAVLRAQM

EVYCSDFHAERAAREKIHEEKEQLALQLAILLLKENNDIEEGGSRQSLMEMQC

RHGVKEMFKDFQLRQPPLVPSRKGETPPSGTSSAFSSYFNNKVGIPQEHVDH

DDFDANQLLNKINEPPKPAPRQGSGRDQPLNSKKKKRLLSFRDVDFEEDSDG

SGKVDKMLLQELSEKLELAEQALASKQLQMDEMKQTLAKQEEDLETMAVLRA

QMEVYCSDFHAERAAREKIHEEKEQLALQLAILLLKENNDIEEGGSRQSLMEM

QCRHGVKEMFKDFQLRQPPLVPSRKGETPPSGTSSAFSSYFNNKVGIPQEHV

DHDDFDANQLLNKINEPPKPAPRQGSGRDQPLNSKKKKRLLSFRDVDFEEDS

DGSGKVDKMLLQELSEKLELAEQALASKQLQMDEMKQTLAKQEEDLETMAVL

RAQMEVYCSDFHAERAAREKIHEEKEQLALQLAILLLKENNDIEEGGSRQSLM

EMQCRHGVKEMFKDFQLRQPPLVPSRKGETPPSGTSSAFSSYFNNKVGIPQE

HVDHDDFDANQLLNKINEPPKPAPRQGSGRDQPLNSKKKKRLLSFRDVDFEE

-continued

DSDGSGKVDKMLLQELSEKLELAEQALASKQLQMDEMKQTLAKQEEDLETMA

VLRAQMEVYCSDFHAERAAREKIHEEKEQLALQLAILLKENNDIEEGGSRQS

LMEMQCRHGVKEMFKDFQLRQPPLVPSRKGETPPSGTSSAFSSYFNNKVGIP

QEHVDHDDFDANQLLNKINEPPKPAPRQGSGRDQPLNSKKKKRLLSFRDVDF

EEDSD.

SEQ ID NO: 58 is amino acid sequence of an embodiment of an M5M6BR polypeptide
(MBD-MVIBD-MBD-MVIBD-MBD-MVIBD-MBD-MVIBD)
RDQPLNSKKKKRLLSFRDVDFEEDSDGSGKVDKMLLQELSEKLELAEQALAS

KQLQMDEMKQTLAKQEEDLETMAVLRAQMEVYCSDFHAERAAREKIHEEKEQ

LALQLAILLKENNDIEEGGSRQSLMEMQCRHGVKEMFKDFQLRQPPLVPSRK

GETPPSGTSSAFSSYFNNKVGIPQEHVDHDDFDANQLLNKINEPPKPAPRQG

SGRDQPLNSKKKKRLLSFRDVDFEEDSDGSGKVDKMLLQELSEKLELAEQAL

ASKQLQMDEMKQTLAKQEEDLETMAVLRAQMEVYCSDFHAERAAREKIHEEK

EQLALQLAILLKENNDIEEGGSRQSLMEMQCRHGVKEMFKDFQLRQPPLVPS

RKGETPPSGTSSAFSSYFNNKVGIPQEHVDHDDFDANQLLNKINEPPKPAPR

QGSGRDQPLNSKKKKRLLSFRDVDFEEDSDGSGKVDKMLLQELSEKLELAEQ

ALASKQLQMDEMKQTLAKQEEDLETMAVLRAQMEVYCSDFHAERAAREKIHE

EKEQLALQLAILLKENNDIEEGGSRQSLMEMQCRHGVKEMFKDFQLRQPPLV

PSRKGETPPSGTSSAFSSYFNNKVGIPQEHVDHDDFDANQLLNKINEPPKPA

PRQGSGRDQPLNSKKKKRLLSFRDVDFEEDSDGSGKVDKMLLQELSEKLELA

EQALASKQLQMDEMKQTLAKQEEDLETMAVLRAQMEVYCSDFHAERAAREKI

HEEKEQLALQLAILLKENNDIEEGGSRQSLMEMQCRHGVKEMFKDFQLRQPP

LVPSRKGETPPSGTSSAFSSYFNNKVGIPQEHVDHDDFDANQLLNKINEPPK

PAPRQ.

SEQ ID NO: 59 is amino acid sequence of an embodiment of an M5M6BR polypeptide
(MVIBD-MVIBD-MVIBD-MBD-MBD-MBD)
KVDKMLLQELSEKLELAEQALASKQLQMDEMKQTLAKQEEDLETMAVLRAQM

EVYCSDFHAERAAREKIHEEKEQLALQLAILLKENNDIEEGGSRQSLMEMQC

RHGVKEMFKDFQLRQPPLVPSRKGETPPSGTSSAFSSYFNNKVGIPQEHVDH

DDFDANQLLNKINEPPKPAPRQGSGKVDKMLLQELSEKLELAEQALASKQLQ

MDEMKQTLAKQEEDLETMAVLRAQMEVYCSDFHAERAAREKIHEEKEQLALQ

LAILLKENNDIEEGGSRQSLMEMQCRHGVKEMFKDFQLRQPPLVPSRKGETP

PSGTSSAFSSYFNNKVGIPQEHVDHDDFDANQLLNKINEPPKPAPRQGSGKV

DKMLLQELSEKLELAEQALASKQLQMDEMKQTLAKQEEDLETMAVLRAQMEV

YCSDFHAERAAREKIHEEKEQLALQLAILLKENNDIEEGGSRQSLMEMQCRH

GVKEMFKDFQLRQPPLVPSRKGETPPSGTSSAFSSYFNNKVGIPQEHVDHDD

FDANQLLNKINEPPKPAPRQGSGRDQPLNSKKKKRLLSFRDVDFEEDSDGSG

RDQPLNSKKKKRLLSFRDVDFEEDSDGSGRDQPLNSKKKKRLLSFRDVDFEE

DSDGSG.

DETAILED DESCRIPTION

The invention, in part, relates to molecules and compounds that can be used to target the cell body of cells in which they are present. In addition, the invention in some aspects includes expression of fusion proteins comprising a targeting polypeptide of the invention and one or more cargo polypeptides in a cell. In some embodiments of the invention, a cargo polypeptide is also referred to as a "polypeptide of interest" to express in a cell. In some aspects of the invention a cargo polypeptide is a membrane polypeptide such as a channel polypeptide or an ion pump polypeptide. A cargo may be an opsin polypeptide, including a stimulus-activated opsin polypeptide, such as a light-activated polypeptide. In some embodiments of the invention, a fusion protein comprises: a targeting polypeptide of the invention, a cargo polypeptide of interest to express in a cell, and optionally a detectable label polypeptide. The invention, in part, also relates to methods of treating diseases and conditions in subject that include expressing fusion proteins in cells in a subject, wherein a fusion protein expressed in one or more cells in the subject comprise a targeting polypeptide of the invention and a polypeptide of interest.

The invention, in part, relates to soma-targeted opsin molecules, that are selectively expressed in the cell body and weakly expressed on the dendrites or axons, therefore effectively eliminating crosstalk, or signal overlap, of multiple expressed opsin molecules. A number of soma-targeting polypeptides have now been identified and used in methods described herein. In a non-limiting example, it has now been demonstrated that a short amino terminal segment of the kainate receptor KA2 subunit or functional variants thereof, can be expressed with an opsin polypeptide, such as the channelrhodopsin CoChR, in a fusion protein and used in methods to selectively traffick the CoChR polypeptide to the cell body of neurons in the mammalian cortex.

Another soma-targeting polypeptide that has now been identified comprises one or more myosin 5-myosin 6 binding repeat polypeptides or functional variants thereof. The term: myosin 5-myosin 6 binding repeat is also referred to herein as "M5M6BR". It has now been demonstrated that the M5M6BR polypeptide or functional variant thereof can be expressed in a fusion protein with a cargo molecule, such as an opsin polypeptide, in a cell, and the M5M6BR polypeptide trafficks the cargo molecule to the cell soma.

Another soma-targeting polypeptide that has now been identified comprises an rSK-1-tail polypeptide or functional variants thereof. It has now been demonstrated that the rSK-1-tail polypeptide or functional variant thereof can be expressed in cell as part of a fusion protein that also includes a cargo molecule, such as an opsin polypeptide, and the rSK-1-tail polypeptide trafficks the cargo molecule to the cell soma.

Certain embodiments of methods and compositions of the invention can be used in combination with holographic 2P stimulation for activation and/or imaging of targeted polypeptide functions. Fusion proteins of the invention that comprise an opsin and a soma-targeting polypeptide of the invention, for example a KA2 targeting polypeptide, a M5M6BR polypeptide, or a rSK-1-tail polypeptide can be used in methods for optogenetic stimulation of single cells in mammalian brain slices, with millisecond temporal resolution, effectively without cross-talk activation of nearby cells. The term: "KA2 polypeptide of the invention" used herein in reference to targeting polypeptides, includes the KA2 polypeptide set forth as SEQ ID NO: 1 and polypeptides that are functional variants of the KA2 polypeptide of SEQ ID NO: 1.

The term "M5M6BR polypeptide of the invention" as used herein in reference to targeting polypeptides, includes the 1, 2, 3, or more of the myosin-5 binding repeat (MBR) polypeptide set forth herein as SEQ ID NO: 22 and 1, 2, 3, or more of the myosin-6 binding repeat (MVIBD) polypeptide set forth as SEQ ID NO: 23. In some aspects of the invention, a M5M6BR comprises two or more MBR polypeptides, or functional variants thereof, in series and two or more MVIBD polypeptides, or functional variants thereof, in series. Non-limiting examples of M5M6BR polypeptides of the invention are SEQ ID Nos: 32 and 51-59, which each illustrate different combinations of MVIBD and MBR polypeptides. Aspects of the invention include compositions and methods that include M5M6BR molecules and functional variants thereof. The amino acid sequence of the MVIBD and MBD polypeptides included in embodiments of M5M6BR soma-targeting polypeptides of the invention are independently selected. For example, in some aspects of compositions and methods of the invention, each MBD polypeptide in a M5M6BR soma-targeting polypeptide has an amino acid sequence set forth herein as SEQ ID NO: 22 and each MVIBD polypeptide in the M5M6BR soma-targeting polypeptide has the amino acid sequence set forth herein as SEQ ID NO: 23. M5M6BR sequences can be considered to be parent M5M6BR sequences for functional variants derived therefrom. Non-limiting examples of parent M5M6BR polypeptides of the invention are SEQ ID Nos: 32 and 51-59. As used herein the terms "parent M5M6BR polypeptide" encompasses polypeptides of the invention comprising 1, 2, 3, or more of the myosin-5 binding repeat (MBD) polypeptide set forth herein as SEQ ID NO: 22 and 1, 2, 3, or more of the myosin-6 binding repeat (MVIBD) polypeptide set forth as SEQ ID NO: 23. Sequence modifications to the amino acid sequence of a parent M5M6BR polypeptide of the invention can result in a functional variant of that parent M5M6BR polypeptide. It will be understood that a parent M5M6BR polypeptides may differ from another parent M5M6BR polypeptide in characteristics such as: number, order, and arrangement of MBD and MVIBD polypeptides and may also differ in linker sequences and/or other included sequence elements.

In some aspects of the invention, one or more MBD or MVIBD polypeptides may have an amino acid sequence that is different from SEQ ID NO: 22 or SEQ ID NO: 23, respectively. For example, though not intended to be limiting, a M5M6BR soma-targeting polypeptide may include one or more MBD polypeptides having the sequence set forth as SEQ ID NO: 22, one or more MBD functional variants, one or more MVIBD polypeptides having the sequence set forth as SEQ ID NO: 23 and/or, one or more MVIBD functional variants. The term "independently selected" as used herein in the context of components for an M5M6BR polypeptide means that the practitioner may determine the order and amino acid sequence of each MBD and MVIBD polypeptide included in a M5M6BR soma-targeting polypeptide of the invention can be chosen independent of the others included in the M5M6BR. In some aspects of the invention, a M5M6BR polypeptide includes: two or more MBD polypeptides with the same amino acid sequence; two or more MVIBD polypeptides with the same amino acid sequence; two or more MBD polypeptides with different amino acid sequences; and/or two or more MVIBD polypeptides with different amino acid sequences. The skilled artisan will be readily able to select and use different combinations of MBD and MVIBD polypeptide and functional variants thereof as components of M5M6BR soma-targeting polypeptides of the invention.

In reference to M5M6BR polypeptides of the invention, the term "tandem" is used herein to describe two polypeptides that are in series with each other in an M5M6BR polypeptide. In a non-limiting example, an M5M6BR polypeptide of the invention that comprises the sequences: "MBR"-linker-"MBR" (see SEQ ID NO: 28) and "MVIBD" linker-"MVIBD" (see SEQ ID NO: 29) and may be referred to as comprising tandem MBR sequences and tandem MVIBD sequences, respectively. In some aspects of the invention, MBR, MVIBD, and other polypeptides may be connected to adjacent polypeptides and amino acid sequences with a linker amino acid sequence. An example of a linker amino acid sequence is: GSG and additional linker sequences are known and routinely used in the art and are suitable for use in compositions and methods of the invention. Linker sequences are also referred to as "spacer" sequences. In some aspects of compositions and methods of the invention, an M5M6BR polypeptide comprises one, two or more MBR polypeptides, one, two, or more MVIBD polypeptides, and one, two, or more linker polypeptides. Non-limiting examples of fusion proteins comprising an MVIBD polypeptide of the invention are set forth as SEQ ID Nos: 43-48.

The term "rSK-1-tail polypeptide of the invention" as used herein in reference to targeting polypeptides, includes the amino acid sequence set forth as SEQ ID NO: 31, and functional variants thereof. rSK-1-tail polypeptide set forth as SEQ ID NO: 31 is encoded by the polynucleotide sequence set forth as SEQ ID NO: 30. Non-limiting examples of constructs of the invention that comprise a rSK-1-tail polypeptide are set forth as SEQ ID Nos: 33-37. Non-limiting examples of fusion proteins of the invention that comprise a RSK-1-tail polypeptide are set forth as SEQ ID Nos: 36 and 38.

A fusion protein of the invention may, in some aspects, comprise an opsin polypeptide and a KA2 targeting polypeptide set forth herein as SEQ ID NO: 1 or a functional variant thereof, a M5M6BR polypeptide described herein or a functional variant thereof, or a rSK-1-tail polypeptide set forth herein as SEQ ID NO: 31 or a functional variant thereof. A non-limiting example of a fusion protein of the invention comprises a CoChR polypeptide and a soma-targeting polypeptide of the invention, such as but not limited to a KA2 polypeptide, or functional variant thereof. A non-limiting example of a fusion protein of the invention is called: somatic CoChR (soCoChR), which has the amino acid sequence set forth herein as SEQ ID NO: 20, encoded by the mammalian-codon optimized nucleic acid sequence set forth herein as: SEQ ID NO: 21. CoChR, the amino acid sequence is set forth there as SEQ ID NO: 18, which is encoded by the mammalian codon optimized nucleic acid sequence set forth herein as: SEQ ID NO: 19. The CoChR polypeptide is a channelrhodopsin originally derived from the species Chloromonas oogama, see: Klapoetke, N. et al. (2014) Nat Methods March; 11(3): 338-346, the content of which is incorporated by reference herein in its entirety. Another non-limiting example of a fusion protein of the invention comprises a CsChrimson polypeptide and a M5M6BR polypeptide such as in the sequences set forth herein as SEQ ID NO: 25 and 27, which are encoded by SEQ ID Nos: 24 and 26, respectively.

The invention also includes, in some aspects, use of optimized 2P optics with a fusion protein of the invention comprising a soma-targeting polypeptide of the invention, such as, but not limited to: a KA2 polypeptide set forth as SEQ ID NO: 1, or a functional variant thereof, and an opsin polypeptide, which can permit a diverse set of neural codes and computations to be probed in systems and circuit neuroscience. As used herein components of a fusion protein, such as, but not limited to: one or more of a KA2 polypeptide, a M5M6BR polypeptide, an rSK-1-tail polypeptide, an opsin polypeptide, an additional targeting polypeptide, and a detectable label polypeptide, may be referred to being "fused" to each other. For example, when referring to a KA2 polypeptide and an opsin that are part of a fusion protein, the KA2 polypeptide may be referred to as being "fused" to the opsin polypeptide. As used herein, the term "and functional variant thereof" in used a phrase such as: "KA2 polypeptide, M5M6BR polypeptide, rSK-1-tail polypeptide and functional variants thereof" is intended to encompass: functional variants of the KA2 polypeptide, functional variants of a parent M5M6BR polypeptide, and functional variants of the rSK-1-tail polypeptide.

In some aspects of the invention, one or more cargo polypeptides of interest to express in a cell can be directed by a soma-targeting polypeptide of the invention, such as KA2 polypeptides, M5M6BR polypeptides, rSK-1-tail polypeptides and functional variants thereof of the invention, to the cell body of the cell in which they are expressed. As used herein, the term "directed" used in reference to a cargo polypeptide of interest that is part of a fusion protein that also includes a soma-targeting polypeptide of the invention such as a KA2 polypeptide, M5M6BR polypeptide, rSK-1-tail polypeptide—or functional variant thereof of the invention, means the polypeptide of interest is localized in the cell body of the cell in which the fusion protein is expressed, due to the function of the soma-targeting polypeptide. As herein, the term "directed" and "directing" are used interchangeably with the terms "targeted" and "targeting". A soma-targeting polypeptide of the invention, such as a KA2 polypeptide, M5M6BR polypeptide, rSK-1-tail polypeptide of the invention directs the localization of the expressed polypeptide of interest to the soma of the cell in which it is expressed. The ability to direct the location of the expressed polypeptide of interest to a specific cell region, the soma, results in improved efficiencies of specific delivery and localization of polypeptides of interest in cells. A soma-targeting polypeptide of the invention, such as a KA2 polypeptide, M5M6BR polypeptide, rSK-1-tail polypeptide or functional variants thereof may be used in embodiments of the invention for directed delivery of a membrane polypeptide of interested such as a membrane channel polypeptide or an ion pump polypeptide in a cell. In certain aspects of the invention, a polypeptide of interest is an opsin polypeptide, which may be a light-driven microbial opsin.

Compositions of the invention may include a soma-targeting molecule of the invention, such as a KA2 molecule, M5M6BR molecule, rSK-1-tail molecule or functional variant thereof, and an opsin molecule, and one or more additional molecules. In some embodiments of the invention, a soma-targeting molecule of the invention, such as a KA2 molecule, M5M6BR molecule, rSK-1-tail molecule or functional variant thereof is a polypeptide. In certain embodiments of the invention, a KA2 molecule M5M6BR molecule, rSK-1-tail molecule or functional variant thereof is a polynucleotide with a nucleic acid sequence that encodes a KA2 polypeptide, M5M6BR polypeptide, rSK-1-tail polypeptide or a functional variant thereof. The KA2 polypeptide set forth as SEQ ID NO: 1, and encoded by SEQ ID NO: 2, is also referred to herein as "KA2(1-150)", with the "1-150" referring to amino acid residues 1-150 of a full-length amino acid sequence of a 979 amino acid kainate receptor subunit 2, also referred to as "KA2" and "grik5", is set forth herein as SEQ ID NO: 16, and encoded by the nucleic acid sequence set forth herein as SEQ ID NO: 17.

Cargo sequences (polypeptides and/or polynucleotides), which also referred to herein as sequences of interest, may include opsins such as channelrhodopsin, halorhodopsin, Archaerhodopsin, and *Leptosphaeria* rhodopsin polypeptides and their encoding polynucleotides, numerous of which are well known in the art as tools for optical control of membrane potential in electrically excitable cells and that are routinely expressed in fusion proteins and used in optogenetic methods and compositions.

Expression of such an opsin in a cell permits modulation of the cell's membrane potential when the cell is contacted with a suitable light, or other stimulatory means. Methods to prepare and express a light-activated opsin in a cell, and in a subject, are well known in the art, as are methods to select and apply a suitable wavelength of light to the cell in which the opsin is expressed in order to activate the expressed opsin channel or ion pump in the cell. In some aspects of the invention, one or more soma-targeting polypeptides of the invention, such as a KA2 polypeptide, M5M6BR polypeptide, rSK-1-tail polypeptide or functional variants thereof may be used to direct one or more independently selected opsins expressed in a cell and/or subject. In certain aspects of the invention different wavelengths of light may be applied to a cell or cells comprising one or more fusion proteins, respectively, in order to activate the independently selected opsins, which may be activated by different wavelengths of light. Methods of adjusting illumination variables are well-known in the art and representative methods can be found in publications such as: Lin, J., et al., Biophys. J. 2009 Mar. 4; 96(5):1803-14; Wang, H., et al., 2007 Proc Natl Acad Sci USA. 2007 May 8; 104(19):8143-8. Epub 2007 May 1; the content of each of which is incorporated herein by reference in its entirety. It will be understood that an opsin polypeptide that is activated or inhibited by light or that is activated or inhibited by another stimulation means can be used in aspects of compositions and methods of the invention.

In certain implementations, the invention comprises methods for preparing and using genes encoding light-activated opsins such as light-activated ion channel polypeptides and light-activated ion pumps in vectors that also include a nucleic acid molecule that encodes a soma-targeting polypeptide of the invention, such as a KA2 polypeptide, M5M6BR polypeptide, rSK-1-tail polypeptide or functional variant thereof. The invention, in part, also includes polynucleotides comprising nucleic acid sequences that encode a soma-targeting polypeptide of the invention, such as a KA2 polypeptide, M5M6BR polypeptide, rSK-1-tail polypeptide or functional variant thereof of the invention as well as vectors and constructs that comprise such nucleic acid sequences. In some embodiments the invention includes expression in cells, tissues, and subjects of polypeptides encoded by the nucleic acid sequences.

Targeting Sequences and Functional Variants

As used herein the term "targeting sequence" means a soma-targeting sequence of the invention, such as a KA2 polypeptide or encoding nucleic acid molecule, M5M6BR polypeptide or encoding nucleic acid molecule, rSK-1-tail polypeptide or encoding nucleic acid molecule or functional variants thereof of the invention or a functional variant of a soma-targeting polypeptide or encoding nucleic acid molecule of the invention, such as a KA2 polypeptide or encoding nucleic acid molecule, M5M6BR polypeptide or encoding nucleic acid molecule, rSK-1-tail polypeptide or encoding nucleic acid molecule, or functional variants thereof of the invention. The term "variant" as used herein in the context of polypeptide molecules and/or polynucleotide molecules, describes a molecule with one or more of the following characteristics: (1) the variant differs in sequence from the molecule of which it is a variant, (2) the variant is a fragment of the molecule of which it is a variant and is identical in sequence to the fragment of which it is a variant, and/or (3) the variant is a fragment and differs in sequence from the fragment of the molecule of which it is a variant. As used herein, the term "parent" in reference to a sequence means a sequence from which a variant originates. For example, though not intended to be limiting: SEQ ID NO: 1 is the parent sequence for a KA2 functional variant of the invention and SEQ ID NO: 31 is the parent sequence for a rSK-1-tail functional variant of the invention, etc. As used herein a parent M5M6BR sequence is a sequence comprising one or more MVD polypeptides that has an amino acid sequence set forth herein as SEQ ID NO: 22 and one or more MVIBD polypeptides that has the amino acid sequence set forth herein as SEQ ID NO: 23. Thus, in some aspects of the invention a parent M5M6BR polypeptide has a sequence set forth as SEQ ID NO: 32, 51-59, though, as described above herein, the term parent M5M6BR polypeptide is understood to include additional polypeptides that comprise 1, 2, 3, or more of the myosin-5 binding repeat (MBD) polypeptide set forth herein as SEQ ID NO: 22 and 1, 2, 3, or more of the myosin-6 binding repeat (MVIBD) polypeptide set forth as SEQ ID NO: 23.

A soma-targeting polypeptide of the invention, such as a KA2 polypeptide, M5M6BR polypeptide, rSK-1-tail polypeptide of the invention may have the amino acid sequence set forth herein. For example, a KA2 targeting polypeptide of the invention may have the amino acid sequence set forth herein as SEQ ID NO: 1, or may be a functional variant of the KA2 targeting polypeptide that has a sequence that is modified from that of SEQ ID NO: 1. A M5M6BR targeting polypeptide of the invention may be a parent M5M6BR polypeptide as described herein, or may be a functional variant of the parent M5M6BR targeting polypeptide that has a sequence that is modified from that of its parent. In another example, a rSK-1-tail targeting polypeptide of the invention may have the amino acid sequence set forth as SEQ ID NO: 31, or may be a functional variant of the rSK-1-tail targeting polypeptide that has a sequence that is modified from that of SEQ ID NO: 31.

As used herein the term "modified" or "modification" in reference to a polypeptide sequence or a polynucleotide sequence refers to a change of 1, 2, 3, 4, 5, 6, 7, 8, 9, 10, 11, 12, 13, 14, 15, 16, 17, 18, 18, 20, 21, 22, 23, 24, 25, or more amino acids or nucleic acids, respectively in the sequence as compared to the soma-targeting polypeptide of the invention, such as a KA2 polypeptide set forth herein as SEQ ID NO: 1, a parent M5M6BR polypeptide as described herein, or an rSK-1-tail polypeptide set forth herein as SEQ ID NO: 31, or any of their encoding nucleic acid sequence. As used herein, a sequence change or modification may be one or more of a substitution, deletion, insertion or a combination thereof. For example, though not intended to be limiting: the amino acid sequence of a variant KA2 polypeptide may be identical to the KA2 sequence set forth as SEQ ID NO: 1 except that it has one, two, three, four, five, or more amino acid substitutions, deletions, insertions, or combinations thereof. SEQ ID NO: 10 is a non-limiting example of a functional variant of the KA2 polypeptide of SEQ ID NO: 1 that includes an amino acid substitution.

The invention, in some aspects also includes soma-targeting polypeptides of the invention, such as a KA2 polypeptide, an M5M6BR polypeptide, an rSK-1-tail polypeptide, and functional variants thereof, and their encoding nucleic acid molecules, that have one or more substitutions or other modifications from molecules described herein, while retaining at least a portion of the function of the parent molecule of which they are a variant. For example, a soma-targeting polypeptides of the invention, such as a KA2 polypeptide, an M5M6BR polypeptide, an rSK-1-tail polypeptide sequence can be modified with one or more substitutions, deletions, insertions, combinations thereof, or other modifications and can be tested using methods described herein for characteristics including, but not limited to: expression, cell localization, targeting of one or more polypeptides of interest to the soma of a cell in which they are expressed, and the ability to direct an opsin polypeptide (co-expressed as part of a fusion protein) to the cell body (soma) of the cell in which the fusion protein comprising the soma-targeting polypeptide variant and the opsin are expressed. A functional variant will have at least a portion of the targeting function of soma-targeting polypeptides of the invention, such as a KA2 polypeptide, an M5M6BR polypeptide, an rSK-1-tail polypeptide from which it was derived, which is also referred to herein as its "parent sequence"). In certain aspects of the invention, a KA2, M5M6BR, or rSK-1-tail functional variant has at least 5%, 10%, 15%, 20%, 25%, 30%, 35%, 40%, 45%, 50%, 55%, 60%, 65%, 70%, 75%, 80%, 85%, 90%, 95%, 100%, 105%, 110%, 120%, 130%, 140%, 150%, 160%, 170%, 180%, 190%, or 200% (including all integers in the stated range) of a level of function of the KA2 polypeptide, M5M6BR polypeptide, or rSK-1-tail polypeptide respectively, from which it was derived, which in some embodiments of the invention is SEQ ID NO: 1 for a KA2 functional variant, a parent M5M6BR sequence for a M5M6BR functional variant, and SEQ ID NO: 31 for a rSK-1-tail functional variant. In some aspects of the invention, a functional variant of a soma-targeting polypeptides of the invention, such as a KA2 polypeptide, an M5M6BR polypeptide, an rSK-1-tail polypeptide has more than 200% of the function of its parent polypeptide. For example, though not intended to be limiting, in some aspects of the invention, a functional variant of the KA2 polypeptide set forth as SEQ ID NO: 1 has more than 200% of the function of the KA2 polypeptide set forth as SEQ ID NO: 1. A non-limiting example of a functional variant of SEQ ID NO: 1, that includes the amino acid sequence set forth as SEQ ID NO: 1, but with a Y→A amino acid substitution at residue corresponding to amino acid 76 in SEQ ID NO: 1. The Y76A substituted KA2 polypeptide us a functional variant of KA2 polypeptide set forth as SEQ ID NO: 1, and can be used as a targeting KA2 polypeptide in compositions and methods of the invention.

It will be understood that in some embodiments of the invention, a functional variant of a soma-targeting polypeptide of the invention, such as a KA2 polypeptide, an M5M6BR polypeptide, an rSK-1-tail polypeptide may have an amino acid sequence that corresponds to the amino acid sequence of its parent KA2 polypeptide (a non-limiting example of which is SEQ ID NO: 1), its parent M5M6BR polypeptide (non-limiting examples of which are SEQ ID NO: 32, 51-59), or its parent rSK-1-tail polypeptide (a non-limiting example of which is SEQ ID NO: 31), or a variant thereof, but without 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74 amino acids corresponding to the amino acid sequence of the parent KA2 polypeptide, parent M5M6BR polypeptide, or parent rSK-1-tail polypeptide, respectively. For example, though not intended to be limiting, SEQ ID NO: 12 consists of amino acids 1-100 of SEQ ID NO: 1. SEQ ID NO: 12 has been tested and identified as a functional variant of SEQ ID NO: 1 that can be used as a soma-targeting polypeptide in methods and compositions of the invention. In some aspects of the invention, a functional variant of a soma-targeting polypeptide of the invention, such as a KA2 polypeptide, an M5M6BR polypeptide, or an rSK-1-tail polypeptide, set forth herein as SEQ ID NO: 1, a parent M5M6BR sequence, SEQ ID NO: 31, respectively may be a fragment of the parent polypeptide set forth herein wherein the fragment has at least 75%, 80%, 85%, 90%, 95%, 97%, 98%, 99%, or 100% sequence identity to the region of the amino acid sequence of the parent sequence which it aligns. As a non-limiting example, a functional variant of a KA2 polypeptide set forth herein as SEQ ID NO: 1, may be a fragment of SEQ ID NO: 1 wherein the fragment has at least 75%, 80%, 85%, 90%, 95%, 97%, 98%, 99%, or 100% sequence identity to the region of the amino acid sequence of SEQ ID NO: 1 which it aligns.

It has been determined that amino acids 1-75 of SEQ ID NO: 1 may be more able to tolerate sequence modification than can be tolerated by amino acids 76-150, or amino acids 76-100 of SEQ ID NO: 1. In some aspects of the invention, a functional variant of SEQ ID NO: 1 may have at least 45%, 50%, 55%, 60%, 65%, 70%, 75%, 80%, 85%, 90%, 95%, 96%, 97%, 98%, 99%, or 100% identity to amino acids 1-75 of SEQ ID NO: 1 as set forth herein. In certain aspects of the invention, a functional variant of SEQ ID NO: 1 may have at least 80%, 85%, 90%, 95%, 96%, 97%, 98%, 99%, or 100% identity to the amino acids 76-100 or 76-150 of SEQ ID NO: 1 as set forth herein. In conjunction with the teaching provided herein, a skilled artisan will be able to use art-known procedures to envision, prepare, and utilize additional targeting KA2 polypeptides that retain a portion of the amino acid sequence set forth herein as SEQ ID NO: 1, SEQ ID NO: 3, SEQ ID NO: 10, SEQ ID NO: 12, or SEQ ID NO:16.

In certain aspects of the invention a functional variant of a soma-targeting polypeptides of the invention, such as a KA2 polypeptide, an M5M6BR polypeptide, an rSK-1-tail polypeptide may comprise a sequence set forth as SEQ ID NO: 1, a parent M5M6BR sequence, or SEQ ID NO: 31, respectively or a fragment thereof that includes one or more additional amino acids. For example, though not intended to be limiting, a functional variant may include one or more additional amino acids at the C terminus and/or N terminus that are not present in SEQ ID NO: 1, the parent M5M6BR sequence, SEQ ID NO: 31 or a fragment thereof. For example, though not intended to be limiting, SEQ ID NO: 3 is the amino acid sequence of a polypeptide that is longer than the sequence set forth herein as SEQ ID NO: 1 that includes amino acids 1-150 of SEQ ID NO: 1 and additional C-terminus amino acids. The polypeptide having the sequence set forth as SEQ ID NO: 3 includes amino acids 1-360 of a full-length KA2 polypeptide, which is set forth herein as SEQ ID NO: 16. SEQ ID NO: 3 is a non-limiting example of a functional variant of SEQ ID NO: 1 that has been determined to function as a soma-targeting polypeptide in methods and compositions of the invention. In conjunction with the teaching provided herein, a skilled artisan can use art-known methods to envision, prepare, and utilize additional targeting KA2 polypeptides that retain a portion of the amino acid sequence set forth herein as SEQ ID NO: 1 and are greater in length than SEQ ID NO: 1.

In invention in certain aspects, includes compositions and methods comprising a soma-targeting polypeptide of the invention, such as a KA2 polypeptide, an M5M6BR polypeptide, an rSK-1-tail polypeptide that is a fragment of the amino acid sequence set forth as SEQ ID NO: 1, the parent M5M6BR sequence, or SEQ ID NO: 31, respectively, or is greater in length than SEQ ID NO: 1, a parent M5M6BR sequence, or SEQ ID NO: 31, respectively, and retains at least a portion of the targeting function of the SEQ ID NO:

1, the parent M5M6BR sequence, or SEQ ID NO: 31 polypeptide, respectively, to direct a cargo polypeptide to the soma of a cell in which a fusion protein comprising the KA2, M5M6BR, or rSK-1-tail polypeptide variant and the cargo polypeptide is expressed. A functional variant of the soma-targeting polypeptide of the invention, such as a KA2 polypeptide, an M5M6BR polypeptide, an rSK-1-tail polypeptide that is a fragment of the amino acid sequence set forth as SEQ ID NO: 1, the parent M5M6BR sequence, or SEQ ID NO: 31, respectively may be shorter or longer than the sequence of SEQ ID NO: 1, the parent M5M6BR sequence, or SEQ ID NO: 31, respectively, as set forth herein.

A variant polypeptide (also referred to herein as a "modified" polypeptide) may include one or more deletions, point mutations, truncations, amino acid substitutions and/or additions of amino acids or non-amino acid moieties. Modifications of a polypeptide of the invention, such as soma-targeting polypeptide of the invention, such as a KA2 polypeptide, an M5M6BR polypeptide, an rSK-1-tail polypeptide set forth as SEQ ID NO: 1, the parent M5M6BR sequence, or SEQ ID NO: 31, respectively, may be made in certain aspects of the invention by modification of the nucleic acid sequence that encodes the polypeptide. Modifications of the molecules of the invention also embrace fusion proteins comprising all or part of the amino acid sequence set forth as SEQ ID NO: 1, the parent M5M6BR sequence, SEQ ID NO: 31, or functional variants thereof.

In certain embodiments of the invention, a polypeptide variant may be a polypeptide that is modified specifically to alter a feature of the polypeptide that may be, but need not be related to its physiological activity. For example, though not intended to be limiting, one or more amino acid residues may substituted, deleted, or added to a soma-targeting polypeptide of the invention, such as a KA2 polypeptide, an M5M6BR polypeptide, an rSK-1-tail polypeptide resulting in a KA2, M5M6BR, or rSK-1-tail polypeptide variant having one or more of: increased stability, increased targeting efficiency; a least a portion of the targeting efficiency of the KA2, M5M6BR, rSK-1-tail polypeptide set forth as SEQ ID NO: 1, the parent M5M6BR sequence, and SEQ ID NO: 31, respectively, etc. As used herein the term "targeting efficiency" when used in relation to a soma-targeting polypeptide of the invention, such as a KA2 polypeptide, an M5M6BR polypeptide, an rSK-1-tail polypeptide or functional variant thereof means the ability of the polypeptide to direct one or more additional polypeptides, for example though not intended to be limiting: an opsin polypeptide, a detectable label polypeptide, etc. to the cell body of a cell in which the soma-targeting polypeptide of the invention, such as a KA2 polypeptide, a M5M6BR polypeptide, a rSK-1-tail polypeptide, or a functional variant thereof is expressed in a fusion protein that also comprises the one or more additional polypeptides. In conjunction with teaching provided herein, a skilled artisan can use art-known methods to envision, prepare, and utilize additional functional variants of a soma-targeting polypeptide of the invention, such as a KA2 polypeptide, an M5M6BR polypeptide, an rSK-1-tail polypeptide comprising an amino acid sequence set forth as SEQ ID NO: 1, the parent M5M6BR sequence, or SEQ ID NO: 31, respectively, but with one, two, three, four, or more amino acid substitutions, deletions, additions, or combinations thereof.

Polypeptides suitable for use in methods of the invention can be synthesized with modifications and/or modifications can be made in a polypeptide by selecting and introducing an amino acid substitution, deletion, or addition. Modified polypeptides then can be tested for one or more activities [e.g., delivery of cargo (for example: delivery of an opsin polypeptide); stability; accurate direction of the soma-targeting polypeptide of the invention, such as a KA2 polypeptide, an M5M6BR polypeptide, an rSK-1-tail polypeptide and its cargo (for example: directing an opsin polypeptide co-expressed in a fusion protein with the soma-targeting polypeptide) to the soma of a cell in which the molecules are expressed, etc.) to determine which modification provides a modified polypeptide with the desired properties and function.

The skilled artisan will also realize that conservative amino acid substitutions may be made in a soma-targeting polypeptide of the invention, such as a KA2 polypeptide, an M5M6BR polypeptide, an rSK-1-tail polypeptide of the invention to provide functional variant polypeptides, i.e., a variant KA2, M5M6BR, or rSK-1-tail polypeptide that retains at least a portion of the functional capability of the un-modified polypeptide. As used herein, a "conservative amino acid substitution" refers to an amino acid substitution that does not alter the relative charge or size characteristics of the polypeptide in which the amino acid substitution is made. Conservative substitutions of amino acids may, in some embodiments of the invention, include substitutions made amongst amino acids within the following groups: (a) M, I, L, V; (b) F, Y, W; (c) K, R, H; (d) A, G; (e) S, T; (f) Q, N; and (g) E, D. Polypeptide variants can be prepared according to methods for altering polypeptide sequence and known to one of ordinary skill in the art such. Non-limiting examples of functional variants of a soma-targeting polypeptide of the invention, such as a KA2 polypeptide, an M5M6BR polypeptide, an rSK-1-tail polypeptide of the invention are KA2, M5M6BR, and rSK-1-tail polypeptides comprising conservative amino acid substitutions of the KA2, M5M6BR, and rSK-1-tail polypeptides, respectively.

The invention, in part, includes functional variants of a nucleic acid sequences that encode soma-targeting polypeptides of the invention, such as a KA2 polypeptide, an M5M6BR polypeptide, an rSK-1-tail polypeptide comprising amino acid sequences set forth as SEQ ID NO: 1, the parent M5M6BR sequence, or SEQ ID NO: 31, respectively. In some aspects of the invention, a functional variant of a KA2, M5M6BR, or rSK-1-tail nucleic acid sequence of the invention has at least 75%, 80%, 85%, 90%, 95%, 96%, 97%, 98%, or 99% identity to the nucleic acid sequence that encodes SEQ ID NO: 1, the parent M5M6BR sequence, or SEQ ID NO: 31, respectively, and the nucleic acid sequence of the functional variant encodes a polypeptide that is a functional variant of a KA2, M5M6BR, or rSK-1-tail polypeptide, as described elsewhere herein. In certain embodiments of the invention, a functional variant of a polynucleotide has at least 85%, 90%, 95%, 97%, 98%, 99%, or 100% nucleic acid sequence identity to the polynucleotide sequence of which it is a variant. In some aspects of the invention, a functional variant of the polynucleotide set forth herein as SEQ ID NO: 2 may have 45%, 50%, 55%, 60%, 65%, 70%, 75%, 80%, 85%, 90%, 95%, 96%, 97%, 98%, 99%, or 100% identity to the nucleic acid sequence that encodes amino acids 1-75 of SEQ ID NO: 1 as set forth herein. In certain aspects of the invention, a functional variant of SEQ ID NO: 2 may have at least 80%, 85%, 90%, 95%, 96%, 97%, 98%, 99%, or 100% identity to the nucleic acid sequence that encodes amino acids 76-100 or 76-150 of SEQ ID NO: 1. In conjunction with the teaching provided herein, a skilled artisan will be able to use art-known procedures to envision, prepare, and utilize additional targeting KA2, M5M6BR, and rSK-1-tail polypeptides that retain a portion of the amino acid sequence set forth herein as SEQ ID NO: 1, a parent M5M6BR sequence, and SEQ ID NO: 31, respectively.

Sequence identity can be determined using standard techniques known in the art. To determine the percent identity (similarity) of two amino acid sequences the sequences are aligned for optimal comparison purposes (e.g., gaps may be introduced in the sequence of one protein for optimal alignment with the other protein). The amino acid residues at corresponding amino acid positions are then compared. When a position in one sequence is occupied by the same amino acid residue as the corresponding position in the other sequence, then the molecules have identity/similarity at that position. The percent identity or percent similarity between the two sequences is a function of the number of identical positions shared by the sequences (i.e., % identity or % similarity=number of identical positions/total number of positions×100). Such an alignment can be performed using any one of a number of well-known computer algorithms designed and used in the art for such a purpose. Similarly, percent identity/similarity of polynucleotide sequences encoding a polypeptide of the invention can be determined using art-known alignment and comparison methods for nucleic acid molecules.

Standard art-known methods can be used to prepare variants of the soma-targeting polypeptide of the invention, such as a KA2 polypeptide, an M5M6BR polypeptide, an rSK-1-tail polypeptide that is a fragment of the amino acid sequence set forth as SEQ ID NO: 1, the parent M5M6BR sequence, or other M5M6BR binding repeat combination, or SEQ ID NO: 31, respectively and their respective encoding nucleic acid sequences. A site or region for introducing an amino acid sequence modification may be predetermined, and the mutation per se need not be predetermined. For example, to optimize the performance of a mutation at a given site, random mutagenesis may be conducted at the target codon or region and the expressed polypeptide screened for the level of desired function or activity. Techniques for making substitution mutations at predetermined sites in DNA having a known sequence are well known, for example, M13 primer mutagenesis and PCR mutagenesis. Variant sequences may in some embodiments of the invention be prepared by site specific mutagenesis of nucleic acids in the DNA encoding a polypeptide of the invention, using cassette or PCR mutagenesis or other techniques known in the art, to produce DNA encoding the polypeptide. In certain embodiments of the invention, activity of variant or fragment of a polynucleotide or polypeptide can be tested by cloning the gene encoding the altered polypeptide into a bacterial or mammalian expression vector, introducing the vector into an appropriate host cell, expressing the altered polypeptide, and testing for a functional capability of the polypeptide as disclosed herein. Additional methods for generating recombinant polypeptides are known in the art may include use of prokaryotic and eukaryotic expression systems including but not limited to bacterial and mammalian expression systems.

It is understood in the art that the codon systems in different organisms can be slightly different, and that therefore where the expression of a given protein from a given organism is desired, the nucleic acid sequence can be modified for expression within that organism. Thus, in some embodiments, a targeting polypeptide and/or fusion protein of the invention is encoded by a mammalian-codon-optimized nucleic acid sequence, which may in some embodiments be a human-codon optimized nucleic acid sequence. An aspect of the invention provides a nucleic acid sequence that encodes a fusion protein comprising a KA2 polypeptide or variant thereof of the invention, and that is optimized for expression with a mammalian cell. In certain aspects of the invention, a nucleic acid sequence is optimized for expression in a human cell.

As used herein, the terms "protein" and "polypeptide" are used interchangeably and thus the term polypeptide may be used to refer to a full-length protein and may also be used to refer to a fragment of a full-length protein, and/or functional variants thereof. As used herein, the terms "polynucleotide" and "nucleic acid sequence" may be used interchangeably and may comprise genetic material including, but not limited to: RNA, DNA, mRNA, cDNA, etc., which may include full length sequences, functional variants, and/or fragments thereof.

Targeted Molecules (Also Referred to as: Cargo Molecules)

Molecules that can be targeted to a specific location in a cell, such as the cell body, include, but are not limited to: opsin polypeptides, detectable label polypeptides, fluorescent polypeptides, additional trafficking polypeptides, etc. As used herein a polypeptide that is targeted to a location using a soma-targeting polypeptide of the invention, such as a KA2 polypeptide, an M5M6BR polypeptide, an rSK-1-tail polypeptide or functional variant thereof of the invention is also interchangeably referred to herein as a "cargo" polypeptide.

Non-limiting examples of detectable label cargo polypeptides include: green fluorescent protein (GFP); enhanced green fluorescent protein (EGFP), red fluorescent protein (RFP); yellow fluorescent protein (YFP), dtTomato, mCherry, DsRed, mRuby, cyan fluorescent protein (CFP); far red fluorescent proteins, etc. Numerous fluorescent proteins and their encoding nucleic acid sequences are known in the art and routine methods can be used to include such sequences in fusion proteins and vectors, respectively, of the invention.

Additional sequences that may be included in a fusion protein of the invention are trafficking sequences, including, but not limited to: Kir2.1 sequences and functional variants thereof, KGC sequences, ER2 sequences, etc. Examples of trafficking polypeptides, which may also be referred to herein as "export" polypeptides, that may be used in certain embodiments of the invention include, but are not limited to: SEQ ID NOs: 7 and 9. Examples of nucleic acid sequences that encode trafficking polypeptides that may be used in some embodiments of the invention include, but are not limited to: SEQ ID NOs: 6 and 8. Additional trafficking polypeptides and their encoding nucleic acid sequences are known in the art and routine methods can be used to include and use such sequences in fusion proteins and vectors, respectively, of the invention.

Another type of cargo molecule that may be included in compositions and used in methods of the invention is an opsin molecule. As used herein, the term "opsin" means an opsin molecule that when expressed in a cell functions as a membrane channel, an ion pump, or other identified structure, based on its sequence. A non-limiting example of an opsin useful in compositions and methods of the invention is a light-activated opsin. As used herein the term "opsin" may include any opsin having a sequence that is one or more of: a wild type opsin sequence, a modified opsin sequence, a mutated opsin sequence, a chimeric opsin sequence, a synthetic opsin sequence, a functional fragment of an opsin sequence that may include one or more additions, deletions, substitutions, or other modifications to the sequence of the parent opsin sequence from which the variant sequence originates, and a functional variant of an opsin sequence that may include one or more additions, deletions, substitutions, or other modifications to the sequence of the parent opsin sequence from which the variant sequence originates.

Methods of preparing and using opsin molecules and functional variants thereof are well known in the art and such opsins may be used in aspects of the invention. Examples of categories opsin molecules, whose members may be included in compositions of the invention and used in methods of the invention include, but are not limited to light-activated microbial opsins such as halorhodopsins, channelrhodopsins, Archaerhodopsins, and *Leptosphaeria* rhodopsins, members of each of which are well known in the art. Non-limiting examples of opsins that may be included embodiments of compositions, vectors, and used in methods of the invention are: CoChR, ChR2, ChR88, ChR90, ChR64, ChR86, ChR87, ChR90, Chrimson, ChrimsonR, Chronos, CsChrimson, ReaChR, GtACR, SwiChRca, iChloC, ChloC, ChIEF, V1C1, ChR2-2A-Halo, VChR1, Halo57, Jaws, Halo (also known as: NpHR), eNpH; R, eNpHR 3.0, Arch, eArch 3.0, ArchT, ArchT 3.0, Mac, Mac 3.0, and functional mutants (also referred to as "functional variants" thereof. [see Klapoetke et al. (2014) Nature Methods 11(3), 338-346; for review see: Yizhar, O. et al. (2011) Neuron Vol. 71:9-34; the content of each of which is incorporated by reference herein in its entirety.] Additional opsin polypeptides and their encoding nucleic acid sequences are known in the art and routine methods can be used to include and use such sequences and functional variants thereof in fusion proteins and vectors, respectively, of the invention.

Delivery of Targeting and Cargo Polypeptides

Delivery of a targeting molecule to a cell and/or expression of a targeting polypeptide and its cargo in a cell can be done using art-known delivery means. In some embodiments of the invention a targeting polypeptide and cargo polypeptide of the invention are included in a fusion protein. It is well known in the art how to prepare and utilize fusion proteins that comprise one or more polypeptide sequences. In certain embodiments of the invention, a fusion protein can be used to deliver a targeting polypeptide, such as a soma-targeting polypeptide of the invention, such as a KA2 polypeptide, an M5M6BR polypeptide, an rSK-1-tail polypeptide or functional variant thereof of the invention to a cell and may, in some embodiments, be used to deliver a cargo polypeptide such as an opsin polypeptide to a specific region of a cell in which the fusion protein is expressed. A fusion protein of the invention can be expressed in a specific cell type, tissue type, organ type, and/or region in a subject, or in vitro, for example in culture, in a slice preparation, etc. Preparation, delivery, and use of a fusion protein and its encoding nucleic acid sequences are well known in the art. Routine methods can be used in conjunction with teaching herein to express a targeting polypeptide, one or more cargo polypeptides, and optionally additional polypeptides, in a desired cell, tissue, or region in vitro or in a subject.

It is an aspect of the invention to provide a light-activated opsin polypeptide of the invention that is non-toxic, or substantially non-toxic in cells in which it is expressed. In the absence of light, a light-activated opsin polypeptide of the invention does not significantly alter cell health or ongoing electrical activity in the cell in which it is expressed. In some embodiments of the invention, a light-activated opsin polypeptide of the invention is genetically introduced into a cellular membrane, and reagents and methods are provided herein for genetically targeted expression of light-activated opsin polypeptides. Genetic targeting using a soma-targeting polypeptide of the invention, such as a KA2 polypeptide, an M5M6BR polypeptide, an rSK-1-tail polypeptide or a functional variant thereof of the invention, can be used to deliver a light-activated opsin polypeptide to specific cell types, to specific cell subtypes, to specific spatial regions within an organism, and to sub-cellular regions within a cell, including, the soma of a cell. Routine genetic procedures can also be used to control parameters of expression, such as but not limited to: the amount of a light-activated opsin polypeptide expressed, the timing of the expression, etc.

In some embodiments of the invention a reagent for genetically targeted expression of a light-activated opsin polypeptide is a vector comprising a gene encoding a soma-targeting polypeptide of the invention, such as a KA2 polypeptide, an M5M6BR polypeptide, an rSK-1-tail polypeptide or functional variant thereof of the invention, and gene encoding an opsin polypeptide. As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One type of vector is an episoma, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert an opsin polypeptide and a soma-targeting polypeptide of the invention, such as a KA2 polypeptide, an M5M6BR polypeptide, an rSK-1-tail polypeptide or functional variant thereof of the invention into dividing and non-dividing cells and can insert an opsin polypeptide and a soma-targeting polypeptide of the invention, such as a KA2 polypeptide, an M5M6BR polypeptide, an rSK-1-tail polypeptide or functional variant thereof of the invention into a cell that is an in vivo, in vitro, or ex vivo cell.

Vectors useful in methods of the invention may include additional sequences including, but not limited to, one or more signal sequences and/or promoter sequences, or a combination thereof. In certain embodiments of the invention, a vector may be a lentivirus, adenovirus, adeno-associated virus, or other vector that comprises a gene encoding an opsin polypeptide and a gene encoding a soma-targeting polypeptide of the invention, such as a KA2 polypeptide, an M5M6BR polypeptide, an rSK-1-tail polypeptide or functional fragment thereof of the invention. An adeno-associated virus (AAV) such as AAV8, AAV1, AAV2, AAV4, AAV5, AAV9, are non-limiting examples of vectors that may be used to express a fusion protein of the invention in a cell and/or subject. Expression vectors and methods of their preparation and use are well known in the art. Non-limiting examples of suitable expression vectors and methods for their use are provided herein.

Promoters that may be used in methods and vectors of the invention include, but are not limited to, cell-specific promoters or general promoters. Non-limiting examples promoters that can be used in vectors of the invention are: ubiquitous promoters, such as, but not limited to: CMV, CAG, CBA, and EF1a promoters; and tissue-specific promoters, such as but not limited to: Synapsin, CamKIIa, GFAP, RPE, ALB, TBG, MBP, MCK, TNT, and aMHC promoters. Methods to select and use ubiquitous promoters and tissue-specific promoters are well known in the art. A non-limiting example of a tissue-specific promoter that can be used to express a light-activated opsin polypeptide in a cell such as a neuron is a synapsin promoter, which can be used to express an opsin polypeptide and soma-targeting polypeptide of the invention, such as a KA2 polypeptide, an M5M6BR polypeptide, an rSK-1-tail polypeptide or functional variant thereof, in embodiments of methods of the invention. Additional tissue-specific promoters and general promoters are well known in the art and, in addition to those provided herein, may be suitable for use in compositions and methods of the invention.

Imaging

According to principles of this invention, the performance of a soma-targeting polypeptide of the invention, such as a KA2 polypeptide, an M5M6BR polypeptide, an rSK-1-tail polypeptide of the invention can be used to target a polypeptide such as, but not limited to, an opsin polypeptide, to the soma of a cell. Stimulation of a targeted opsin with a suitable stimulation means to activate the opsin in the cell soma can be imaged using methods of the invention. Some aspects of methods of the invention comprise use of 1-photon (1P) photostimulation, 2-photon (2P) stimulation, 2P holographic stimulation, or other suitable stimulation/imaging method. Methods of the invention also include, in some aspects, acquiring a 2P image stack of a cell in which a fusion peptide of the invention is expressed, and reconstructing a 3-dimensional (3-D) volume of the region surrounding the imaged cell. A soma-targeting polypeptide of the invention, such as a KA2 polypeptide, an M5M6BR polypeptide, an rSK-1-tail polypeptide or functional variant of the invention can be used in methods to deliver a light-activated opsin to a cell, and the soma-targeting polypeptide of the invention, such as a KA2 polypeptide, an M5M6BR polypeptide, an rSK-1-tail polypeptide or functional variant thereof selectively traffics (also referred to herein as "targets") the opsin to the cell body of the cell. Examples of a cell in which a fusion protein comprising a soma-targeting polypeptide of the invention, such as a KA2 polypeptide, an M5M6BR polypeptide, an rSK-1-tail polypeptide or functional variant thereof and an opsin polypeptide can be delivered include but are not limited to: a single isolated cell, a cell in culture, an in vitro cell, an in vivo cell, an ex vivo cell, a cell in a tissue, a cell in a subject, a cell in an organ, a cell in a cultured tissue, a cell in a neural network, a cell in a brain slice, a neuron, etc.

A soma-targeting polypeptide of the invention, such as a KA2 polypeptide, an M5M6BR polypeptide, an rSK-1-tail polypeptide or functional variant thereof expressed as part of a fusion protein that also includes one or more light-activated opsin polypeptide, fluorescent polypeptide, detectable label polypeptide, etc. permits stimulation and imaging of the cell in which the fusion protein is expressed. In some aspects of the invention, imaging methods include optogenetic stimulation of one or more cells with millisecond temporal resolution, without statistically significant cross-talk activation of nearby cells. Some embodiments of methods of the invention include expressing in a cell a fusion protein comprising a soma-targeting polypeptide of the invention, such as a KA2 polypeptide, an M5M6BR polypeptide, an rSK-1-tail polypeptide or functional variant thereof and one or more other polypeptides, a non-limiting example of which is a cargo polypeptide such as an opsin. Expression of a fusion protein of the invention in a cell results in delivery and localization of the cargo polypeptide in the cell body of the cell. Because little or no delivery of the opsin occurs outside of the cell body of a cell in which a fusion protein of the invention is expressed, it is possible to optically activate the cell, even in the presence of other cells, with sub-millisecond precision. Certain embodiments of stimulation and imaging methods of the invention are described herein, and certain means for optimizing such methods are provided in the Examples section. It will also be understood that alternative stimulation and imaging methods may be compatible with compositions and methods of the invention.

Methods of Using Targeting Molecules and Cargo Molecules

Targeting polypeptides of the invention, such as a soma-targeting polypeptide of the invention, such as a KA2 polypeptide, an M5M6BR polypeptide, an rSK-1-tail polypeptide and functional variants thereof, are well suited for directing one or more cargo polypeptides that are expressed in a fusion protein with the targeting polypeptide, to the cell body of a cell in which the fusion protein is expressed. In some embodiments of the invention, a cargo polypeptide that is a light-activated opsin polypeptide can be expressed in a localized manner, in the soma of the cell. Expression of the opsin in the cell body can be used to modulate electrical activity of the cell. Because embodiments of compositions and methods of the invention result in specific targeting of the expressed cargo to the soma of the cell in which it is expressed, some aspects of methods of the invention can be used to selectively activate a single cell in which a fusion protein of the invention is expressed. For example, though not intended to be limiting: a fusion protein that comprises a KA2 polypeptide or variant thereof of the invention, such as CoChR-KA2(1-150)-GFP, also referred to herein as: soCoChR, can be expressed in a cell, which results in the localization of the CoChR polypeptide and GFP in the cell soma. Contacting the cell in which the soCoChR polypeptide is expressed with suitable light to activate the CoChR light-activated opsin polypeptide in the cell permits modulation of the electrical activity of the cell. Other non-limiting examples of fusion proteins of the invention that can be expressed in cells and used in methods of the invention are set forth as SEQ ID NOs: 25 and 27. Cells in which an opsin/targeting polypeptide fusion protein of the invention is expressed can be contacted with suitable light to activate the opsin, thereby modulating electrical activity in the cell. It will be understood that the type and level of modulation of electrical activity and ion flux in a cell will depend, in part, on the light-activated opsin that is expressed in the cell as part of the fusion protein of the invention. Art-known methods can be used to select suitable stimulation parameters such as type of stimulation, illumination wavelength, intensity, pulse rate, etc. for use with compositions and methods of the invention expressed in cells and membranes. See for example: U.S. Pat. Nos. 8,957,028; 9,309,296; 9,284,353; 9,249,234; 9,101,690; PCT Pub. No. WO2013/07123; US Pat Pub No. 20120214188; US Pat Pub. No. 20160039902; US Pat Pub No. 20140223679; Packer, A. M. et al., 2012 Nature Methods December 9(12):1202-1205; and Oron, D. et al., Progress in Brain Research, Chapter 7, Volume 196, 2012, Pages 119-143: the content of each of which is incorporated by references in its entirety herein.

Certain aspects of the invention include methods for modulating one or more characteristics of a cell, such as, but not limited to: electrical activity in a cell and ion flux across a cell membrane. Compositions and methods of the invention can be used in a cell and/or a subject as a means with which to: modulate ion flux across a membrane of a cell, treat a disease or conditions in the cell or subject, identify a candidate agent that when contacted with a cell expressing a fusion protein of the invention modulates electrical activity in the cell, identify a candidate agent that when contacted with a cell expressing a fusion protein of the invention modulates ion flux across a membrane of the cell, etc. In some aspects of the invention, methods and apparatuses are provided that can be used to image and detect an effect of activating an opsin polypeptide that is expressed in a cell as part of a fusion protein of the invention. Numerous methods for using one or more light-activated opsin polypeptides expressed in a host cell and/or a host subject are known in the art and the compositions and methods of the invention may be used in conjunction with such methods to enhance selective activation and imaging of a cell in which a fusion protein of the invention is expressed.

Methods and compositions of the invention permit selective expression of an opsin polypeptide in a cell body and its activation, with little or no cross-talk from other cells. As used herein the term "cross-talk" when used in the context of cell activation means activation of one or more cells whose processes physically touch the cell in which a fusion protein of the invention is expressed. A soma-targeting polypeptide of the invention, such as a KA2 polypeptide, an M5M6BR polypeptide, an rSK-1-tail polypeptide or functional variant thereof of the invention, when expressed in a cell as part of a fusion protein that also comprises a light-activated opsin polypeptide, results in selective targeting of the opsin polypeptide to the cell body of the cell in which it is expressed. Selective targeting by the soma-targeting polypeptide of the invention, such as a KA2 polypeptide, an M5M6BR polypeptide, an rSK-1-tail polypeptide or functional variant thereof of the invention directs an opsin polypeptide to the soma of the cell in which a fusion protein comprising the targeting and opsin polypeptides are expressed, and permits imaging of opsin activity in single cells even within a plurality of cells and/or in cellular networks without cross-talk. Methods and compositions of the invention provide an efficient and selective means to localize and image activity of activated opsin polypeptides that are expressed in fusion proteins of the invention.

Working operation of a prototype of this invention has been demonstrated in vitro and in vivo, by genetically expressing a fusion protein comprising an opsin polypeptide and a soma-targeting polypeptide of the invention, such as a KA2 polypeptide, an M5M6BR polypeptide, an rSK-1-tail polypeptide or functional variant thereof of the invention in cells, illuminating the cells with suitable wavelengths of light to activate the opsin, and demonstrating rapid changes in electrical activity and/or ion flux in the cell in response to the light, as well as rapid release from the changes upon cessation of light. Depending on the particular implementation, methods of the invention allow directed localization of an opsin in the soma of a cell and stimulus control of cellular functions in vivo, ex vivo, and in vitro.

Cells and Subjects

A cell used in methods and with sequences of the invention may be an excitable cell or a non-excitable cell. A cell in which a fusion protein comprising a light-activated opsin polypeptide and a soma-targeting polypeptide of the invention, such as a KA2 polypeptide, an M5M6BR polypeptide, an rSK-1-tail polypeptide or functional variant thereof of the invention may be expressed and may be used in methods of the invention include prokaryotic and eukaryotic cells. Useful cells include, but are not limited to, vertebrate cells, which in some embodiments of the invention may be mammalian cells. Examples of cells in which a fusion protein comprising an opsin polypeptide and a soma-targeting polypeptide of the invention, such as a KA2 polypeptide, an M5M6BR polypeptide, an rSK-1-tail polypeptide or functional variant thereof of the invention may be expressed are excitable cells, which include cells able to produce and respond to electrical signals. Examples of excitable cell types include, but are not limited to neurons, muscles, cardiac cells, and secretory cells (such as pancreatic cells, adrenal medulla cells, pituitary cells, etc.). A cell in which a fusion protein of the invention is expressed may be a single cell, an isolated cell, a cell that is one of a plurality of cells, aa cell that is one in a network of two or more interconnected cells, a cell that is one of two or more cells that are in physical contact with each other, etc.

Non-limiting examples of cells that may be used in methods of the invention include: nervous system cells, cardiac cells, circulatory system cells, visual system cells, auditory system cells, secretory cells, endocrine cells, and muscle cells. In some embodiments, a cell used in conjunction with the invention may be a healthy normal cell, which is not known to have a disease, disorder or abnormal condition. In some embodiments, a cell used in conjunction with methods and compositions of the invention may be an abnormal cell, for example, a cell obtained from a subject diagnosed as having a disorder, disease, or condition, including, but not limited to a degenerative cell, a neurological disease-bearing cell, a cell model of a disease or condition, an injured cell, etc. In some embodiments of the invention, a cell may be a control cell. In some aspects of the invention a cell can be a model cell for a disease or condition.

A fusion protein comprising a light-activated opsin polypeptide and a soma-targeting polypeptide of the invention, such as a KA2 polypeptide, an M5M6BR polypeptide, an rSK-1-tail polypeptide or functional variant thereof of the invention may be expressed in one or more cells from culture, cells in solution, cells obtained from subjects, and/or cells in a subject (in vivo cells). Light-activated opsin polypeptides expressed in fusion proteins of the invention may be expressed and activated in cultured cells, cultured tissues (e.g., brain slice preparations, etc.), and in living subjects, etc. As used herein, the term "subject" may refer to a: human, non-human primate, cow, horse, pig, sheep, goat, dog, cat, rodent, fly or other host organism. As used herein the term "host" means the subject or cell in which a fusion protein of the invention is expressed. In some aspects of the invention a host is a vertebrate subject. In certain embodiments of the invention, a host is a mammal. In certain aspects of the invention a host is an invertebrate subject.

Controls and Candidate Compound Testing

Using certain embodiments of compositions and methods of the invention, one or more light-activated opsin polypeptides of the invention can be expressed in a localized region of a cell, for example the soma, and methods to stimulate and image the response in the cell to activation of the light-activated opsin polypeptide can be utilized to assess changes in cells, tissues, and subjects in which they are expressed. Some embodiments of the invention include directed delivery of light-activated opsins to the soma of a cell to identify effects of one or more candidate compounds on the cell, tissue, and/or subject in which the light-activated opsin is expressed. Results of testing one or more activities of a light-activated opsin polypeptide of the invention can be advantageously compared to a control.

As used herein a control may be a predetermined value, which can take a variety of forms. It can be a single cut-off value, such as a median or mean. It can be established based upon comparative groups, such as cells or tissues that include the light-activated opsin polypeptide of the invention and are contacted with light, but are not contacted with the candidate compound and the same type of cells or tissues that under the same testing condition are contacted with the candidate compound. Another example of comparative groups may include cells or tissues that have a disorder or condition and groups without the disorder or condition. Another comparative group may be cells from a group with a family history of a disease or condition and cells from a group without such a family history. A predetermined value can be arranged, for example, where a tested population is divided equally (or unequally) into groups based on results of testing. Those skilled in the art are able to select appropriate control groups and values for use in comparative methods of the invention. In certain aspects of the invention, a control is a cell that does not include a fusion protein of the invention and an activity in such a cell can be compared to the activity in a cell that does include a fusion protein of the invention.

As a non-limiting example of use of a light-activated opsin polypeptide to identify a candidate therapeutic agent or compound, a fusion protein comprising light-activated opsin polypeptide and a soma-targeting polypeptide of the invention, such as a KA2 polypeptide, an M5M6BR polypeptide, an rSK-1-tail polypeptide or functional variant thereof of the invention may be expressed in an excitable cell in culture or in a subject and the excitable cell may be contacted with a light that activates the light-activated opsin polypeptide and with a candidate therapeutic compound. In one embodiment of the invention, a test cell in which a fusion protein comprising a light-activated opsin polypeptide and a soma-targeting polypeptide of the invention, such as a KA2 polypeptide, an M5M6BR polypeptide, an rSK-1-tail polypeptide or functional variant thereof of the invention is expressed is contacted with a light that depolarizes the cell or otherwise alters ion flux across a membrane in the cell and the cell is also contacted with a candidate compound. The cell, tissue, and/or subject that include the cell can be monitored for the presence or absence of a change that occurs in test conditions versus a control condition. For example, in a cell, an activity modulation in the test cell may be a change in the depolarization of the test cell, a change in a depolarization-mediated cell characteristic in the test cell, a change in ion flux across a membrane of the test cell, each of which can be compared to the activity in control cell, and a change that is different in the test cell compared to the control cell, may indicate that the candidate compound has an effect on the test cell, tissue and/or subject that includes the cell. In some embodiments of the invention, an activity of a cell may be one or more of: an action potential, a pH change, release of a neurotransmitter, etc. and may in some embodiments, include a downstream effect on one or more additional cells, which occurs due to the modulation of an activity in the host cell in which the fusion protein comprising the light-activated opsin and a soma-targeting polypeptide of the invention, such as a KA2 polypeptide, an M5M6BR polypeptide, an rSK-1-tail polypeptide or functional variant thereof of the invention are expressed. Art-known methods can be used to assess electrical activity and ion flux activity and changes and modulation of such activities upon stimulation and activation of a light-activated opsin polypeptide expressed in a cell, with or without additional contact with a candidate compound.

Candidate-compound identification methods of the invention may be carried out in a cell in a subject or in cultured or in vitro cells. Candidate-compound identification methods of the invention that are performed in a subject, may include expressing a fusion protein comprising a light-activated opsin polypeptide and a soma-targeting polypeptide of the invention, such as a KA2 polypeptide, an M5M6BR polypeptide, an rSK-1-tail polypeptide or functional variant thereof in a subject, contacting the cell in the subject with a light under suitable conditions to activate the light-activated opsin polypeptide, and administering to the subject a candidate compound. The subject is then monitored to determine whether any change occurs that differs from a control effect in a subject. Candidate-compound identification methods of the invention that are performed in vitro may include expressing a fusion protein comprising a light-activated opsin polypeptide and a soma-targeting polypeptide of the invention, such as a KA2 polypeptide, an M5M6BR polypeptide, an rSK-1-tail polypeptide or functional variant thereof of the invention in a cell, which may or may not be a cultured cell, contacting the cell with a light under suitable conditions to activate the light-activated opsin polypeptide and alter electrical activity in the cell and/or ion flux across a membrane of the cell, and contacting the cell with a candidate compound. The cell is then monitored to determine whether any change occurs that differs from a control effect in a substantially similar cell that is not contacted with the candidate compound. Thus, for example, a cell expressing the light-activated opsin polypeptide can, in the presence of a candidate compound, be contacted with a light appropriate to activate the light-activated opsin polypeptide. Contact of the light-activated opsin polypeptide with the candidate compound may also occur at one or more time points prior to, at the same time as, or subsequent to contact with the light appropriate to activate the light-activated opsin polypeptide. A result of such contact with the candidate compound can be measured and compared to a control value as a determination of the presence or absence of an effect of the candidate compound on an activity in the cell, such, but not limited to: an electrical activity and/or ion flux activity.

Methods of identifying effects of candidate compounds using fusion proteins of the invention may also include additional steps and assays to further characterizing an identified activity change in the cell, tissue, or subject when the cell is contacted with suitable light and the candidate compound. In some embodiments of the invention, testing in a cell, tissue, or subject can also include testing one or more cells that each comprises one or more independently selected light-activated opsin polypeptides, such that one, two, three, or more different light-activated opsins polypeptides are expressed in two or more cells that may be in close spatial proximity with each other, may be in physical contact with each other, or may be spatially distant from each other. In some aspects of the invention, at least one, two, three, four, or more of the additional light-activated opsin polypeptides are activated by contact with light having a different wavelength than used to activate other of the additional ion channel opsin polypeptides.

In a non-limiting example of a candidate drug identification method of the invention, cells in which a fusion protein comprising a light-activated opsin polypeptide and soma-targeting polypeptide of the invention, such as a KA2 polypeptide, an M5M6BR polypeptide, an rSK-1-tail polypeptide or functional variant thereof of the invention are contacted with suitable light, and are depolarized, thus triggering release of a neurotransmitter from the cell, then candidate therapeutic compounds are applied that modulate the response of the cell to depolarization (determined for example using patch clamping methods or other suitable art-known means). These and other methods enable therapeutic compound screening using light to activate the opsin of interest that is localized in the cell body of the cell in which it is expressed.

In some embodiments of the invention, a fusion protein comprising a light-activated opsin polypeptide and soma-targeting polypeptide of the invention, such as a KA2 polypeptide, an M5M6BR polypeptide, an rSK-1-tail polypeptide or functional variant thereof of the invention can be used in test systems and assays for assessing membrane protein trafficking and physiological function in cells and subjects and the use of use of light-activated opsin to modulate electrical activity of a cell and/or to modulate ion flux across a membrane of the cell. Implementation of fusion proteins in cells, activating light-activated opsin polypeptides by contact with a suitable light and contact parameters, identifying modulation of an activity of a cell such as depolarization, APs, ion flux, hyperpolarization etc. are routinely practiced in the art and in combination with methods and compositions of the invention can be used to identify and test candidate therapeutic agents.

In certain aspects of the invention, a fusion protein comprising a light-activated opsin polypeptide and soma-targeting polypeptide of the invention, such as a KA2 polypeptide, an M5M6BR polypeptide, an rSK-1-tail polypeptide or functional variant thereof of the invention can be expressed in a cell and/or subject and used to assess or diagnose a disease or condition in the subject.

Methods of Treating

Some aspects of the invention include methods of treating a disorder or condition in a cell, tissue, or subject using fusion protein comprising an opsin and a soma-targeting polypeptide of the invention, such as a KA2 polypeptide, an M5M6BR polypeptide, an rSK-1-tail polypeptide or functional variant thereof of the invention. Treatment methods of the invention may include administering to a subject in need of such treatment, a therapeutically effective amount of a vector encoding a fusion protein comprising a light-activated opsin polypeptide and a soma-targeting polypeptide of the invention, such as a KA2 polypeptide, an M5M6BR polypeptide, an rSK-1-tail polypeptide or functional variant thereof of the invention, to treat the disorder. In certain aspects of the invention, a therapeutically effective amount of a cell comprising a fusion protein of the invention may be administered to a subject in a treatment method of the invention. It will be understood that a treatment may be a prophylactic treatment or may be a treatment administered following the diagnosis of a disease or condition. A treatment of the invention may reduce or eliminate a symptom or characteristic of a disorder, disease, or condition or may eliminate the disorder, disease, or condition itself. It will be understood that a treatment of the invention may reduce or eliminate progression of a disease, disorder or condition and may in some instances result in the regression of the disease, disorder, or condition. A treatment need not entirely eliminate the disease, disorder, or condition to be effective.

In certain aspects of the invention, a means of expressing in a cell of a subject, a fusion protein comprising a soma-targeting polypeptide of the invention, such as a KA2 polypeptide, an M5M6BR polypeptide, an rSK-1-tail polypeptide or functional variant thereof and an opsin polypeptide may comprise: administering to a cell a vector that encodes a fusion protein comprising the opsin polypeptide and a soma-targeting polypeptide of the invention, such as a KA2 polypeptide, an M5M6BR polypeptide, an rSK-1-tail polypeptide or functional variant thereof of the invention; administering to a subject a cell in which a fusion protein of the invention is present; or administering a fusion protein of the invention to a subject. Delivery or administration of a fusion protein of the invention may include administration of a pharmaceutical composition that comprises cell, wherein the cell expresses the opsin polypeptide fused to a soma-targeting polypeptide of the invention, such as a KA2 polypeptide, an M5M6BR polypeptide, an rSK-1-tail polypeptide or functional variant thereof of the invention. Administration of an opsin and targeting soma-targeting polypeptide of the invention, such as a KA2 polypeptide, an M5M6BR polypeptide, an rSK-1-tail polypeptide or functional variant thereof of the invention, may, in some aspects of the invention include administration of a pharmaceutical composition comprising a vector, wherein the vector comprises a nucleic acid sequence encoding an opsin polypeptide and a soma-targeting polypeptide of the invention, such as a KA2 polypeptide, an M5M6BR polypeptide, an rSK-1-tail polypeptide or functional variant thereof of the invention, wherein the administration of the vector results in expression of a fusion protein comprising the opsin polypeptide and the soma-targeting polypeptide of the invention, such as a KA2 polypeptide, an M5M6BR polypeptide, an rSK-1-tail polypeptide or functional variant thereof in one or more cells in the subject. In some aspects of the invention, targeted expression of an opsin polypeptide in the soma of a cell may be referred to as "increasing" expression of that opsin polypeptide in the soma of the cell. It will be understood that in some aspects of the invention, the starting level of expression of the opsin in the soma of a cell may be zero and a treatment method of the invention may be used to increase that level above zero. In certain aspects of the invention, for example in a subsequent delivery of a fusion protein of the invention to a cell and/or subject, a level of expression of the opsin the soma of a cell may be greater than zero, with one or more of the opsin polypeptides present in the soma, and a treatment method of the invention may be used to increase the expression level of the opsin polypeptide in the cell soma.

An effective amount of an opsin and a soma-targeting polypeptide of the invention, such as a KA2 polypeptide, an M5M6BR polypeptide, an rSK-1-tail polypeptide or functional variant thereof of the invention is an amount that results in expression of the opsin in the cell body of a cell, in a tissue or subject at a level or amount that is beneficial for the subject. An effective amount may also be determined by assessing physiological effects of administration on a cell or subject such as a decrease in symptoms of a disease or condition to be treated, following administration. Other assays will be known to a skilled artisan and can be employed for measuring a level of a response to a treatment of the invention. The amount of a treatment may be varied for example by increasing or decreasing the amount of the targeted opsin polypeptide administered, by changing the therapeutic composition in which the opsin polypeptide is administered, by changing the route of administration, by changing the dosage timing, by changing expression conditions of a fusion protein of the invention, by changing the activation amounts and parameters of an opsin polypeptide of the invention, and so on. An effective amount will vary with the particular condition being treated, the age and physical condition of the subject being treated; the severity of the condition, the duration of the treatment, the nature of the concurrent therapy (if any), the specific route of administration, and the like factors within the knowledge and expertise of a health practitioner. For example, an effective amount may depend upon the location and number of cells in the subject in which the opsin polypeptide and targeting KA2 polypeptide or functional variant thereof of the invention, is to be expressed. An effective amount may also depend on the location of the tissue to be treated. Factors useful to determine an effective amount of a therapeutic are well known to those of ordinary skill in the art and can be addressed with no more than routine experimentation. It is generally preferred that a maximum dose of a composition to increase the level of a targeted opsin polypeptide, and/or to alter the length or timing of activation of a target opsin polypeptide in a subject (alone or in combination with other therapeutic agents) be used, that is, the highest safe dose or amount according to sound medical judgment. It will be understood by those of ordinary skill in the art, however, that a patient, also referred to herein as a subject, may insist upon a lower dose or tolerable dose for medical reasons, psychological reasons or for virtually any other reasons.

An opsin polypeptide and targeting soma-targeting polypeptide of the invention, such as a KA2 polypeptide, an M5M6BR polypeptide, an rSK-1-tail polypeptide or functional variant thereof of the invention may be administered using art-known methods. The manner and dosage administered may be adjusted by the individual physician, healthcare practitioner, or veterinarian, particularly in the event of any complication. The absolute amount administered will depend upon a variety of factors, including the material selected for administration, whether the administration is in single or multiple doses, and individual subject parameters including age, physical condition, size, weight, and the stage of the disease or condition. These factors are well known to those of ordinary skill in the art and can be addressed with no more than routine experimentation.

Pharmaceutical compositions that deliver a fusion protein comprising an opsin and a soma-targeting polypeptide of the invention, such as a KA2 polypeptide, an M5M6BR polypeptide, an rSK-1-tail polypeptide or functional variant thereof of the invention may be administered alone, in combination with each other, and/or in combination with other drug therapies, or other treatment regimens that are administered to subjects. A pharmaceutical composition used in the foregoing methods may contain an effective amount of a therapeutic compound that will increase the level of a desired opsin polypeptide to a level that produces the desired response in a unit of weight or volume suitable for administration to a subject. In some embodiments of the invention, a pharmaceutical composition of the invention may include a pharmaceutically acceptable carrier.

Pharmaceutically acceptable carriers include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. In certain embodiments of the invention, such preparations may contain salt, buffering agents, preservatives, compatible carriers, aqueous solutions, water, etc. When used in medicine, the salts may be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

One or more of an opsin polypeptide or encoding polynucleotide thereof of the invention, or a cell or vector comprising a nucleic acid sequence encoding an opsin polypeptide and a soma-targeting polypeptide of the invention, such as a KA2 polypeptide, an M5M6BR polypeptide, an rSK-1-tail polypeptide or functional variant thereof of the invention, may be administered, for example in a pharmaceutical composition, directly to a tissue. Direct tissue administration may be achieved by direct injection, and such administration may be done once, or alternatively a plurality of times. If administered multiple times, the polypeptides, polynucleotides, cells, and/or vectors may be administered via different routes. For example, the first (or the first few) administrations may be made directly into the affected tissue while later administrations may be systemic.

A dose of a pharmaceutical composition of the invention that is administered to a subject to increase the level of a desired opsin polypeptide in one or more cells of the subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The amount and timing of activation of an opsin delivered using a targeting a soma-targeting polypeptide of the invention, such as a KA2 polypeptide, an M5M6BR polypeptide, an rSK-1-tail polypeptide or functional variant thereof of the invention (e.g., light wavelength, pulse length, length of light contact, etc.) that has been administered to a subject can also be adjusted based on efficacy of the treatment in a particular subject. Parameters for illumination and activation of an opsin delivered to a subject using a method of the invention, can be determined using teaching herein in conjunction with art-known methods, without requiring undue experimentation.

Various modes of administration known to the skilled artisan can be used to effectively deliver a pharmaceutical composition to increase the level of an opsin polypeptide in the soma of a desired cell in a tissue or body region of a subject. Methods for administering such a composition or pharmaceutical compound of the invention may be topical, intravenous, oral, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., Remington, The Science and Practice of Pharmacy, 2012, Editor: Allen, Loyd V., Jr, $22^{nd}$ Edition) provide modes of administration and formulations for delivery of various pharmaceutical preparations and formulations in pharmaceutical carriers. Other protocols which are useful for the administration of a therapeutic compound of the invention will be known to a skilled artisan, in which the dose amount, schedule of administration, sites of administration, mode of administration (e.g., intra-organ) and the like vary from those presented herein.

Administration of a cell or vector to increase expression of an opsin polypeptide in the soma of one or more cells in a mammal other than a human; and administration and use of a targeted opsin polypeptide using a soma-targeting polypeptide of the invention, such as a KA2 polypeptide, an M5M6BR polypeptide, an rSK-1-tail polypeptide or functional variant thereof of the invention, e.g. for testing purposes or veterinary therapeutic purposes, may be carried out under substantially the same conditions as described above. It will be understood that embodiments of the invention are applicable to both human and animals. Thus this invention is intended to be used in husbandry and veterinary medicine as well as in human therapeutics.

Disorders, Diseases and Conditions

Targeted opsin polypeptides of the invention may be used to direct localized expression of the opsin in the cell body of a cell in which a fusion protein comprising the opsin polypeptide and a soma-targeting polypeptide of the invention, such as a KA2 polypeptide, an M5M6BR polypeptide, an rSK-1-tail polypeptide or functional variant thereof of the invention is expressed and used to alter voltage-associated cell activities. Such methods may be used to treat: blindness, reduced vision, deafness, and/or reduced hearing in a subject. Disorders and conditions that may be treated using methods of the invention include, but are not limited to: partial or complete vision loss; partial or complete hearing loss; injury; memory loss, psychiatric disorders; brain damage; stroke; degenerative neurological condition, such as, but not limited to: Parkinson's disease, Amyotrophic Lateral Sclerosis (ALS), Alzheimer's disease; seizures, etc. In some aspects of the invention, compositions and methods of the invention are used to treat visual system diseases and conditions or to augment normal visual system processes. In certain aspects of the invention, compositions and methods of the invention are used to treat auditory system diseases and conditions or to augment normal auditory processes.

In some embodiments of the invention, a fusion protein comprising a light-activated opsin polypeptide and a soma-targeting polypeptide of the invention, such as a KA2 polypeptide, an M5M6BR polypeptide, an rSK-1-tail polypeptide or functional variant thereof of the invention is administered to a subject who has a partial or complete vision loss and the cell that expresses the opsin can function as a light-sensitive cell in the visual system, thereby permitting a gain of some or all of the lost visual function in the subject. In certain embodiments of the invention, a fusion protein comprising a light-activated opsin polypeptide and a soma-targeting polypeptide of the invention, such as a KA2 polypeptide, an M5M6BR polypeptide, an rSK-1-tail polypeptide or functional variant thereof of the invention is administered to a subject who has a partial or complete hearing loss and the cell that expresses the opsin can function as a light-sensitive cell in the auditory system thereby permitting a gain of some or all of the lost auditory function in the subject.

The present invention in some aspects includes preparing nucleic acid sequences and polynucleotide sequences; expressing in cells and membranes polypeptides encoded by the prepared nucleic acid and polynucleotide sequences; illuminating the cells and/or membranes with suitable light, and which results in modulation of electrical activity and or ion flux in the cells and across membranes. The ability to controllably alter one or more of: voltage across membranes; ion flux across members, cell depolarization, cell hyperpolarization using contact of the expressed opsin polypeptide with light has been demonstrated for numerous opsins that can be included in compositions and methods of the invention. The present invention enables targeted expression and localization of an opsin in the soma of a cell in which it is expressed, which may be in vivo, ex vivo, and in vitro. Compositions and targeting methods of the invention and their use have broad-ranging applications for drug screening, treatments, and research applications, some of which are describe herein.

EXAMPLES

Example 1

Methods
Primary Neuron Culture, Transfection and Transduction

All procedures involving animals were in accordance with the National Institutes of Health Guide for the care and use of laboratory animals and approved by the Massachusetts Institute of Technology Animal Care and Use Committee. Hippocampal neuron culture was prepared from postnatal day 0 or day 1 Swiss Webster (Taconic, Hudson, N.Y. or Charles River, Wilmington, Mass.) mice as previously described [Chow, B. Y., et al., (2010) Nature, 463(7277), 98-102], with the following modifications: Dissected hippocampal tissues were digested with 100 units of papain (Worthington Biochem, Lakewood, N.J.) for 5 minutes and the digestion was stopped with ovomucoid trypsin inhibitor (Worthington Biochem, Lakewood, N.J.). Cells were plated at a density of 30,000 per glass coverslip coated with Matrigel (BD Biosciences, San Jose, Calif.).

For all GFP fusions with opsins or GFP fusions with trafficking sequences during the screen for soma targeting sequences, transfection was performed at 4 days in vitro (DIV) with commercial calcium phosphate kit (Invitrogen, Waltham, Mass.). An additional washing with acidic MEM buffer (pH 6.8-6.9) after calcium phosphate precipitate incubation was added to completely re-suspend residual precipitates [Jiang & Chen (2006) Nature Protocols, 1(2), 695-700]. One µg of DNA was used in the transfections. Neurons were imaged 14-18 DIV (10-14 days post-transfection).

For the mCherry expression the already transfected neurons were transduced 10-14 DIV, with AAV8-Syn-mCherry-WPRE virus by adding 1l of the virus (titer=$1.4 \times 10^{13}$). Merged images were created by overlaying the green (GFP fusion images) with the red (mCherry images). AAV particles were produced by the University of North Carolina Chapel Hill Vector Core. To get panneuronal expression of either CoChR-GFP or soCoChR-GFP in culture (as seen in FIG. 2), hippocampal cultures were transduced 3-4 DIV with either AAV8-Syn-CoChR-GFP-WPRE or AAV8-Syn-soCoChR-GFP-WPRE viruses (at a titer of $4.7 \times 10^{12}$ and $4.0 \times 10^{12}$ respectively) and imaged 14 days later.

Whole-Cell Electrophysiology In Vitro
Current and Voltage Clamp Recordings of Cultured Neurons Whole cell patch clamp recordings in culture were made using Axopatch 200B or Multiclamp 700B amplifier, a Digidata 1440 digitizer, and a PC running pClamp (Molecular Devices, Sunnyvale, Calif.). For in vitro current-clamp recordings, neurons were patched 14-18 DIV (10-14 days post-transfection) to allow for sodium channel maturation. Neurons were bathed in room temperature Tyrode containing 125 mM NaCl, 2 mM KCl, 3 mM $CaCl_2$, 1 mM $MgCl_2$, 10 mM HEPES, 30 mM glucose and the synaptic blockers 0.01 mM NBQX and 0.01 mM GABAzine. The Tyrode pH was adjusted to 7.3 with NaOH and the osmolarity was adjusted to 300 mOsm with sucrose. For in vitro voltage-clamp recordings, neurons were patched 19-21 DIV (17-20 days post-transfection) and were done under similar conditions as current-clamp recordings, except tyrode also contains 1 µM of tetrodotoxin (TTX, Tocris Bioscience, Bristol, UK). No retinal was supplemented for any cultured neuron recordings.

For recordings, borosilicate glass pipettes (Warner Instruments, Hamden, Conn.) with an outer diameter of 1.2 mm and a wall thickness of 0.255 mm were pulled to a resistance of 5-10 MΩ with a P-97 Flaming/Brown micropipette puller (Sutter Instruments, Novato, Calif.) and filled with a solution containing 125 mM K-gluconate, 8 mM NaCl, 0.1 mM $CaCl_2$, 0.6 mM $MgCl_2$, 1 mM EGTA, 10 mM HEPES, 4 mM Mg-ATP, and 0.4 mM Na-GTP. The pipette solution pH was adjusted to 7.3 with KOH and the osmolarity was adjusted to 298 mOsm with sucrose. For voltage clamp experiments, cells were clamped at −65 mV. For current clamp experiments, access resistance was monitored throughout recording. Data was analyzed using Clampfit (Molecular Devices, Sunnyvale, Calif.) and custom MATLAB scripts (Mathworks, Inc., Natick, Mass.).

Current Clamp Recordings of Cultured Neurons During Digital Micromirror Device (DMD) Photostimulation Experiments Whole cell patch clamp recordings were made using Axopatch 200B or Multiclamp 700B amplifier, a Digidata 1440 digitizer, and a PC running pCLAMP (Molecular Devices, Sunnyvale, Calif.). In each experiment, the procedure was to patch (current clamp) cell #1. Then, starting from cell #1, cell #1 and 9 other cells were photostimulated by DMD. Photostimulations were made 10 seconds apart (470 nm; 40.7 mW/mm2) and the responses for the photostimulation were recorded in pCLAMP (n=5 cells from 4 cultures for CoChR-GFP; n=5 cells from 5 cultures for soCoChR-GFP).

Molecular Cloning and Virus Production

All opsin genes were synthesized (Genscript, Piscataway, N.J.) with mammalian codon optimization and subcloned as previously described [Chow, B. Y., et al., (2010). Nature, 463(7277), 98-102; Klapoetke, N. C., et al., (2014). Nature Methods, 11(3), 338-46]. For screening in cultured neuron studies, all genes were subcloned into FCK backbone under CaMKII promoter and with a C-terminal GFP fusion. For soCoChR-GFP, the first 450 bp were cloned 3' to CoChR, with no further trafficking sequences added. For CoChR-$Na_V1.2$ (II/III)-GFP the KGC [Ma, D., et al., (2001). Science, N.Y., 291(5502), 316-9] followed by ER2 [Hofherr, A., et al., (2005). J. Cell Sci., 118(Pt 9), 1935-43] trafficking sequences from the potassium channel Kir2.1, with the resulting molecule being CoChR-KGC-$Na_V1.2$ (II/III)-ER2-GFP as previously described [Chuong, A. S., et al., (2014). Nature Neurosci., 17(8), 1123-9]. For virus production, the genes were cloned into the pAAV plasmid after Synapsin promoter. AAV production (serotype 8) was performed by UNC vector core.

Photostimulation Experiments In Vitro
Whole Field Neural Stimulation

Neuron voltage clamp photo-stimulation experiments were done with a LED mounted on microscope for widefield illumination (Leica 3000B), with nominal wavelength at 480 nm, (X-Cite XLED1, Excelitas Technologies, Waltham, Mass.). The LED spectrum was filtered with the 472/30 nm BrightLine single-band bandpass filter (Semrock, Rochester, N.Y.). Light was triggered by pClamp (Molecular Devices, Sunnyvale, Calif.). Light power was measured at 34.84 mW/mm², through a Leica HCX APO L 40× objective (air, NA=0.6). For each trace recorded, a 10 ms current injection was given (to make sure a neuron could spike), followed by a 1 ms light pulse (480 nm; 34.84 mW/mm²) 5 seconds later.

Stimulation of Cell Bodies with a DMD

Stimulation of neural cell bodies experiments were performed with a Leica 6000 B widefield microscope, mounted with a Mosaic DMD system (Andor, Belfast, UK) and a Zyla 5.5 sCMOS camera (Andor, Belfast, UK). The experiments were performed with an LED with nominal wavelength at 470 nm (Thorlabs, Newton, N.J., M470L2) and power of 40.7 mW/mm². Neurons were imaged and stimulated through a 1 MP-2262-59022XR-360T GFP/mCherry Filter Set (dual GFP/mCherry, Andor, Belfast, UK). For the photostimulation experiment: an image of the green fluorescence was acquired, and cell bodies were then identified based on their donut shaped fluorescence. A cell was chosen randomly to be patched, with the only requirement being in a densely cultured area. This cell was referred to as #1. Thereafter, 9 circles, with a diameter of 20 μm were defined around the nuclei of cell bodies of interest using Metamorph software (Molecular Devices, Sunnyvale, Calif.) with distances ranging between 10-200 μm from cell #1. Then, starting from cell #1, cell #1 and 9 other cells were photostimulated sequentially. Stimulations were made 10 s apart (40.7 mW/mm²).

Imaging In Vitro

GFP-fusions with trafficking sequences, Opsin-GFP and cytosolic mCherry expressed in cultured neurons were imaged with a LED mounted (X-Cite XLED1, Excelitas Technologies, Waltham, Mass.) on a microscope for widefield illumination (Leica 3000B), through either Leica HCX APO L 40× objective (air, NA=0.6) or Leica HCX APO L 20× objective (air, NA=0.5). Imaging was performed with a Hamamatsu Orca Flash 4.0 camera under identical illumination conditions throughout with: 480 nm LED using GFP-3035D filter cube (Semrock, Rochester, N.Y.) for GFP fluorescence (34.84 mW/mm²); 540 nm LED with 543 nm±11 nm excitation filter (Semrock, Rochester, N.Y.) for mCherry fluorescence. Images were taken with an exposure of 300 ms.

Cultured neurons expressing CoChR-GFP or KA2-GFP and KA2(1-150)-GFP were imaged using similar parameters: fluorescence was excited with a 480 nm LED filtered by 472/30 nm BrightLine single-band bandpass filter (Semrock, Rochester, N.Y.) and focused on the sample through a Leica HCX APO L 20× objective (air, NA=0.6), with a power of 25.19 mW/mm². Images were acquired with a Hamamatsu Orca Flash 4.0 with an exposure of 300 ms.

Viral Injections and Whole-Cell Electrophysiology in Brain Slices

All experimental procedures were in accordance with guidelines from European Union and institutional guidelines of the care and use of laboratory animals (Council directive 86/609 European Economic Community) that were approved by the Paris Descartes Ethics Committee for Animal Research (registered number CEEA34.EV. 118.12).

Stereotactic injections of the viral vectors AAV8-Synapsin-CoChR-GFP, AAV8-ChR86-KGC-NaV1.2long-GFP-ER2 and AAV8-soCoChR-GFP were performed in 4 weeks old Swiss mice (Janvier Lab, Saint Berthevin Cedex, FR). Mice were anesthetized with ketamine (80 mg/Kg)-xylazine (5 mg/Kg) solution and a small craniotomy (0.7 mm) was made on the skull overlying V1 cortex. Injection of 1-1.5 μl solution containing the viral vector was made with a cannula at about 80-100 nl/min at 200-250 μm below the dural surface. The craniotomy and the skull were sutured and the mouse recovered from anesthesia.

Brain slices of V1 cortex were prepared from mice at 7-15 weeks after viral injection. Mice were deeply anesthetized with isoflurane 5%, decapitated, and brain was rapidly removed. Sagittal slices of 300 μm were obtained (VT1200S Leica Biosystems, Wetzlar, Germany) in room temperature or ice-cold solution containing the following (in mM): 85 NaCl, 2.5 KCl, 0.5 $CaCl_2$, 4 $MgCl_2$, 65 sucrose, 25 glucose, 0.5 ascorbic acid.

Slices were transferred in a recovery chamber at 350 for 45 minutes containing 20% sucrose solution and 80% ACSF containing the following (in mM): 125 NaCl, 2.5 KCl, 26 NaHCO$_3$, 1.25 NaH$_2$PO$_4$, 1 MgCl$_2$, 1.5 CaCl$_2$, 25 glucose, 0.5 ascorbic acid. All solutions were aerated with 95% O$_2$ and 5% CO$_2$ to a final 7.4 pH.

Slices were placed in a recording chamber under the microscope objective and patched monitoring IR transmitted light images acquired at approximately video rate. Cells were patched at 40-70 μm depth and clamped at −70 mV in voltage- and current-clamp configurations. Cell type was established based on morphology and action potentials firing properties. Electrophysiology data were acquired with a Multiclamp 700B amplifier, a Digidata 1322A digitizer (MolecularDevices) or a National Instrument device, and a PC running pClamp 10 software (Molecular Devices) or Neuromatic software running on IgorPro interface (Wavemetrics, Portland, Oreg.). Voltage and current clamp recordings were filtered at 6 kHz and sampled at 20 kHz.

The following blockers were added to the artificial cerebro-spinal fluid (ACSF) solution in all experiments to block any synaptic effect: strychnine, picrotoxin/gabazine and NBQX (1-5 μM; Abcam, Cambridge, Mass.; Tocris Bioscience, Bristol, UK). Borosilicate glass pipette (o.d. 1.5 mm and i.d. 0.86 mm) were pulled with a micropipette puller (Sutter Instruments, Novato, Calif.) and filled with a solution containing the following (mM): 130 K-gluconate, 7 KCl, 4 MgATP, 0.3 mM NaGTP, 10 Na-phosphocreatine, and 10 mM HEPES (pH adjusted to 7.28 with KOH; osmolarity 280 mOsm). Pipette resistance in the bath was 5-7 MΩ. Data were acquired with a Multiclamp 700B amplifier, a Digidata 1322A digitizer (Molecular Devices) or a National Instrument device, and a PC running pClamp 10 software (Molecular Devices) or Neuromatic software running on IgorPro interface (Wavemetrics, Portland, Oreg.).

Imaging and Photo-Stimulations in Brain Slices

Holographic photostimulation was implemented in two different setups, with two different photostimulation laser sources and imaging system. Setups 1 and 2 were used to acquire the data presented on FIGS. 3 and 4 and the data presented in FIG. 5 was acquired solely with setup 1.

Description of Setups and Holographic Stimulation:

Setup 1

Figure 9:
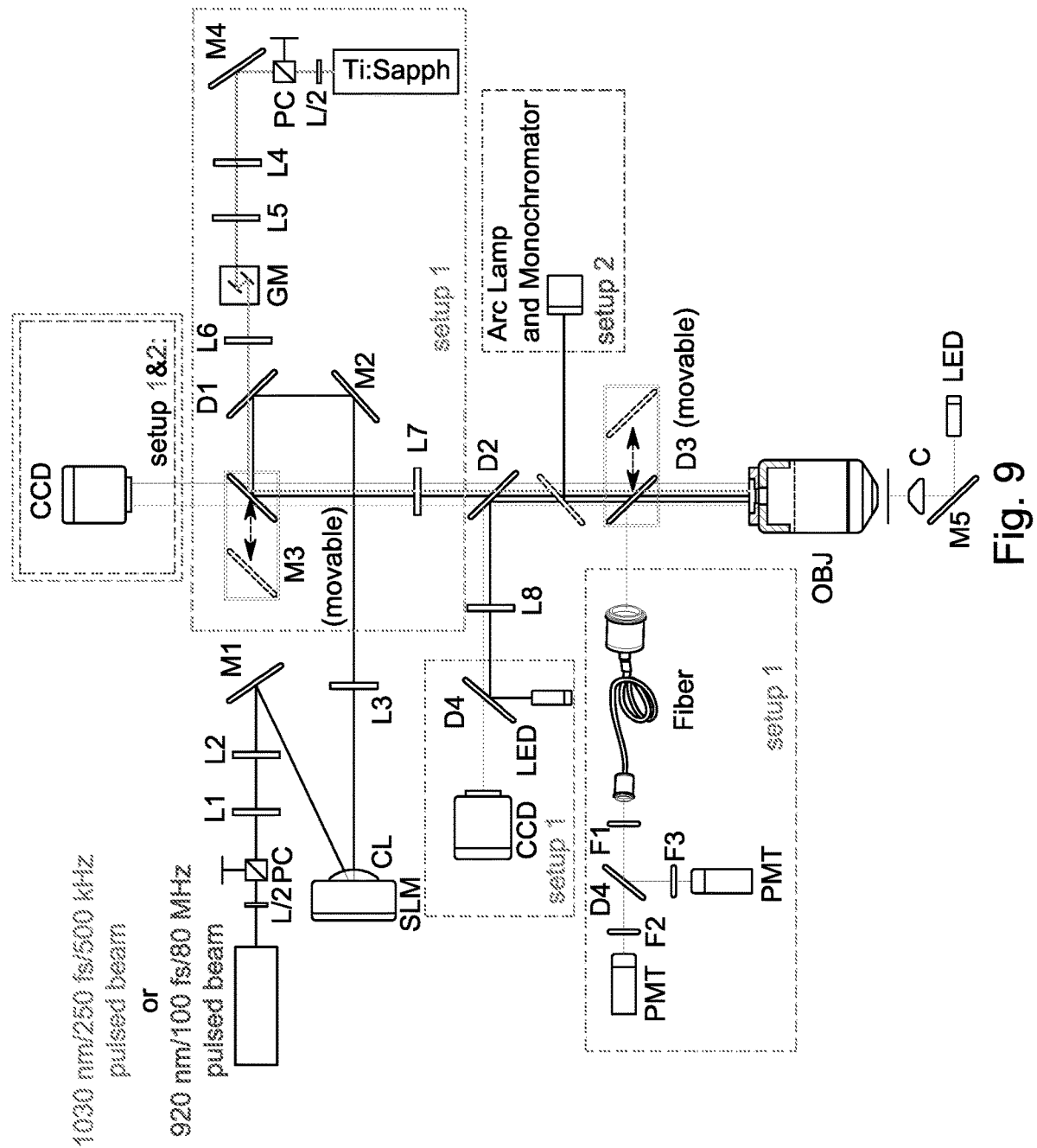
FIG. 9 provides a schematic diagram showing an embodiment of a detailed scheme of the holographic microscopes, for both setup 1 and setup 2. PC, Polarizer Cube; L/2, Half Wave Plate; M, Mirror; L, Lens; SLM, Spatial Light Modulator; CL, Cylindrical Lens; D, Dichroic; GM, Galvanometric Mirrors; F, Filter; OBJ, Objective; C, Condenser. Additional description provided in the Examples section.
Figure 10A:
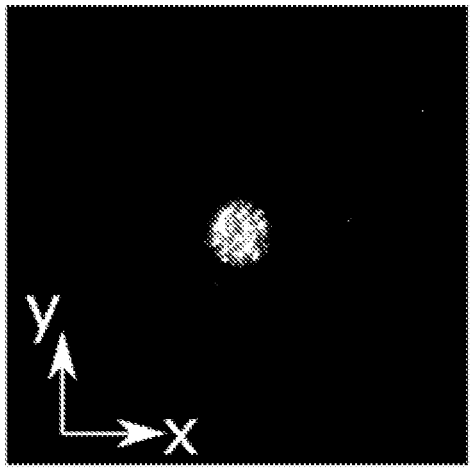
FIG. 10A-J provides photomicrographic images, graphs, and projection images demonstrating axial resolution of 2P holographic spots and diffraction efficiency correction.
Figure 10B:
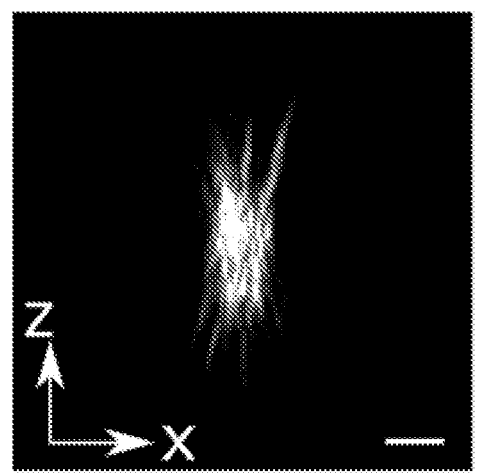
Figure 10C:
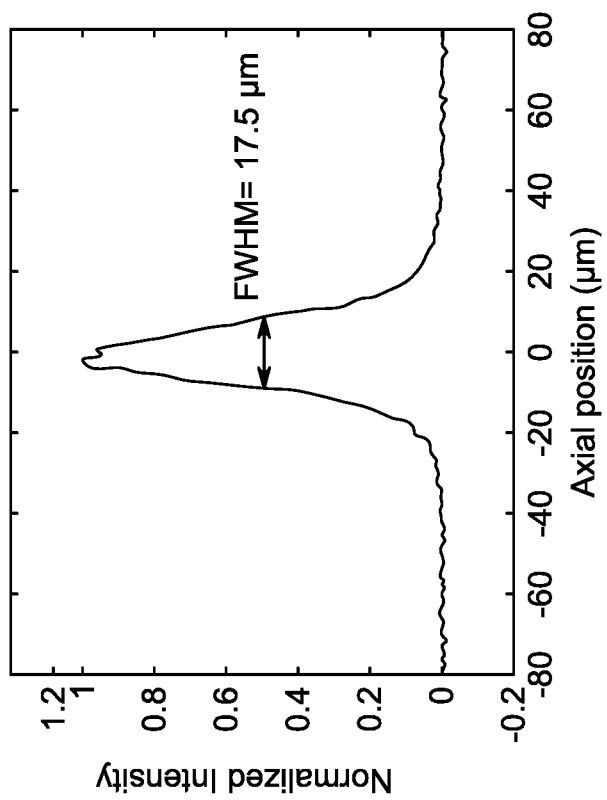
Figure 10D:
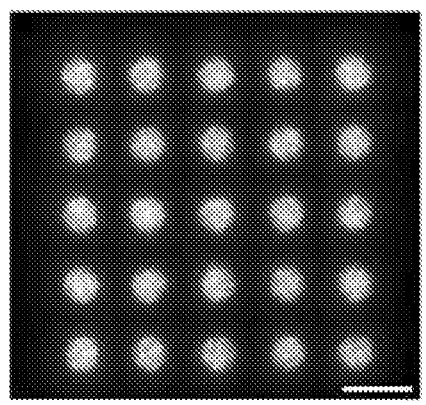
Figure 10E:
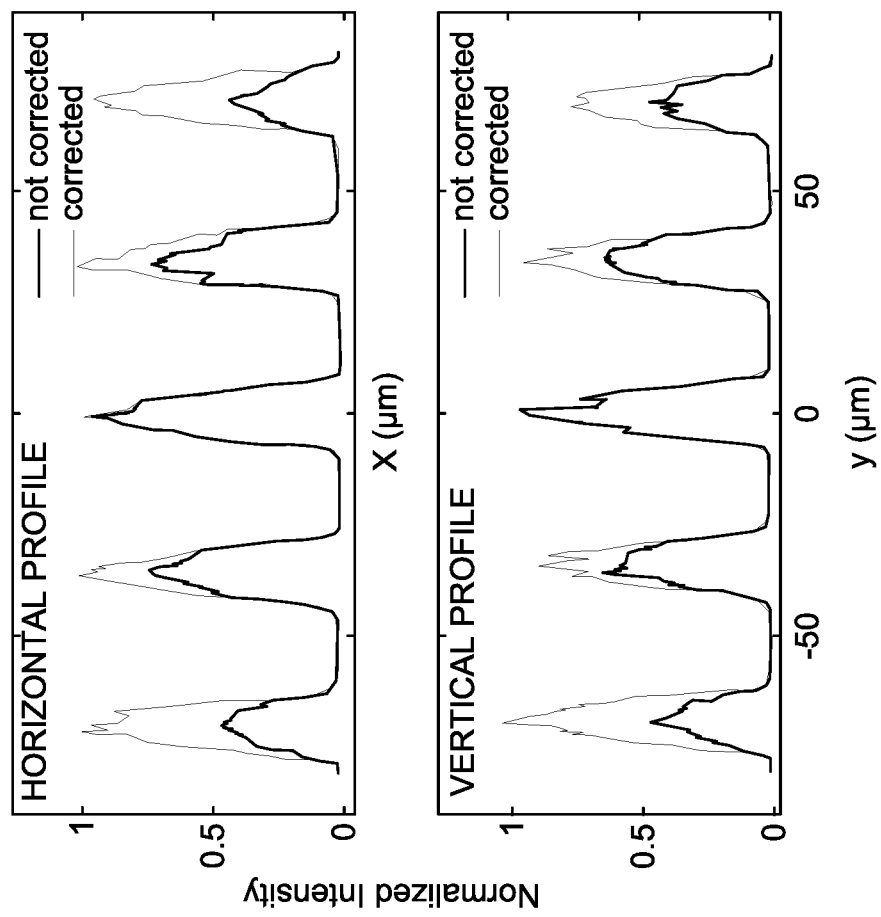
Figures 10F, 10G:
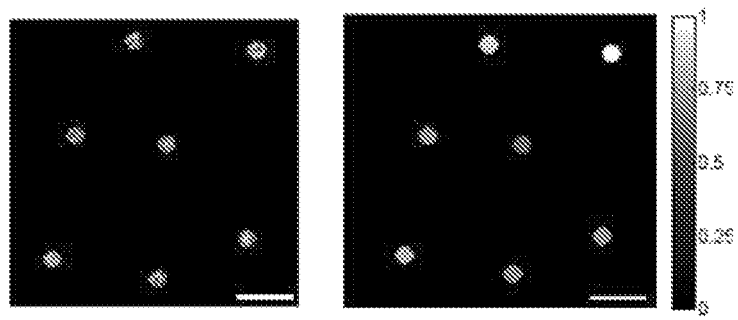
Figure 10H:
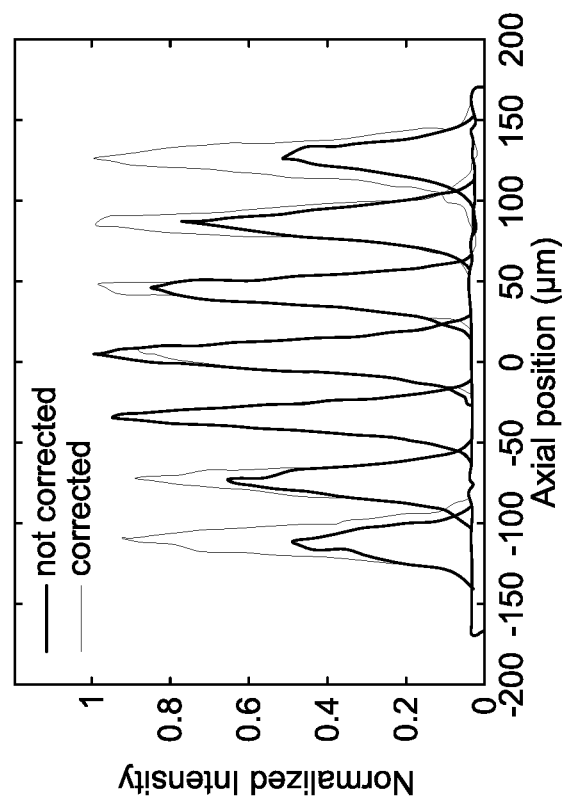
Figure 10I:
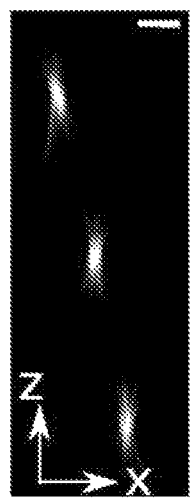
Figure 10J:
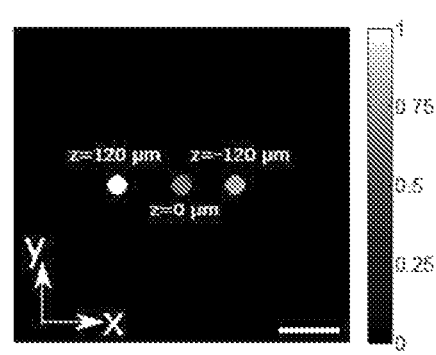

Setup 1 consisted of a homemade system, built around a commercial upright microscope (SliceScope, Scientifica, Clarksburg, N.J.) in which the holographic photo-stimulation path is combined with 3 imaging pathways: a two photon raster-scanning, a single-photon (1P) wide-field epi-fluorescence and an infrared (IR) transmitted light imaging (see detailed scheme in FIG. 9). Two-photon imaging is based on a mode-locked Ti-Sapphire source (Coherent, Santa Clara, Calif. Chameleon Vision II, pulse width 140 fs, tuning range 680 nm-1080 nm). The beam was raster scanned on the sample via a pair of XY galvanometric mirrors (3 mm aperture, 6215H series, Cambridge Technology, Bedford, Mass.) imaged at the back aperture of the microscope objective (40× W APO NIR, Nikon) through an afocal telescope (scan lens: f=100 mm, Thorlabs #AC508-300-B; tube lens: f=300 mm, Thorlabs #AC508-100-B). Fluorescence was collected by a fiber-coupled detection scheme [Ducros, M., et al. (2011). J. Neurosci. Methods, 198(2), 172-80] including a large diameter collector lens (f=75 mm, Thorlabs #LB 1309-A) and a 5 mm diameter liquid light guide (LLG, Series 300, Lumatec, Deisenhofen, DE customized with a f=14.5 mm doublet lens glued at the fiber entrance by Till Photonics, Hillsboro, Oreg. and an anti-reflective coating provided at the fiber exit). The fiber exit was imaged onto two photomultiplier tubes GaAsP (H10770-40 SEL, Hamamatsu, Bridgewater, N.J. H10770-40 SEL, active area 5 mm) by a set of three matching aspheres lenses (f=23.5 mm, Melles Griot #LAG-32.5-23.5-C). Following the fiber exit, fluorescence light was filtered by an infrared-light blocking filter (FF01-750sp, Semrock, Rochester, N.Y.), split into two channels by a dichroic mirror (FF555-Di03, Semrock, Rochester, N.Y.) and detected through two emission filters (FF01-510/84 and FF02-617/73, Semrock, Rochester, N.Y.). 2P imaging laser power was tuned by combining an electrically-controlled liquid crystal variable phase retarder (LRC-200-IR1, Meadowlark Optics, Frederick, Colo.) and a polarizer cube (BB-050-IR1, Meadowlark Optics, Frederick, Colo.).

1P imaging was based on the illumination provided by a LED source (M470L2, Thorlabs, Newton, N.J.), whose emission spectra was filtered by a bandwidth excitation filter (FF01-452/45, Semrock, Rochester, N.Y.) and coupled to a diffuser (DG10-1500, Thorlabs, Newton, N.J.) and an achromatic lens (f=30 mm, #LA1805 Thorlabs, Newton, N.J.) to provide homogeneous widefield illumination on the sample. 1P excited fluorescence was collected through a tube lens (f=200 mm), separated from the excitation light using a dichroic mirror (FF510-Di02, Semrock, Rochester, N.Y.) and detected by a CCD camera (Orca-05G, Hamamatsu, Bridgewater, N.J.) after passing through a visible bandwidth filter (FF01-609/181, Semrock, Rochester, N.Y.).

Fluorescence induced either by 2P raster scanning or 1P widefield illumination was collected by PMTs or CCD respectively, having in the detection pathway a switchable dichroic mirror (FF705-Di01, 70×50 mm custom size, Semrock, Rochester, N.Y.).

Transmitter IR oblique illumination imaging was provided by an IR-LED source (M780L2, Thorlabs, Newton, N.J.) installed at the rear port of the microscope via a DODT-contrast tube (DODT tube, Scientifica, Clarksburg, N.J.) coupled with a condenser focusing the light on the sample, that, after transmission through the sample, was collected with an IR CCD (IR-1000, DAGE-MTI, Michigan City, Ind.).

The 2P photo-activation consisted in the spatial patterning of arbitrary light patterns on cellular substructure obtained with Computer Generated Holography, based on phase modulation of the laser wavefront via the use of a Spatial Light Modulator (SLM).

The laser source used consisted on a femtosecond pulsed beam delivered by a fiber laser source (pulse width 250 fs, repetition rate 500 kHz, pulse energy 20 μJ, wavelength 1030 nm; Satsuma, Amplitude Systems, Boston, Mass.). The beam was enlarged by a telescope and reflected on the sensitive area of a reconfigurable liquid crystal on silicon spatial light modulator (LCOS-SLM, X10468-07 Hamamatsu Photonics, Bridgewater, N.J.). The reflected beam was projected on the back focal plane of the objective with an afocal telescope (f=300 mm, Thorlabs #AC508-300-B and f=500 mm Thorlabs #AC508-500-B). The SLM was controlled by a custom-designed software (Lutz et al. 2008) based on a Gerchberg and Saxton (GS) iterative algorithm [Gerchberg, R. W., & Saxton, W. O. (1972). Optik, 35(2), 237-246] which converts an arbitrary intensity pattern on the sample plane to a specific phase profile to be addressed at the SLM plane.

Additionally, adding lens-phase modulations to 2D-phase holograms enables remote axial displacements and 3D position of laterally shaped targets [Haist, T., et al., (1997). Opt. Commun. 140, 299-308]. This allowed subcellular processes to be targeted following their path in x-y-z (FIG. 3) and to address sequentially or simultaneously multiple targets in multiple planes (FIG. 5). Zero-order of diffraction was eliminated by introducing a cylindrical lens [Hernandez, O., et al., (2014) Optics Letters Vol. 39, Issue 20, pp. 5953-5956]. 2P imaging scan and 2P photo-activation beams were combined through a large dichroic mirror (Chroma T970dcspxr, 50 mm×70 mm custom sized, Chroma, Bellows Falls, Vt.).

Setup 2

An analogous holographic photostimulation was also implemented and used on another system, setup 2, coupled with widefield epifluorescence imaging.

This system was built on Olympus BX51WI—upright microscope, provided wide field epifluorescence imaging based on the illumination with an Arc Lamp, (OptoSource Illuminator, Cairn Research, Faversham, UK, coupled with a monochromator Optoscan Monochromator, Cairn Research, Faversham, UK), and an Orca Flash 4.0 Hamamatsu CCD camera.

The holographic photo-activation laser source consists of a conventional pulsed Ti:Sapphire laser, used at 920 nm (pulse width: 100 fs, repetition rate: 80 MHz, Mai-Tai, Deep-See, Spectra Physics, Santa Clara, Calif.). The holographic path was analogues to the one described for setup 1: a beam expander enlarged the beam in front of the Spatial Light Modulator (LCOS-SLM X10468-02), whose plane was projected at the back focal plane of a 40×-NA 0.8 objective LUM PLAN FI/IR, Olympus) by an afocal telescope (f=750 mm, Thorlabs #AC508-750-B and f=500 mm Thorlabs #AC508-500-B). The holographic beams was coupled on the optical axis of the microscope by a dichroic mirror (FF670, SDi01, 25*36 mm, Semrock, Rochester, N.Y.).

Power Conversion Between Setup 1 and Setup 2

The differences between the two laser sources in setups 1 and 2, in terms of wavelength, pulse width and repetition rate, required a proper calibration in order to compare the average photo-stimulation power density between experiments performed on the two setups. An empirical estimate was used to identify a scaling conversion factor k between the power of the two system: $P_1$ on setup 1 and $P_2$ on setup 2, based on the measurements of the rise-time of the photoinduced current (see also FIG. 4): the ratio between the power of the two setups was measured under an excitation that induced the same current rise-time. The conversion factor obtained was $k=P_2/Py_1 \approx 5.2$ meaning that the regenerative amplifier of setup 1 is around 5 times more efficient in the excitation of CoChR than the conventional Ti:Sapphire laser of setup 2.

This empirical estimation of the conversion factor k was similar to the theoretical evaluation of the same conversion factor, obtained taking into account the laser specifications and preliminary measurements of the 2P CoChR absorption spectrum (details below herein).

Diffraction Efficiency Corrections

Holographic patterns suffer from limited diffraction efficiency, meaning that the intensity of an holographic spot decreases the more is moved away from the center of the field of view or away from the nominal focal plane of the objective. For the measurements reported in FIG. 3 and FIG. 5, it was crucial to target cells or sub-cellular regions in the field of view with the same illumination intensity. In order to achieve this, specific corrective algorithms were implemented.

In the case of sequential targeting of different locations, homogenization of light distribution was achieved by generating, together with the main holographic spots, also an extra-spot at the edge of the field of view. By adjusting its size, the power of the main spot could be modulated, correcting the power inhomogeneity due to diffraction efficiency (see FIG. 9). The extra spot was blocked at an intermediate image plane after the Spatial Light Modulator, preventing it to reach the sample. In the case of simultaneous illumination of multiple locations, the input pattern given to the Iterative GS algorithm was modified in order to redistribute at will the power intensities between different spots. More power was sent to the more peripheral location and less to the more central ones, in order to compensate the diffraction efficiency and assure the same excitation density all over the pattern (see FIG. 9). Finally, to assure the delivery of the same excitation power density between the sequential stimulation with single spot and the simultaneous one, the laser power was properly adjusted taking into the total number of spots and their location.

Holographic Photostimulation Along Neurites

Patched cells in slices were loaded with Alexa594 Hydrazide dye (15-20 µM; Invitrogen, Waltham, Mass.) to visualize the cell's morphology. The patched neuron loaded with Alexa594 was imaged with a 2P scanning imaging system (imaging laser at 800 nm, setup 1) or widefield illumination (at 570 nm, setup 2). A z-stack of the fluorescence emission was acquired in order to reconstruct the 3D morphology of the neurites (in a range of typically +40 µm) and target them with holographic illumination specific x-y-z position along neurites.

The photo-stimulation protocol consists of sequentially displacing 10 µm diameter holographic stimulation spots from the distal end of the process towards the soma, with a step-size of approximately 10 µm. 2P stimulation consisted of 30 ms pulses with an illumination power density corresponding to the power threshold density required to trigger one action potential when stimulating the whole soma. Practically, the power threshold density was obtained by progressively increasing the excitation power up to a value that allowed to reliably (in three consecutive trials) trigger one action potential.

Measurement of Opsin and Photoinduced AP Kinetic Parameters

Neurons expressing CoChR-GFP or soCoChR-GFP were patched and photostimulated with holographic spots whose diameter was between 10 and 15 µm covering the whole soma. The kinetics of the response was monitored in both current clamp and voltage clamp. The photostimulation consisted of pulses of holographic illumination with a duration varying from 300 ms at a low power and down to a few ms at a higher power. The reported risetime corresponds to the time constant of a mono-exponential fit of the ascending part of the photoinduced current. The reported data have been obtained using both setups 1 and 2, and the two x-axes represented the averaged photostimulation power density values corresponding to each setup. A conversion factor k=5.2) was used to rescale from the two setups so that their power was equivalent.

To estimate the asymptotic value of the risetime, the risetime versus power curve was fit with the expression $t_{rise}=c_1/(P+c_2)^2+c_3$, with P the photostimulation power density, $c_1$, $c_2$ and $c_3$ free parameters in the fit, and the exponent 2 in the denominator to take into account the quadratic dependency of the opsin excitation under 2P illumination. The coefficient was taken as the asymptotic values of the risetime for each cells, and then averaged across cells. Only cells considered in the average were cells in which the risetime versus power curve had sufficiently number of experimental points (>) to assure the reliability of the fit.

The AP latency was defined as the time delay between the onset of 2P stimulation and the peak of the photostimulated AP. The plotted values were obtained by averaging AP latencies across 5 photo-stimulations (separated by 30 s). The duration of the photostimulation pulse was initially set for 30 ms for low stimulation power ($22\pm19$ µW/µm$^2$). For higher photostimulation power ($107\pm29$ µW/µm$^2$), the duration of photo-stimulation was decreased below 30 ms. The reported jittering was calculated as the standard deviation of the AP latency computed on series of 5 consequent photo-stimulations. The values were extracted from the same data used to obtain the latency values.

Cell-Somata Holographic Photostimulations in Slices

Opsin expressing cells were visualized with a 2P scanning imaging system (imaging laser at $\lambda$=920 nm in setup 1) and patched. Thereafter, a z-stack of the GFP fluorescence emission in the volume around the patched cell was acquired in order to identify neighboring positive cells. In slices expressing soCoChR-GFP expressing, cells were clearly distinguishable, because their somata were predominantly fluorescent with minimal neurophil fluorescence. In contrast, slices expressing CoChR-GFP presented a diffused and homogeneous green fluorescence, in which cells could be recognizable as dark spots (spots with lower fluorescence compared to the background).

In the volume around the patched cells, an ensemble of neighboring fluorescent cells was randomly identified and selected, and the selected cells were targeted with 10-15 m holographic spots. Depending on the field of view and cell distribution, 5 to 8 cells were selected. These cells, in the vicinity of the patched cell, were sequentially stimulated with a holographic spot (for 30 ms, 5 s apart) and the generated membrane depolarization in the soma was recorded (photo-stimulation power: 40 µW/µm$^2$ for CoChR-GFP, 43 µW/µm$^2$ for CoChR-GFP, setup 1). The last cell to be photostimulated for each stimulation sequence was the patched cell. Blockers were added to the ACSF solution in all experiments to block any synaptic effect (strychnine, picrotoxin/gabazine and NBQX (1-5 µM; Abcam, Cambridge, Mass.; Tocris Bioscience, Bristol, UK).

For simultaneous illumination experiments, a CoChR-GFP cell or soCoChR-GFP cell was patched and the membrane voltage was recorded in whole-cell current-clamp configuration as in 7 CoChR-GFP cells or soCoChR-GFP cells in the vicinity of the patched cell were simultaneously illuminated with 7 holographic spots for 30 ms and the generated membrane depolarization in the soma was recorded. The same power was delivered to each spot composing the pattern, thanks to diffraction efficiency compensating algorithm (see Methods above, herein). Additionally, the total laser power was adjusted in order to guarantee that the same excitation power density was delivered during the sequential photostimulation of single cells or the simultaneous illuminations of multiple cells (see FIG. 9).

3D Holographic Pattern Reconstruction

To reconstruct 3D holographic illumination for multiple cell photo-stimulation, a dual microscope configuration was used: below the main objective a second objective (NA 1.2, water-immersion, 60×) was placed. While the main objective focused the holographic pattern on a layer of rhodamine 6G (spin coated on a glass coverslip), the second objective collected the fluorescence generated by the rhodamine layer that was then recorded on a CCD camera. By changing the vertical position of the main objective, the whole x-y-z distribution of the holographic excitation is reconstructed. The resulting mages were processed with ImageJ.

Image Analysis Determining the Fluorescence Brightness from the Soma to the Neurites Images for this analysis were taken 14-18 DIV (10-14 days post-transfection). The image analysis was performed in ImageJ. For each neuron, the first step was to define the boundaries of the soma. To that end, a 20 µm diameter circle was drawn near the soma, inside which there was no apparent fluorescence from the soma or from neurites. The average fluorescence in the circle was defined as background fluorescence.

Pixels with fluorescence intensity of at least 10% above background levels were considered to be part of the soma and processes, and the boundary between soma and its processes was defined by the apparent cell morphology. Then, a polygon was drawn along the defined soma boundary and measured the average fluorescence inside of it, and subtracted the previously calculated background value. The resulting value was considered soma fluorescence. To measure the fluorescence intensities along the neurites, 1 µm$^2$ rectangles were defined along the neurite that were up to 100 µm away from soma at increments of 10 µm. The distance between each rectangle and the soma was measured along the neurites (not the minimal linear distance from the soma, since neurites were curved). The background value was then defined exactly as described above for the soma. It was made certain that the pixel intensity values at the boundaries of the rectangle were at least 10% above background levels, to be considered inside the neurite. The fluorescence intensity in each rectangle was averaged, then subtracted the background, then divided it by the average soma fluorescence and plotted resulting ratio with respect to their distances along the neurites. The ratios for each distance were averaged across neurites and data was plotted (using Matlab) as average and standard error of the mean (For CoChR-GFP, n=5 neurites taken from 5 cells taken from 2 cultures. For soCoChR-GFP, n=5 neurites taken from 5 cells taken from 3 cultures. For CoChR-Na$_V$1.2 (II/III)-GFP, n=5 neurites taken from 5 cells taken from 4 cultures).

Results

Creation of a Somatic Opsin—

Procedures were carried out to screen, via a multi-stage pipeline, for soma-targeting sequences that could localize opsins to neuronal cell bodies. Nine somatically expressed proteins (see Table 1 for a list of the proteins, and the various fragments and fusions explored below) were chosen for further consideration: myelin proteolipid proteins srPLP and DM20 [Jacobs, E. C., et al., (2003). Dev. Neurosci., 25(2-4), 96-104], the potassium channel K$_V$2.1 [Lim, S. T., et al., (2000). Neuron, 25(2), 385-397], sodium channels Na$_V$1.2 and Na$_V$1.6 [Garrido, J. J., et al., (2003). Science, 300(5628), 2091-4], the adhesion molecule L1 with the soma-retention causing mutation R184Q [Schafer, M. K. E., et al., (2010). Neurobiol. of Disease, 40(1), 222-37], the dynein adaptor protein Bicaudal-D (BicD) truncated after 50 codons (out of 782; this truncation impairs transport of FMRP out of the soma) [Bianco, A., et al., (2010). Current Biology: CB, 20(16), 1487-92], the adaptor protein Ankyrin$_G$ [Zhang, X., & Bennett, V. (1998). J. Cell Biol., 142(6), 1571-81], and the kainate receptor subunit KA2 [Valluru, L., et al., (2005). J. Biol. Chem., 280(7), 6085-93].

TABLE 1 soma-targeting candidate proteins

| Name of protein | Was the protein fused to a fluorescent protein or an immunoepitope tag? If yes, was it an N-terminal or a C-terminal fusion? * | Which was the soma targeting motif or peptide found? | Was the soma-targeting fragment fused to a fluorescent protein or an immunoepitope tag? If yes, was it an N-terminal or a C-terminal fusion? * | How far from the soma, approximately, was the fluorescence detected using visual inspection? | Did the sequence target an opsin to the soma or to the axon initial segment? If yes, what was the construct used? | Linker used between CoChR and the localization sequence |
|---|---|---|---|---|---|---|
| $Na_V1.6$ | Yes. N-terminal with GFP [i] | $Na_V1.6$(II-III) [i], a 27 amino acid sequence, from the intracellular loop between transmembrane domains II and III. | Yes. N-terminal [i] An N-terminal fusion was made. | 20-70 μm | Yes, to the axon hillock; ChR2-GFP-Nav1.6(II-III) [ii] | N/A |
| $Na_V1.2$ | Yes. N-terminal with GFP [i] | $Na_V1.2$(II-III) [i], a 27 amino acid sequence, from the intracellular loop between transmembrane domains II and III. | Yes. N-terminal [i] We made an N-terminal fusion. | 20-50 μm | Yes, to the axon hillock; ChR2-YFP-Nav1.2(II-III) [v] | Ggsggt |
| Soma restricted proteolipid (srPLP) | No. The protein was labeled with antibodies [iii] We made both N and C terminal fusions with GFP. | N/A | N/A | >100 μm | N/A | N/A |
| DM20 | No. The protein was labeled with antibodies [iii] Both N and C terminal fusions with GFP were made. | N/A | N/A | >100 μm | N/A | N/A |
| $Ankyrin_G$ | Yes. N-terminal with GFP [iv] | $Ankyrin_G$(837) [vi], from the N-terminal fragment of $Ankyrin_G$. | No. N-terminal Fusions were made with ChR2 or with eNpHR [vi]. We made both N and C fusions. | 20-50 μm The C-terminal fusion had a 10-fold higher expression than the N-terminal one. | Yes, to the soma. $Ankyrin_G$(837)-ChR2-mCherry and $Ankyrin_G$(1-2512)-eNpHR-GFP [vi]. CoChR-$Ankyrin_G$(1-2512)-GFP was made that was somatic and enabled photostimulation in expressing neurons. Was not packaged in AAVs due to its large size. | Ggsggt |

TABLE 1-continued soma-targeting candidate proteins

| Name of protein | Was the protein fused to a fluorescent protein or an immunoepitope tag? If yes, was it an N-terminal or a C-terminal fusion? * | Which was the soma targeting motif or peptide found? | Was the soma-targeting fragment fused to a fluorescent protein or an immunoepitope tag? If yes, was it an N- terminal or a C-terminal fusion? * | How far from the soma, approximately, was the fluorescence detected using visual inspection? | Did the sequence target an opsin to the soma or to the axon initial segment? If yes, what was the construct used? | Linker used between CoChR and the localization sequence |
|---|---|---|---|---|---|---|
| L1-R184Q | Yes, N-terminal with GFP [vii]. Both N and C fusions with GFP were made. | N/A | N/A | 50-100 μm | N/A | N/A |
| $K_v2.1$ | Yes, a HA-tag was fused to the N-terminus of $K_v2.1$. [viii]. | $K_v2.1$-motif, a 22 amino acid sequence [ii] from the C-terminal domain of $K_v2.1$. | No. C-terminal Fusions were made with ChR2 [ii]. A C-terminal fusion with GFP was made. | 60-150 μm | Yes. To the soma. ChR2-YFP-Kv2.1-motif and NpHR-YFP-Kv2.1-motif [ii] | N/A |
| KA2 | Yes, a myc-tag was fused to the N-terminus of KA2. Both N and C fusions with GFP were made.. | KA2(1-150). To find it, KA2 was fragmented into (from N terminal to C terminal) into KA2_PART 1 (360 amino acids), KA2_PART 2 (360 amino acids) and KA2_PART 3 (259 amino acids. | Yes, C and N terminal fusions of KA2(1-150) with GFP were made. | 20-50 μm | Yes, to the soma. The following were cloned: KA2(1-150)-CoChR-GFP (average current in expressing cells was 130 pA ± 34 pA), and CoChR--KA2(1-150)-GFP average current in expressing cells was 720 pA ± 156 pA) which was named soCoChR. | ggsggtggsggt (SEQ ID NO: 5) |
| BiCD$^{r5}$ | No, however FMRP was localized to the soma in neurons of fly larvae expressing BiCDr5 [ix]. | Yes, in the BiCD$^{r5}$ allele there is a stop codon after the first 50 codons (out of 782) [x]. | No. Both N and C fusions with GFP were made. | >100 μm | N/A | N/A |

*N-terminal fusion means targeting-sequence-GFP or targeting-sequence-opsin, C-terminal fusion is GFP-targeting-sequence or opsin-targeting-sequence. Citations:

[i] Garrido, J. J., et al., (2003) Science (New York, N.Y.), 300(5628), 2091-4;

[ii] Wu, C., et al., (2013). PloS One, 8(6), e66332. doi:10.1371/journal.pone.0066332;

[iii] Jacobs, E. C., et al., (2003) Dev. Neurosci., 25(2-4), 96-104;

[iv] Zhang, X., & Bennett, V. (1998) J. Cell Biol., 142(6), 1571-81;

[v] Grubb, M. S., & Burrone, J. (2010) PloS One, 5(10), e13761. doi:10.1371/journal.pone.0013761;

[vi] Greenberg, K. P., et al., (2011) Neuron, 69(4), 713-20;

[vii] SchAfer, M. K. E., et al., (2010) Neurobiol. of Disease, 40(1), 222-37;

[viii] Lim, S. T., et al., (2000) Neuron, 25(2), 385-397;

[ix] Bianco, A., et al., (2010) Current Biology: CB, 20(16), 1487-92; and

[x] Ran, B., et al., (1994) Development (Cambridge, England), 120(5), 1233-42.

In some studies, neuron somatic localization had been explored further by fusing the proteins to reporters—namely, $Na_v1.2$, $Na_v1.6$, L1-R184Q and AnkyrinG were fused to fluorescent proteins (FPs) [Garrido, J. J., et al., (2003) Science (New York, N.Y.), 300(5628), 2091-4; Schafer, M. K. E., et al., (2010) Neurobiol. of Disease, 40(1), 222-37; and Zhang, X., & Bennett, V. (1998) J. Cell Biol., 142(6), 1571-81], KA2 to a myc-tag [Vallum, L., et al., (2005). J. Biol. Chem., 280(7), 6085-93], and $K_v2.1$ to an HA-tag [Lim, S. T., et al., (2000). Neuron, 25(2), 385-397].

and GFP and Table 2a-b for statistical analysis of this comparison), but KA2(1-75) did not (see Table 1 for summary). Table 2a-b provides Two-way repeated measures (RM) ANOVA for normalized GFP brightness at different positions along neurites of three GFP variants. For GFP, n=5 neurites from 3 cells from 2 cultures. For KA2-GFP, n=5 neurites from 3 cells from 2 cultures. For KA2(1-150)-GFP, n=5 neurites from 3 cells from 2 cultures. Molecule (GFP variant) and distance (distance along neurite) were used as two factors for normalized GFP brightness.

Table 2a-b: Analysis of Data in FIG. 6

TABLE 2a

Figure 6A:
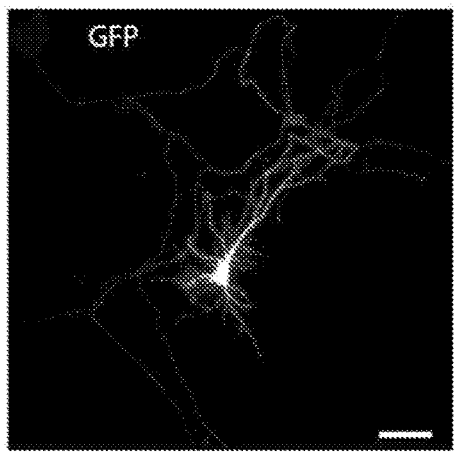
FIG. 6A-F provides photomicrographic images and bar plots demonstrating that an N-terminal domain of kainate receptor subunit 2 is retained in the soma.
Figure 6D:
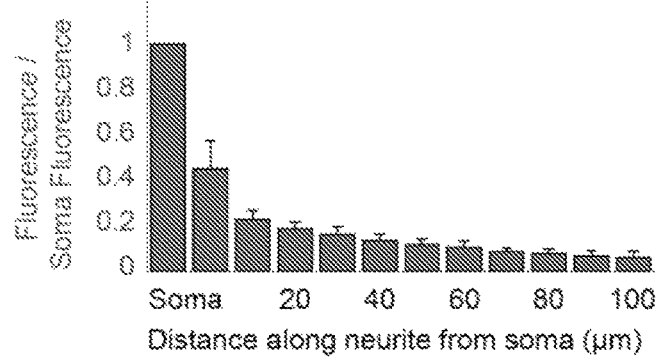
Figure 6B:
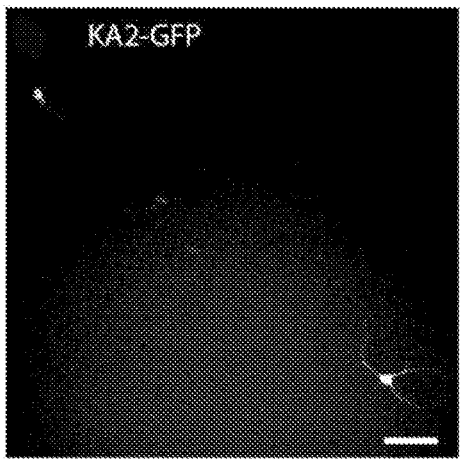
Figure 6E:
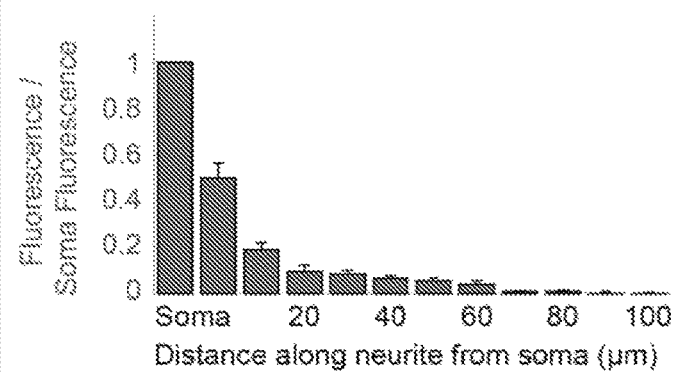
Figure 6C:
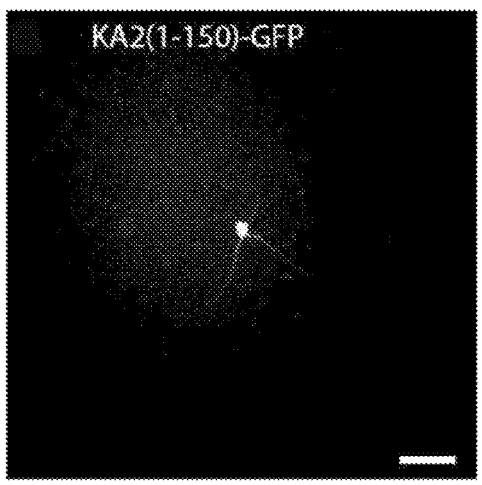
Figure 6F:
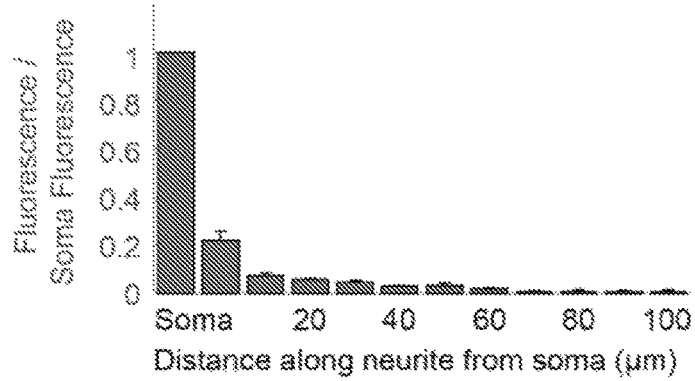
Figure 8B:
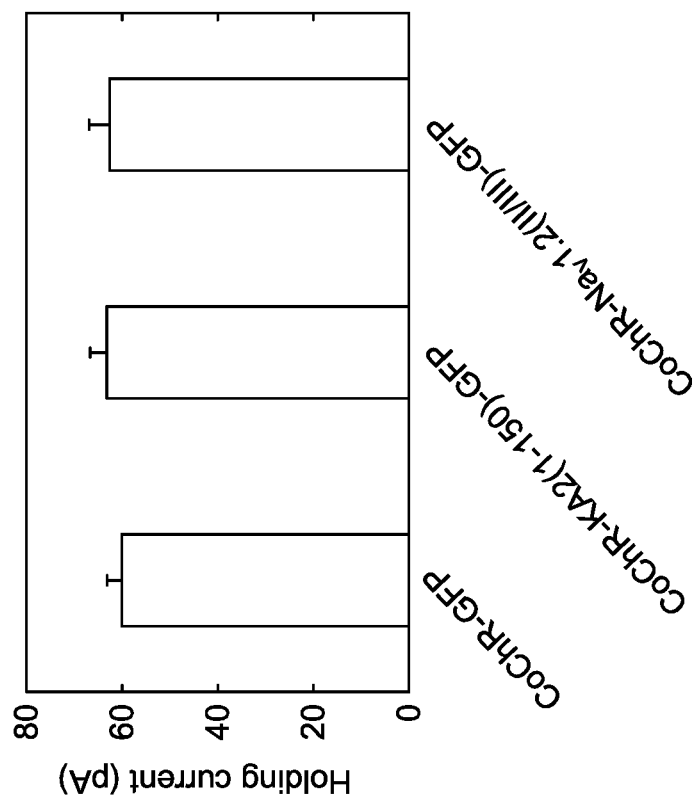
FIG. 8A-D provides bar plots showing examples of membrane properties of neurons expressing somatic vs. untargeted opsins. Cultured hippocampal neurons expressing CoChR-GFP (n=10 cells from 3 cultures), soCoChR-GFP (n=10 cells from 3 cultures) and CoChR-Na$_V$1.2 (II/III)-GFP (n=10 cells from 3 cultures) were patched 14 days following AAV transduction.
Figure 8A:
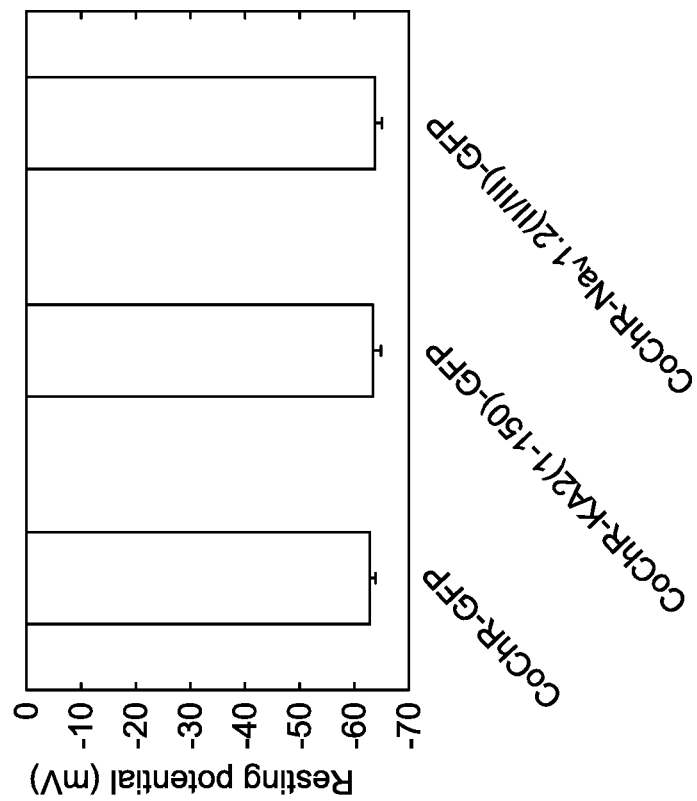
Figure 8D:
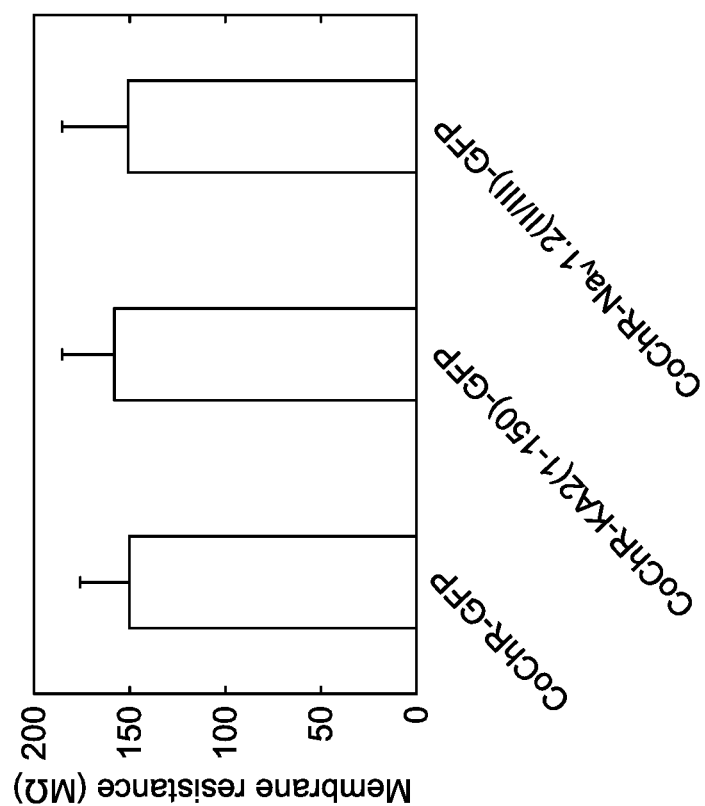
Figure 8C:
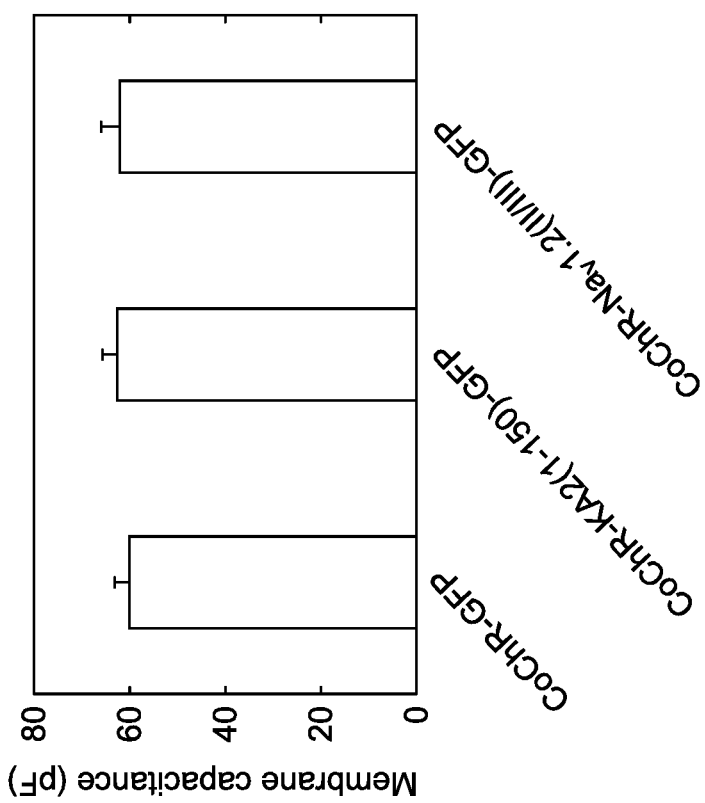

Statistical analysis for FIG. 6, FIG. 6D, E, and F - GFP brightness versus position along a neurite, normalized to GFP brightness at the soma.

| Source | Sum of squares | Degrees of freedom | Mean squares | F-statistic | P-value |
|---|---|---|---|---|---|
| Molecule | 0.433 | 2 | 0.21667 | 12.00 | 0.0039 |
| Distance | 2.051 | 10 | 0.20506 | 46.20 | 0 |
| Molecule × Distance | 0.239 | 20 | 0.01197 | 4.97 | $1.15 \times 10^{-7}$ |
| Molecule × Neurite | 0.144 | 8 | 0.01805 | — | — |
| Distance × Neurite | 0.178 | 40 | 0.00444 | — | — |
| Molecule × Distance × Neurite | 0.193 | 80 | 0.00240 | — | — |

TABLE 2b

Tukey's post hoc test for normalized GFP brightness along neurites after two-way RM ANOVA, with GFP as control group.

| Molecule | Tukey HSD Q statistic | P-Value | # of brightness measurements on neurites | Mean | s.e.m |
|---|---|---|---|---|---|
| KA2-GFP | 4.2524 | 0.0085525 | 55 | 0.0946 | 0.0201 |
| KA2(1-150)-GFP | 6.9380 | 0.0010053 | 55 | 0.0464 | 0.0089 |

For some of the above soma-restricting proteins, key fragments were shown to be sufficient to cause soma targeting of a reporter (see Table 1).

Experiments were performed in which green fluorescent protein (GFP) was fused to the full length clones of the 4 soma-targeting proteins described above for which no key fragment was reported (srPLP, DM20, L1-R84Q, and KA2), as well as to the reported fragments for the other 5 soma-targeting proteins (see Table 1). These GFP fusions were transfected into cultured hippocampal neurons, and it was visually observed that two of the 9 sequences tested appeared to target GFP primarily to the cell body (summarized in Table 1).

Two proteins were chosen for further consideration, KA2 and NaV1.2(II/III)-GFP. Because KA2 is a 979 amino acid protein, and was therefore unwieldy from a viral packaging standpoint, KA2 was divided into 3 parts. This resulted in fragments (listed from N terminal to C terminal) of length 360 amino acids [containing one transmembrane domain] [Marchler-Bauer, A., et al., (2014). Nucleic Acids Research, 43(D1)], 360 amino acids (containing 3 transmembrane domains), and 259 amino acids [containing one transmembrane domain and an arginine-rich ER retention sequence] [Ren, Z., et al., (2003). J. Neurosci., 23(16), 6608-6616]. GFP fused to the first fragment was somatic, but GFP fused to the latter two were not (see Table 1 for a summary). The N-terminal 150 amino acids of fragment 1, which was termed KA2(1-150), was tried and it was determined that this targeted GFP to the cell body (see FIG. 6 for comparison of the fluorescence between KA2-GFP, KA2(1-150)-GFP As for NaV1.2(II/III), an earlier study using this to target ChR2-YFP [Grubb, M. S., & Burrone, J. (2010). PloS One, 5(10), e13761. doi:10.1371/journal.pone.0013761] to the axon hillock of neurons revealed photocurrents significantly smaller than those of ChR2-YFP YFP [Grubb, M. S., & Burrone, J. (2010). PloS One, 5(10), e13761. doi:10.1371/journal.pone.0013761], and furthermore alterations of neuron excitability were found [Zhang, Z., et al., (2015). PloS One, 10(11), e0142052. doi:10.1371/journal.pone.0142052], so this motif was retained for comparison purposes (See FIG. 7 for images of CoChR-$Na_v1.2$(II/III)-GFP and Table 3 for statistics), but did not pursue it beyond the culture phase. Table 3a-g shows two-sample Kolmogorov-Smirnov (K-S) tests with Bonferroni correction for normalized GFP brightness at different positions along neurites. The overall significance level α was set to 0.05, and the significance level of each individual K-S test was a/11=0.0045. P values less than 0.0045 were highlighted in bold. For CoChR-GFP, n=7 neurites from 5 cells from 2 cultures. For CoChR-KA2(1-150)-GFP, n=9 neurites from 7 cells from 3 cultures. For CoChR-$Na_v1.2$(II/III)-GFP, n=5 neurites from 5 cells from 4 cultures.

Table 3a-g provides results of statistical analysis for FIG. 1 and FIG. 7. FIGS. 1M and 1N—GFP brightness versus position along a neurite, normalized to GFP brightness at the soma, analysis in Table 3a-c. FIG. 1P, photocurrent analysis in Table 3d-e. FIG. 1Q—τoff, analysis in Table 3f-g.

TABLE 3a

CoChR-GFP vs CoChR-KA2(1-150)-GFP:

| | Distance along neurite from soma | | | | | |
|---|---|---|---|---|---|---|
| | 0 | 10 | 20 | 30 | 40 | 50 |
| p-value | 0.00018 | 0.00018 | 0.01112 | 0.01714 | 0.01112 | 0.00126 |

| | Distance along neurite from soma | | | | | |
|---|---|---|---|---|---|---|
| | 60 | 70 | 80 | 90 | 100 | — |
| p-value | 0.00221 | 0.00036 | 0.00213 | 0.00213 | 0.00213 | — |

TABLE 3b

CoChR-GFP vs CoChR-NaV1.2(II/III)-GFP:

| | Distance along neurite from soma | | | | | |
|---|---|---|---|---|---|---|
| | 0 | 10 | 20 | 30 | 40 | 50 |
| p-value | 0.2999 | 0.61557 | 0.2999 | 0.05179 | 0.01038 | 0.01038 |

TABLE 3b-continued

CoChR-GFP vs CoChR-NaV1.2(II/III)-GFP:

| | Distance along neurite from soma | | | | | |
|---|---|---|---|---|---|---|
| | 60 | 70 | 80 | 90 | 100 | — |
| p-value | 0.01833 | 0.01833 | 0.05292 | 0.05292 | 0.2587 | — |

TABLE 3c

CoChR-KA2(1-150)-GFP vs CoChR-NaV1.2(II/III)-GFP:

| | Distance along neurite from soma | | | | | |
|---|---|---|---|---|---|---|
| | 0 | 10 | 20 | 30 | 40 | 50 |
| p-value | 0.12085 | 0.12085 | 0.30923 | 0.30923 | 0.90097 | 0.56102 |

| | Distance along neurite from soma | | | | | |
|---|---|---|---|---|---|---|
| | 60 | 70 | 80 | 90 | 100 | — |
| p-value | 0.56102 | 0.56102 | 0.12085 | 0.56102 | 0.12085 | — |

TABLE 3d

One-way analysis of variance (ANOVA) for photocurrent values:

| Molecule | # of cells |
|---|---|
| CoChR-GFP | 13 |
| CoChR-KA2(1-150)-GFP | 13 |
| CoChR-$Na_V$1.2(II/III)-GFP | 10 |

| Source | Sum of squares | Degrees of freedom | Mean squares | F-statistic | P-value |
|---|---|---|---|---|---|
| Between groups | 2431100 | 2 | 1215600 | 3.45 | 0.0437 |
| Within groups | 11638000 | 33 | 352660 | — | — |
| Total | 14069000 | 35 | — | — | — |

TABLE 3e

CoChR-GFP used as control group for Tukey's post hoc test after ANOVA.

| Molecule | Tukey HSD Q statistic | P-Value | # of cells | Mean | s.e.m |
|---|---|---|---|---|---|
| CoChR-KA2(1-150)-GFP | 0.6254 | 0.5566126 | 13 | 720 pA | 156 pA |
| CoChR-$Na_V$1.2(II/III)-GFP | 3.5295 | 0.0455040 | 10 | 273 pA | 44 pA |

Figure 1Q:
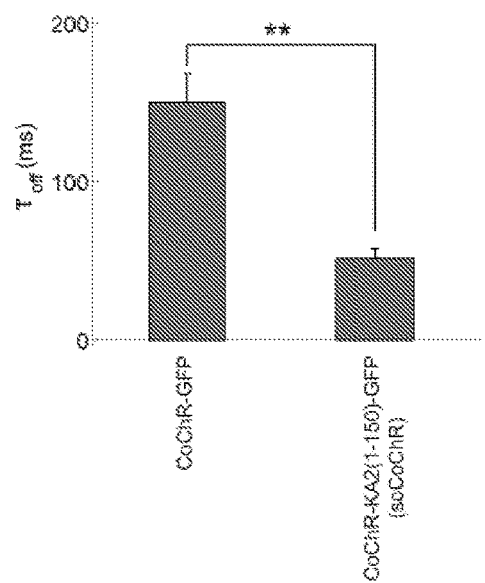

TABLE 3f shows results of analysis illustrated in FIG. 1Q - $\tau$off.
One-way analysis of variance (ANOVA) for $\tau$off values:

| Molecule | # of cells |
|---|---|
| CoChR-GFP | 10 |
| CoChR-KA2(1-150)-GFP | 11 |
| CoChR-$Na_V$1.2(II/III)-GFP | 10 |

| Source | Sum of squares | Degrees of freedom | Mean squares | F-statistic | P-value |
|---|---|---|---|---|---|
| Between groups | 49536 | 2 | 24768 | 16.78 | 0.00002 |
| Within groups | 41329 | 28 | 1476 | — | — |
| Total | 90865 | 30 | — | — | — |

TABLE 3g

CoChR-GFP used as control group for Tukey's post hoc test after ANOVA.

| Molecule | Tukey HSD Q statistic | P-Value | # of cells | Mean | s.e.m |
|---|---|---|---|---|---|
| CoChR-KA2(1-150)-GFP | 7.3747 | 0.0010053 | 11 | 52 ms | 6 ms |
| CoChR-Na$_V$1.2(II/III)-GFP | 6.8399 | 0.0010053 | 10 | 57 ms | 13 ms |

KA2(1-150) was fused to the C-terminus of CoChR, a powerful opsin that had amongst the largest photocurrents described to date [Klapoetke, N. C., et al., (2014). Nature Methods, 11(3), 338-46], and examined the resulting localization, finding that CoChR-KA2(1-150)-GFP appeared to be primarily at and near the cell body (FIG. 1G-J), as compared to wild-type CoChR-GFP (FIG. 1C-F). Quantitatively, at 50 μm from the edge of the cell body, CoChR-KA2(1-150)-GFP fluorescence was 4.67±1.29% of the average brightness across the cell body, in contrast to 35.56±8.33% for the wild-type opsin (mean±standard error of the mean; n=5 neurites taken from 5 cells from 3 cultures for the KA2 fusion, n=5 neurites taken from 5 cells from 2 cultures for the wild-type, FIG. 1M-N). It was found that for most distances between 0 to 100 μm from the edge of the cell body, in CoChR-KA2(1-150)-GFP expressing cells the neurite fluorescence was significantly lower than in CoChR-GFP expressing cells (n=9 neurites from 7 cells from 3 cultures for CoChR-KA2(1-150)-GFP; n=7 neurites from 5 cells from 2 cultures for CoChR-GFP; see Table 3 for Bonferroni-corrected Kolmogorov-Smirnov tests run for each bin).

Photo-current measurements (FIGS. 1O & 1P; 5 ms light pulses at 480 nm, 34.84 mW/mm$^2$) revealed that CoChR-GFP and CoChR-KA2(1-150)-GFP had average photocurrents of 1029±217 pA and 720 pA+156 pA respectively (mean±standard error of the mean, n=10 and 13 cells each from 3 and 3 cultures for CoChR-GFP and CoChR-KA2(1-150)-GFP respectively; see Table 3 for full statistics). As previously reported in Klapoetke, N. C., et al., (2014). Nature Methods, 11(3), 338-46, CoChR-GFP under 1P wide field activation has a long photo-current decay time (FIG. 1Q; $\tau_{off}$=150±18 ms, value is mean±standard error of the mean). This value was shorter in CoChR-KA2(1-150)-GFP (52±6 ms; mean±standard error of the mean; n=10 neurons from 3 cultures, 11 neurons from 3 cultures for CoChR-GFP and CoChR-KA2(1-150)-GFP respectively; FIG. 1Q; see Table 3 for full statistics), perhaps because the patch pipette is measuring just the decay of currents near the cell body, and not all the currents propagating in from the neurites that would be driven by wild-type opsin. The passive membrane properties for neurons containing CoChR-GFP (n=10 cells from 3 cultures) and CoChR-KA2(1-150)-GFP (n=10 cells from 3 cultures) were not significantly different (P>0.05 for these membrane properties: resting potential, membrane capacitance, holding current and membrane resistance; see FIG. 8 for comparison between the membrane properties of the targeted and non-targeted molecules in this study; see Table 5 for full statistics.

Table 5a-: Statistical Analysis for FIG. 8

TABLE 5a

One-way analysis of variance (ANOVA) for resting potential:

| Molecule | # of cells |
|---|---|
| CoChR-GFP | 10 |
| CoChR-KA2(1-150)-GFP | 10 |
| CoChR-Na$_V$1.2(II/III)-GFP | 10 |

| Source | Sum of squares | Degrees of freedom | Mean squares | F-statistic | P-value |
|---|---|---|---|---|---|
| Between groups | 6.318 | 2 | 3.159 | 0.196 | 0.8232 |
| Within groups | 435.3 | 27 | 16.12 | — | — |
| Total | 441.6 | 29 | — | — | — |

TABLE 5b

One-way analysis of variance (ANOVA) for membrane capacitance:

| Molecule | # of cells |
|---|---|
| CoChR-GFP | 10 |
| CoChR-KA2(1-150)-GFP | 10 |
| CoChR-Na$_V$1.2(II/III)-GFP | 10 |

| Source | Sum of squares | Degrees of freedom | Mean squares | F-statistic | P-value |
|---|---|---|---|---|---|
| Between groups | 40.20 | 2 | 20.10 | 0.170 | 0.8448 |
| Within groups | 3198 | 27 | 118.4 | — | — |
| Total | 3238 | 29 | — | — | — |

TABLE 5c

One-way analysis of variance (ANOVA) for holding current:

| Molecule | # of cells |
|---|---|
| CoChR-GFP | 10 |
| CoChR-KA2(1-150)-GFP | 10 |
| CoChR-Na$_V$1.2(II/III)-GFP | 10 |

| Source | Sum of squares | Degrees of freedom | Mean squares | F-statistic | P-value |
|---|---|---|---|---|---|
| Between groups | 75.27 | 2 | 37.63 | 0.0820 | 0.9215 |
| Within groups | 12390 | 27 | 459.0 | — | — |
| Total | 12470 | 29 | — | — | — |

TABLE 5d

One-way analysis of variance (ANOVA) for membrane resistance:

| Molecule | # of cells |
|---|---|
| CoChR-GFP | 10 |
| CoChR-KA2(1-150)-GFP | 10 |
| CoChR-Na$_v$1.2(II/III)-GFP | 10 |

| Source | Sum of squares | Degrees of freedom | Mean squares | F-statistic | P-value |
|---|---|---|---|---|---|
| Between groups | 332.6 | 2 | 166.3 | 0.0188 | 0.9814 |
| Within groups | 238600 | 27 | 8837 | — | — |
| Total | 238900 | 29 | — | — | — |

Somatic CoChR Enables Single Cell Optogenetic Control Using 1P Photo-stimulation To test whether CoChR-KA2(1-150)-GFP, which was named: soma-targeted CoChR (soCoChR for short), could mediate 1-photon stimulation of cultured hippocampal neurons without stimulating nearby cells, a single cell was patched under wide-field fluorescence microscopy, and a digital micromirror device (DMD) was used to consecutively photo-stimulate the patched cell and its neighbors with 20 micron diameter filled circles of 470 nm light of power 40.7 mW/mm$^2$ and duration of 1 ms, aiming for the cell body (FIG. 2A-B for a scheme of the experiment), under synaptic blockade. It was found that for light of this power, both CoChR-GFP or soCoChR-GFP expressing cells (n=5 and 5 respectively; FIG. 2C-D for images of opsin-expressing neurons), illuminating the cell body of the patched cell always yielded an action potential (AP) in that cell. Furthermore, while patching a CoChR-GFP expressing cell and photostimulating the neighboring non-patched CoChR-GFP expressing cells' somata, an action potential (AP) was recorded when photostimulating 62.0±16.3% of the cells (FIG. 2E, 2H; mean+s.e.m.; n=5 patched cells from 4 cultures); in contrast, while patching a soCoChR cell, photostimulating the neighboring non-patched cells' somata never resulted in an AP (P<0.01; FIG. 2F, 2H; n=5 patched cells from 5 cultures). Analyzing the data further, resulted in identification of depolarizations of ≥0.5 mV above baseline (defined as the average voltage over the 100 ms preceding the voltage change, see Methods described above herein) in patched cells within CoChR-GFP-expressing networks when 96.0±2.4% of the nearby cells were stimulated (FIG. 2E, 2I; mean±s.e.m.), in contrast to 4.0±4.0% of the nearby-cell stimulations for soCoChR-expressing neurons (P<0.001; FIG. 2F, 2I; mean±s.e.m.).

Two-Photon Holographic Control of Brain Slices with soCoChR-Expressing Neurons

Next, the potential for soCoChR to mediate single cell optogenetic control in intact mouse brain slices was assessed. To avoid the possibility of out of focus light exciting distant neurons, 2P activation was used, and to optimize temporal resolution holographic light control was used. Holographic 2P activation was implemented in two different microscopes (schematized at a high level in FIG. 3A; with further detail in FIG. 9). In setup 1, a custom made 2P scanning system was combined with a 2P computer generated holography (CGH) setup, using a high energy amplified fiber laser (λ=1030 nm; exit average power=10 W; repetition rate=500 kHz; pulse duration=250 fs) as excitation source. In setup 2, a 1P epifluorescence microscope was combined with a 2P CGH system using as excitation source a conventional mode locked Ti:Sapphire fs laser (λ=920 nm; exit average power=1.6 W; repetition rate=80 MHz; pulse duration=100 fs). Setup 1 was designed to achieve simultaneous activation of multiple cells, since the high output power and low repetition rate of the laser source enabled high energy pulses to be simultaneously delivered over the cell body surface, while keeping average power low. Setup 2, in contrast, had lower power, but used only conventional and commonly available laser hardware.

Figure 3A:
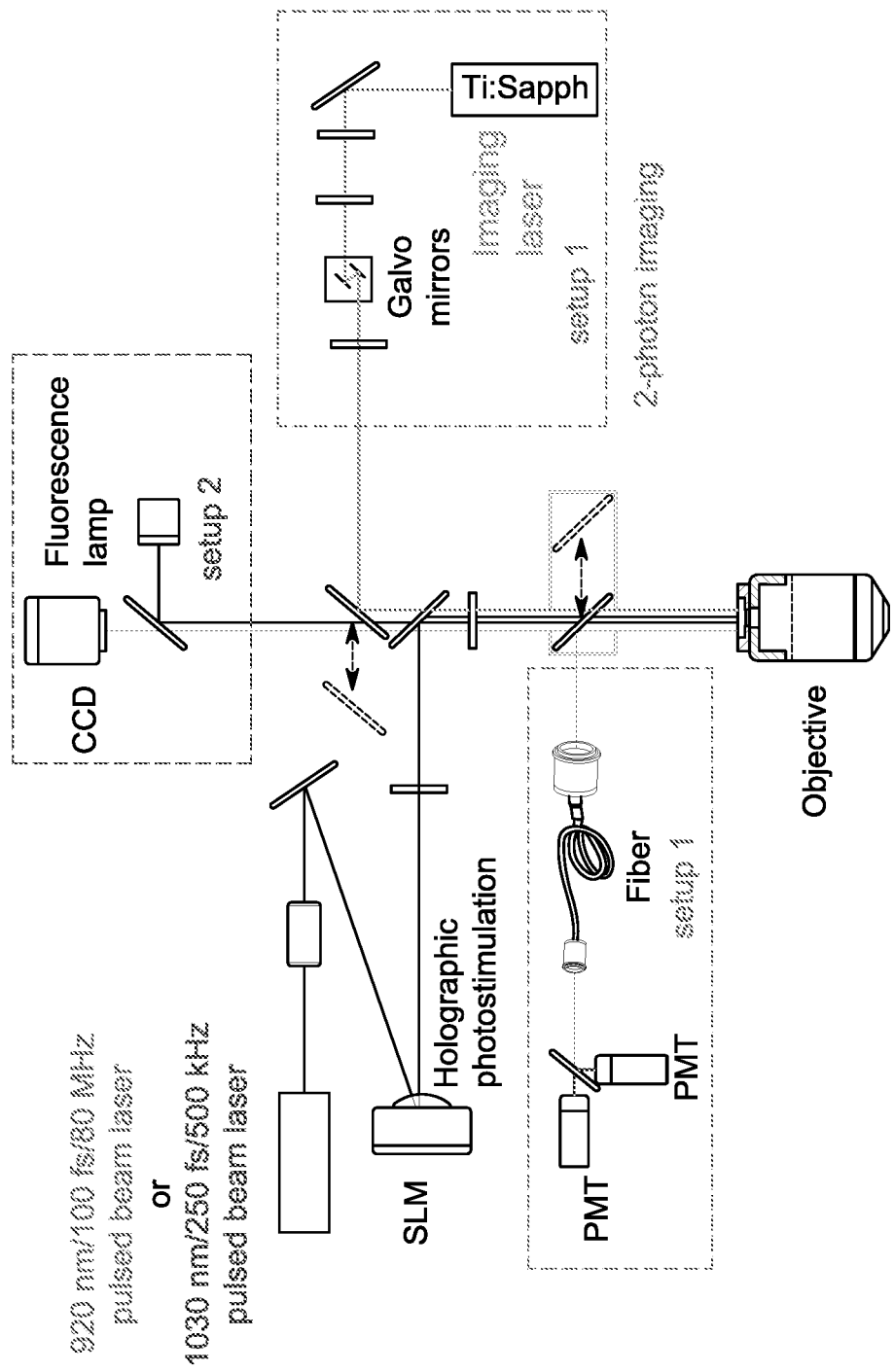
FIG. 3A-D provides schematic diagrams, traces, and a bar plot of embodiments of the invention showing that photocurrents of neurites expressing soCoChR-GFP are significantly smaller than in neurites expressing CoChR-GFP, in neurons virally expressing these opsins in mouse cortical brain slice.
Figure 3B:
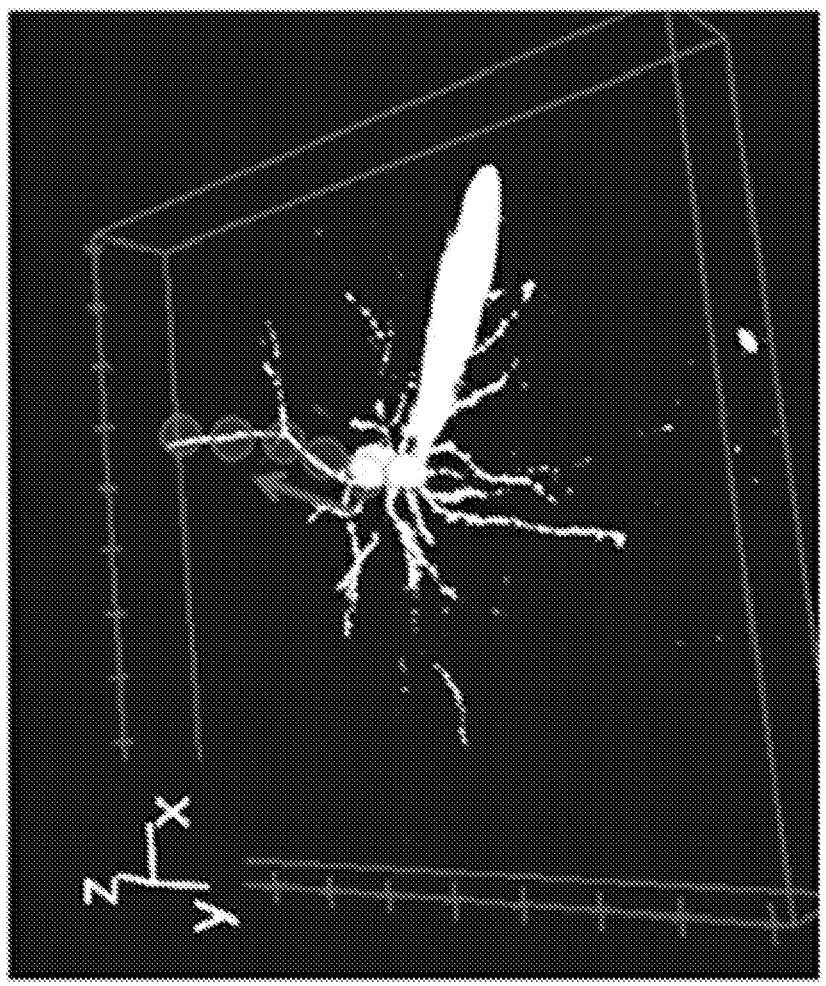
Figure 3C:
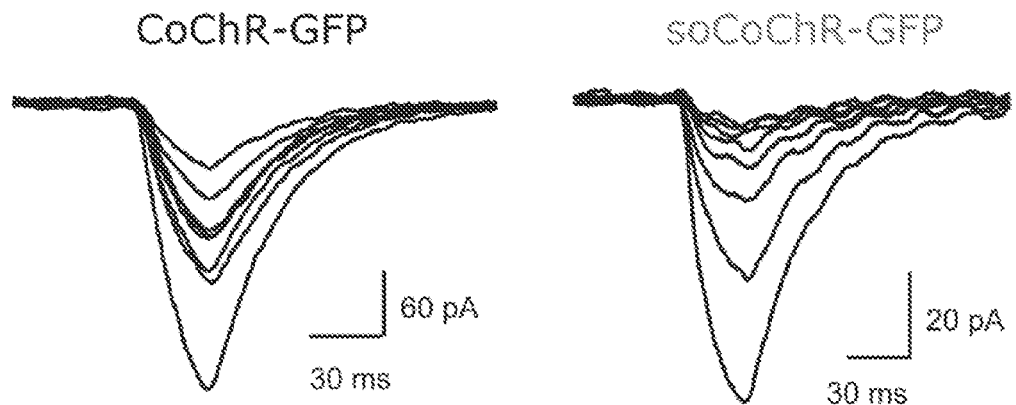
Figure 3D:
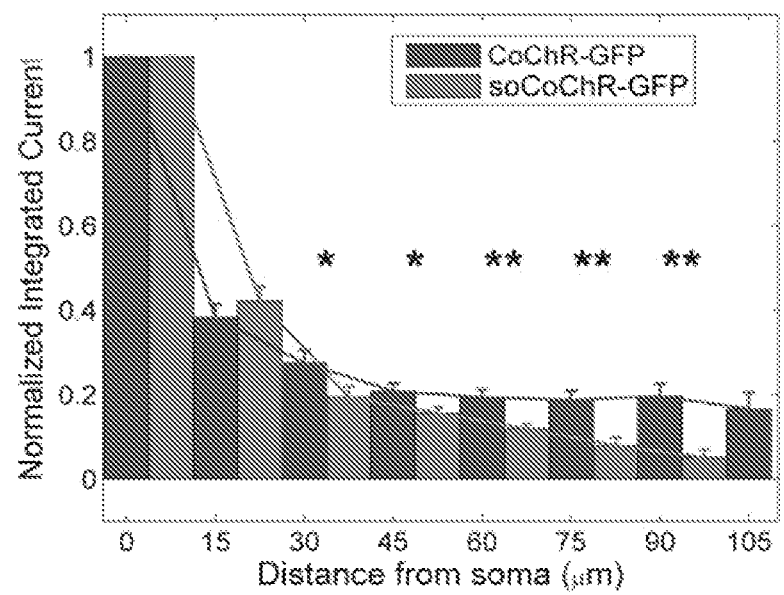
Figure 4A:
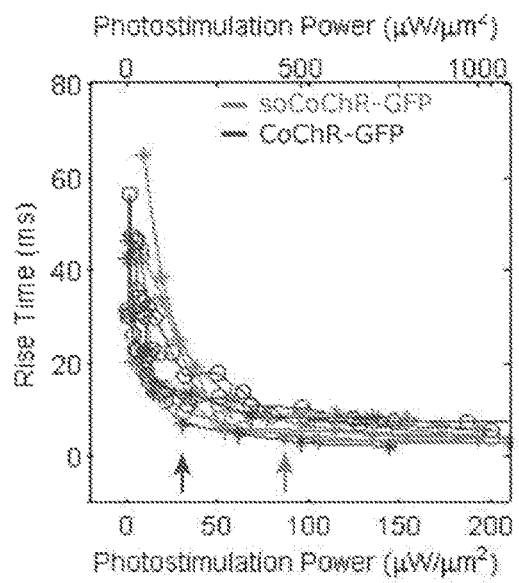
FIG. 4A-C provides graphs illustrating the 2P power necessary to enable millisecond control of cortical neuron activation in mouse brain slice.
Figure 4B:
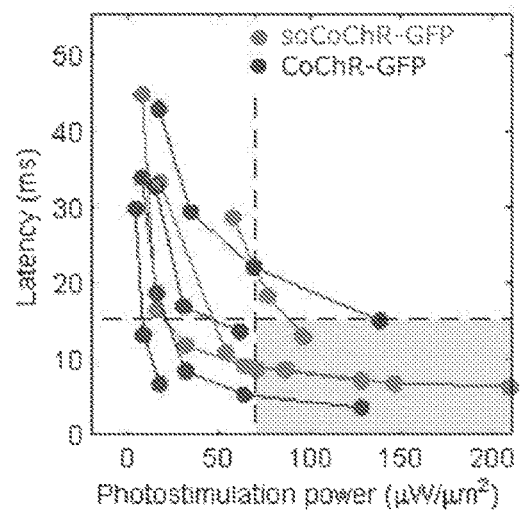

The spatial confinement of soCoChR vs. CoChR was quantified by measuring the photostimulated current integral while steering a 10 μm diameter holographic spot away from the soma of a patched neuron in ~10 μm steps along a neurite of a mouse cortical brain slice, with synaptic blockers applied (FIGS. 3B and C). 2P photo-stimulation power density was set, for each cell, at the minimum value necessary to reliably (in three consecutive trials) trigger one action potential using a 30 ms photo-stimulation pulse illuminating the whole soma (threshold power for CoChR-GFP: 28±10 μW/μm$^2$ and 92±93 using setups 1 and 2 respectively; n=7 cells in setup 1 and n=10 cells in setup 2; threshold power for soCoChR-GFP: 83±39 μW/μm$^2$ and 261±190 μW/μm$^2$ for soCoChRGFP using setups 1 and 2 respectively; n=4 cells in setup 1 and n=9 cells in setup 2). For each illumination position along each neurite, the measured current integral to the corresponding value measured at the soma was normalized. The normalized current integral decayed more sharply along neurites expressing soCoChR-GFP than along neurites expressing CoChR-GFP (P<0.05 at sites 30 μm from soma and beyond; P<0.01 at sites 60 μm from the soma and beyond; n=16 neurites in from 7 CoChR-GFP cells from 6 mice; n=22 neurites from 13 soCoChR-GFP cells from 9 mice, FIG. 3D). Thus, photo-evoked currents fall off more rapidly for soCoChR-bearing neurites than those bearing the wild-type, a crucial condition to support neuronal stimulation with single cell resolution. Table 4 provides information on analysis used to prepare results shown in FIG. 3. FIG. 3D shows normalized photocurrent integral generated by a photostimulation spot placed on a neurites at different distance from the soma for CoChR-GFP and CoChR-KA2(1-150)-GFP expressing cells. The current integral is normalized to the current integral value obtained with the photostimulation spot at the soma. Two-sample Kolmogorov-Smirnov test for normalized photocurrent for photostimulation along neurites. For CoChR-GFP, n=16 neurites from 7 cells from 6 mice; for CoChR-KA2 (1-150)-GFP, n=22 processes from 13 cells, from 9 mice.

TABLE 4

Statistical analysis for FIG. 3

| | Distance along neurite from soma | | | | | | | |
|---|---|---|---|---|---|---|---|---|
| | 0-Soma | 15 | 30 | 45 | 60 | 75 | 90 | 105 |
| p-value | 1 | 0.64 | 0.038 | 0.022 | 0.0016 | 0.0029 | 0.0004 | 0.0004 |

Millisecond-Timescale Activation of Neurons in Brain Slices

Illumination conditions were then identified that enabled the triggering of action potentials with millisecond temporal jitter in cells expressing soCoChR-GFP vs. CoChR-GFP. The rise time ($\tau_{on}$) and decay time ($\tau_{off}$) of photocurrents generated by a holographic spot covering the cell body of an opsin-expressing neuron were measured while illumination power was increased. For both CoChR-GFP and soCoChR-GFP expressing neurons, $\tau_{on}$ decreased with increasing illumination power (FIG. 4A), reaching an asymptotic value (see methods above herein) of 5.7±2.6 ms in CoChR-GFP cells (n=4 cells from 4 mice) and 4.1±2.5 ms in soCoChR-GFP cells (n=4 cells from 4 mice). $\tau_{off}$ values were almost independent of the illumination power and equal to 37±13 ms in CoChR-GFP (n=4 cells out of 4 mice) and 33.3±5.6 ms in soCoChR-GFP (n=4 cells out of 4 mice). Notably, these numbers were similar, in contrast to what was seen for 1P widefield illumination in cultured neurons (FIG. 1Q), suggesting that restricting light illumination to the soma effectively equalized the decay times of photo-evoked currents for targeted vs. non-targeted opsins.

Figure 4C:
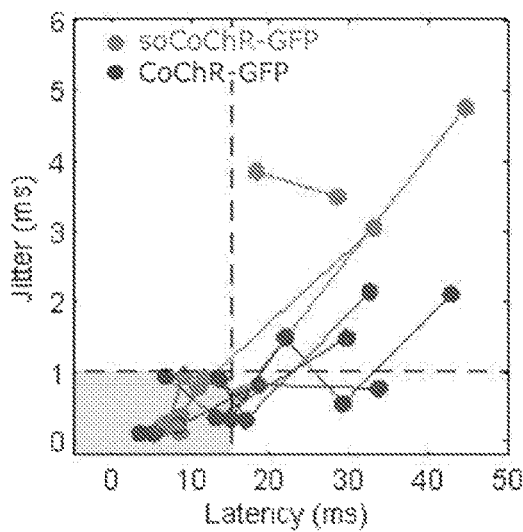

As a next step in understanding the temporal properties of 2P CGH excitation of soCoChR-bearing neurons, steps were taken to assess how AP latency (defined as the time interval between the onset of photo-activation and the peak of the action potential) and AP jitter (defined as the standard deviation of the aforementioned latency) depended on the illumination power, for both wild-type and soma-targeted soCoChR. Increasing the photo-stimulation power density at values above 70 $\mu W/\mu m^2$ on setup 1 (or 360 $\mu W/\mu m^2$ on setup 2) enabled for both CoChR-GFP and soCoChR-GFP-expressing neurons a spike latency below 15 ms (FIG. 4B), and a spike jitter of under 1 ms (FIG. 4C).

Figure 5A:
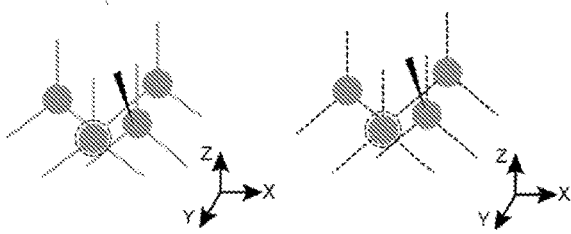
Figure 5B:
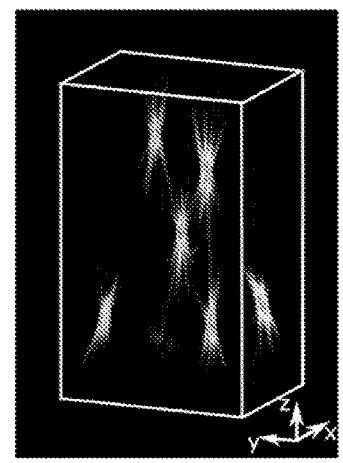

Single Cell Activation of soCoChR-Bearing Neurons in Brain Slices Using 3D Holography Finally, experiments were performed to assess whether soCoChR-bearing neurons in combination with 2P holographic stimulation could enable millisecond-precision single-cell optogenetics in brain slices. Crosstalk experiments were performed as described above herein, patching an opsin-expressing neuron and attempting to activate both the patched neurons and nearby neurons (but, for this experiment, using only setup 1; experiment schematically represented in FIG. 5A). An opsin-expressing neuron was patched, with synaptic transmission blocked, and acquired a 2P image stack to reconstruct the 3D volume (~200×200×80 $\mu m^3$) surrounding the patched cell. 3D holographic illumination allowed to sequentially or simultaneously target multiple locations in such volume (FIG. 5B). Five to seven neighboring neurons in this volume (FIG. 5C) were randomly selected. These cells were then sequentially illuminated with a 10 $\mu m$ holographic spot while recording from the patched cell. In each sequence, for both CoChR-GFP or soCoChR-GFP, the patched cell responded with an action potential when the holographic spot was placed on its cell body. For CoChR-GFP expressing cells, in 44±5% of the cells nearby to a patched cell (n=5 patched cells from 3 mice, FIG. 5D-E), illumination evoked an AP in the patched cell, whereas for soCoChR-GFP expressing cells, illumination of neighboring cells one at a time never evoked an action potential in the patched cell (P<0.01; n=4 patched cells from 4 mice; FIG. 5D-E). Thus, soCoChR used in combination with 2P CGH illumination could ensure zero-crosstalk, single cell stimulation of neurons in intact brain circuitry, even ensuring submillisecond jitter of the spikes.

Although individually illuminating neighboring soCoChR-GFP expressing cells did not evoke APs in the patched cell, the illumination still induced a depolarization of 4±2 mV in the patched cell (FIG. 5D; n=4 cells from 4 mice). Accordingly, experiments were performed to assess whether simultaneous stimulation of multiple neighboring cells could push a patched neuron to fire one or more action potentials, by exciting between 5 and 8 randomly selected neighboring cells, but simultaneously this time. Multiple illumination spots were generated, each with power density equal to the one used for the corresponding experiment with sequential cell stimulation (73±33 $\mu W/\mu m^2$ and 150±76 $\mu W/\mu m^2$ for CoChR-GFP and soCoChR-GFP expressing cells respectively; see also Methods above herein and FIG. 9). For CoChR-GFP, in 60% of the cells we observed multiple action potentials when the 7-8 neighboring cells were stimulated (n=5 patched cells from 3 mice; FIG. 5F-G). In contrast, for soCoChR-GFP multiple action potentials were never observed when 5-7 neighboring cells were stimulated (n=3 patched cells from 3 mice; FIG. 5F-G). Single action potentials were observed in 100% and 33% of patched cells, for CoChR-GFP and soCoChR-GFP respectively (n=5 cells from 3 mice and 3 cells from 3 mice, respectively) in this simultaneous neuron excitation condition.

DISCUSSION

The studies herein have demonstrated that optical activation of single cells in dense mammalian neural circuitry, with submillisecond precision, is possible without causing stray spiking in neighboring neurons—a long-sought goal in the usage of optogenetics to examine the connections and functions of single neurons in the intact brain. This result has been achieved through molecular engineering—creating a soma-targeted version of the powerful opsin CoChR, or soCoChR for short—as well as optimal 2-photon computer generated holographic (CGH) control of individual neurons. These studies and resulting methods and compositions of the invention, enable optogenetics to be performed with single cell precision, key to enabling individual connections to be assessed and mapped throughout intact circuits as a function of brain state, plasticity, or disease.

The experiments included screening potential trafficking (also referred to herein as targeting) sequences from 9 different soma-localized molecules, first testing entire molecules as well as fragments with GFP, then CoChR, a powerful opsin previously discovered [Klapoetke, N. C., et al., (2014). Nature Methods, 11(3), 338-46]. It was identified that the first 150 amino acids on the N-terminus of the kainate receptor subunit 2 enabled efficient target of CoChR to the soma, restricting CoChR expression to the first 20-50 $\mu m$ of dendrites and axons, without alteration of cellular function. Going forward, as more and more soma-localized proteins are found, the screening methods of the invention, as disclosed herein, may allow for even better targeted optogenetics. The experiments demonstrated that it was possible to get zero-crosstalk two-photon excitation of individual cells without driving action potentials in neighbors, but activating many neighbors at once could cause a nearby neuron to be excited to the point of spiking.

Single cell optogenetics can be a powerful tool for mapping the connectivity of neurons within functional networks, a topic of great interest in the understanding of how individual cells work together in networks to implement neural computation. With zero-cross-talk single cell optogenetics, it is possible to patch one neuron and photo-stimulate many neighboring cells, measuring synaptic strength as well as synaptic release kinetics, or perhaps also to image neural activity network-wide (e.g., with novel red calcium reporters [Dana, H., et al., (2016). eLife, 5, e12727] in response to each neuron within the network being excited in turn. Thus, the methods and compositions of the invention will be useful for bridging the structural and functional domains of the field of connectomics, important for ultimately realizing its impact on the understanding of behavior and disease.

For soCoChR-GFP-expressing neurons it has now been demonstrated that APs could be generated reliably by using either a conventional mode locked fs Ti:Sapphire laser (λ=920 nm, repetition rate 80 MHz, exit power=1.6 W) or an amplified fiber laser (λ=1030 nm, repetition rate 500 kHz, exit power=10 W). The first approach is of easier implementation, because such laser sources are common in 2P microscopy in laboratories and imaging facilities. However, the studies disclosed herein found, in agreement with previous experiments using ChR2 [Papagiakoumou, E., et al., (2010) Nature Methods, 7(10), 848-854; Prakash, R. et al., (2012) Nature Methods, 9(12), 1171-9] or C1V1 [Begue, A., et al., (2013). Biomedical Optics Express, 4(12), 2869-79], that reaching the AP threshold with soCoChR at depth of about 50 µm requires an excitation power of about 30 mW/cell. This value, considering an available exit power after the objective of about 200 mW (at 920 nm), may limit to about 6-7 cells the maximum number of simultaneously achievable targets. Conversely, amplified fiber lasers enable higher 2P absorption compared to typical mode-locked Ti:Sapphire laser oscillators due to lower pulse repetition rates of the femtosecond laser (two-photon excited signal, $S \propto P_{avg}(f\tau)^{-1}$, with f repetition rate, τ pulse width and $P_{avg}$ average beam power [Xu, C., & Webb, W. W. (1996). J. Optical Soc. of America B, 13(3), 481. doi: 10.1364/JOSAB. 13.000481; Zipfel, W. R., et al., (2003). Nature Biotech., 21(11), 1369-1377]. This feature enabled reducing to ~80 µW/µm² (corresponding to about 7 mW/cell) the AP spiking threshold and therefore, considering the several-Watt exit power of amplified fiber laser (corresponding in the set up disclosed herein to ~2 W after the objective) would make it possible to simultaneously photostimulate up to 200 cells. Overall these results indicate that targeted CoChR can be used for optogenetic neuronal control with single cell resolution and sub-millisecond temporal precision using optimized 2P CGH optics. Performances similar to the one achieved with targeted CoChR and 2P holographic illumination might be reached by other opsins when fused to the KA2(1-150) motif, e.g. Jaws for neuronal inhibition. Thus, additional opsins can be targeted using a KA2 polypeptide or functional variants thereof as described herein.

Example 2

Studies were performed and novel soma-targeting molecular strategies were developed. These strategies include use of expression of protein sequences in cells. The methods included novel expression of protein sequences that when fused to different opsin polypeptides (for example, but not limited to: CoChR, CsChrimson, Chronos, Jaws, etc.) resulted in transport of the opsin polypeptides into the soma of the cell in which they are expressed. The resulting opsins were found to be both somatic and functional. Two different molecular targeting strategies were tested and found to successfully deliver the opsin polypeptide to the soma of the cell in which they were expressed.

One strategy included use of myosin binding repeats. Myosin 5 binding repeat (MBD) is known to lead to the trafficking of cargo to dendrites [Lewis, T. et al., Nat Neurosci. 2009 May; 12(5): 568-576], and myosin 6 binding repeat (MVIBD) is known to lead to the trafficking of cargo to axons [Lewis, T. et al., (2011) PLoS Biology March Vol. 9, Issue 3 e1001021]. Experiments were performed to assess the use of multiple MBD and MVIBD repeated components as part of fusion proteins that additionally included cargo polypeptides, for example detectable labels, opsins, etc. The term: M5M6BR is used herein to refer to myosin binding repeat-containing soma-targeting polypeptides (also called soma-targeting polypeptides herein). Studies were performed to prepare and use M5M6BR polypeptides to deliver cargo polypeptides to soma. Experiments included expressing, in cells, different combinations of binding repeat sequences fused to a cargo polypeptide of interest. Studies were performed to assess the ability of various numbers, arrangements, and combinations of binding repeats in methods to localize a cargo polypeptide to the soma of the cell. Methods used to prepare sequences, to express fusion proteins in cells, and to assess localization of the cargo polypeptide in the cell included procedures as described in Example 1 herein.

When the two sequences (MVIBD and MBD, for example) were fused to an opsin and to one another in tandem and repeated more than once (for example MVIBD-MBD)-MVIBD)-MBD) they resulted in clustering of the opsins at the neural cell body (soma). Studies were performed using various combinations and numbers of MVIBD and MBD polypeptides to prepare and use M5M6BR polypeptides of the invention. Each of the following M5M6BR soma-targeting polypeptide was tested using methods described herein: MVIBD-MBD; MBD-MVIBD; MVIBD-MBD-MVIBD-MBD; MBD-MVIBD-MBD-MVIBD; MVIBD-MBD-MVIBD-MBD-MVIBD-MBD; MBD-MVIBD-MBD-MVIBD-MBD-MVIBD; MVIBD-MBD-MVIBD-MBD-MVIBD-MBD; MBD-MVIBD-MBD-MVIBD-MBD-MVIBD; MVIBD-MVIBD-MBD-MBD; MVIBD-MVIBD-MVIBD-MBD-MBD-MBD, with MBD and MVIBD representing polypeptides set forth herein as: SEQ ID NOs: 22 and 23, respectively. Tested sequences included at least those set forth as SEQ ID NO: 32, and 51-59. Linking amino acids were included between polypeptides in M5M6BRs tested. FIGS. 11 and 12 illustrate results of soma-targeting M5M6BR experiments.

Results of the studies demonstrated the effectiveness of the use of the M5M6BR polypeptides as soma-directing polypeptides. Results also indicated that in general, a longer series of MVIBD and MBD polypeptides resulted in higher levels of puncta in the soma of the tested cells, as compared to shorter series of MVIBD and MBD polypeptides.

A second strategy that was tested included the use of the tail region of the potassium calcium-activated channel subfamily N member 1 (Kcnn1) from the rat (*Rattus norvegicus*), rSK-1-tail. Studies were performed in which this sequence, fused to an opsin polypeptide, was expressed in a cell. Methods used to prepare sequences, to express fusion proteins in cells, and to assess localization of the cargo polypeptide in the cell included procedures as described in Example 1 herein. The results of the studies demonstrated that the rSK-1-tail sequence, when fused to an opsin resulted in transport of the opsin polypeptide to the soma of the cell in which it was expressed.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated by reference in their entirety herein.

What is claimed is:

1. A corn position comprising a fusion protein comprising a soma-targeting polypeptide fused to an opsin polypeptide, wherein the soma-targeting polypeptide comprises a KA2 polypeptide, wherein the KA2 polypeptide amino acid sequence consists of SEQ ID NO: 1, 3, 10, 12, 14 or an amino acid sequence with at least 90% sequence identity to SEQ ID NO: 1, 3, 10, 12, or 14, respectively.

2. The composition of claim 1, wherein the soma-targeting sequence of the KA2 polypeptide has the amino acid sequence of SEQ ID NO: 3, 10, 12 or 14.

3. The composition of claim 1, wherein the opsin polypeptide is a channelrhodopsin polypeptide.

4. The composition of claim 1, further comprising a pharmaceutically acceptable carrier.

5. The composition of claim 1, wherein the fusion protein further comprises a detectable label.

6. A cell comprising the composition of claim 1.

7. A method of modulating electrical activity in a cell, the method comprising:
   a) expressing in a host cell a fusion protein comprising a soma-targeting polypeptide and an opsin polypeptide, wherein the soma-targeting polypeptide comprises a KA2 polypeptide, wherein the KA2 polypeptide amino acid sequence consists of SEQ ID NO: 1, 3, 10, 12, 14 or an amino acid sequence with at least 90% sequence identity to the amino acid sequence of SEQ ID NO: 1, 3, 10, 12, or 14, respectively, and
   b) contacting the expressed opsin polypeptide with a light under suitable conditions to activate the opsin polypeptide and modulate an electrical activity in the host cell.

8. The method of claim 7, wherein the host cell is a vertebrate cell.

9. The method of claim 7, wherein the host cell is a mammalian cell.

* * * * *

UNITED STATES PATENT AND TRADEMARK OFFICE
CERTIFICATE OF CORRECTION

| | |
|---|---|
| PATENT NO. | : 11,324,824 B2 |
| APPLICATION NO. | : 16/306627 |
| DATED | : May 10, 2022 |
| INVENTOR(S) | : Shemesh et al. |

It is certified that error appears in the above-identified patent and that said Letters Patent is hereby corrected as shown below:

In the Specification

In Column 1, Lines 12-15, delete:
"This invention was made with government support under NIH 6928706 and NIH 6931693 awarded by the National Institutes of Health. The government has certain rights in the invention."

And insert:
-- This invention was made with government support under NS087724, R01 MH103910, and R24 MH106075 awarded by the National Institutes of Health. The government has certain rights in the invention. --.

Signed and Sealed this
Fourth Day of November, 2025

John A. Squires
*Director of the United States Patent and Trademark Office*